US008017559B2

(12) United States Patent
Etzerodt et al.

(10) Patent No.: US 8,017,559 B2
(45) Date of Patent: Sep. 13, 2011

(54) COMBINATORIAL LIBRARIES OF PROTEINS HAVING THE SCAFFOLD STRUCTURE OF C-TYPE LECTIN-LIKE DOMAINS

(75) Inventors: Michael Etzerodt, Hinnerup (DK); Thor Las Holtet, Rønde (DK); Niels Jonas Heilskov Graversen, Åbyhøj (DK); Hans Christian Thøgersen, Mundelstrup (DK)

(73) Assignee: Anaphore, Inc., San Diego, CA (US)

( * ) Notice: Subject to any disclaimer, the term of this patent is extended or adjusted under 35 U.S.C. 154(b) by 501 days.

(21) Appl. No.: 11/633,040

(22) Filed: Dec. 4, 2006

(65) Prior Publication Data

US 2007/0275393 A1 Nov. 29, 2007

Related U.S. Application Data

(62) Division of application No. 10/450,472, filed as application No. PCT/DK01/00825 on Dec. 13, 2001, now abandoned.

(60) Provisional application No. 60/272,098, filed on Feb. 28, 2001.

(30) Foreign Application Priority Data

Dec. 13, 2000 (DK) ................................ 2000 01872

(51) Int. Cl.
*C40B 20/04* (2006.01)
*C40B 50/18* (2006.01)
(52) U.S. Cl. ............. 506/4; 506/3; 506/2; 506/1; 435/6; 435/7.1; 435/7.2
(58) Field of Classification Search .................. 506/1–4; 435/6, 7.1, 7.2
See application file for complete search history.

(56) References Cited

U.S. PATENT DOCUMENTS 5,593,882 A    1/1997   Erbe et al.
5,679,548 A *  10/1997  Barbas et al. ................. 435/69.6

FOREIGN PATENT DOCUMENTS

| EP | 0 947 582 A1 | 6/1999 |
| WO | 94/18227 A2 | 8/1994 |
| WO | 9856906 A | 12/1998 |
| WO | 99/24617 A1 | 5/1999 |
| WO | 00/20574 A3 | 4/2000 |
| WO | 02/48189 A2 | 6/2002 |
| WO | 02/48189 A3 | 6/2002 |

OTHER PUBLICATIONS

Reiter, Yoram et al.: "An Antibody Single-domain Phage Display Library of a Native Heavy Chain Variable Region: Isolation of Functional Single-domain VH Molecules with a Unique Interface," J. Mol. Biol., 290:685-698 (1999).

Nuttall, Stewart D. et al.: "Design and Expression of Soluble CTLA-4 Variable Domain as a Scaffold for the Display of Functional Polypeptides," Protein Structure, Function and Genetics, 36: 271-227 (1999).
Hassan, Helle et al.: "The Lectin Domain of UDP-N-acetyl-D-galactosamine: Polypeptide N-acetylagalactosaminyltransferase-T4 Directs its Glycopeptice Specificites," Journal of Biological Chemistry, vol. 275, No. 49, pp. 38197-38205 (2000).
Vestweber, Dietmar et al.: "Mechanisms That Regulate the Function of the Selections and Their Ligands," Physiological Reviews, vol. 79, No. 1, Jan. 1999, pp. 181-213.
Evans, Stephen V. and Mackenzie, C. Roger: "Characterization of protein-glycolipid recognition at the membrane bilayer," Journal of Molecular Recognition, 12: 155-168 (1999).
Skerra, Arne: "Review Engineered protein scaffolds for molecular recognition," Journal of Molecular Recognition, vol. 13, pp. 167-187 (2000).
Vita, Claudio: "Engineering novel proteins by transfer of active sites to natural scaffolds," Current Opinion in Biotechnology, vol. 8, pp. 429-434 (1997).
International Preliminary Examination Report for International Application No. PCT/DK01/00825.
International Search Report for International Application No. PCT/DK01/00825.
Aspberg et al. "The C-type lectin domains of lecticans, a family of aggregating chondroitin sulfate proteoglycans, bind tenascin-R by protein-protein interactions independent of carbohydrate moiety," Proc. Natl. Acad. Sci., USA, vol. 94, pp. 10116-10121, Sep. 1997.
Bass et al. "Hormone Phage: An Enrichment Method for Variant Proteins With Altered Binding Properties," Proteins: Structure, Function, and Genetics 8:309-314, 1990.
Benhar et al., "Highly Efficient Selection of Phage Antibodies Mediated by Display of Antigen as Lpp-OmpA' Fusions on Live Bacteria, " J. Mol. Biol. (2000) 301, pp. 893-904.
Berglund et al., "The gene structure of tetranectin, a plasminogen binding protein, "FEBS Letters, vol. 309, No. 1, pp. 15-19, Aug. 1992.
Bertrand et al., "Crystal structure of human lithostathine, the pancreatic inhibitor of stone formation," The EMBO Journal, vol. 15, No. 11, pp. 2678-2684, 1996.
Bettler et al., "Immunoglobulin E-binding Site in Fc, Receptor (FcRii/CD23) identified by Homolog-scanning Mutagenesis," The Journal of Biological Chemistry, vol. 267, No. 1, Issue of Jan. 5, pp. 185-191, 1992.

(Continued)

*Primary Examiner* — T. D. Wessendorf
(74) *Attorney, Agent, or Firm* — McDonnell Boehnen Hulbert & Berghoff LLP

(57) ABSTRACT

The present invention provides novel polypeptides having the scaffold structure of a C-type lectin-like domain (CTLD) and a randomized loop region for specifically binding a variety of target compounds and also provides nucleic acids encoding the polypeptides. The present invention further provides combinatorial CTLD libraries, methods for constructing the libraries, and methods for screening the libraries to identify and isolate the novel CTLD polypeptides. Specifically, the invention provides libraries of nucleic acids encoding polypeptides having a scaffold CTLD with a randomized loop region, as well as nucleic acid sequences, vectors, and methods for preparing and expressing the libraries. Exemplary nucleic acids useful in the combinatorial libraries are derived from tetranectin and other proteins having a CTLD.

22 Claims, 37 Drawing Sheets

OTHER PUBLICATIONS

Blanck et al., "Introduction of Selectin-like Binding Specificity into a Homologus Mannosebinding Protein," The Journal of Biological Chemistry, vol. 271, No. 13, Issue of Mar. 19, 1996, pp. 7289-729.

Burrows et al., "Selective binding of N-acetylglucosamine to the chicken hepatic lectin," Biochem J., 324, pp. 673-680, 1997.

Chiba et al., "Introduction of Mannose Binding Protein-type Phosphatidylinositol Recognition into Pulmonary Surfactant Protein A," Biochemistry, 38, pp. 7321-7331.

Christensen et al., "Sequence-specific binding of the N-terminal three-finger fragment of Xenopus transcription factor IIIA to the internal control region of a 5S RNA gene," FEBS Letters, vol. 281, No. 1, 2, pp. 181-184, FEBS 09586, Apr. 1991.

Cyr et al., "A library of Bacteriophage-displayed antibody fragments directed against proteins of the inner ear" PNAS (USA), vol. 97, No. 5, Feb. 29, 2000, pp. 2276-228.

Drickamer, "Engineering galactose-binding activity into a C-type mannose-binding protein" Nature vol. 360, Nov. 12, 1992, pp. 183-186.

Drickamer et al., "Biology of Animal Lectins," Annu Rev. Cell Biol., 1993, 9:237-264.

Drickamer "C-type lectin-like domains," Current Opinion in Structural Biology, 1999, 9:585-590.

Dunn, "Phage display of proteins" Current Opinion in Biotechnology, 1996, 7:547-553.

Ernst et al., "Expanding baculovirus surface display: Modification of the native coat protein gp64 of Autographa californica NPV," Eur. J.Biochem., 267, pp. 4033-4039, 2000.

Ewart et al., "The ice-binding Site of Atlantic Herring Antifreeze Protein Corresponds to the Carbohydrate-Binding Site of C-type Lectins," Biochemistry, 37, pp. 4080-4085, 1998.

Feinberg et al., "Structure of a C-type Carbohydrate Recognition Domain from the Macrophage Mannose Receptor," The Journal of Biologycal Chemistry, vol. 275, Jul. 14, 2000, pp. 21539-52548.

Fujii et al., "Evolving catalytic antibodies in a phage-displayed combinatorial library "Nature Biotechnology, vol. 16, May 1998, pp. 463-467.

Gates et al., Affinity Selective Isolation of Ligands from Peptide Libraries Through Display on a lac Repressor "Headpiece Dimer", J. Mol. Biol. , 255, 1996, pp. 373-386.

Graversen et al., "The Plasminogen Binding Site of the C-type Lectin Tetrnectin is located in the Carbohydrate Recognition Domain, and Binding is Sensitive to Both Calcium and Lysine, " The Journal of Biological Chemistry, vol. 273, Oct. 30, 1998, pp. 29241-29246.

Graversen et al., "Multational Analysis of Affinity and Selectivity of Kringle-Tetranectin Interaction. Grafting novel kringle affinity onto the tetranectin lectin scaffold," The Journal of Biological Chemistry, vol. 275, Dec. 1, 2000, pp. 37390-37396.

Griffiths et al., "Strategies for selection of antibodies by phage display" Current Opinion Biotech, vol. 9, 1998, pp. 102-108.

Holtet et al., :Tetranectin, a trimeric plasminogen-binding C-type lectin, Protein Science, 1997, 6:1511-1515.

Honma et al., "The Mannose-Binding Protein a Region of Glutamic Acid 185-Alanine 221 can Functionally Replace the Surfactant Protein a Region of Glutamic Acid 195-Phenyllalanine 228 without Loss of Interaction With Lipids and Alveolar Type II Cells," Biochemistry, 36, 1997, pp. 7176-7184.

Huang et al., "Design of Potent β-Lactamase Inhibitors by Phage Display of βLactamase Inhibitory Protein", The Journal of Biological Chemistry, vol. 275, May 19, 2000, pp. 14964-14968.

Hufton et al., "Development and application of cytotoxic T lymphocyte-associated antigen 4 as a protein scaffold for the generation of novel binding ligands, " FEBS Letters 475, pp. 225-231, 2000.

Hakannson et al., "Crystal structure of the trimetric alpha-helical coiled coil and the three lectin domains of human lung surfactant protein D," Structure Folding and Design, vol. 7, No. 3, 1999, pp. 255-264.

Iobst et al., "Binding of Sugar Ligands to Ca 2+ dependent Animal Lectins: I. Analysis of Mannose Binding by Site Directed Mutagenesis and NMR" The Journal of Biological Chemistry, vol. 269, Jun. 3, 1994, pp. 15505-15511.

Iobst et al., "Binding of Sugar Ligands to Ca 2+ dependent Animal Lectins: II. Generation of Hight-Affinity Galactose Binding by Site-Directed Mutagenesis," The Journal of Biological Chemistry, vol. 269, Jun. 3, 1994, pp. 15512-15519.

Iobst et al., "Selective Sugar Binding to the Carbohydrate Recognition Domains of the Rat Hepatic and Macrophage Asialoglycoprotein Receptors," The Journal of Biological Chemistry, vol. 271, Mar. 22, 1996, pp. 6686-6693.

Jaquinod et al., "Mass Spectrometric Characterisation of Post-Translational Modification and Genetic Variation in Human Tetranectin," Biol. Chem. vol. 380 Nov. 1990, pp. 1307-1314.

Kastrup et al., "Structure of the C-Type Lectin Carbohydrate Recognition Domain of Human Tetranectin," Acta Crystallographica Section D, 54, pp. 757-766.

Kogan et al., "A Single Amino Acid Residue Can Determine the Ligand Specificity of E-selectin, " The Journal of Biologycal Chemistry, vol. 270, Jun. 9, 1995, pp. 14047-14055.

Kolatkar et aL, "Mechanism of N-Acetylgalactosamine Binding to a C-type Animal Lectin Carbohydrate-recognition Domain," The Journal of Biological Chemistry, vol. 273, Jul. 31, 1998, pp. 19502-19508.

Lorentsen et al., "The heparin-bin ding site in tetranectin is located in the N-terminal region and binding does not involve the carbohydrate recognition domain," Biochem J., 347, 2000, pp. 83-87.

Marks et al., "Molecular Evolution of Proteins on Filamentous Phage: Mimicking the Strategy of the Immune System,"The Journal of Biological Chemistry, vol. 267, Aug. 15, 1992, pp. 16007-16010.

Mann et at., "The amino-acid sequence of the abalone (Haliotis Laevigata) nacre protein perlucin: Detection of a Functional C-type Lectin Domain with Galactose/mannose specificity," Eur. J. Biochem., 267, pp. 5257-5264. 2000.

McCormack et al., The Carbohydrate Recognition Domain of the Surfactant Protein A Mediates Binding to the Major Surface Glycoprotein of Pneumocystis carinii, Biochemistry, 36, 97, pp. 8092-8099.

Meer et al., "Crystal Structure of the Carbohydrate Recognition Domain of the Hi Subunit of the Asialoglycoprotein Receptor,"J. Mol. Biol., 300, 2000, pp. 857-865.

Mikawa et al., "Surface Display of Proteins on Bacteriophage λ Heads,"J. Mot. Biol, 262, 1996, pp. 21-30.

Mio et at., "Isolation and Characterization of a cDNA for Human, Mouse, and Rat Full-Length Stem Cell Growth Factor, a New Member of C-Type Lectin Superfamily," Biochemical and Biophysical Research Communications, 249, 1998, pp. 124-130.

Mizuno et at., "Structure of coagulation factors IX/X-binding protein, a heterodimer of C-type Lectin dornains,"Nature Structural Biology, vol. 4, Jun. 1997, pp. 438-441.

Ng et al., "Ca 2+ Dependent Structural Changes in C-type Mannose-Binding Proteins," Biochemistry, 37, 1998, pp. 17965-17976.

Ng et al. "Coupling of Prolyl Peptide Bond Isomerization and Ca 2+ Binding in a C-type Mannose-Binding Protein," Biochemistry, 37, 1998, pp. 17977-17989.

Nielsen et al., "Crystal structure of tetranectin, a trimeric plasminogen-binding protein with an helical alpha-helical coiled coil, " FEBS Letters, 412, 1997, pp. 388-396.

Nissim et al. "Antibody fragments from a 'single pot' phage display library as immunochemical reagents" The EMBO Journal, vol. 13, 1994, pp. 692-698.

Ogasawara et al. "Altered Carbohydrate Recognition Specificity Engineered into surfactant Protein D Reveals Different Binding Mechanisms for Phosphalidylinositol and Glucosylceramide," The Journal of Biological Chemistry, vol. 270, Jun. 16, 1995, pp. 14725-14732.

Ohtani et at., "Molecular Cloning of a Novel Human Collectin from Liver (CL-L1)," The journal of Biological Chemistry, vol. 274, May 7, 1999, pp. 13681-13689.

Pattanajitvilai et al., "Mutational Analysis of Arg[197] of Rat Surfactant Protein A: HIS[197] Creates Specific Lipid Uptake Defects," The Journal of Biological Chemistry, vol. 273, Mar. 6, 1998, pp. 5702-5707.

Roget et at., "The Structure of a Tunicate C-type Lectin from Polyandrocarpa misakiensis: Complexed with D-Galactose, "J. Mol. Biol., 290, 1999, pp. 867-879.

Revelle et al., "Structure-Function Analysis of P-selectin-Sialyl Lewis Binding Interactions:Mutagenic Alteration of Ligand Binding Specificity, "The Journal of Biological Chemistry, vol. 271, Feb. 23, 1996, pp. 4289-4297.

Sano et al. "Analysis of Chimeric Proteins Identifies the Regions in the Carbohydrate Recoqnition Domains of Rat Lung Collectins That are Essential for Interactions with Phospholipids, Glycolipids, and Alveolar Type II Cells," The Journal of Biological Chemistry, vol. 273, Feb. 2, 1998, pp. 4783.4789.

Schaffitzel et al., "Ribosome display: an in vitro method for selection and evolution of antibodies from libraries, "Journal of Immunological Methods, 231, 1999, pp. 119-135.

Sheriff et aI, "Human mannose-binding protein carbohydrate recognition domain trimerizes through a triple α-helical coiled-coil," Nature, Structural Biology, vol. 1, Nov. 1994, pp. 789-794.

Sorensen et al., "Cloning of a cDNA encoding murine tetranectin (Recombinant DNA; homology, plasminogen binding cancer; tumor invasion)," Gene, 152, 1995, pp. 243-245.

Torgersen et al., "Mechanism of Ligand Binding to E- and P-selectin Analyzed Using Selectin/Mannose-binding Protein Chimeras," The Journal of Biological Chemistry, vol. 273, Mar. 13, pp. 6254-6261.

Tormo et al., "Crystal structure of a lectin-like natural killer cell receptor bound to its MHC class I ligand," Nature, vol. 402, Dec. 9, 1999, pp. 623-631.

Tsunezawa et al., "Site-directed mutagenesis of surfactant protein A reveals dissociation of lipid aggregation and lipid uptake by alveolar type II cells," Biochimica et Biophysica Acta 1387,1998, pp. 433-446.

Weis et al., "Structure of the Calcium-Dependent Lectin Domain from a Rat Mannose-Binding Protein Determined by MAD Phasing,"Science, vol. 254, Dec. 13, 1991, pp. 1608-1615.

Weis et al. "Structural Basis of Lectin-Carbohydrate Recognition," Annu. Rev. Biochem, 65, 1996, pp. 441-473.

Whitehorn et al., "A Generic Method for Expression and Use of "Tagged" Soluble Versions of Cell Surface Receptors," Biotechnology, vol. 13, Nov. 1995, pp. 1215-1219.

Bodder et al., "Yeast surface display for screening combinatorial polypeptide libraries," Nature Biotech, 1997, vol. 15, pp. 553-557.

McCafferty et al., "Phage-enzymes: expression and affinity chromatography of functional alkaline phosphatase on the surface of bacteriophage, "Prot. Eng., 1991, vol. 4, pp. 955-961.

McCormack et al. "Surfactant protein A amino acids Glu195 and Arg197 are essential for receptor binding, phospholipid aggregation, regulation of secretion, and the facilitated uptake of phospholipid by type II cels," J. Biol. Chem., vol. 269, 1997, pp. 29801-29807.

Wragg et al., "Identification of amino acid residues that determine pH dependence of ligand binding to the asialog!ycoprotein receptor during endocytosis," J. BioI. Chem., 1999, vol. 274, pp. 35400-35406.

Zhang et al. "Cloning, mapping and genomic organization of a fish C-type lectin gene from homozygous clones of rainbow trout (Oncorhynchos Mykiss,)," Biochem. et Biophys. Acta, vol. 1494, pp. 14-22.

Doi et al., "Screening of conformationally constrained random polypeptide libraries displayed on a protein scaffold," CMLS Cellular and Molecular Life Sciences, Birkhauser Verlag, Basel, CH, vol. 54, No. 5, May 1998, pp. 394-404.

* cited by examiner

(SEQ ID NO: 291)
(SEQ ID NO: 290)
(SEQ ID NO: 292)
(SEQ ID NO: 293)

Fig. 3

```
          A L Q T V V L K Q T K V H M K V F L A P T Q T K F P H E A S                30
hCTLD   GCCCTGCAGACGGTCGTCCTGAAGCAGACCAAGGTCCACATGAAGGTCTTCCTGGCCCCAACCCAGACCAAGTTCCCACGAGGCCAGC      90
mCTLD   GCCCTACAGACAGTGGTCCTGAAGGGCACCAAGGTGCACCTGAACTTCCTGAAGGTGAACCTGAAGACCCAGCCCAAGTTCATGAGGCCAGC
          A L Q T V V L K G T K V H L N F L K V N L K T Q P K F M R P A               30

E D C I S R G G T L G S T P Q Q S E N D A L Y E Y L R Q S V                60
 91    GAGGACTGCATCTCGCGGGGCGGCACCCTCGGCAGCACCCCTCAGCAGTCGGAGAACGACGCCCTCTATGAGTACTTGCGCCAGAGCGTG    180
       GAGGACTGCATCTCGCAACTGCATCTGGCTGGTGCTGAGATCTGGCTGGGTGAACGGAGAACGCGGTGCCCTCTTCGAGTACGCCAGGCACAGCGTG
          E D C I S Q L H L A G A E I W L V L R S G G A L F E Y A R H S V               60

D C N R A E I W L G L N D M A A R G T W V D M T G T R I A Y K                90
181    GACTGCAACAGGGCCGAGATCTGGCTGGGCCTCAACGACATGGCCGCCCGGGGCACCTGGGTGGACATGACCGGCACCCGGATCGCCTACAAG   270
       GGCAACAGGGCCGAGATCCGGCTGGGAGACATGAACGCAGCCGAGGCATGGGTTCCTCAGGGCCAAGGCCAAGGCAACGGCTACAAG
          G N R A E I R L G D M N A A E A W V L Q G Q G Q G A N G Y K

Bgl II                                              Kpn I

N W E T E I T A Q P D G G K T E N C A V L S G A A N G K W F                120
271    AACTGGGAGACTGAGATCACCGCCCAGCCCGATGGCGGCAAGACCGAGAACTGCGCCGTTCTGTCTGGAGCAGCAAACGGCAAGTGGTTC    360
       AACTGGGAGACCGAGATCACCGCCCAGCCCGATGGCGGCAAGGCCGAGAACTGCGCGGCCCTGTCCGGCGCCGCCAACGGCAAGTGGTTC
          N W E T E I T A Q P D G G K A E N C A A L S G A A N G K W F

D K R C R D D L P Y I C Q F G I V *                                       (SEQ ID NO: 295)
361    GACAAGCGCTGCCGCGATGACCTGCCCTACATCTGCCAGTTCGGCATCGTGTAG                                      (SEQ ID NO: 294)
       GACAAGCGGTGCCGCGATCAATTGCCCTACATCTGCCAGTTTGCCATTGTCTAG                                      (SEQ ID NO: 296)
          D K R C R D Q L P Y I C Q F A I V *                                        (SEQ ID NO: 297)
                Hun I
```

Fig. 4 pT7H6FX-htlec

G S I E G R G R P E P T V V K V E A E I W G P R Q L P V I C Q P G I V *  (SEQ ID NO: 2)
GATCCATCGAGGGTAGGCGACCGGAGCCGACCGTCGTC---AAAGTC---GAGCCCGAGATCTGG---GGTACCCGC---CAATTGCCTACAATCTGCCAGTCGGGATCGTGTA  (SEQ ID NO: 1)

(SEQ ID NO: 299)  BamHI    BglII    KpnI    MunI
(SEQ ID NO: 298)
                                                    M G S H H H H H H
                                                    CATATGGGATCGCATCACCATCACCATCACGGATCCACG
                                                                                        HindIII
                                                                                        AGCTTGAATTC  (SEQ ID NO: 300)

```
  1  GSIEGRGEPPTQKPKKIVNAKKDVQVNVTKLKMF
 31  EELKSRLDTLAFTLAQEVALKEQASEDLQVHGT
 61  TKVHMKKVFPQKTKTPHEYLRHERSVGEIWLKGT
 91  LSTPQMAEGTWDMTGTRIAKWGANGKMKGTGQP
121  LNDMAAEKTENCAVLSGANGKWFDKRCRDQLP
151  PDGGKTENWFDKRCRDQLP
181  YICQFGIV
```

(SEQ ID NO: 2)

Fig. 6

FX-htCTLD

```
  1 GSIEGRALQTVVLKGTKVHMKVFLAFTQTK
 31 TEHEASBDNKDCISRGGTLSNDDMAABGTSENDALYB
 61 YLRQYKGNEAEIWTEITAQPDGKTENCAVLSGA
 91 TRIAYKNWETEITAQPDLPYICQFPGIV
121 ANGKWFDKRCRDQLPYICQFPGIV
```

(SEQ ID NO: 4)

Fig. 8

PhTN

```
  1 P A M A E P P T Q K P K K I V N A K K D V V N T C K M P G T K E L V T
 31 K S R M C F L A E T L A Q E V A L K E Q A L Q E B T V S R I H S R G T L N D
 61 H P Q P T G S E N D V Q L M T F H R Q S E D C I S R A E B I T R G L M D D
 91 M A A E G T A A D W A L Y E Y L R Q K A K N W E T B I T A Q P D G
121 P Q K T E N C A V L S G A A M Q K W F D K R C R D Q L P Y I
151 Q K T E N C A V L S G A A M Q K W F D K R C R D Q L P Y I
181 Q F G I V A A A
```

(SEQ ID NO: 9)

Fig.10

```
phTN3
  1 PAMAALQTVCLKGTPLKVHMKCFLAFTQTKTF
 31 HEASEDCISRGGTSMDTPOKTGSENDALYEYL
 61 ROSVGHABIWLGLMDGGMAKTOEMCAVDMTGAR
 91 AYKNETEHTAQPDDKTIQFICOFGIVAAAN
121 GKWFDKRCRDQLPYIOFGIVAAAN (SEQ ID NO: 11)
```

Fig. 12 phtlec

```
  1 PAMAEPPTQ QEVTKPKKIV NAKKDVNTKV LKGMFKGTLF TDGC
 31 KSRLDTLAFT QEVALKFHEA SEDCLQTVAL QGMKGTLSND DH
 61 HMKVFLAFTK KVTKVLRGSV KNEABIWETH IDQPYIC
 91 PQTGSENDAL YBVLRQWTKO TRIAYKWFDKRCRD
121 MAABGTWDMT GCAVLSGAANGKWFDKRCRD
151 GKTENCAVLS GAANG
181 QFGIVAAA (SEQ ID NO: 13)
```

Fig.14

PhtcTLD

```
  1 PAMAALQTVVLKGTKVHMKVFLAFTQTKTF
 31 HEASEDCISRGGTLSTPQMAAEGTWDALYEYL
 61 RQSVGNEAEHIWLGNDMAEGTENCAVLSGAAN
 91 IAYKWETEITAQPDGKTEGIVAAADMTGTR
121 GKWFDKRCRDQLPYICQFGIVAAAN
```
(SEQ ID NO: 15)

Fig.16

```
FX-mt1ec
  1 GSIQGRGESPTPKAKKAAKKDLVSSKMF
 31 EEKVNRMKVLAQEVLAFTQPKTHEARHSYAKKQALEKDCHTVAQHIKG
 61 TLGTPQSELENEALFEYAKKQALEKDCHTVAQHIKG
 91 LGTPOSELENEALFEYAKHSVKQDNAEIWLG
121 LNDMAEGAWDMTGTLAYKNWERITQ
151 PDGKAENCAALSAANCKWFDKRCRDQLP
181 YICQFAIV (SEQ ID NO: 29)
```

Fig. 19

FX-mtCTLD

```
  1 GSIQGRALQTVVLKGTKVNLKVLLAFTQPK
 31 TFHEASEDCISQWLGGTLGNDMPQSELBNBALFE
 61 YARHSVGNDARIWHTTPDGGKARNCAALSGA
 91 TLLAYKNEBTEIDPGKARNCAALSGA
121 ANGKWFDKRCRDQLPYICQFAIV (SEQ ID NO: 31)
```

Fig.21

```
Pmtlec
  1 PAMAESPTPKAKKAANAKQKKDLVSSKMFEELKVT
 31 KNRMDVLAQEVKALLKHEARHSVKALDTVLKGNDG
 61 MLKVLAPKFYARLFHEASEDWGGLQHITLNDPYI
 91 PQSELENEALFEYARHSVKNWPDKRCRDOLPYIC
121 MAAENCAAWDMTGILAYKMWPDKRCRDOLPYIC
151 GKABNCAALSGAANGMWPDKRCRDOLPYIC
181 QFAIVAAA   (SEQ ID NO: 36)
```

Fig. 23

```
PmtCHLD
  1 PAMAALQTVVLKGTKVNLPKVLLAFTQPKTF
 31 HEASEDCISQGWLGTPPDMAAEGKAENWCAMWEALFEYA
 61 RHSVCNDAEIWLGLNDGGKAAEGAEGNCAAVDMTGTL
 91 LAYKNWETEHTQPYICQFAIVAALSGAAN
121 GKWFDKRCRDOLPYICQPAIVAAA       (SEQ ID NO: 38)
```

Fig. 25

```
pIMDP
  1 PAMANKLHAFSMGKKSGHIPKFVTNKKVTNKERKIPMP
 31 FSKVKTSKALLSELRGTDBVTEGDMYLRGIHKGLWRIQLTMOWEYP
 61 VAKTSKDEPNDHGSBDPAAGHIPQVEGBDAAGHNKDEGBD... 
```

*(SEQ ID NO: 59)*

Fig.30

```
PhSP-D
  1 P A M A K K V B L F P N G Q S V G E K I F K T A G P V K P Q S
 31 W K Q K N E A L C T Q G Q L A S P R S A A K W Y K E Q E S
 61 L V V A V Y S N W A P G E N G M T D S K T D G C V B I F T G E W
 91 L W L N D R A C E K R L V C B F A A
121 N D R A C E K R L V C B F A A A
                                              (SEQ ID NO: 61)
```

Fig. 32

SEQUENCE LISTING

```
<160> NUMBER OF SEQ ID NOS: 352

<210> SEQ ID NO 1
<211> LENGTH: 571
<212> TYPE: DNA
<213> ORGANISM: Homo sapiens
<220> FEATURE:
<221> NAME/KEY: CDS
<222> LOCATION: (1)..(564)
<223> OTHER INFORMATION: FX-htlec encoding insert

<400> SEQUENCE: 1 gga tcc atc gag ggt agg ggc gag cca cca acc cag aag ccc aag aag        48
Gly Ser Ile Glu Gly Arg Gly Glu Pro Pro Thr Gln Lys Pro Lys Lys
1               5                   10                  15 att gta aat gcc aag aaa gat gtt gtg aac aca aag atg ttt gag gag        96
Ile Val Asn Ala Lys Lys Asp Val Val Asn Thr Lys Met Phe Glu Glu
            20                  25                  30 ctc aag agc cgt ctg gac acc ctg gcc cag gag gtg gcc ctg ctg aag       144
Leu Lys Ser Arg Leu Asp Thr Leu Ala Gln Glu Val Ala Leu Leu Lys
        35                  40                  45 gag cag cag gcc ctg cag acg gtc gtc ctg aag ggg acc aag gtg cac       192
Glu Gln Gln Ala Leu Gln Thr Val Val Leu Lys Gly Thr Lys Val His
    50                  55                  60
```

```
atg aaa gtc ttt ctg gcc ttc acc cag acg aag acc ttc cac gag gcc      240
Met Lys Val Phe Leu Ala Phe Thr Gln Thr Lys Thr Phe His Glu Ala
 65              70                  75                  80 agc gag gac tgc atc tcg cgc ggg ggc acc ctg agc acc cct cag act      288
Ser Glu Asp Cys Ile Ser Arg Gly Gly Thr Leu Ser Thr Pro Gln Thr
                 85                  90                  95 ggc tcg gag aac gac gcc ctg tat gag tac ctg cgc cag agc gtg ggc      336
Gly Ser Glu Asn Asp Ala Leu Tyr Glu Tyr Leu Arg Gln Ser Val Gly
            100                 105                 110 aac gag gcc gag atc tgg ctg ggc ctc aac gac atg gcg gcc gag ggc      384
Asn Glu Ala Glu Ile Trp Leu Gly Leu Asn Asp Met Ala Ala Glu Gly
        115                 120                 125 acc tgg gtg gac atg acc ggt acc cgc atc gcc tac aag aac tgg gag      432
Thr Trp Val Asp Met Thr Gly Thr Arg Ile Ala Tyr Lys Asn Trp Glu
130                 135                 140 act gag atc acc gcg caa ccc gat ggc ggc aag acc gag aac tgc gcg      480
Thr Glu Ile Thr Ala Gln Pro Asp Gly Gly Lys Thr Glu Asn Cys Ala
145                 150                 155                 160 gtc ctg tca ggc gcg gcc aac ggc aag tgg ttc gac aag cgc tgc cgc      528
Val Leu Ser Gly Ala Ala Asn Gly Lys Trp Phe Asp Lys Arg Cys Arg
                165                 170                 175 gat caa ttg ccc tac atc tgc cag ttc ggg atc gtg taagctt              571
Asp Gln Leu Pro Tyr Ile Cys Gln Phe Gly Ile Val
            180                 185

<210> SEQ ID NO 2
<211> LENGTH: 188
<212> TYPE: PRT
<213> ORGANISM: Homo sapiens

<400> SEQUENCE: 2

Gly Ser Ile Glu Gly Arg Gly Glu Pro Pro Thr Gln Lys Pro Lys Lys
 1               5                  10                  15

Ile Val Asn Ala Lys Lys Asp Val Val Asn Thr Lys Met Phe Glu Glu
             20                  25                  30

Leu Lys Ser Arg Leu Asp Thr Leu Ala Gln Glu Val Ala Leu Leu Lys
         35                  40                  45

Glu Gln Gln Ala Leu Gln Thr Val Val Leu Lys Gly Thr Lys Val His
     50                  55                  60

Met Lys Val Phe Leu Ala Phe Thr Gln Thr Lys Thr Phe His Glu Ala
 65                  70                  75                  80

Ser Glu Asp Cys Ile Ser Arg Gly Gly Thr Leu Ser Thr Pro Gln Thr
                 85                  90                  95

Gly Ser Glu Asn Asp Ala Leu Tyr Glu Tyr Leu Arg Gln Ser Val Gly
            100                 105                 110

Asn Glu Ala Glu Ile Trp Leu Gly Leu Asn Asp Met Ala Ala Glu Gly
        115                 120                 125

Thr Trp Val Asp Met Thr Gly Thr Arg Ile Ala Tyr Lys Asn Trp Glu
    130                 135                 140

Thr Glu Ile Thr Ala Gln Pro Asp Gly Gly Lys Thr Glu Asn Cys Ala
145                 150                 155                 160

Val Leu Ser Gly Ala Ala Asn Gly Lys Trp Phe Asp Lys Arg Cys Arg
                165                 170                 175

Asp Gln Leu Pro Tyr Ile Cys Gln Phe Gly Ile Val
            180                 185

<210> SEQ ID NO 3
<211> LENGTH: 436
```

```
<212> TYPE: DNA
<213> ORGANISM: Homo sapiens
<220> FEATURE:
<221> NAME/KEY: CDS
<222> LOCATION: (1)..(429)
<223> OTHER INFORMATION: FX-htCTLD encoding insert

<400> SEQUENCE: 3 gga tcc atc gag ggt agg gcc ctg cag acg gtc gtc ctg aag ggg acc      48
Gly Ser Ile Glu Gly Arg Ala Leu Gln Thr Val Val Leu Lys Gly Thr
1               5                   10                  15 aag gtg cac atg aaa gtc ttt ctg gcc ttc acc cag acg aag acc ttc      96
Lys Val His Met Lys Val Phe Leu Ala Phe Thr Gln Thr Lys Thr Phe
                20                  25                  30 cac gag gcc agc gag gac tgc atc tcg cgc ggg ggc acc ctg agc acc     144
His Glu Ala Ser Glu Asp Cys Ile Ser Arg Gly Gly Thr Leu Ser Thr
            35                  40                  45 cct cag act ggc tcg gag aac gac gcc ctg tat gag tac ctg cgc cag     192
Pro Gln Thr Gly Ser Glu Asn Asp Ala Leu Tyr Glu Tyr Leu Arg Gln
        50                  55                  60 agc gtg ggc aac gag gcc gag atc tgg ctg ggc ctc aac gac atg gcg     240
Ser Val Gly Asn Glu Ala Glu Ile Trp Leu Gly Leu Asn Asp Met Ala
65                  70                  75                  80 gcc gag ggc acc tgg gtg gac atg acc ggt acc cgc atc gcc tac aag     288
Ala Glu Gly Thr Trp Val Asp Met Thr Gly Thr Arg Ile Ala Tyr Lys
                85                  90                  95 aac tgg gag act gag atc acc gcg caa ccc gat ggc ggc aag acc gag     336
Asn Trp Glu Thr Glu Ile Thr Ala Gln Pro Asp Gly Gly Lys Thr Glu
                100                 105                 110 aac tgc gcg gtc ctg tca ggc gcg gcc aac ggc aag tgg ttc gac aag     384
Asn Cys Ala Val Leu Ser Gly Ala Ala Asn Gly Lys Trp Phe Asp Lys
            115                 120                 125 cgc tgc cgc gat caa ttg ccc tac atc tgc cag ttc ggg atc gtg         429
Arg Cys Arg Asp Gln Leu Pro Tyr Ile Cys Gln Phe Gly Ile Val
        130                 135                 140 taagctt                                                              436

<210> SEQ ID NO 4
<211> LENGTH: 143
<212> TYPE: PRT
<213> ORGANISM: Homo sapiens

<400> SEQUENCE: 4

Gly Ser Ile Glu Gly Arg Ala Leu Gln Thr Val Val Leu Lys Gly Thr
1               5                   10                  15

Lys Val His Met Lys Val Phe Leu Ala Phe Thr Gln Thr Lys Thr Phe
                20                  25                  30

His Glu Ala Ser Glu Asp Cys Ile Ser Arg Gly Gly Thr Leu Ser Thr
            35                  40                  45

Pro Gln Thr Gly Ser Glu Asn Asp Ala Leu Tyr Glu Tyr Leu Arg Gln
        50                  55                  60

Ser Val Gly Asn Glu Ala Glu Ile Trp Leu Gly Leu Asn Asp Met Ala
65                  70                  75                  80

Ala Glu Gly Thr Trp Val Asp Met Thr Gly Thr Arg Ile Ala Tyr Lys
                85                  90                  95

Asn Trp Glu Thr Glu Ile Thr Ala Gln Pro Asp Gly Gly Lys Thr Glu
                100                 105                 110

Asn Cys Ala Val Leu Ser Gly Ala Ala Asn Gly Lys Trp Phe Asp Lys
            115                 120                 125

Arg Cys Arg Asp Gln Leu Pro Tyr Ile Cys Gln Phe Gly Ile Val
        130                 135                 140
```

<210> SEQ ID NO 5
<211> LENGTH: 47
<212> TYPE: DNA
<213> ORGANISM: Artificial
<220> FEATURE:
<223> OTHER INFORMATION: Description of Artificial Sequence: Primer

<400> SEQUENCE: 5
cggctgagcg gcccagccgg ccatggccga gccaccaacc cagaagc        47

<210> SEQ ID NO 6
<211> LENGTH: 27
<212> TYPE: DNA
<213> ORGANISM: Artificial
<220> FEATURE:
<223> OTHER INFORMATION: Description of Artificial Sequence: Primer

<400> SEQUENCE: 6
cctgcggccg ccacgatccc gaactgg        27

<210> SEQ ID NO 7
<211> LENGTH: 43
<212> TYPE: DNA
<213> ORGANISM: Artificial
<220> FEATURE:
<223> OTHER INFORMATION: Description of Artificial Sequence: Primer

<400> SEQUENCE: 7
cggctgagcg gcccagccgg ccatggccgc cctgcagacg gtc        43

<210> SEQ ID NO 8
<211> LENGTH: 570
<212> TYPE: DNA
<213> ORGANISM: Homo sapiens
<220> FEATURE:
<221> NAME/KEY: CDS
<222> LOCATION: (8)..(565)
<223> OTHER INFORMATION: PhTN encoding insert

<400> SEQUENCE: 8

```
ggcccag ccg gcc atg gcc gag cca cca acc cag aag ccc aag aag att       49
        Pro Ala Met Ala Glu Pro Pro Thr Gln Lys Pro Lys Lys Ile
         1               5                  10 gta aat gcc aag aaa gat gtt gtg aac aca aag atg ttt gag gag ctc       97
Val Asn Ala Lys Lys Asp Val Val Asn Thr Lys Met Phe Glu Glu Leu
 15              20                  25                  30 aag agc cgt ctg gac acc ctg gcc cag gag gtg gcc ctg ctg aag gag      145
Lys Ser Arg Leu Asp Thr Leu Ala Gln Glu Val Ala Leu Leu Lys Glu
                 35                  40                  45 cag cag gcc ctg cag acg gtc tgc ctg aag ggg acc aag gtg cac atg      193
Gln Gln Ala Leu Gln Thr Val Cys Leu Lys Gly Thr Lys Val His Met
             50                  55                  60 aaa tgc ttt ctg gcc ttc acc cag acg aag acc ttc cac gag gcc agc      241
Lys Cys Phe Leu Ala Phe Thr Gln Thr Lys Thr Phe His Glu Ala Ser
         65                  70                  75 gag gac tgc atc tcg cgc ggg ggc acc ctg agc acc cct cag act ggc      289
Glu Asp Cys Ile Ser Arg Gly Gly Thr Leu Ser Thr Pro Gln Thr Gly
     80                  85                  90 tcg gag aac gac gcc ctg tat gag tac ctg cgc cag agc gtg ggc aac      337
Ser Glu Asn Asp Ala Leu Tyr Glu Tyr Leu Arg Gln Ser Val Gly Asn
 95                 100                 105                 110 gag gcc gag atc tgg ctg ggc ctc aac gac atg gcg gcc gag ggc acc      385
Glu Ala Glu Ile Trp Leu Gly Leu Asn Asp Met Ala Ala Glu Gly Thr
```

```
            115                 120                 125
tgg gtg gac atg acc ggc gcc cgc atc gcc tac aag aac tgg gag act    433
Trp Val Asp Met Thr Gly Ala Arg Ile Ala Tyr Lys Asn Trp Glu Thr
            130                 135                 140 gag atc acc gcg caa ccc gat ggc ggc aag acc gag aac tgc gcg gtc    481
Glu Ile Thr Ala Gln Pro Asp Gly Gly Lys Thr Glu Asn Cys Ala Val
        145                 150                 155 ctg tca ggc gcg gcc aac ggc aag tgg ttc gac aag cgc tgc cgc gat    529
Leu Ser Gly Ala Ala Asn Gly Lys Trp Phe Asp Lys Arg Cys Arg Asp
    160                 165                 170 cag ctg ccc tac atc tgc cag ttc ggg atc gtg gcg gccgc              570
Gln Leu Pro Tyr Ile Cys Gln Phe Gly Ile Val Ala
175                 180                 185
```

<210> SEQ ID NO 9
<211> LENGTH: 186
<212> TYPE: PRT
<213> ORGANISM: Homo sapiens

<400> SEQUENCE: 9

```
Pro Ala Met Ala Glu Pro Pro Thr Gln Lys Pro Lys Lys Ile Val Asn
1               5                   10                  15

Ala Lys Lys Asp Val Val Asn Thr Lys Met Phe Glu Glu Leu Lys Ser
            20                  25                  30

Arg Leu Asp Thr Leu Ala Gln Val Ala Leu Leu Lys Glu Gln Gln
        35                  40                  45

Ala Leu Gln Thr Val Cys Leu Lys Gly Thr Lys Val His Met Lys Cys
    50                  55                  60

Phe Leu Ala Phe Thr Gln Thr Lys Thr Phe His Glu Ala Ser Glu Asp
65                  70                  75                  80

Cys Ile Ser Arg Gly Gly Thr Leu Ser Thr Pro Gln Thr Gly Ser Glu
                85                  90                  95

Asn Asp Ala Leu Tyr Glu Tyr Leu Arg Gln Ser Val Gly Asn Glu Ala
            100                 105                 110

Glu Ile Trp Leu Gly Leu Asn Asp Met Ala Ala Glu Gly Thr Trp Val
        115                 120                 125

Asp Met Thr Gly Ala Arg Ile Ala Tyr Lys Asn Trp Glu Thr Glu Ile
    130                 135                 140

Thr Ala Gln Pro Asp Gly Gly Lys Thr Glu Asn Cys Ala Val Leu Ser
145                 150                 155                 160

Gly Ala Ala Asn Gly Lys Trp Phe Asp Lys Arg Cys Arg Asp Gln Leu
                165                 170                 175

Pro Tyr Ile Cys Gln Phe Gly Ile Val Ala
            180                 185
```

<210> SEQ ID NO 10
<211> LENGTH: 438
<212> TYPE: DNA
<213> ORGANISM: Homo sapiens
<220> FEATURE:
<221> NAME/KEY: CDS
<222> LOCATION: (8)..(433)
<223> OTHER INFORMATION: PhTN3 encoding insert

<400> SEQUENCE: 10

```
ggcccag ccg gcc atg gcc gcc ctg cag acg gtc tgc ctg aag ggg acc    49
        Pro Ala Met Ala Ala Leu Gln Thr Val Cys Leu Lys Gly Thr
            1               5                   10 aag gtg cac atg aaa tgc ttt ctg gcc ttc acc cag acg aag acc ttc    97
Lys Val His Met Lys Cys Phe Leu Ala Phe Thr Gln Thr Lys Thr Phe
```

```
                 15                  20                  25                  30 cac gag gcc agc gag gac tgc atc tcg cgc ggg ggc acc ctg agc acc        145
His Glu Ala Ser Glu Asp Cys Ile Ser Arg Gly Gly Thr Leu Ser Thr
                35                  40                  45 cct cag act ggc tcg gag aac gac gcc ctg tat gag tac ctg cgc cag        193
Pro Gln Thr Gly Ser Glu Asn Asp Ala Leu Tyr Glu Tyr Leu Arg Gln
            50                  55                  60 agc gtg ggc aac gag gcc gag atc tgg ctg ggc ctc aac gac atg gcg        241
Ser Val Gly Asn Glu Ala Glu Ile Trp Leu Gly Leu Asn Asp Met Ala
        65                  70                  75 gcc gag ggc acc tgg gtg gac atg acc ggc gcc cgc atc gcc tac aag        289
Ala Glu Gly Thr Trp Val Asp Met Thr Gly Ala Arg Ile Ala Tyr Lys
    80                  85                  90 aac tgg gag act gag atc acc gcg caa ccc gat ggc ggc aag acc gag        337
Asn Trp Glu Thr Glu Ile Thr Ala Gln Pro Asp Gly Gly Lys Thr Glu
95                 100                 105                 110 aac tgc gcg gtc ctg tca ggc gcg gcc aac ggc aag tgg ttc gac aag        385
Asn Cys Ala Val Leu Ser Gly Ala Ala Asn Gly Lys Trp Phe Asp Lys
                115                 120                 125 cgc tgc cgc gat cag ctg ccc tac atc tgc cag ttc ggg atc gtg gcg        433
Arg Cys Arg Asp Gln Leu Pro Tyr Ile Cys Gln Phe Gly Ile Val Ala
            130                 135                 140 gccgc                                                                   438

<210> SEQ ID NO 11
<211> LENGTH: 142
<212> TYPE: PRT
<213> ORGANISM: Homo sapiens

<400> SEQUENCE: 11

Pro Ala Met Ala Ala Leu Gln Thr Val Cys Leu Lys Gly Thr Lys Val
1               5                  10                  15

His Met Lys Cys Phe Leu Ala Phe Thr Gln Thr Lys Thr Phe His Glu
                20                  25                  30

Ala Ser Glu Asp Cys Ile Ser Arg Gly Gly Thr Leu Ser Thr Pro Gln
            35                  40                  45

Thr Gly Ser Glu Asn Asp Ala Leu Tyr Glu Tyr Leu Arg Gln Ser Val
        50                  55                  60

Gly Asn Glu Ala Glu Ile Trp Leu Gly Leu Asn Asp Met Ala Ala Glu
65                  70                  75                  80

Gly Thr Trp Val Asp Met Thr Gly Ala Arg Ile Ala Tyr Lys Asn Trp
                85                  90                  95

Glu Thr Glu Ile Thr Ala Gln Pro Asp Gly Gly Lys Thr Glu Asn Cys
            100                 105                 110

Ala Val Leu Ser Gly Ala Ala Asn Gly Lys Trp Phe Asp Lys Arg Cys
        115                 120                 125

Arg Asp Gln Leu Pro Tyr Ile Cys Gln Phe Gly Ile Val Ala
    130                 135                 140

<210> SEQ ID NO 12
<211> LENGTH: 570
<212> TYPE: DNA
<213> ORGANISM: Homo sapiens
<220> FEATURE:
<221> NAME/KEY: CDS
<222> LOCATION: (8)..(565)
<223> OTHER INFORMATION: Phtlec encoding insert

<400> SEQUENCE: 12 ggcccag ccg gcc atg gcc gag cca cca acc cag aag ccc aag aag att        49
```

```
            Pro Ala Met Ala Glu Pro Pro Thr Gln Lys Pro Lys Lys Ile
            1               5                   10
gta aat gcc aag aaa gat gtt gtg aac aca aag atg ttt gag gag ctc        97
Val Asn Ala Lys Lys Asp Val Val Asn Thr Lys Met Phe Glu Glu Leu
 15              20                  25                  30
aag agc cgt ctg gac acc ctg gcc cag gag gtg gcc ctg ctg aag gag       145
Lys Ser Arg Leu Asp Thr Leu Ala Gln Glu Val Ala Leu Leu Lys Glu
                 35                  40                  45
cag cag gcc ctg cag acg gtc gtc ctg aag ggg acc aag gtg cac atg       193
Gln Gln Ala Leu Gln Thr Val Val Leu Lys Gly Thr Lys Val His Met
             50                  55                  60
aaa gtc ttt ctg gcc ttc acc cag acg aag acc ttc cac gag gcc agc       241
Lys Val Phe Leu Ala Phe Thr Gln Thr Lys Thr Phe His Glu Ala Ser
         65                  70                  75
gag gac tgc atc tcg cgc ggg ggc acc ctg agc acc cct cag act ggc       289
Glu Asp Cys Ile Ser Arg Gly Gly Thr Leu Ser Thr Pro Gln Thr Gly
     80                  85                  90
tcg gag aac gac gcc ctg tat gag tac ctg cgc cag agc gtg ggc aac       337
Ser Glu Asn Asp Ala Leu Tyr Glu Tyr Leu Arg Gln Ser Val Gly Asn
 95                  100                 105                 110
gag gcc gag atc tgg ctg ggc ctc aac gac atg gcg gcc gag ggc acc       385
Glu Ala Glu Ile Trp Leu Gly Leu Asn Asp Met Ala Ala Glu Gly Thr
                 115                 120                 125
tgg gtg gac atg acc ggt acc cgc atc gcc tac aag aac tgg gag act       433
Trp Val Asp Met Thr Gly Thr Arg Ile Ala Tyr Lys Asn Trp Glu Thr
             130                 135                 140
gag atc acc gcg caa ccc gat ggc ggc aag acc gag aac tgc gcg gtc       481
Glu Ile Thr Ala Gln Pro Asp Gly Gly Lys Thr Glu Asn Cys Ala Val
         145                 150                 155
ctg tca ggc gcg gcc aac ggc aag tgg ttc gac aag cgc tgc cgc gat       529
Leu Ser Gly Ala Ala Asn Gly Lys Trp Phe Asp Lys Arg Cys Arg Asp
     160                 165                 170
caa ttg ccc tac atc tgc cag ttc ggg atc gtg gcg gccgc                 570
Gln Leu Pro Tyr Ile Cys Gln Phe Gly Ile Val Ala
 175                 180                 185

<210> SEQ ID NO 13
<211> LENGTH: 186
<212> TYPE: PRT
<213> ORGANISM: Homo sapiens

<400> SEQUENCE: 13

Pro Ala Met Ala Glu Pro Pro Thr Gln Lys Pro Lys Lys Ile Val Asn
1               5                   10                  15

Ala Lys Lys Asp Val Val Asn Thr Lys Met Phe Glu Glu Leu Lys Ser
                20                  25                  30

Arg Leu Asp Thr Leu Ala Gln Glu Val Ala Leu Leu Lys Glu Gln Gln
            35                  40                  45

Ala Leu Gln Thr Val Val Leu Lys Gly Thr Lys Val His Met Lys Val
        50                  55                  60

Phe Leu Ala Phe Thr Gln Thr Lys Thr Phe His Glu Ala Ser Glu Asp
65                  70                  75                  80

Cys Ile Ser Arg Gly Gly Thr Leu Ser Thr Pro Gln Thr Gly Ser Glu
                85                  90                  95

Asn Asp Ala Leu Tyr Glu Tyr Leu Arg Gln Ser Val Gly Asn Glu Ala
            100                 105                 110

Glu Ile Trp Leu Gly Leu Asn Asp Met Ala Ala Glu Gly Thr Trp Val
        115                 120                 125

Asp Met Thr Gly Thr Arg Ile Ala Tyr Lys Asn Trp Glu Thr Glu Ile
```

-continued

```
                    130                 135                 140
Thr Ala Gln Pro Asp Gly Gly Lys Thr Glu Asn Cys Ala Val Leu Ser
145                 150                 155                 160

Gly Ala Ala Asn Gly Lys Trp Phe Asp Lys Arg Cys Arg Asp Gln Leu
                165                 170                 175

Pro Tyr Ile Cys Gln Phe Gly Ile Val Ala
            180                 185

<210> SEQ ID NO 14
<211> LENGTH: 438
<212> TYPE: DNA
<213> ORGANISM: Homo sapiens
<220> FEATURE:
<221> NAME/KEY: CDS
<222> LOCATION: (8)..(433)
<223> OTHER INFORMATION: PhtCTLD encoding insert

<400> SEQUENCE: 14 ggcccag ccg gcc atg gcc gcc ctg cag acg gtc gtc ctg aag ggg acc        49
        Pro Ala Met Ala Ala Leu Gln Thr Val Val Leu Lys Gly Thr
         1               5                  10 aag gtg cac atg aaa gtc ttt ctg gcc ttc acc cag acg aag acc ttc        97
Lys Val His Met Lys Val Phe Leu Ala Phe Thr Gln Thr Lys Thr Phe
 15                  20                  25                  30 cac gag gcc agc gag gac tgc atc tcg cgc ggg ggc acc ctg agc acc       145
His Glu Ala Ser Glu Asp Cys Ile Ser Arg Gly Gly Thr Leu Ser Thr
                     35                  40                  45 cct cag act ggc tcg gag aac gac gcc ctg tat gag tac ctg cgc cag       193
Pro Gln Thr Gly Ser Glu Asn Asp Ala Leu Tyr Glu Tyr Leu Arg Gln
                 50                  55                  60 agc gtg ggc aac gag gcc gag atc tgg ctg ggc ctc aac gac atg gcg       241
Ser Val Gly Asn Glu Ala Glu Ile Trp Leu Gly Leu Asn Asp Met Ala
             65                  70                  75 gcc gag ggc acc tgg gtg gac atg acc ggt acc cgc atc gcc tac aag       289
Ala Glu Gly Thr Trp Val Asp Met Thr Gly Thr Arg Ile Ala Tyr Lys
 80                  85                  90 aac tgg gag act gag atc acc gcg caa ccc gat ggc ggc aag acc gag       337
Asn Trp Glu Thr Glu Ile Thr Ala Gln Pro Asp Gly Gly Lys Thr Glu
 95                 100                 105                 110 aac tgc gcg gtc ctg tca ggc gcg gcc aac ggc aag tgg ttc gac aag       385
Asn Cys Ala Val Leu Ser Gly Ala Ala Asn Gly Lys Trp Phe Asp Lys
                115                 120                 125 cgc tgc cgc gat caa ttg ccc tac atc tgc cag ttc ggg atc gtg gcg       433
Arg Cys Arg Asp Gln Leu Pro Tyr Ile Cys Gln Phe Gly Ile Val Ala
                130                 135                 140 gccgc                                                                  438

<210> SEQ ID NO 15
<211> LENGTH: 142
<212> TYPE: PRT
<213> ORGANISM: Homo sapiens

<400> SEQUENCE: 15

Pro Ala Met Ala Ala Leu Gln Thr Val Val Leu Lys Gly Thr Lys Val
 1               5                  10                  15

His Met Lys Val Phe Leu Ala Phe Thr Gln Thr Lys Thr Phe His Glu
                 20                  25                  30

Ala Ser Glu Asp Cys Ile Ser Arg Gly Gly Thr Leu Ser Thr Pro Gln
             35                  40                  45

Thr Gly Ser Glu Asn Asp Ala Leu Tyr Glu Tyr Leu Arg Gln Ser Val
         50                  55                  60
```

```
Gly Asn Glu Ala Glu Ile Trp Leu Gly Leu Asn Asp Met Ala Ala Glu
 65                  70                  75                  80

Gly Thr Trp Val Asp Met Thr Gly Thr Arg Ile Ala Tyr Lys Asn Trp
                 85                  90                  95

Glu Thr Glu Ile Thr Ala Gln Pro Asp Gly Gly Lys Thr Glu Asn Cys
            100                 105                 110

Ala Val Leu Ser Gly Ala Ala Asn Gly Lys Trp Phe Asp Lys Arg Cys
        115                 120                 125

Arg Asp Gln Leu Pro Tyr Ile Cys Gln Phe Gly Ile Val Ala
    130                 135                 140

<210> SEQ ID NO 16
<211> LENGTH: 555
<212> TYPE: DNA
<213> ORGANISM: Mus musculus
<220> FEATURE:
<221> NAME/KEY: misc_feature
<223> OTHER INFORMATION: EcoRI to HindIII insert containing mtlec
      encoding part

<400> SEQUENCE: 16
ggaattcgag tcacccactc ccaaggccaa gaaggctgca aatgccaaga aagatttggt      60
gagctcaaag atgtcgagga gctcaagaac aggatggatg tcctggccca ggaggtggcc    120
ctgctgaagg agaagcaggc cttacagact gtggtcctga agggcaccaa ggtgaacttg    180
aaggtcctcc tggccttcac ccaaccgaag accttccatg aggcgagcga ggactgcatc    240
tcgcaagggg gcacgctggg cacccccgcag tcagagctag agaacgaggc gctgttcgag    300
tacgcgcgcc acagcgtggg caacgatgcg gagatctggc tgggcctcaa cgacatggcc    360
gcggaaggcg cctgggtgga catgaccggt accctcctgg cctacaagaa ctgggagacg    420
gagatcacga cgcaacccga cggcggcaaa gccgagaact cgccgccct gtctggcgca    480 gccaacggca agtggttcga caagcgatgc cgcgatcaat gccctacat ctgccagttt    540 gccattgtga agctt                                                   555

<210> SEQ ID NO 17
<211> LENGTH: 77
<212> TYPE: DNA
<213> ORGANISM: Artificial
<220> FEATURE:
<223> OTHER INFORMATION: Description of Artificial Sequence:
      oligonucleotide

<400> SEQUENCE: 17
cggaattcga gtcacccact cccaaggcca agaaggctgc aaatgccaag aaagatttgg     60
tgagctcaaa gatgttc                                                  77

<210> SEQ ID NO 18
<211> LENGTH: 94
<212> TYPE: DNA
<213> ORGANISM: Artificial
<220> FEATURE:
<223> OTHER INFORMATION: Description of Artificial Sequence:
      oligonucleotide

<400> SEQUENCE: 18
gcggatccag gcctgcttct ccttcagcag ggccacctcc tgggccagga catccatcct     60
gttcttgagc tcctcgaaca tctttgagct cacc                                94

<210> SEQ ID NO 19
```

```
<211> LENGTH: 97
<212> TYPE: DNA
<213> ORGANISM: Artificial
<220> FEATURE:
<223> OTHER INFORMATION: Description of Artificial Sequence:
      oligonucleotide

<400> SEQUENCE: 19
gcaggcctta cagactgtgt gcctgaaggg caccaaggtg aacttgaagt gcctcctggc    60
cttcacccaa ccgaagacct tccatgaggc gagcgag                            97

<210> SEQ ID NO 20
<211> LENGTH: 93
<212> TYPE: DNA
<213> ORGANISM: Artificial
<220> FEATURE:
<223> OTHER INFORMATION: Description of Artificial Sequence:
      oligonucleotide

<400> SEQUENCE: 20
ccgcatgctt cgaacagcgc ctcgttctct agctctgact gcggggtgcc cagcgtgccc    60
ccttgcgaga tgcagtcctc gctcgcctca tgg                                93

<210> SEQ ID NO 21
<211> LENGTH: 61
<212> TYPE: DNA
<213> ORGANISM: Artificial
<220> FEATURE:
<223> OTHER INFORMATION: Description of Artificial Sequence:
      oligonucleotide

<400> SEQUENCE: 21
ggttcgaata cgcgcgccac agcgtgggca acgatgcgga gatctaaatg ctcccaattg    60
c                                                                   61

<210> SEQ ID NO 22
<211> LENGTH: 55
<212> TYPE: DNA
<213> ORGANISM: Artificial
<220> FEATURE:
<223> OTHER INFORMATION: Description of Artificial Sequence:
      oligonucleotide

<400> SEQUENCE: 22
ccaagcttca caatggcaaa ctggcagatg tagggcaatt gggagcattt agatc         55

<210> SEQ ID NO 23
<211> LENGTH: 86
<212> TYPE: DNA
<213> ORGANISM: Artificial
<220> FEATURE:
<223> OTHER INFORMATION: Description of Artificial Sequence:
      oligonucleotide

<400> SEQUENCE: 23
cggagatctg gctgggcctc aacgacatgg ccgcggaagg cgcctgggtg gacatgaccg    60
gtaccctcct ggcctacaag aactgg                                        86

<210> SEQ ID NO 24
<211> LENGTH: 130
<212> TYPE: DNA
<213> ORGANISM: Artificial
<220> FEATURE:
<223> OTHER INFORMATION: Description of Artificial Sequence:
      oligonucleotide
```

-continued

```
<400> SEQUENCE: 24
gggcaattga tcgcggcatc gcttgtcgaa cctcttgccg ttggctgcgc cagacagggc    60
ggcgcagttc tcggctttgc cgccgtcggg ttgcgtcgtg atctccgtct cccagttctt   120
gtaggccagg                                                          130

<210> SEQ ID NO 25
<211> LENGTH: 40
<212> TYPE: DNA
<213> ORGANISM: Artificial
<220> FEATURE:
<223> OTHER INFORMATION: Description of Artificial Sequence: Primer

<400> SEQUENCE: 25
ctgggatcca tccagggtcg cgagtcaccc actcccaagg                          40

<210> SEQ ID NO 26
<211> LENGTH: 27
<212> TYPE: DNA
<213> ORGANISM: Artificial
<220> FEATURE:
<223> OTHER INFORMATION: Description of Artificial Sequence: Primer

<400> SEQUENCE: 26
ccgaagctta cacaatggca aactggc                                        27

<210> SEQ ID NO 27
<211> LENGTH: 39
<212> TYPE: DNA
<213> ORGANISM: Artificial
<220> FEATURE:
<223> OTHER INFORMATION: Description of Artificial Sequence: Primer

<400> SEQUENCE: 27
ctgggatcca tccagggtcg cgccttacag actgtggtc                           39

<210> SEQ ID NO 28
<211> LENGTH: 568
<212> TYPE: DNA
<213> ORGANISM: Mus musculus
<220> FEATURE:
<221> NAME/KEY: CDS
<222> LOCATION: (1)..(561)
<223> OTHER INFORMATION: FX-mtlec encoding insert

<400> SEQUENCE: 28 gga tcc atc cag ggt cgc gag tca ccc act ccc aag gcc aag aag gct     48
Gly Ser Ile Gln Gly Arg Glu Ser Pro Thr Pro Lys Ala Lys Lys Ala
 1               5                  10                  15 gca aat gcc aag aaa gat ttg gtg agc tca aag atg ttc gag gag ctc     96
Ala Asn Ala Lys Lys Asp Leu Val Ser Ser Lys Met Phe Glu Glu Leu
            20                  25                  30 aag aac agg atg gat gtc ctg gcc cag gag gtg gcc ctg ctg aag gag    144
Lys Asn Arg Met Asp Val Leu Ala Gln Glu Val Ala Leu Leu Lys Glu
        35                  40                  45 aag cag gcc tta cag act gtg gtc ctg aag ggc acc aag gtg aac ttg    192
Lys Gln Ala Leu Gln Thr Val Val Leu Lys Gly Thr Lys Val Asn Leu
    50                  55                  60 aag gtc ctc ctg gcc ttc acc caa ccg aag acc ttc cat gag gcg agc    240
Lys Val Leu Leu Ala Phe Thr Gln Pro Lys Thr Phe His Glu Ala Ser
65                  70                  75                  80 gag gac tgc atc tcg caa ggg ggc acg ctg ggc acc ccg cag tca gag    288
Glu Asp Cys Ile Ser Gln Gly Gly Thr Leu Gly Thr Pro Gln Ser Glu
                85                  90                  95
```

```
cta gag aac gag gcg ctg ttc gag tac gcg cgc cac agc gtg ggc aac      336
Leu Glu Asn Glu Ala Leu Phe Glu Tyr Ala Arg His Ser Val Gly Asn
            100                 105                 110 gat gcg gag atc tgg ctg ggc ctc aac gac atg gcc gcg gaa ggc gcc      384
Asp Ala Glu Ile Trp Leu Gly Leu Asn Asp Met Ala Ala Glu Gly Ala
        115                 120                 125 tgg gtg gac atg acc ggt acc ctc ctg gcc tac aag aac tgg gag acg      432
Trp Val Asp Met Thr Gly Thr Leu Leu Ala Tyr Lys Asn Trp Glu Thr
    130                 135                 140 gag atc acg acg caa ccc gac ggc ggc aaa gcc gag aac tgc gcc gcc      480
Glu Ile Thr Thr Gln Pro Asp Gly Gly Lys Ala Glu Asn Cys Ala Ala
145                 150                 155                 160 ctg tct ggc gca gcc aac ggc aag tgg ttc gac aag cga tgc cgc gat      528
Leu Ser Gly Ala Ala Asn Gly Lys Trp Phe Asp Lys Arg Cys Arg Asp
                165                 170                 175 caa ttg ccc tac atc tgc cag ttt gcc att gtg taagctt                  568
Gln Leu Pro Tyr Ile Cys Gln Phe Ala Ile Val
                180                 185

<210> SEQ ID NO 29
<211> LENGTH: 187
<212> TYPE: PRT
<213> ORGANISM: Mus musculus

<400> SEQUENCE: 29

Gly Ser Ile Gln Gly Arg Glu Ser Pro Thr Pro Lys Ala Lys Lys Ala
1               5                   10                  15

Ala Asn Ala Lys Lys Asp Leu Val Ser Ser Lys Met Phe Glu Glu Leu
            20                  25                  30

Lys Asn Arg Met Asp Val Leu Ala Gln Glu Val Ala Leu Leu Lys Glu
        35                  40                  45

Lys Gln Ala Leu Gln Thr Val Val Leu Lys Gly Thr Lys Val Asn Leu
    50                  55                  60

Lys Val Leu Leu Ala Phe Thr Gln Pro Lys Thr Phe His Glu Ala Ser
65                  70                  75                  80

Glu Asp Cys Ile Ser Gln Gly Gly Thr Leu Gly Thr Pro Gln Ser Glu
                85                  90                  95

Leu Glu Asn Glu Ala Leu Phe Glu Tyr Ala Arg His Ser Val Gly Asn
            100                 105                 110

Asp Ala Glu Ile Trp Leu Gly Leu Asn Asp Met Ala Ala Glu Gly Ala
        115                 120                 125

Trp Val Asp Met Thr Gly Thr Leu Leu Ala Tyr Lys Asn Trp Glu Thr
    130                 135                 140

Glu Ile Thr Thr Gln Pro Asp Gly Gly Lys Ala Glu Asn Cys Ala Ala
145                 150                 155                 160

Leu Ser Gly Ala Ala Asn Gly Lys Trp Phe Asp Lys Arg Cys Arg Asp
                165                 170                 175

Gln Leu Pro Tyr Ile Cys Gln Phe Ala Ile Val
                180                 185

<210> SEQ ID NO 30
<211> LENGTH: 436
<212> TYPE: DNA
<213> ORGANISM: Mus musculus
<220> FEATURE:
<221> NAME/KEY: CDS
<222> LOCATION: (1)..(429)
<223> OTHER INFORMATION: FX-mtCTLD encoding insert

<400> SEQUENCE: 30
```

```
gga tcc atc cag ggt cgc gcc tta cag act gtg gtc ctg aag ggc acc    48
Gly Ser Ile Gln Gly Arg Ala Leu Gln Thr Val Val Leu Lys Gly Thr
1               5                   10                  15 aag gtg aac ttg aag gtc ctc ctg gcc ttc acc caa ccg aag acc ttc    96
Lys Val Asn Leu Lys Val Leu Leu Ala Phe Thr Gln Pro Lys Thr Phe
            20                  25                  30 cat gag gcg agc gag gac tgc atc tcg caa ggg ggc acg ctg ggc acc   144
His Glu Ala Ser Glu Asp Cys Ile Ser Gln Gly Gly Thr Leu Gly Thr
        35                  40                  45 ccg cag tca gag cta gag aac gag gcg ctg ttc gag tac gcg cgc cac   192
Pro Gln Ser Glu Leu Glu Asn Glu Ala Leu Phe Glu Tyr Ala Arg His
    50                  55                  60 agc gtg ggc aac gat gcg gag atc tgg ctg ggc ctc aac gac atg gcc   240
Ser Val Gly Asn Asp Ala Glu Ile Trp Leu Gly Leu Asn Asp Met Ala
65                  70                  75                  80 gcg gaa ggc gcc tgg gtg gac atg acc ggt acc ctc ctg gcc tac aag   288
Ala Glu Gly Ala Trp Val Asp Met Thr Gly Thr Leu Leu Ala Tyr Lys
                85                  90                  95 aac tgg gag acg gag atc acg acg caa ccc gac ggc ggc aaa gcc gag   336
Asn Trp Glu Thr Glu Ile Thr Thr Gln Pro Asp Gly Gly Lys Ala Glu
            100                 105                 110 aac tgc gcc gcc ctg tct ggc gca gcc aac ggc aag tgg ttc gac aag   384
Asn Cys Ala Ala Leu Ser Gly Ala Ala Asn Gly Lys Trp Phe Asp Lys
        115                 120                 125 cga tgc cgc gat caa ttg ccc tac atc tgc cag ttt gcc att gtg       429
Arg Cys Arg Asp Gln Leu Pro Tyr Ile Cys Gln Phe Ala Ile Val
    130                 135                 140 taagctt                                                            436

<210> SEQ ID NO 31
<211> LENGTH: 143
<212> TYPE: PRT
<213> ORGANISM: Mus musculus

<400> SEQUENCE: 31

Gly Ser Ile Gln Gly Arg Ala Leu Gln Thr Val Val Leu Lys Gly Thr
1               5                   10                  15

Lys Val Asn Leu Lys Val Leu Leu Ala Phe Thr Gln Pro Lys Thr Phe
            20                  25                  30

His Glu Ala Ser Glu Asp Cys Ile Ser Gln Gly Gly Thr Leu Gly Thr
        35                  40                  45

Pro Gln Ser Glu Leu Glu Asn Glu Ala Leu Phe Glu Tyr Ala Arg His
    50                  55                  60

Ser Val Gly Asn Asp Ala Glu Ile Trp Leu Gly Leu Asn Asp Met Ala
65                  70                  75                  80

Ala Glu Gly Ala Trp Val Asp Met Thr Gly Thr Leu Leu Ala Tyr Lys
                85                  90                  95

Asn Trp Glu Thr Glu Ile Thr Thr Gln Pro Asp Gly Gly Lys Ala Glu
            100                 105                 110

Asn Cys Ala Ala Leu Ser Gly Ala Ala Asn Gly Lys Trp Phe Asp Lys
        115                 120                 125

Arg Cys Arg Asp Gln Leu Pro Tyr Ile Cys Gln Phe Ala Ile Val
    130                 135                 140

<210> SEQ ID NO 32
<211> LENGTH: 47
<212> TYPE: DNA
<213> ORGANISM: Artificial
<220> FEATURE:
<223> OTHER INFORMATION: Description of Artificial Sequence: Primer
```

<400> SEQUENCE: 32

```
cggctgagcg gcccagccgg ccatggccga gtcacccact cccaagg          47
```

<210> SEQ ID NO 33
<211> LENGTH: 27
<212> TYPE: DNA
<213> ORGANISM: Artificial
<220> FEATURE:
<223> OTHER INFORMATION: Description of Artificial Sequence: Primer

<400> SEQUENCE: 33

```
cctgcggccg ccacgatccc gaactgg                                27
```

<210> SEQ ID NO 34
<211> LENGTH: 46
<212> TYPE: DNA
<213> ORGANISM: Artificial
<220> FEATURE:
<223> OTHER INFORMATION: Description of Artificial Sequence: Primer

<400> SEQUENCE: 34

```
cggctgagcg gcccagccgg ccatggccgc cttacagact gtggtc           46
```

<210> SEQ ID NO 35
<211> LENGTH: 570
<212> TYPE: DNA
<213> ORGANISM: Mus musculus
<220> FEATURE:
<221> NAME/KEY: CDS
<222> LOCATION: (8)..(565)
<223> OTHER INFORMATION: Pmtlec encoding insert

<400> SEQUENCE: 35

```
ggcccag ccg gcc atg gcc gag tca ccc act ccc aag gcc aag aag gct    49
        Pro Ala Met Ala Glu Ser Pro Thr Pro Lys Ala Lys Lys Ala
          1               5                   10 gca aat gcc aag aaa gat ttg gtg agc tca aag atg ttc gag gag ctc    97
Ala Asn Ala Lys Lys Asp Leu Val Ser Ser Lys Met Phe Glu Glu Leu
 15                  20                  25                  30 aag aac agg atg gat gtc ctg gcc cag gag gtg gcc ctg ctg aag gag   145
Lys Asn Arg Met Asp Val Leu Ala Gln Glu Val Ala Leu Leu Lys Glu
                 35                  40                  45 aag cag gcc tta cag act gtg gtc ctg aag ggc acc aag gtg aac ttg   193
Lys Gln Ala Leu Gln Thr Val Val Leu Lys Gly Thr Lys Val Asn Leu
             50                  55                  60 aag gtc ctc ctg gcc ttc acc caa ccg aag acc ttc cat gag gcg agc   241
Lys Val Leu Leu Ala Phe Thr Gln Pro Lys Thr Phe His Glu Ala Ser
 65                  70                  75 gag gac tgc atc tcg caa ggg ggc acg ctg ggc acc ccg cag tca gag   289
Glu Asp Cys Ile Ser Gln Gly Gly Thr Leu Gly Thr Pro Gln Ser Glu
 80                  85                  90 cta gag aac gag gcg ctg ttc gag tac gcg cgc cac agc gtg ggc aac   337
Leu Glu Asn Glu Ala Leu Phe Glu Tyr Ala Arg His Ser Val Gly Asn
 95                 100                 105                 110 gat gcg gag atc tgg ctg ggc ctc aac gac atg gcc gcg gaa ggc gcc   385
Asp Ala Glu Ile Trp Leu Gly Leu Asn Asp Met Ala Ala Glu Gly Ala
                115                 120                 125 tgg gtg gac atg acc ggt acc ctc ctg gcc tac aag aac tgg gag acg   433
Trp Val Asp Met Thr Gly Thr Leu Leu Ala Tyr Lys Asn Trp Glu Thr
            130                 135                 140 gag atc acg acg caa ccc gac ggc ggc aaa gcc gag aac tgc gcc gcc   481
Glu Ile Thr Thr Gln Pro Asp Gly Gly Lys Ala Glu Asn Cys Ala Ala
145                 150                 155
```

```
ctg tct ggc gca gcc aac ggc aag tgg ttc gac aag cga tgc cgc gat      529
Leu Ser Gly Ala Ala Asn Gly Lys Trp Phe Asp Lys Arg Cys Arg Asp
    160                 165                 170 caa ttg ccc tac atc tgc cag ttt gcc att gtg gcg gccgc              570
Gln Leu Pro Tyr Ile Cys Gln Phe Ala Ile Val Ala
175                 180                 185

<210> SEQ ID NO 36
<211> LENGTH: 186
<212> TYPE: PRT
<213> ORGANISM: Mus musculus

<400> SEQUENCE: 36

Pro Ala Met Ala Glu Ser Pro Thr Pro Lys Ala Lys Lys Ala Ala Asn
1               5                   10                  15

Ala Lys Lys Asp Leu Val Ser Ser Lys Met Phe Glu Glu Leu Lys Asn
                20                  25                  30

Arg Met Asp Val Leu Ala Gln Glu Val Ala Leu Leu Lys Glu Lys Gln
            35                  40                  45

Ala Leu Gln Thr Val Val Leu Lys Gly Thr Lys Val Asn Leu Lys Val
50                  55                  60

Leu Leu Ala Phe Thr Gln Pro Lys Thr Phe His Glu Ala Ser Glu Asp
65                  70                  75                  80

Cys Ile Ser Gln Gly Gly Thr Leu Gly Thr Pro Gln Ser Glu Leu Glu
                85                  90                  95

Asn Glu Ala Leu Phe Glu Tyr Ala Arg His Ser Val Gly Asn Asp Ala
            100                 105                 110

Glu Ile Trp Leu Gly Leu Asn Asp Met Ala Ala Glu Gly Ala Trp Val
        115                 120                 125

Asp Met Thr Gly Thr Leu Leu Ala Tyr Lys Asn Trp Glu Thr Glu Ile
130                 135                 140

Thr Thr Gln Pro Asp Gly Gly Lys Ala Glu Asn Cys Ala Ala Leu Ser
145                 150                 155                 160

Gly Ala Ala Asn Gly Lys Trp Phe Asp Lys Arg Cys Arg Asp Gln Leu
                165                 170                 175

Pro Tyr Ile Cys Gln Phe Ala Ile Val Ala
            180                 185

<210> SEQ ID NO 37
<211> LENGTH: 438
<212> TYPE: DNA
<213> ORGANISM: Mus musculus
<220> FEATURE:
<221> NAME/KEY: CDS
<222> LOCATION: (8)..(433)
<223> OTHER INFORMATION: PmtCTLD encoding insert

<400> SEQUENCE: 37 ggcccag ccg gcc atg gcc gcc tta cag act gtg gtc ctg aag ggc acc      49
        Pro Ala Met Ala Ala Leu Gln Thr Val Val Leu Lys Gly Thr
            1               5                   10 aag gtg aac ttg aag gtc ctc ctg gcc ttc acc caa ccg aag acc ttc      97
Lys Val Asn Leu Lys Val Leu Leu Ala Phe Thr Gln Pro Lys Thr Phe
15                  20                  25                  30 cat gag gcg agc gag gac tgc atc tcg caa ggg ggc acg ctg ggc acc     145
His Glu Ala Ser Glu Asp Cys Ile Ser Gln Gly Gly Thr Leu Gly Thr
                35                  40                  45 ccg cag tca gag cta gag aac gag gcg ctg ttc gag tac gcg cgc cac     193
Pro Gln Ser Glu Leu Glu Asn Glu Ala Leu Phe Glu Tyr Ala Arg His
            50                  55                  60
```

```
agc gtg ggc aac gat gcg gag atc tgg ctg ggc ctc aac gac atg gcc        241
Ser Val Gly Asn Asp Ala Glu Ile Trp Leu Gly Leu Asn Asp Met Ala
         65                  70                  75 gcg gaa ggc gcc tgg gtg gac atg acc ggt acc ctc ctg gcc tac aag        289
Ala Glu Gly Ala Trp Val Asp Met Thr Gly Thr Leu Leu Ala Tyr Lys
 80                  85                  90 aac tgg gag acg gag atc acg acg caa ccc gac ggc ggc aaa gcc gag        337
Asn Trp Glu Thr Glu Ile Thr Thr Gln Pro Asp Gly Gly Lys Ala Glu
 95                 100                 105                 110 aac tgc gcc gcc ctg tct ggc gca gcc aac ggc aag tgg ttc gac aag        385
Asn Cys Ala Ala Leu Ser Gly Ala Ala Asn Gly Lys Trp Phe Asp Lys
                115                 120                 125 cga tgc cgc gat caa ttg ccc tac atc tgc cag ttt gcc att gtg gcg        433
Arg Cys Arg Asp Gln Leu Pro Tyr Ile Cys Gln Phe Ala Ile Val Ala
            130                 135                 140 gccgc                                                                   438
```

<210> SEQ ID NO 38
<211> LENGTH: 142
<212> TYPE: PRT
<213> ORGANISM: Mus musculus

<400> SEQUENCE: 38

```
Pro Ala Met Ala Ala Leu Gln Thr Val Val Leu Lys Gly Thr Lys Val
 1               5                  10                  15

Asn Leu Lys Val Leu Leu Ala Phe Thr Gln Pro Lys Thr Phe His Glu
            20                  25                  30

Ala Ser Glu Asp Cys Ile Ser Gln Gly Gly Thr Leu Gly Thr Pro Gln
        35                  40                  45

Ser Glu Leu Glu Asn Glu Ala Leu Phe Glu Tyr Ala Arg His Ser Val
    50                  55                  60

Gly Asn Asp Ala Glu Ile Trp Leu Gly Leu Asn Asp Met Ala Ala Glu
 65                  70                  75                  80

Gly Ala Trp Val Asp Met Thr Gly Thr Leu Leu Ala Tyr Lys Asn Trp
                85                  90                  95

Glu Thr Glu Ile Thr Thr Gln Pro Asp Gly Gly Lys Ala Glu Asn Cys
            100                 105                 110

Ala Ala Leu Ser Gly Ala Ala Asn Gly Lys Trp Phe Asp Lys Arg Cys
        115                 120                 125

Arg Asp Gln Leu Pro Tyr Ile Cys Gln Phe Ala Ile Val Ala
    130                 135                 140
```

<210> SEQ ID NO 39
<211> LENGTH: 116
<212> TYPE: DNA
<213> ORGANISM: Artificial
<220> FEATURE:
<223> OTHER INFORMATION: Description of Artificial Sequence: oligonucleotide
<220> FEATURE:
<221> NAME/KEY: misc_feature
<222> LOCATION: (17)..(18)
<223> OTHER INFORMATION: randomised
<220> FEATURE:
<221> NAME/KEY: misc_feature
<222> LOCATION: (20)..(21)
<223> OTHER INFORMATION: randomised
<220> FEATURE:
<221> NAME/KEY: misc_feature
<222> LOCATION: (23)..(24)
<223> OTHER INFORMATION: randomised
<220> FEATURE:
<221> NAME/KEY: misc_feature

```
<222> LOCATION: (26)..(27)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised
<220> FEATURE:
<221> NAME/KEY: misc_feature
<222> LOCATION: (50)..(51)
<223> OTHER INFORMATION: randomised
<220> FEATURE:
<221> NAME/KEY: misc_feature
<222> LOCATION: (53)..(54)
<223> OTHER INFORMATION: randomised
<220> FEATURE:
<221> NAME/KEY: misc_feature
<222> LOCATION: (98)..(99)
<223> OTHER INFORMATION: randomised

<400> SEQUENCE: 39
cgcctacaag aactggnnsn nsnnsnnsnn snnscaaccc gatnnsnnsn nsnnsgagaa    60
ctgcgcggtc ctgtcaggcg cggccaacgg caagtggnns gacaagcgct gccgcg       116

<210> SEQ ID NO 40
<211> LENGTH: 31
<212> TYPE: DNA
<213> ORGANISM: Artificial
<220> FEATURE:
<223> OTHER INFORMATION: Description of Artificial Sequence:
      oligonucleotide

<400> SEQUENCE: 40
gaccggtacc cgcatcgcct acaagaactg g                                   31

<210> SEQ ID NO 41
<211> LENGTH: 30
<212> TYPE: DNA
<213> ORGANISM: Artificial
<220> FEATURE:
<223> OTHER INFORMATION: Description of Artificial Sequence:
      oligonucleotide

<400> SEQUENCE: 41
gtagggcaat tgatcgcggc agcgcttgtc                                     30

<210> SEQ ID NO 42
<211> LENGTH: 94
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (17)..(18)
<223> OTHER INFORMATION: randomised
<220> FEATURE:
<221> NAME/KEY: misc_feature
<222> LOCATION: (20)..(21)
<223> OTHER INFORMATION: randomised
<220> FEATURE:
```

```
<221> NAME/KEY: misc_feature
<222> LOCATION: (23)..(24)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised

<400> SEQUENCE: 42
gctgggcctc aacgacnnsn nsnnsgagnn snnstgggtg gacatgaccg gtacccgcat      60
cgcctacaag aactgggaga ctgagatcac cgcg                                 94

<210> SEQ ID NO 43
<211> LENGTH: 102
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (63)..(64)
<223> OTHER INFORMATION: randomised
<220> FEATURE:
<221> NAME/KEY: misc_feature
<222> LOCATION: (66)..(67)
<223> OTHER INFORMATION: randomised
<220> FEATURE:
<221> NAME/KEY: misc_feature
<222> LOCATION: (69)..(70)
<223> OTHER INFORMATION: randomised
<220> FEATURE:
<221> NAME/KEY: misc_feature
<222> LOCATION: (72)..(73)
<223> OTHER INFORMATION: randomised

<400> SEQUENCE: 43
cgcggcagcg cttgtcgaac cacttgccgt tggccgcgcc tgacaggacc gcgcagttct      60
csnnsnnsnn snnatcgggt tgcgcggtga tctcagtctc cc                        102

<210> SEQ ID NO 44
<211> LENGTH: 31
<212> TYPE: DNA
<213> ORGANISM: Artificial
<220> FEATURE:
<223> OTHER INFORMATION: Description of Artificial Sequence:
      oligonucleotide

<400> SEQUENCE: 44
cgaggccgag atctggctgg gcctcaacga c                                    31

<210> SEQ ID NO 45
<211> LENGTH: 31
<212> TYPE: DNA
<213> ORGANISM: Artificial
<220> FEATURE:
<223> OTHER INFORMATION: Description of Artificial Sequence:
      oligonucleotide

<400> SEQUENCE: 45
gggcaacgag gccgagatct ggctgggcct c                                    31

<210> SEQ ID NO 46
<211> LENGTH: 19
<212> TYPE: DNA
<213> ORGANISM: Artificial
```

```
<220> FEATURE:
<223> OTHER INFORMATION: Description of Artificial Sequence:
      oligonucleotide

<400> SEQUENCE: 46
cctgaccctg cagcgcttg                                                     19

<210> SEQ ID NO 47
<211> LENGTH: 81
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (26)..(27)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised

<400> SEQUENCE: 47
cgagatctgg ctgggcctca acgacnnsnn snnsnnsnns nnsgagggca cctgggtgga        60
catgaccggt acccgcatcg c                                                  81

<210> SEQ ID NO 48
<211> LENGTH: 78
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (26)..(27)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised

<400> SEQUENCE: 48
cgagatctgg ctgggcctca acgacnnsnn snnsnnsnns gagggcacct gggtggacat        60
```
gaccggtacc cgcatcgc                                                        78

<210> SEQ ID NO 49
<211> LENGTH: 94
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (17)..(18)
<223> OTHER INFORMATION: randomised
<220> FEATURE:
<221> NAME/KEY: misc_feature
<222> LOCATION: (20)..(21)
<223> OTHER INFORMATION: randomised
<220> FEATURE:
<221> NAME/KEY: misc_feature
<222> LOCATION: (23)..(24)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised

<400> SEQUENCE: 49
gctgggcctc aacgacnnsn nsnnsgagnn snnstgggtg gacatgaccg gtacccgcat         60
cgcctacaag aactgggaga ctgagatcac cgcg                                    94

<210> SEQ ID NO 50
<211> LENGTH: 18
<212> TYPE: DNA
<213> ORGANISM: Artificial
<220> FEATURE:
<223> OTHER INFORMATION: Description of Artificial Sequence:
      oligonucleotide

<400> SEQUENCE: 50
gcgatgcggg taccggtc                                                      18

<210> SEQ ID NO 51
<211> LENGTH: 89
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (54)..(55)
<223> OTHER INFORMATION: randomised
<220> FEATURE:
<221> NAME/KEY: misc_feature
<222> LOCATION: (57)..(58)
<223> OTHER INFORMATION: randomised
<220> FEATURE:
<221> NAME/KEY: misc_feature
<222> LOCATION: (60)..(61)
<223> OTHER INFORMATION: randomised
<220> FEATURE:
<221> NAME/KEY: misc_feature
<222> LOCATION: (63)..(64)
<223> OTHER INFORMATION: randomised
<220> FEATURE:
<221> NAME/KEY: misc_feature
<222> LOCATION: (66)..(67)
<223> OTHER INFORMATION: randomised
<220> FEATURE:
<221> NAME/KEY: misc_feature

```
<222> LOCATION: (69)..(70)
<223> OTHER INFORMATION: randomised

<400> SEQUENCE: 51
gcatcgccta caagaactgg gagactgaga tcaccgcgca acccgatggc ggcnnsnnsn      60
nsnnsnnsnn sgagaactgc gcggtcctg                                       89

<210> SEQ ID NO 52
<211> LENGTH: 86
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (54)..(55)
<223> OTHER INFORMATION: randomised
<220> FEATURE:
<221> NAME/KEY: misc_feature
<222> LOCATION: (57)..(58)
<223> OTHER INFORMATION: randomised
<220> FEATURE:
<221> NAME/KEY: misc_feature
<222> LOCATION: (60)..(61)
<223> OTHER INFORMATION: randomised
<220> FEATURE:
<221> NAME/KEY: misc_feature
<222> LOCATION: (63)..(64)
<223> OTHER INFORMATION: randomised
<220> FEATURE:
<221> NAME/KEY: misc_feature
<222> LOCATION: (66)..(67)
<223> OTHER INFORMATION: randomised

<400> SEQUENCE: 52
gcatcgccta caagaactgg gagactgaga tcaccgcgca acccgatggc ggcnnsnnsn      60
nsnnsnnsga gaactgcgcg gtcctg                                          86

<210> SEQ ID NO 53
<211> LENGTH: 34
<212> TYPE: DNA
<213> ORGANISM: Artificial
<220> FEATURE:
<223> OTHER INFORMATION: Description of Artificial Sequence:
      oligonucleotide

<400> SEQUENCE: 53
catgaccggt acccgcatcg cctacaagaa ctgg                                 34

<210> SEQ ID NO 54
<211> LENGTH: 66
<212> TYPE: DNA
<213> ORGANISM: Artificial
<220> FEATURE:
<223> OTHER INFORMATION: Description of Artificial Sequence:
      oligonucleotide

<400> SEQUENCE: 54
cctgaccctg cagcgcttgt cgaaccactt gccgttggcc gcgcctgaca ggaccgcgca      60
gttctc                                                                66

<210> SEQ ID NO 55
<211> LENGTH: 45
<212> TYPE: DNA
<213> ORGANISM: Artificial
<220> FEATURE:
<223> OTHER INFORMATION: Description of Artificial Sequence:
      oligonucleotide
```

```
<400> SEQUENCE: 55
ggtacctaag tgacgatatc ctgacctaac tgcagggatc aattg                          45

<210> SEQ ID NO 56
<211> LENGTH: 343
<212> TYPE: DNA
<213> ORGANISM: Homo sapiens
<220> FEATURE:
<221> NAME/KEY: CDS
<222> LOCATION: (8)..(274)
<223> OTHER INFORMATION: Human PhtCPB insert

<400> SEQUENCE: 56 ggcccag ccg gcc atg gcc gcc ctc cag acg gtc tgc ctg aag ggg acc        49
        Pro Ala Met Ala Ala Leu Gln Thr Val Cys Leu Lys Gly Thr
        1               5                   10 aag gtg cac atg aaa tgc ttt ctg gcc ttc acc cag acg aag acc ttc        97
Lys Val His Met Lys Cys Phe Leu Ala Phe Thr Gln Thr Lys Thr Phe
15                  20                  25                  30 cac gag gcc agc gag gac tgc atc tcg cgc ggg ggc acc ctg agc acc       145
His Glu Ala Ser Glu Asp Cys Ile Ser Arg Gly Gly Thr Leu Ser Thr
                35                  40                  45 cct cag act ggc tcg gag aac gac gcc ctg tat gag tac ctg cgc cag       193
Pro Gln Thr Gly Ser Glu Asn Asp Ala Leu Tyr Glu Tyr Leu Arg Gln
        50                  55                  60 agc gtg ggc aac gag gcc gag atc tgg ctg ggc ctc aac gac atg gcg       241
Ser Val Gly Asn Glu Ala Glu Ile Trp Leu Gly Leu Asn Asp Met Ala
65                  70                  75 gcc gag ggc acc tgg gtg gac atg acc ggt acc taagtgacga tatcctgacc      294
Ala Glu Gly Thr Trp Val Asp Met Thr Gly Thr
            80                  85 taactgcagg gatcaattgc cctacatctg ccagttcggg atcgtgtag                  343

<210> SEQ ID NO 57
<211> LENGTH: 89
<212> TYPE: PRT
<213> ORGANISM: Homo sapiens

<400> SEQUENCE: 57

Pro Ala Met Ala Ala Leu Gln Thr Val Cys Leu Lys Gly Thr Lys Val
1               5                   10                  15

His Met Lys Cys Phe Leu Ala Phe Thr Gln Thr Lys Thr Phe His Glu
            20                  25                  30

Ala Ser Glu Asp Cys Ile Ser Arg Gly Gly Thr Leu Ser Thr Pro Gln
        35                  40                  45

Thr Gly Ser Glu Asn Asp Ala Leu Tyr Glu Tyr Leu Arg Gln Ser Val
    50                  55                  60

Gly Asn Glu Ala Glu Ile Trp Leu Gly Leu Asn Asp Met Ala Ala Glu
65                  70                  75                  80

Gly Thr Trp Val Asp Met Thr Gly Thr
                85

<210> SEQ ID NO 58
<211> LENGTH: 405
<212> TYPE: DNA
<213> ORGANISM: Rattus rattus
<220> FEATURE:
<221> NAME/KEY: CDS
<222> LOCATION: (8)..(400)
<223> OTHER INFORMATION: Rat PrMBP insert

<400> SEQUENCE: 58
```

```
ggcccag ccg gcc atg gcc aac aag ttg cat gcc ttc tcc atg ggt aaa      49
        Pro Ala Met Ala Asn Lys Leu His Ala Phe Ser Met Gly Lys
        1               5                   10 aag tct ggg aag aag ttc ttt gtg acc aac cat gaa agg atg ccc ttt      97
Lys Ser Gly Lys Lys Phe Phe Val Thr Asn His Glu Arg Met Pro Phe
15                  20                  25                  30 tcc aaa gtc aag gcc ctg tgc tca gag ctc cga ggc act gtg gct atc     145
Ser Lys Val Lys Ala Leu Cys Ser Glu Leu Arg Gly Thr Val Ala Ile
                35                  40                  45 ccc aag aat gct gag gag aac aag gcc atc caa gaa gtg gct aaa acc     193
Pro Lys Asn Ala Glu Glu Asn Lys Ala Ile Gln Glu Val Ala Lys Thr
            50                  55                  60 tct gcc ttc cta ggc atc acg gac gag gtg act gaa ggc caa ttc atg     241
Ser Ala Phe Leu Gly Ile Thr Asp Glu Val Thr Glu Gly Gln Phe Met
        65                  70                  75 tat gtg aca ggg ggg agg ctc acc tac agc aac tgg aaa aag gat gag     289
Tyr Val Thr Gly Gly Arg Leu Thr Tyr Ser Asn Trp Lys Lys Asp Glu
80                  85                  90 ccc aat gac cat ggc tct ggg gaa gac tgt gtc act ata gta gac aac     337
Pro Asn Asp His Gly Ser Gly Glu Asp Cys Val Thr Ile Val Asp Asn
95                  100                 105                 110 ggt ctg tgg aat gac atc tcc tgc caa gct tcc cac acg gct gtc tgc     385
Gly Leu Trp Asn Asp Ile Ser Cys Gln Ala Ser His Thr Ala Val Cys
                115                 120                 125 gag ttc cca gcc gcg gccgc                                            405
Glu Phe Pro Ala Ala
            130
```

<210> SEQ ID NO 59
<211> LENGTH: 131
<212> TYPE: PRT
<213> ORGANISM: Rattus rattus

<400> SEQUENCE: 59

```
Pro Ala Met Ala Asn Lys Leu His Ala Phe Ser Met Gly Lys Lys Ser
1               5                   10                  15

Gly Lys Lys Phe Phe Val Thr Asn His Glu Arg Met Pro Phe Ser Lys
            20                  25                  30

Val Lys Ala Leu Cys Ser Glu Leu Arg Gly Thr Val Ala Ile Pro Lys
        35                  40                  45

Asn Ala Glu Glu Asn Lys Ala Ile Gln Glu Val Ala Lys Thr Ser Ala
    50                  55                  60

Phe Leu Gly Ile Thr Asp Glu Val Thr Glu Gly Gln Phe Met Tyr Val
65                  70                  75                  80

Thr Gly Gly Arg Leu Thr Tyr Ser Asn Trp Lys Lys Asp Glu Pro Asn
                85                  90                  95

Asp His Gly Ser Gly Glu Asp Cys Val Thr Ile Val Asp Asn Gly Leu
            100                 105                 110

Trp Asn Asp Ile Ser Cys Gln Ala Ser His Thr Ala Val Cys Glu Phe
        115                 120                 125

Pro Ala Ala
    130
```

<210> SEQ ID NO 60
<211> LENGTH: 408
<212> TYPE: DNA
<213> ORGANISM: Homo sapiens
<220> FEATURE:
<221> NAME/KEY: CDS
<222> LOCATION: (8)..(403)

<223> OTHER INFORMATION: Human PhSP-D insert

<400> SEQUENCE: 60

```
ggcccag ccg gcc atg gcc aag aaa gtt gag ctc ttc cca aat ggc caa        49
        Pro Ala Met Ala Lys Lys Val Glu Leu Phe Pro Asn Gly Gln
        1               5                   10 agt gtg ggg gag aag att ttc aag aca gca ggc ttt gta aaa cca ttt        97
Ser Val Gly Glu Lys Ile Phe Lys Thr Ala Gly Phe Val Lys Pro Phe
15              20                  25                  30 acg gag gca cag ctg ctg tgc aca cag gct ggt gga cag ttg gcc tct       145
Thr Glu Ala Gln Leu Leu Cys Thr Gln Ala Gly Gly Gln Leu Ala Ser
                35                  40                  45 cca cgc tct gcc gct gag aat gcc gcc ttg caa cag ctg gtc gta gct       193
Pro Arg Ser Ala Ala Glu Asn Ala Ala Leu Gln Gln Leu Val Val Ala
            50                  55                  60 aag aac gag gct gct ttc ctg agc atg act gat tcc aag aca gag ggc       241
Lys Asn Glu Ala Ala Phe Leu Ser Met Thr Asp Ser Lys Thr Glu Gly
65                  70                  75 aag ttc acc tac ccc aca gga gag tcc ctg gtc tat tcc aac tgg gcc       289
Lys Phe Thr Tyr Pro Thr Gly Glu Ser Leu Val Tyr Ser Asn Trp Ala
        80                  85                  90 cca ggg gag ccc aac gat gat ggc ggg tca gag gac tgt gtg gag atc       337
Pro Gly Glu Pro Asn Asp Asp Gly Gly Ser Glu Asp Cys Val Glu Ile
95                  100                 105                 110 ttc acc aat ggc aag tgg aat gac agg gct tgt gga gaa aag cgt ctt       385
Phe Thr Asn Gly Lys Trp Asn Asp Arg Ala Cys Gly Glu Lys Arg Leu
                115                 120                 125 gtg gtc tgc gag ttc gcg gccgc                                         408
Val Val Cys Glu Phe Ala
            130
```

<210> SEQ ID NO 61
<211> LENGTH: 132
<212> TYPE: PRT
<213> ORGANISM: Homo sapiens

<400> SEQUENCE: 61

```
Pro Ala Met Ala Lys Lys Val Glu Leu Phe Pro Asn Gly Gln Ser Val
1               5                   10                  15

Gly Glu Lys Ile Phe Lys Thr Ala Gly Phe Val Lys Pro Phe Thr Glu
            20                  25                  30

Ala Gln Leu Leu Cys Thr Gln Ala Gly Gly Gln Leu Ala Ser Pro Arg
        35                  40                  45

Ser Ala Ala Glu Asn Ala Ala Leu Gln Gln Leu Val Val Ala Lys Asn
    50                  55                  60

Glu Ala Ala Phe Leu Ser Met Thr Asp Ser Lys Thr Glu Gly Lys Phe
65                  70                  75                  80

Thr Tyr Pro Thr Gly Glu Ser Leu Val Tyr Ser Asn Trp Ala Pro Gly
                85                  90                  95

Glu Pro Asn Asp Asp Gly Gly Ser Glu Asp Cys Val Glu Ile Phe Thr
            100                 105                 110

Asn Gly Lys Trp Asn Asp Arg Ala Cys Gly Glu Lys Arg Leu Val Val
        115                 120                 125

Cys Glu Phe Ala
    130
```

<210> SEQ ID NO 62
<211> LENGTH: 49
<212> TYPE: DNA
<213> ORGANISM: Artificial

-continued

<220> FEATURE:
<223> OTHER INFORMATION: Description of Artificial Sequence:
      oligonucleotide

<400> SEQUENCE: 62
cggctgagcg gcccagccgg ccatggccaa caagttgcat gccttctcc         49

<210> SEQ ID NO 63
<211> LENGTH: 34
<212> TYPE: DNA
<213> ORGANISM: Artificial
<220> FEATURE:
<223> OTHER INFORMATION: Description of Artificial Sequence:
      oligonucleotide

<400> SEQUENCE: 63
gcactcctgc ggccgcggct gggaactcgc agac                         34

<210> SEQ ID NO 64
<211> LENGTH: 48
<212> TYPE: DNA
<213> ORGANISM: Artificial
<220> FEATURE:
<223> OTHER INFORMATION: Description of Artificial Sequence:
      oligonucleotide

<400> SEQUENCE: 64
cggctgagcg gcccagccgg ccatggccaa gaaagttgag ctcttccc          48

<210> SEQ ID NO 65
<211> LENGTH: 36
<212> TYPE: DNA
<213> ORGANISM: Artificial
<220> FEATURE:
<223> OTHER INFORMATION: Description of Artificial Sequence:
      oligonucleotide

<400> SEQUENCE: 65
gcactcctgc ggccgcgaac tcgcagacca caagac                       36

<210> SEQ ID NO 66
<211> LENGTH: 65
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised
<220> FEATURE:
<221> NAME/KEY: misc_feature
<222> LOCATION: (44)..(45)
<223> OTHER INFORMATION: randomised

<400> SEQUENCE: 66
gccaccggtg acgtagatga attggccttc snsnnsnns nnsnngtccg tgatgcctag   60
gaagg 65

```
<210> SEQ ID NO 67
<211> LENGTH: 68
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised

<400> SEQUENCE: 67
```
gccaccggtg acgtagatga attggccttc snnsnnsnns nnsnnsnngt ccgtgatgcc 60
taggaagg 68

```
<210> SEQ ID NO 68
<211> LENGTH: 62
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (23)..(24)
<223> OTHER INFORMATION: randomised
<220> FEATURE:
<221> NAME/KEY: misc_feature
<222> LOCATION: (26)..(27)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised

<400> SEQUENCE: 68
```

```
gccaccggtg acgtagatga asnnsnnsnn snnsnnsnns nncgtgatgc ctaggaaggc    60
ag                                                                  62
```

<210> SEQ ID NO 69
<211> LENGTH: 40
<212> TYPE: DNA
<213> ORGANISM: Artificial
<220> FEATURE:
<223> OTHER INFORMATION: Description of Artificial Sequence:
      oligonucleotide

<400> SEQUENCE: 69

```
ccagttgctg tatttcaggc tgccaccggt gacgtagatg                         40
```

<210> SEQ ID NO 70
<211> LENGTH: 34
<212> TYPE: DNA
<213> ORGANISM: Artificial
<220> FEATURE:
<223> OTHER INFORMATION: Description of Artificial Sequence:
      oligonucleotide

<400> SEQUENCE: 70

```
gcctgaaata cagcaactgg aagaaagacg aacc                               34
```

<210> SEQ ID NO 71
<211> LENGTH: 68
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised
<220> FEATURE:
<221> NAME/KEY: misc_feature
<222> LOCATION: (44)..(45)
<223> OTHER INFORMATION: randomised

<400> SEQUENCE: 71

```
ctggaagaaa gacgaaccga atgaccatgg cnnsnnsnns nnsnnsgaag actgtgtcac    60
tatagtag                                                            68
```

<210> SEQ ID NO 72
<211> LENGTH: 71
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)

<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised

<400> SEQUENCE: 72
ctggaagaaa gacgaaccga atgaccatgg cnnsnnsnns nnsnnsnnsg aagactgtgt    60
cactatagta g    71

<210> SEQ ID NO 73
<211> LENGTH: 59
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (23)..(24)
<223> OTHER INFORMATION: randomised
<220> FEATURE:
<221> NAME/KEY: misc_feature
<222> LOCATION: (26)..(27)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised

<400> SEQUENCE: 73
ctggaagaaa gacgaaccga atnnsnnsnn snnsnnsgaa gactgtgtca ctatagtag    59

<210> SEQ ID NO 74
<211> LENGTH: 17
<212> TYPE: DNA
<213> ORGANISM: Artificial
<220> FEATURE:
<223> OTHER INFORMATION: Description of Artificial Sequence:
      oligonucleotide

<400> SEQUENCE: 74
cggctgagcg gcccagc    17

<210> SEQ ID NO 75
<211> LENGTH: 17
<212> TYPE: DNA
<213> ORGANISM: Artificial
<220> FEATURE:
<223> OTHER INFORMATION: Description of Artificial Sequence:
      oligonucleotide

<400> SEQUENCE: 75

```
gcactcctgc ggccgcg                                              17

<210> SEQ ID NO 76
<211> LENGTH: 69
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised

<400> SEQUENCE: 76
ctcaccggtc ggatacgtga acttgccctc tgtsnnsnns nnsnnsnnat cagtcatgct    60
caggaaagc                                                             69

<210> SEQ ID NO 77
<211> LENGTH: 72
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised
<220> FEATURE:
<221> NAME/KEY: misc_feature
<222> LOCATION: (50)..(51)
<223> OTHER INFORMATION: randomised

<400> SEQUENCE: 77
ctcaccggtc ggatacgtga acttgccctc tgtsnnsnns nnsnnsnnsn natcagtcat    60
gctcaggaaa gc                                                         72

<210> SEQ ID NO 78
<211> LENGTH: 60
```

```
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (23)..(24)
<223> OTHER INFORMATION: randomised
<220> FEATURE:
<221> NAME/KEY: misc_feature
<222> LOCATION: (26)..(27)
<223> OTHER INFORMATION: randomised
<220> FEATURE:
<221> NAME/KEY: misc_feature
<222> LOCATION: (29)..(30)
<223> OTHER INFORMATION: randomised
<220> FEATURE:
<221> NAME/KEY: misc_feature
<222> LOCATION: (32)..(33)
<223> OTHER INFORMATION: randomised
<220> FEATURE:
<221> NAME/KEY: misc_feature
<222> LOCATION: (35)..(36)
<223> OTHER INFORMATION: randomised
<220> FEATURE:
<221> NAME/KEY: misc_feature
<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised

<400> SEQUENCE: 78
ctcaccggtc ggatacgtga asnnsnnsnn snnsnnsnns nnagtcatgc tcaggaaagc      60

<210> SEQ ID NO 79
<211> LENGTH: 39
<212> TYPE: DNA
<213> ORGANISM: Artificial
<220> FEATURE:
<223> OTHER INFORMATION: Description of Artificial Sequence:
      oligonucleotide

<400> SEQUENCE: 79
cagttggaat agaccaggga ctcaccggtc ggatacgtg                            39

<210> SEQ ID NO 80
<211> LENGTH: 65
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (30)..(31)
<223> OTHER INFORMATION: randomised
<220> FEATURE:
<221> NAME/KEY: misc_feature
<222> LOCATION: (33)..(34)
<223> OTHER INFORMATION: randomised
<220> FEATURE:
<221> NAME/KEY: misc_feature
<222> LOCATION: (36)..(37)
<223> OTHER INFORMATION: randomised
<220> FEATURE:
<221> NAME/KEY: misc_feature
<222> LOCATION: (39)..(40)
<223> OTHER INFORMATION: randomised
<220> FEATURE:
<221> NAME/KEY: misc_feature
<222> LOCATION: (42)..(43)
<223> OTHER INFORMATION: randomised
```

<400> SEQUENCE: 80
gggccccagg ggagcccaac gatgatggcn nsnnsnnsnn snnsgaggac tgtgtggaga    60
tcttc    65

<210> SEQ ID NO 81
<211> LENGTH: 68
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (30)..(31)
<223> OTHER INFORMATION: randomised
<220> FEATURE:
<221> NAME/KEY: misc_feature
<222> LOCATION: (33)..(34)
<223> OTHER INFORMATION: randomised
<220> FEATURE:
<221> NAME/KEY: misc_feature
<222> LOCATION: (36)..(37)
<223> OTHER INFORMATION: randomised
<220> FEATURE:
<221> NAME/KEY: misc_feature
<222> LOCATION: (39)..(40)
<223> OTHER INFORMATION: randomised
<220> FEATURE:
<221> NAME/KEY: misc_feature
<222> LOCATION: (42)..(43)
<223> OTHER INFORMATION: randomised
<220> FEATURE:
<221> NAME/KEY: misc_feature
<222> LOCATION: (45)..(46)
<223> OTHER INFORMATION: randomised

<400> SEQUENCE: 81
gggccccagg ggagcccaac gatgatggcn nsnnsnnsnn snnsnnsgag gactgtgtgg    60
agatcttc    68

<210> SEQ ID NO 82
<211> LENGTH: 68
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (30)..(31)
<223> OTHER INFORMATION: randomised
<220> FEATURE:
<221> NAME/KEY: misc_feature
<222> LOCATION: (33)..(34)
<223> OTHER INFORMATION: randomised
<220> FEATURE:
<221> NAME/KEY: misc_feature
<222> LOCATION: (36)..(37)
<223> OTHER INFORMATION: randomised
<220> FEATURE:
<221> NAME/KEY: misc_feature
<222> LOCATION: (39)..(40)
<223> OTHER INFORMATION: randomised
<220> FEATURE:
<221> NAME/KEY: misc_feature
<222> LOCATION: (42)..(43)
<223> OTHER INFORMATION: randomised
<220> FEATURE:
<221> NAME/KEY: misc_feature
<222> LOCATION: (45)..(46)
<223> OTHER INFORMATION: randomised

<400> SEQUENCE: 82

```
gggcccagg ggagcccaac gatgatggcn nsnnsnnsnn snnsnnsgag gactgtgtgg      60
agatcttc                                                             68

<210> SEQ ID NO 83
<211> LENGTH: 56
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (21)..(22)
<223> OTHER INFORMATION: randomised
<220> FEATURE:
<221> NAME/KEY: misc_feature
<222> LOCATION: (24)..(25)
<223> OTHER INFORMATION: randomised
<220> FEATURE:
<221> NAME/KEY: misc_feature
<222> LOCATION: (27)..(28)
<223> OTHER INFORMATION: randomised
<220> FEATURE:
<221> NAME/KEY: misc_feature
<222> LOCATION: (30)..(31)
<223> OTHER INFORMATION: randomised
<220> FEATURE:
<221> NAME/KEY: misc_feature
<222> LOCATION: (33)..(34)
<223> OTHER INFORMATION: randomised

<400> SEQUENCE: 83 gggcccagg ggagcccaac nnsnnsnnsn nsnnsgagga ctgtgtggag atcttc         56

<210> SEQ ID NO 84
<211> LENGTH: 77
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (21)..(22)
<223> OTHER INFORMATION: randomised
<220> FEATURE:
<221> NAME/KEY: misc_feature
<222> LOCATION: (24)..(25)
<223> OTHER INFORMATION: randomised
<220> FEATURE:
<221> NAME/KEY: misc_feature
<222> LOCATION: (27)..(28)
<223> OTHER INFORMATION: randomised
<220> FEATURE:
<221> NAME/KEY: misc_feature
<222> LOCATION: (30)..(31)
<223> OTHER INFORMATION: randomised
<220> FEATURE:
<221> NAME/KEY: misc_feature
<222> LOCATION: (33)..(34)
<223> OTHER INFORMATION: randomised
<220> FEATURE:
<221> NAME/KEY: misc_feature
<222> LOCATION: (36)..(37)
<223> OTHER INFORMATION: randomised

<400> SEQUENCE: 84
gcatcgccta caagaactgg nnsnnsnnsn nsnnsnnsca acccgatggc ggcaagaccg    60
agaactgcgc ggtcctg                                                   77

<210> SEQ ID NO 85
<211> LENGTH: 83
<212> TYPE: DNA
```

```
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (24)..(25)
<223> OTHER INFORMATION: randomised
<220> FEATURE:
<221> NAME/KEY: misc_feature
<222> LOCATION: (27)..(28)
<223> OTHER INFORMATION: randomised
<220> FEATURE:
<221> NAME/KEY: misc_feature
<222> LOCATION: (30)..(31)
<223> OTHER INFORMATION: randomised
<220> FEATURE:
<221> NAME/KEY: misc_feature
<222> LOCATION: (33)..(34)
<223> OTHER INFORMATION: randomised
<220> FEATURE:
<221> NAME/KEY: misc_feature
<222> LOCATION: (36)..(37)
<223> OTHER INFORMATION: randomised
<220> FEATURE:
<221> NAME/KEY: misc_feature
<222> LOCATION: (39)..(40)
<223> OTHER INFORMATION: randomised

<400> SEQUENCE: 85
gcatcgccta caagaactgg gagnnsnnsn nsnnsnnsnn sgcgcaaccc gatggcggca      60
agaccgagaa ctgcgcggtc ctg                                             83

<210> SEQ ID NO 86
<211> LENGTH: 80
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (24)..(25)
<223> OTHER INFORMATION: randomised
<220> FEATURE:
<221> NAME/KEY: misc_feature
<222> LOCATION: (27)..(28)
<223> OTHER INFORMATION: randomised
<220> FEATURE:
<221> NAME/KEY: misc_feature
<222> LOCATION: (30)..(31)
<223> OTHER INFORMATION: randomised
<220> FEATURE:
<221> NAME/KEY: misc_feature
<222> LOCATION: (33)..(34)
<223> OTHER INFORMATION: randomised
<220> FEATURE:
<221> NAME/KEY: misc_feature
<222> LOCATION: (36)..(37)
<223> OTHER INFORMATION: randomised

<400> SEQUENCE: 86
gcatcgccta caagaactgg gagnnsnnsn nsnnsnnsgc gcaacccgat ggcggcaaga      60
ccgagaactg cgcggtcctg                                                 80

<210> SEQ ID NO 87
<211> LENGTH: 75
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
```

<222> LOCATION: (38)..(39)
<223> OTHER INFORMATION: randomised
<220> FEATURE:
<221> NAME/KEY: misc_feature
<222> LOCATION: (41)..(42)
<223> OTHER INFORMATION: randomised
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised
<220> FEATURE:
<221> NAME/KEY: misc_feature
<222> LOCATION: (50)..(51)
<223> OTHER INFORMATION: randomised
<220> FEATURE:
<221> NAME/KEY: misc_feature
<222> LOCATION: (53)..(54)
<223> OTHER INFORMATION: randomised
<220> FEATURE:
<221> NAME/KEY: misc_feature
<222> LOCATION: (56)..(57)
<223> OTHER INFORMATION: randomised

<400> SEQUENCE: 87
gtagggcaat tgatcgctgc agcgcttgtc gaaccasnns nnsnnsnnsn nsnnsnncag    60
gaccgcgcag ttctc                                                    75

<210> SEQ ID NO 88
<211> LENGTH: 84
<212> TYPE: DNA
<213> ORGANISM: Artificial
<220> FEATURE:
<223> OTHER INFORMATION: Description of Artificial Sequence:
      oligonucleotide
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised
<220> FEATURE:
<221> NAME/KEY: misc_feature
<222> LOCATION: (50)..(51)
<223> OTHER INFORMATION: randomised
<220> FEATURE:
<221> NAME/KEY: misc_feature
<222> LOCATION: (53)..(54)
<223> OTHER INFORMATION: randomised
<220> FEATURE:
<221> NAME/KEY: misc_feature
<222> LOCATION: (56)..(57)
<223> OTHER INFORMATION: randomised
<220> FEATURE:
<221> NAME/KEY: misc_feature
<222> LOCATION: (59)..(60)
<223> OTHER INFORMATION: randomised

<400> SEQUENCE: 88
gtagggcaat tgatcgctgc agcgcttgtc gaaccacttg ccsnnsnnsn nsnnsnnsnn    60
gcctgacagg accgcgcagt tctc                                          84

<210> SEQ ID NO 89
<211> LENGTH: 81
<212> TYPE: DNA
<213> ORGANISM: Artificial
<220> FEATURE:
<223> OTHER INFORMATION: Description of Artificial Sequence:
      oligonucleotide

```
<220> FEATURE:
<221> NAME/KEY: misc_feature
<222> LOCATION: (44)..(45)
<223> OTHER INFORMATION: randomised
<220> FEATURE:
<221> NAME/KEY: misc_feature
<222> LOCATION: (47)..(48)
<223> OTHER INFORMATION: randomised
<220> FEATURE:
<221> NAME/KEY: misc_feature
<222> LOCATION: (50)..(51)
<223> OTHER INFORMATION: randomised
<220> FEATURE:
<221> NAME/KEY: misc_feature
<222> LOCATION: (53)..(54)
<223> OTHER INFORMATION: randomised
<220> FEATURE:
<221> NAME/KEY: misc_feature
<222> LOCATION: (56)..(57)
<223> OTHER INFORMATION: randomised

<400> SEQUENCE: 89
gtagggcaat tgatcgctgc agcgcttgtc gaaccacttg ccsnnsnnsn nsnnsnngcc    60
tgacaggacc gcgcagttct c                                             81

<210> SEQ ID NO 90
<211> LENGTH: 20
<212> TYPE: DNA
<213> ORGANISM: Artificial
<220> FEATURE:
<223> OTHER INFORMATION: Description of Artificial Sequence:
      oligonucleotide

<400> SEQUENCE: 90
gtagggcaat tgatcgctgc                                               20

<210> SEQ ID NO 91
<211> LENGTH: 34
<212> TYPE: DNA
<213> ORGANISM: Artificial
<220> FEATURE:
<223> OTHER INFORMATION: Description of Artificial Sequence:
      oligonucleotide

<400> SEQUENCE: 91
catgaccggt acccgcatcg cctacaagaa ctgg                               34

<210> SEQ ID NO 92
<211> LENGTH: 53
<212> TYPE: PRT
<213> ORGANISM: Homo sapiens

<400> SEQUENCE: 92

Trp Ile Gly Leu Arg Trp Gln Gly Lys Val Lys Gln Cys Asn Ser Glu
1               5                   10                  15

Trp Ser Asp Gly Ser Ser Val Ser Tyr Glu Asn Trp Ile Glu Ala Glu
            20                  25                  30

Ser Lys Thr Cys Leu Gly Leu Glu Lys Glu Thr Asp Phe Arg Lys Trp
        35                  40                  45

Val Asn Ile Tyr Cys
    50

<210> SEQ ID NO 93
<211> LENGTH: 59
<212> TYPE: PRT
<213> ORGANISM: Homo sapiens

<400> SEQUENCE: 93
```

```
Trp Ile Gly Leu Thr Asp Gln Asn Gly Pro Trp Arg Trp Val Asp Gly
1               5                   10                  15

Thr Asp Phe Glu Lys Gly Phe Lys Asn Trp Ala Pro Leu Gln Pro Asp
            20                  25                  30

Asn Trp Phe Gly His Gly Leu Gly Gly Gly Asp Cys Ala His Ile
                35                  40                  45

Thr Thr Gly Gly Phe Trp Asn Asp Asp Val Cys
        50                  55
```

<210> SEQ ID NO 94
<211> LENGTH: 56
<212> TYPE: PRT
<213> ORGANISM: Homo sapiens

<400> SEQUENCE: 94

```
Trp Ile Gly Leu His Asp Pro Lys Lys Asn Arg Arg Trp His Trp Ser
1               5                   10                  15

Ser Gly Ser Leu Val Ser Tyr Lys Ser Trp Gly Ile Gly Ala Pro Ser
            20                  25                  30

Ser Val Asn Pro Gly Tyr Cys Val Ser Leu Thr Ser Ser Thr Gly Phe
                35                  40                  45

Gln Lys Trp Lys Asp Val Pro Cys
        50                  55
```

<210> SEQ ID NO 95
<211> LENGTH: 56
<212> TYPE: PRT
<213> ORGANISM: Homo sapiens

<400> SEQUENCE: 95

```
Trp Ile Gly Leu Thr Asp Glu Asn Gln Glu Gly Glu Trp Gln Trp Val
1               5                   10                  15

Asp Gly Thr Asp Thr Arg Ser Ser Phe Thr Phe Trp Lys Glu Gly Glu
            20                  25                  30

Pro Asn Asn Arg Gly Phe Asn Glu Asp Cys Ala His Val Trp Thr Ser
                35                  40                  45

Gly Gln Trp Asn Asp Val Tyr Cys
        50                  55
```

<210> SEQ ID NO 96
<211> LENGTH: 54
<212> TYPE: PRT
<213> ORGANISM: Homo sapiens

<400> SEQUENCE: 96

```
Trp Ile Gly Leu Arg Asn Leu Asp Leu Lys Gly Glu Phe Ile Trp Val
1               5                   10                  15

Asp Gly Ser His Val Asp Tyr Ser Asn Trp Ala Pro Gly Glu Pro Thr
            20                  25                  30

Ser Arg Ser Gln Gly Glu Asp Cys Val Met Met Arg Gly Ser Gly Arg
                35                  40                  45

Trp Asn Asp Ala Phe Cys
        50
```

<210> SEQ ID NO 97
<211> LENGTH: 60
<212> TYPE: PRT
<213> ORGANISM: Homo sapiens

<400> SEQUENCE: 97

Trp Ile Gly Leu Thr Asp Lys Asp Ser Glu Gly Thr Trp Lys Trp Val
1               5                   10                  15

Asp Gly Thr Pro Leu Thr Thr Ala Phe Trp Ser Thr Asp Glu Pro Asn
                20                  25                  30

Asp Gly Ala Val Asn Gly Glu Asp Cys Val Ser Leu Tyr Tyr His Thr
            35                  40                  45

Gln Pro Glu Phe Lys Asn Trp Asn Asp Leu Ala Cys
        50                  55                  60

<210> SEQ ID NO 98
<211> LENGTH: 59
<212> TYPE: PRT
<213> ORGANISM: Homo sapiens

<400> SEQUENCE: 98

Trp Ile Gly Leu Thr Asp Gln Gly Thr Glu Gly Asn Trp Arg Trp Val
1               5                   10                  15

Asp Gly Thr Pro Phe Asp Tyr Val Gln Ser Arg Arg Phe Trp Arg Lys
                20                  25                  30

Gly Gln Pro Asp Trp Arg His Gly Asn Gly Glu Arg Glu Asp Cys Val
            35                  40                  45

His Leu Gln Arg Met Trp Asn Asp Met Ala Cys
        50                  55

<210> SEQ ID NO 99
<211> LENGTH: 49
<212> TYPE: PRT
<213> ORGANISM: Homo sapiens

<400> SEQUENCE: 99

Trp Ile Gly Leu Ser Tyr Ser Glu Glu His Thr Ala Trp Leu Trp Glu
1               5                   10                  15

Asn Gly Ser Ala Leu Ser Gln Tyr Leu Ser Phe Glu Thr Phe Asn Thr
                20                  25                  30

Lys Asn Cys Ile Ala Tyr Asn Pro Asn Gly Asn Ala Leu Asp Glu Ser
            35                  40                  45

Cys

<210> SEQ ID NO 100
<211> LENGTH: 57
<212> TYPE: PRT
<213> ORGANISM: Homo sapiens

<400> SEQUENCE: 100

Trp Ile Gly Leu Asn Asp Arg Thr Ile Glu Gly Asp Phe Arg Trp Ser
1               5                   10                  15

Asp Gly His Pro Met Gln Phe Glu Asn Trp Arg Pro Asn Gln Pro Asp
                20                  25                  30

Asn Phe Phe Ala Ala Gly Glu Asp Cys Val Val Met Ile Trp His Glu
            35                  40                  45

Lys Gly Glu Trp Asn Asp Val Pro Cys
        50                  55

<210> SEQ ID NO 101
<211> LENGTH: 61
<212> TYPE: PRT
<213> ORGANISM: Homo sapiens

<400> SEQUENCE: 101

```
Trp Ile Gly Leu His Asp Pro Thr Gln Gly Thr Glu Pro Asn Gly Glu
1               5                   10                  15

Gly Trp Glu Trp Ser Ser Ser Asp Val Met Asn Tyr Phe Ala Trp Glu
            20                  25                  30

Arg Asn Pro Ser Thr Ile Ser Ser Pro Gly His Cys Ala Ser Leu Ser
            35                  40                  45

Arg Ser Thr Ala Phe Leu Arg Trp Lys Asp Tyr Asn Cys
50                  55                  60
```

<210> SEQ ID NO 102
<211> LENGTH: 57
<212> TYPE: PRT
<213> ORGANISM: Homo sapiens

<400> SEQUENCE: 102

```
Trp Ile Gly Leu Asn Asp Arg Ile Val Glu Gln Asp Phe Gln Trp Thr
1               5                   10                  15

Asp Asn Thr Gly Leu Gln Tyr Glu Asn Trp Arg Glu Asn Gln Pro Asp
            20                  25                  30

Asn Phe Phe Ala Gly Gly Glu Asp Cys Val Val Leu Val Ser His Glu
            35                  40                  45

Ile Gly Lys Trp Asn Asp Val Pro Cys
50                  55
```

<210> SEQ ID NO 103
<211> LENGTH: 60
<212> TYPE: PRT
<213> ORGANISM: Homo sapiens

<400> SEQUENCE: 103

```
Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Arg Gln Lys Asp Glu Asp Cys Val Glu Ile Tyr Ile Lys Arg
            35                  40                  45

Glu Lys Asp Val Gly Met Trp Asn Asp Glu Arg Cys
50                  55                  60
```

<210> SEQ ID NO 104
<211> LENGTH: 48
<212> TYPE: PRT
<213> ORGANISM: Homo sapiens

<400> SEQUENCE: 104

```
Trp Ile Gly Val Phe Arg Asn Ser Ser His His Pro Trp Val Thr Met
1               5                   10                  15

Asn Gly Leu Ala Phe Lys His Glu Ile Lys Asp Ser Asp Asn Ala Glu
            20                  25                  30

Leu Asn Cys Ala Val Leu Gln Val Asn Arg Leu Lys Ser Ala Gln Cys
            35                  40                  45
```

<210> SEQ ID NO 105
<211> LENGTH: 55
<212> TYPE: PRT
<213> ORGANISM: Homo sapiens

<400> SEQUENCE: 105

```
Trp Met Gly Leu Ser Asp Leu Asn Gln Glu Gly Thr Trp Gln Trp Val
1               5                   10                  15
```

Asp Gly Ser Pro Leu Leu Pro Ser Phe Lys Gln Tyr Trp Asn Arg Gly
            20                  25                  30

Glu Pro Asn Asn Val Gly Glu Asp Cys Ala Glu Phe Ser Gly Asn
                35                  40                  45

Gly Trp Asn Asp Asp Lys Cys
 50                  55

<210> SEQ ID NO 106
<211> LENGTH: 52
<212> TYPE: PRT
<213> ORGANISM: Homo sapiens

<400> SEQUENCE: 106

Trp Ile Gly Leu Phe Arg Asn Val Glu Gly Thr Trp Leu Trp Ile Asn
 1               5                  10                  15

Asn Ser Pro Val Ser Phe Val Asn Trp Asn Thr Gly Asp Pro Ser Gly
                20                  25                  30

Glu Arg Asn Asp Cys Val Ala Leu His Ala Ser Ser Gly Phe Trp Ser
                35                  40                  45

Asn Ile His Cys
 50

<210> SEQ ID NO 107
<211> LENGTH: 58
<212> TYPE: PRT
<213> ORGANISM: Homo sapiens

<400> SEQUENCE: 107

Trp Leu Gly Leu Asn Asp Met Ala Ala Glu Gly Thr Trp Val Asp Met
 1               5                  10                  15

Thr Gly Ala Arg Ile Ala Tyr Lys Asn Trp Glu Thr Glu Ile Thr Ala
                20                  25                  30

Gln Pro Asp Gly Gly Lys Thr Glu Asn Cys Ala Val Leu Ser Gly Ala
                35                  40                  45

Ala Asn Gly Lys Trp Phe Asp Lys Arg Cys
 50                  55

<210> SEQ ID NO 108
<211> LENGTH: 73
<212> TYPE: PRT
<213> ORGANISM: Homo sapiens

<400> SEQUENCE: 108

Trp Leu Gly Val His Asp Arg Arg Ala Glu Gly Leu Tyr Leu Phe Glu
 1               5                  10                  15

Asn Gly Gln Arg Val Ser Phe Phe Ala Trp His Arg Ser Pro Arg Pro
                20                  25                  30

Glu Leu Gly Ala Gln Pro Ser Ala Ser Pro His Pro Leu Ser Pro Asp
                35                  40                  45

Gln Pro Asn Gly Gly Thr Leu Glu Asn Cys Val Ala Gln Ala Ser Asp
 50                  55                  60

Asp Gly Ser Trp Trp Asp His Asp Cys
 65                  70

<210> SEQ ID NO 109
<211> LENGTH: 57
<212> TYPE: PRT
<213> ORGANISM: Homo sapiens

<400> SEQUENCE: 109

```
Trp Leu Gly Ala Ser Asp Leu Asn Ile Glu Gly Arg Trp Leu Trp Glu
1               5                   10                  15

Gly Gln Arg Arg Met Asn Tyr Thr Asn Trp Ser Pro Gly Gln Pro Asp
            20                  25                  30

Asn Ala Gly Gly Ile Glu His Cys Leu Glu Leu Arg Arg Asp Leu Gly
            35                  40                  45

Asn Tyr Leu Trp Asn Asp Tyr Gln Cys
50                  55
```

<210> SEQ ID NO 110
<211> LENGTH: 59
<212> TYPE: PRT
<213> ORGANISM: Homo sapiens

<400> SEQUENCE: 110

```
Trp Met Gly Leu His Asp Gln Asn Gly Pro Trp Lys Trp Val Asp Gly
1               5                   10                  15

Thr Asp Tyr Glu Thr Gly Phe Lys Asn Trp Arg Pro Glu Gln Pro Asp
            20                  25                  30

Asp Trp Tyr Gly His Gly Leu Gly Gly Glu Asp Cys Ala His Phe
            35                  40                  45

Thr Asp Asp Gly Arg Trp Asn Asp Asp Val Cys
50                  55
```

<210> SEQ ID NO 111
<211> LENGTH: 47
<212> TYPE: PRT
<213> ORGANISM: Homo sapiens

<400> SEQUENCE: 111

```
Trp Met Gly Leu Ser Asn Val Trp Asn Gln Cys Asn Trp Gln Trp Ser
1               5                   10                  15

Asn Ala Ala Met Leu Arg Tyr Lys Ala Trp Ala Glu Glu Ser Tyr Cys
            20                  25                  30

Val Tyr Phe Lys Ser Thr Asn Asn Lys Trp Arg Ser Arg Ala Cys
            35                  40                  45
```

<210> SEQ ID NO 112
<211> LENGTH: 50
<212> TYPE: PRT
<213> ORGANISM: Homo sapiens

<400> SEQUENCE: 112

```
Trp Val Gly Leu Ser Tyr Asp Asn Lys Lys Asp Trp Ala Trp Ile
1               5                   10                  15

Asp Asn Arg Pro Ser Lys Leu Ala Leu Asn Thr Arg Lys Tyr Asn Ile
            20                  25                  30

Arg Asp Gly Gly Cys Met Leu Leu Ser Lys Thr Arg Leu Asp Asn Gly
            35                  40                  45

Asn Cys
50
```

<210> SEQ ID NO 113
<211> LENGTH: 58
<212> TYPE: PRT
<213> ORGANISM: Homo sapiens

<400> SEQUENCE: 113

```
Trp Val Gly Ala Asp Asn Leu Gln Asp Gly Ala Tyr Asn Phe Asn Trp
1               5                   10                  15
```

```
Asn Asp Gly Val Ser Leu Pro Thr Asp Ser Asp Leu Trp Ser Pro Asn
            20                  25                  30
Glu Pro Ser Asn Pro Gln Ser Trp Gln Leu Cys Val Gln Ile Trp Ser
            35                  40                  45
Lys Tyr Asn Leu Leu Asp Val Gly Cys
        50                  55
```

<210> SEQ ID NO 114
<211> LENGTH: 53
<212> TYPE: PRT
<213> ORGANISM: Homo sapiens

<400> SEQUENCE: 114

```
Tyr Leu Gly Met Ile Glu Asp Gln Thr Pro Gly Asp Phe His Tyr Leu
1               5                   10                  15
Asp Gly Ala Ser Val Asn Tyr Thr Asn Trp Tyr Pro Gly Glu Pro Arg
            20                  25                  30
Gly Gln Gly Lys Glu Lys Cys Val Glu Met Tyr Thr Asp Gly Thr Trp
            35                  40                  45
Asn Asp Arg Gly Cys
    50
```

<210> SEQ ID NO 115
<211> LENGTH: 56
<212> TYPE: PRT
<213> ORGANISM: Homo sapiens

<400> SEQUENCE: 115

```
Tyr Leu Ser Met Asn Asp Ile Ser Thr Glu Gly Arg Phe Thr Tyr Pro
1               5                   10                  15
Thr Gly Glu Ile Leu Val Tyr Ser Asn Trp Ala Asp Gly Glu Pro Asn
            20                  25                  30
Asn Ser Asp Glu Gly Gln Pro Glu Asn Cys Val Glu Ile Phe Pro Asp
            35                  40                  45
Gly Lys Trp Asn Asp Val Pro Cys
        50                  55
```

<210> SEQ ID NO 116
<211> LENGTH: 57
<212> TYPE: PRT
<213> ORGANISM: Homo sapiens

<400> SEQUENCE: 116

```
Tyr Leu Ser Met Asn Asp Ile Ser Lys Glu Gly Lys Phe Thr Tyr Pro
1               5                   10                  15
Thr Gly Gly Ser Leu Asp Tyr Ser Asn Trp Ala Pro Gly Glu Pro Asn
            20                  25                  30
Asn Arg Ala Lys Asp Glu Gly Pro Glu Asn Cys Leu Glu Ile Tyr Ser
            35                  40                  45
Asp Gly Asn Trp Asn Asp Ile Glu Cys
        50                  55
```

<210> SEQ ID NO 117
<211> LENGTH: 54
<212> TYPE: PRT
<213> ORGANISM: Homo sapiens

<400> SEQUENCE: 117

```
Phe Leu Gly Ile Thr Asp Glu Val Thr Glu Gly Gln Phe Met Tyr Val
1               5                   10                  15
```

```
Thr Gly Gly Arg Leu Thr Tyr Ser Asn Trp Lys Lys Asp Glu Pro Asn
            20                  25                  30

Asp His Gly Ser Gly Glu Asp Cys Val Thr Ile Val Asp Asn Gly Leu
            35                  40                  45

Trp Asn Asp Ile Ser Cys
 50

<210> SEQ ID NO 118
<211> LENGTH: 54
<212> TYPE: PRT
<213> ORGANISM: Homo sapiens

<400> SEQUENCE: 118

Phe Leu Ser Met Thr Asp Ser Lys Thr Glu Gly Lys Phe Thr Tyr Pro
 1               5                  10                  15

Thr Gly Glu Ser Leu Val Tyr Ser Asn Trp Ala Pro Gly Glu Pro Asn
            20                  25                  30

Asp Asp Gly Gly Ser Glu Asp Cys Val Glu Ile Phe Thr Asn Gly Lys
            35                  40                  45

Trp Asn Asp Arg Ala Cys
 50

<210> SEQ ID NO 119
<211> LENGTH: 55
<212> TYPE: PRT
<213> ORGANISM: Homo sapiens

<400> SEQUENCE: 119

Phe Ile Gly Val Asn Asp Leu Glu Arg Glu Gly Gln Tyr Met Phe Thr
 1               5                  10                  15

Asp Asn Thr Pro Leu Gln Asn Tyr Ser Asn Trp Asn Glu Gly Glu Pro
            20                  25                  30

Ser Asp Pro Tyr Gly His Glu Asp Cys Val Glu Met Leu Ser Ser Gly
            35                  40                  45

Arg Trp Asn Asp Thr Glu Cys
 50                  55

<210> SEQ ID NO 120
<211> LENGTH: 59
<212> TYPE: PRT
<213> ORGANISM: Homo sapiens

<400> SEQUENCE: 120

Phe Val Gly Leu Ser Asp Pro Glu Gly Gln Arg His Trp Gln Trp Val
 1               5                  10                  15

Asp Gln Thr Pro Tyr Asn Glu Ser Ser Thr Phe Trp His Pro Arg Glu
            20                  25                  30

Pro Ser Asp Pro Asn Glu Arg Cys Val Val Leu Asn Phe Arg Lys Ser
            35                  40                  45

Pro Lys Arg Trp Gly Trp Asn Asp Val Asn Cys
 50                  55

<210> SEQ ID NO 121
<211> LENGTH: 45
<212> TYPE: PRT
<213> ORGANISM: Homo sapiens

<400> SEQUENCE: 121

Trp Leu Gly Leu Asn Ala Met Ala Ala Glu Gly Thr Trp Val Asp Met
 1               5                  10                  15
```

Thr Gly Ala Arg Ile Ala Tyr Lys Asn Trp Glu Thr Glu Ile Thr Ala
            20                  25                  30

Gln Pro Asp Gly Gly Lys Thr Glu Asn Cys Ala Val Leu
        35                  40                  45

<210> SEQ ID NO 122
<211> LENGTH: 45
<212> TYPE: PRT
<213> ORGANISM: Homo sapiens

<400> SEQUENCE: 122

Trp Leu Gly Leu Asn Asp Met Ala Ala Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Thr Glu Asn Cys Ala Val Leu
        35                  40                  45

<210> SEQ ID NO 123
<211> LENGTH: 45
<212> TYPE: PRT
<213> ORGANISM: Homo sapiens

<400> SEQUENCE: 123

Trp Leu Gly Leu Asn Asp Met Ala Ala Glu Gly Thr Trp Val Asp Met
1               5                   10                  15

Thr Gly Ala Arg Ile Ala Tyr Ala Asn Trp Glu Thr Glu Ile Thr Ala
            20                  25                  30

Gln Pro Asp Gly Gly Lys Thr Glu Asn Cys Ala Val Leu
        35                  40                  45

<210> SEQ ID NO 124
<211> LENGTH: 45
<212> TYPE: PRT
<213> ORGANISM: Homo sapiens

<400> SEQUENCE: 124

Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ala Thr Ala
            20                  25                  30

Gln Pro Asp Gly Gly Lys Thr Glu Asn Cys Ala Val Leu
        35                  40                  45

<210> SEQ ID NO 125
<211> LENGTH: 45
<212> TYPE: PRT
<213> ORGANISM: Homo sapiens

<400> SEQUENCE: 125

Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Ala Pro Asp Gly Gly Lys Thr Glu Asn Cys Ala Val Leu
        35                  40                  45

<210> SEQ ID NO 126
<211> LENGTH: 45
<212> TYPE: PRT
<213> ORGANISM: Homo sapiens

<400> SEQUENCE: 126

Trp Leu Gly Leu Asn Asp Met Ala Ala Glu Gly Thr Trp Val Asp Met
1               5                  10                  15

Thr Gly Ala Arg Ile Ala Tyr Lys Asn Trp Glu Thr Glu Ile Thr Ala
            20                  25                  30

Gln Pro Ala Gly Gly Lys Thr Glu Asn Cys Ala Val Leu
        35                  40                  45

<210> SEQ ID NO 127
<211> LENGTH: 45
<212> TYPE: PRT
<213> ORGANISM: Homo sapiens

<400> SEQUENCE: 127

Trp Leu Gly Leu Asn Asp Met Ala Ala Glu Gly Thr Trp Val Asp Met
1               5                  10                  15

Thr Gly Ala Arg Ile Ala Tyr Lys Asn Trp Glu Thr Glu Ile Thr Ala
            20                  25                  30

Gln Pro Asp Gly Gly Ala Thr Glu Asn Cys Ala Val Leu
        35                  40                  45

<210> SEQ ID NO 128
<211> LENGTH: 45
<212> TYPE: PRT
<213> ORGANISM: Homo sapiens

<400> SEQUENCE: 128

Trp Leu Gly Leu Asn Asp Met Ala Ala Glu Gly Thr Trp Val Asp Met
1               5                  10                  15

Thr Gly Ala Arg Ile Ala Tyr Lys Asn Trp Glu Thr Glu Ile Thr Ala
            20                  25                  30

Gln Pro Asp Gly Gly Met Thr Glu Asn Cys Ala Val Leu
        35                  40                  45

<210> SEQ ID NO 129
<211> LENGTH: 45
<212> TYPE: PRT
<213> ORGANISM: Homo sapiens

<400> SEQUENCE: 129

Trp Leu Gly Leu Asn Asp Met Ala Ala Glu Gly Thr Trp Val Asp Met
1               5                  10                  15

Thr Gly Ala Arg Ile Ala Tyr Lys Asn Trp Glu Thr Glu Ile Thr Ala
            20                  25                  30

Gln Pro Asp Gly Gly Arg Thr Glu Asn Cys Ala Val Leu
        35                  40                  45

<210> SEQ ID NO 130
<211> LENGTH: 45
<212> TYPE: PRT
<213> ORGANISM: Homo sapiens

<400> SEQUENCE: 130

Trp Leu Gly Leu Asn Asp Met Ala Ala Glu Gly Thr Trp Val Asp Met
1               5                  10                  15

Thr Gly Ala Arg Ile Ala Tyr Lys Asn Trp Glu Thr Glu Ile Thr Ala
            20                  25                  30

Gln Pro Asp Gly Gly Lys Phe Glu Asn Cys Ala Val Leu
        35                  40                  45

```
<210> SEQ ID NO 131
<211> LENGTH: 45
<212> TYPE: PRT
<213> ORGANISM: Homo sapiens

<400> SEQUENCE: 131

Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Met Glu Asn Cys Ala Val Leu
        35                  40                  45

<210> SEQ ID NO 132
<211> LENGTH: 45
<212> TYPE: PRT
<213> ORGANISM: Homo sapiens

<400> SEQUENCE: 132

Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Arg Glu Asn Cys Ala Val Leu
        35                  40                  45

<210> SEQ ID NO 133
<211> LENGTH: 45
<212> TYPE: PRT
<213> ORGANISM: Homo sapiens

<400> SEQUENCE: 133

Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Tyr Glu Asn Cys Ala Val Leu
        35                  40                  45

<210> SEQ ID NO 134
<211> LENGTH: 45
<212> TYPE: PRT
<213> ORGANISM: Homo sapiens

<400> SEQUENCE: 134

Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Thr Ala Asn Cys Ala Val Leu
        35                  40                  45

<210> SEQ ID NO 135
<211> LENGTH: 45
<212> TYPE: PRT
<213> ORGANISM: Homo sapiens

<400> SEQUENCE: 135

Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30
```

```
Gln Pro Asp Gly Gly Lys Thr Asp Asn Cys Ala Val Leu
        35                  40                  45
```

<210> SEQ ID NO 136
<211> LENGTH: 45
<212> TYPE: PRT
<213> ORGANISM: Homo sapiens

<400> SEQUENCE: 136

```
Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Thr Gln Asn Cys Ala Val Leu
        35                  40                  45
```

<210> SEQ ID NO 137
<211> LENGTH: 45
<212> TYPE: PRT
<213> ORGANISM: Homo sapiens

<400> SEQUENCE: 137

```
Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Thr Glu Ala Cys Ala Val Leu
        35                  40                  45
```

<210> SEQ ID NO 138
<211> LENGTH: 45
<212> TYPE: PRT
<213> ORGANISM: Homo sapiens

<400> SEQUENCE: 138

```
Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Arg Tyr Glu Asn Cys Ala Val Leu
        35                  40                  45
```

<210> SEQ ID NO 139
<211> LENGTH: 45
<212> TYPE: PRT
<213> ORGANISM: Homo sapiens

<400> SEQUENCE: 139

```
Trp Leu Gly Leu Asn Asp Met Ala Ala Glu Gly Thr Trp Val Asp Met
1               5                   10                  15

Thr Gly Ala Arg Ile Ala Tyr Lys Asn Trp Glu Thr Glu Ile Thr Ala
            20                  25                  30

Gln Pro Asp Gly Gly Lys Tyr Gln Asn Cys Ala Val Leu
        35                  40                  45
```

<210> SEQ ID NO 140
<211> LENGTH: 45
<212> TYPE: PRT
<213> ORGANISM: Homo sapiens

<400> SEQUENCE: 140

```
Trp Leu Gly Leu Asn Asp Met Ala Ala Glu Gly Thr Trp Val Asp Met
1               5                   10                  15

Thr Gly Ala Arg Ile Ala Tyr Lys Asn Trp Thr Glu Ile Thr Ala
            20                  25                  30

Gln Pro Asp Gly Gly Lys Tyr Glu Asn Cys Ala Val Leu
        35                  40                  45

<210> SEQ ID NO 141
<211> LENGTH: 43
<212> TYPE: PRT
<213> ORGANISM: Ratus sp.

<400> SEQUENCE: 141

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp His Gly Ser Gly Glu Asp Cys Val Thr Ile
        35                  40

<210> SEQ ID NO 142
<211> LENGTH: 43
<212> TYPE: PRT
<213> ORGANISM: Ratus sp.

<400> SEQUENCE: 142

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Glu Pro Asp
            20                  25                  30

Asp His Gly Ser Gly Glu Asp Cys Val Thr Ile
        35                  40

<210> SEQ ID NO 143
<211> LENGTH: 43
<212> TYPE: PRT
<213> ORGANISM: Ratus sp.

<400> SEQUENCE: 143

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Glu Pro Asn
            20                  25                  30

Asp Ala Gly Ser Gly Glu Asp Cys Val Thr Ile
        35                  40

<210> SEQ ID NO 144
<211> LENGTH: 43
<212> TYPE: PRT
<213> ORGANISM: Ratus sp.

<400> SEQUENCE: 144

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Glu Pro Asn
            20                  25                  30

Asp Gly Gly Ser Gly Glu Asp Cys Val Thr Ile
        35                  40

<210> SEQ ID NO 145
<211> LENGTH: 43
```

```
<212> TYPE: PRT
<213> ORGANISM: Ratus sp.

<400> SEQUENCE: 145

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
                20                  25                  30

Asp Trp Gly Ser Gly Glu Asp Cys Val Thr Ile
            35                  40

<210> SEQ ID NO 146
<211> LENGTH: 48
<212> TYPE: PRT
<213> ORGANISM: Ratus sp.

<400> SEQUENCE: 146

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
                20                  25                  30

Asp Trp Tyr Gly His Gly Leu Gly Gly Glu Asp Cys Val Thr Ile
            35                  40                  45

<210> SEQ ID NO 147
<211> LENGTH: 48
<212> TYPE: PRT
<213> ORGANISM: Ratus sp.

<400> SEQUENCE: 147

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
                20                  25                  30

Asp Trp Ala Gly His Gly Leu Gly Gly Glu Asp Cys Val Thr Ile
            35                  40                  45

<210> SEQ ID NO 148
<211> LENGTH: 48
<212> TYPE: PRT
<213> ORGANISM: Ratus sp.

<400> SEQUENCE: 148

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
                20                  25                  30

Asp Trp Gln Gly His Gly Leu Gly Gly Glu Asp Cys Val Thr Ile
            35                  40                  45

<210> SEQ ID NO 149
<211> LENGTH: 48
<212> TYPE: PRT
<213> ORGANISM: Ratus sp.

<400> SEQUENCE: 149

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
                20                  25                  30

Asp Trp Tyr Ala His Gly Leu Gly Gly Gly Glu Asp Cys Val Thr Ile
```

```
                35                  40                  45
```

<210> SEQ ID NO 150
<211> LENGTH: 48
<212> TYPE: PRT
<213> ORGANISM: Ratus sp.

<400> SEQUENCE: 150

```
Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp Trp Tyr Gly Ala Gly Leu Gly Gly Gly Glu Asp Cys Val Thr Ile
        35                  40                  45
```

<210> SEQ ID NO 151
<211> LENGTH: 48
<212> TYPE: PRT
<213> ORGANISM: Ratus sp.

<400> SEQUENCE: 151

```
Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp Trp Tyr Gly Gln Gly Leu Gly Gly Gly Glu Asp Cys Val Thr Ile
        35                  40                  45
```

<210> SEQ ID NO 152
<211> LENGTH: 48
<212> TYPE: PRT
<213> ORGANISM: Ratus sp.

<400> SEQUENCE: 152

```
Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp Trp Tyr Gly Glu Gly Leu Gly Gly Gly Glu Asp Cys Val Thr Ile
        35                  40                  45
```

<210> SEQ ID NO 153
<211> LENGTH: 48
<212> TYPE: PRT
<213> ORGANISM: Ratus sp.

<400> SEQUENCE: 153

```
Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp Trp Tyr Gly Tyr Gly Leu Gly Gly Gly Glu Asp Cys Val Thr Ile
        35                  40                  45
```

<210> SEQ ID NO 154
<211> LENGTH: 47
<212> TYPE: PRT
<213> ORGANISM: Ratus sp.

<400> SEQUENCE: 154

```
Phe Leu Gly Ile Thr Asp Glu Val Thr Glu Gly Gln Phe Met Tyr Val
1               5                   10                  15
```

Thr Gly Gly Arg Leu Thr Tyr Ser Asn Trp Lys Lys Asp Gln Pro Asp
            20                  25                  30

Asp Trp Tyr Gly His Gly Leu Gly Gly Glu Asp Cys Val Thr Ile
            35                  40                  45

<210> SEQ ID NO 155
<211> LENGTH: 43
<212> TYPE: PRT
<213> ORGANISM: Ratus sp.

<400> SEQUENCE: 155

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp Phe Gly Ser Gly Glu Asp Cys Val Thr Ile
            35                  40

<210> SEQ ID NO 156
<211> LENGTH: 48
<212> TYPE: PRT
<213> ORGANISM: Ratus sp.

<400> SEQUENCE: 156

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp Phe Tyr Gly His Gly Leu Gly Gly Gly Glu Asp Cys Val Thr Ile
            35                  40                  45

<210> SEQ ID NO 157
<211> LENGTH: 41
<212> TYPE: PRT
<213> ORGANISM: Ratus sp.

<400> SEQUENCE: 157

Phe Leu Gly Ile Arg Lys Val Asn Asn Val Phe Met Tyr Val Thr Gly
1               5                   10                  15

Gly Arg Leu Thr Tyr Ser Asn Trp Lys Lys Asp Glu Pro Asn Asp His
            20                  25                  30

Gly Ser Gly Glu Asp Cys Val Thr Ile
            35                  40

<210> SEQ ID NO 158
<211> LENGTH: 43
<212> TYPE: PRT
<213> ORGANISM: Ratus sp.

<400> SEQUENCE: 158

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Glu Pro Asn
            20                  25                  30

Asn Arg Gln Lys Asp Glu Asp Cys Val Thr Ile
            35                  40

<210> SEQ ID NO 159
<211> LENGTH: 43
<212> TYPE: PRT
<213> ORGANISM: Ratus sp.

```
<400> SEQUENCE: 159

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Glu Pro Asn
            20                  25                  30

Asp Gly Gly Ser Gly Glu Asp Cys Val Thr Ile
        35                  40

<210> SEQ ID NO 160
<211> LENGTH: 43
<212> TYPE: PRT
<213> ORGANISM: Ratus sp.

<400> SEQUENCE: 160

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Glu Pro Asn
            20                  25                  30

Asp His Gly Ser Gly Glu Asp Cys Val Glu Ile
        35                  40

<210> SEQ ID NO 161
<211> LENGTH: 43
<212> TYPE: PRT
<213> ORGANISM: Ratus sp.

<400> SEQUENCE: 161

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Ala Pro Gly Glu Pro Asn
            20                  25                  30

Asp His Gly Ser Gly Glu Asp Cys Val Thr Ile
        35                  40

<210> SEQ ID NO 162
<211> LENGTH: 43
<212> TYPE: PRT
<213> ORGANISM: Ratus sp.

<400> SEQUENCE: 162

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Ala Asp Asn Glu Pro Asn
            20                  25                  30

Asp His Gly Ser Gly Glu Asp Cys Val Thr Ile
        35                  40

<210> SEQ ID NO 163
<211> LENGTH: 48
<212> TYPE: PRT
<213> ORGANISM: Ratus sp.

<400> SEQUENCE: 163

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Lys Asp Gln Pro Asp
            20                  25                  30

Asp Trp Tyr Gly His Gly Leu Gly Gly Gly Glu Asp Cys Val His Ile
        35                  40                  45
```

```
<210> SEQ ID NO 164
<211> LENGTH: 48
<212> TYPE: PRT
<213> ORGANISM: Ratus sp.

<400> SEQUENCE: 164

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Arg Pro Gly Gln Pro Asp
            20                  25                  30

Asp Trp Tyr Gly His Gly Leu Gly Gly Glu Asp Cys Val His Ile
        35                  40                  45

<210> SEQ ID NO 165
<211> LENGTH: 46
<212> TYPE: PRT
<213> ORGANISM: Ratus sp.

<400> SEQUENCE: 165

Phe Leu Gly Ile Thr Asp Gln Asn Gly Gln Phe Met Tyr Val Thr Gly
1               5                   10                  15

Gly Arg Leu Thr Tyr Ser Asn Trp Lys Lys Asp Gln Pro Asp Asp Trp
            20                  25                  30

Tyr Gly His Gly Leu Gly Gly Gly Glu Asp Cys Val Thr Ile
        35                  40                  45

<210> SEQ ID NO 166
<211> LENGTH: 46
<212> TYPE: PRT
<213> ORGANISM: Ratus sp.

<400> SEQUENCE: 166

Phe Leu Gly Ile Thr Asp Gln Asn Gly Pro Phe Met Tyr Val Thr Gly
1               5                   10                  15

Gly Arg Leu Thr Tyr Ser Asn Trp Lys Lys Asp Gln Pro Asp Asp Trp
            20                  25                  30

Tyr Gly His Gly Leu Gly Gly Glu Asp Cys Val Thr Ile
        35                  40                  45

<210> SEQ ID NO 167
<211> LENGTH: 43
<212> TYPE: PRT
<213> ORGANISM: Ratus sp.

<400> SEQUENCE: 167

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Glu Gly Glu Pro Asn
            20                  25                  30

Asn Arg Gly Ser Gly Glu Asp Cys Val Thr Ile
        35                  40

<210> SEQ ID NO 168
<211> LENGTH: 43
<212> TYPE: PRT
<213> ORGANISM: Ratus sp.

<400> SEQUENCE: 168

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Glu Gly Glu Pro Asn
```

```
                    20                  25                  30

Asn Arg Gly Phe Asn Glu Asp Cys Val Thr Ile
            35                  40

<210> SEQ ID NO 169
<211> LENGTH: 43
<212> TYPE: PRT
<213> ORGANISM: Ratus sp.

<400> SEQUENCE: 169

Phe Leu Gly Ile Thr Asp Glu Val Thr Glu Gly Gln Phe Met Tyr Val
1               5                   10                  15

Thr Gly Gly Arg Leu Thr Tyr Ser Asn Trp Lys Glu Gly Glu Pro Asn
            20                  25                  30

Asn Arg Gly Phe Asn Glu Asp Cys Ala His Val
            35                  40

<210> SEQ ID NO 170
<211> LENGTH: 42
<212> TYPE: PRT
<213> ORGANISM: Ratus sp.

<400> SEQUENCE: 170

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Gln Pro Asp
            20                  25                  30

Gly Gln Gly Lys Glu Lys Cys Val Glu Met
            35                  40

<210> SEQ ID NO 171
<211> LENGTH: 42
<212> TYPE: PRT
<213> ORGANISM: Ratus sp.

<400> SEQUENCE: 171

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Arg
            20                  25                  30

Gly Gln Gly Lys Glu Lys Cys Val Thr Ile
            35                  40

<210> SEQ ID NO 172
<211> LENGTH: 43
<212> TYPE: PRT
<213> ORGANISM: Ratus sp.

<400> SEQUENCE: 172

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Asn
            20                  25                  30

Asp His Gly Ser Gly Glu Asp Cys Val Thr Ile
            35                  40

<210> SEQ ID NO 173
<211> LENGTH: 42
<212> TYPE: PRT
<213> ORGANISM: Ratus sp.

<400> SEQUENCE: 173
```

```
Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Ala Pro Arg
            20                  25                  30

Gly Gln Gly Lys Glu Lys Cys Val Glu Met
            35                  40
```

<210> SEQ ID NO 174
<211> LENGTH: 42
<212> TYPE: PRT
<213> ORGANISM: Ratus sp.

<400> SEQUENCE: 174

```
Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Gly
            20                  25                  30

Gly Gln Gly Lys Glu Lys Cys Val Glu Met
            35                  40
```

<210> SEQ ID NO 175
<211> LENGTH: 42
<212> TYPE: PRT
<213> ORGANISM: Ratus sp.

<400> SEQUENCE: 175

```
Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Arg
            20                  25                  30

Gly Gln Gly Lys Ala Lys Cys Val Glu Met
            35                  40
```

<210> SEQ ID NO 176
<211> LENGTH: 42
<212> TYPE: PRT
<213> ORGANISM: Ratus sp.

<400> SEQUENCE: 176

```
Tyr Leu Gly Met Ile Glu Asp Gln Thr Pro Gly Asp Phe His Tyr Leu
1               5                   10                  15

Asp Gly Ala Ser Val Ser Tyr Thr Asn Trp Tyr Pro Gly Glu Pro Arg
            20                  25                  30

Gly Gln Gly Lys Glu Lys Cys Val Glu Met
            35                  40
```

<210> SEQ ID NO 177
<211> LENGTH: 42
<212> TYPE: PRT
<213> ORGANISM: Ratus sp.

<400> SEQUENCE: 177

```
Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Ala
            20                  25                  30

Gly Gln Gly Lys Glu Lys Cys Val Glu Met
            35                  40
```

<210> SEQ ID NO 178

```
<211> LENGTH: 42
<212> TYPE: PRT
<213> ORGANISM: Ratus sp.

<400> SEQUENCE: 178

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Lys
            20                  25                  30

Gly Gln Gly Lys Glu Lys Cys Val Glu Met
        35                  40

<210> SEQ ID NO 179
<211> LENGTH: 42
<212> TYPE: PRT
<213> ORGANISM: Ratus sp.

<400> SEQUENCE: 179

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro His
            20                  25                  30

Gly Gln Gly Lys Glu Lys Cys Val Glu Met
        35                  40

<210> SEQ ID NO 180
<211> LENGTH: 42
<212> TYPE: PRT
<213> ORGANISM: Ratus sp.

<400> SEQUENCE: 180

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Asp
            20                  25                  30

Gly Gln Gly Lys Glu Lys Cys Val Glu Met
        35                  40

<210> SEQ ID NO 181
<211> LENGTH: 42
<212> TYPE: PRT
<213> ORGANISM: Ratus sp.

<400> SEQUENCE: 181

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Asn
            20                  25                  30

Gly Gln Gly Lys Glu Lys Cys Val Glu Met
        35                  40

<210> SEQ ID NO 182
<211> LENGTH: 42
<212> TYPE: PRT
<213> ORGANISM: Ratus sp.

<400> SEQUENCE: 182

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Gln Pro Arg
            20                  25                  30
```

Gly Gln Gly Lys Glu Lys Cys Val Glu Met
            35                  40

<210> SEQ ID NO 183
<211> LENGTH: 42
<212> TYPE: PRT
<213> ORGANISM: Ratus sp.

<400> SEQUENCE: 183

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Arg
            20                  25                  30

Gly Gln Gly Ala Glu Lys Cys Val Glu Met
            35                  40

<210> SEQ ID NO 184
<211> LENGTH: 42
<212> TYPE: PRT
<213> ORGANISM: Ratus sp.

<400> SEQUENCE: 184

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Arg
            20                  25                  30

Gly Gln Gly Lys Glu Ala Cys Val Glu Met
            35                  40

<210> SEQ ID NO 185
<211> LENGTH: 42
<212> TYPE: PRT
<213> ORGANISM: Ratus sp.

<400> SEQUENCE: 185

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Ala Pro Arg
            20                  25                  30

Gly Gln Gly Ala Glu Ala Cys Val Glu Met
            35                  40

<210> SEQ ID NO 186
<211> LENGTH: 43
<212> TYPE: PRT
<213> ORGANISM: Ratus sp.

<400> SEQUENCE: 186

Tyr Leu Gly Met Ile Glu Asp Gln Thr Pro Gly Asp Phe His Tyr Leu
1               5                   10                  15

Asp Gly Ala Ser Val Asn Tyr Thr Asn Trp Tyr Pro Gly Glu Pro Asn
            20                  25                  30

Asn Asn Gly Gly Ala Glu Asn Cys Val Glu Ile
            35                  40

<210> SEQ ID NO 187
<211> LENGTH: 43
<212> TYPE: PRT
<213> ORGANISM: Ratus sp.

<400> SEQUENCE: 187

Tyr Leu Gly Met Ile Glu Asp Gln Thr Glu Gly Lys Phe Thr Tyr Pro

```
                1               5                  10                 15
Thr Gly Glu Ala Leu Val Tyr Ser Asn Trp Ala Pro Gly Glu Pro Asn
            20                  25                 30

Asn Asn Gly Gly Ala Glu Asn Cys Val Glu Ile
            35                  40

<210> SEQ ID NO 188
<211> LENGTH: 42
<212> TYPE: PRT
<213> ORGANISM: Ratus sp.

<400> SEQUENCE: 188

Tyr Leu Gly Met Ile Glu Asp Gln Thr Glu Gly Gln Phe Met Tyr Val
1               5                   10                  15

Thr Gly Gly Arg Leu Thr Tyr Ser Asn Trp Lys Lys Asp Glu Pro Arg
            20                  25                  30

Gly Gln Gly Lys Glu Lys Cys Val Glu Met
            35                  40

<210> SEQ ID NO 189
<211> LENGTH: 42
<212> TYPE: PRT
<213> ORGANISM: Homo sapiens

<400> SEQUENCE: 189

Tyr Val Gly Leu Thr Glu Gly Pro Ser Pro Gly Asp Phe Arg Tyr Ser
1               5                   10                  15

Asp Gly Thr Pro Val Asn Tyr Thr Asn Trp Tyr Arg Gly Glu Pro Ala
            20                  25                  30

Gly Ala Gly Lys Glu Gln Cys Val Glu Met
            35                  40

<210> SEQ ID NO 190
<211> LENGTH: 42
<212> TYPE: PRT
<213> ORGANISM: Homo sapiens

<400> SEQUENCE: 190

Tyr Val Gly Leu Thr Glu Gly Pro Ser Pro Gly Asp Phe Arg Tyr Ser
1               5                   10                  15

Asp Gly Thr Pro Val Asn Tyr Thr Asn Trp Tyr Arg Gly Glu Pro Ala
            20                  25                  30

Gly Arg Gly Ala Glu Gln Cys Val Glu Met
            35                  40

<210> SEQ ID NO 191
<211> LENGTH: 42
<212> TYPE: PRT
<213> ORGANISM: Homo sapiens

<400> SEQUENCE: 191

Tyr Val Gly Leu Thr Glu Gly Pro Thr Glu Gly Gln Phe Met Tyr Val
1               5                   10                  15

Thr Gly Gly Arg Leu Thr Tyr Ser Asn Trp Lys Lys Asp Glu Pro Arg
            20                  25                  30

Gly Arg Gly Lys Glu Gln Cys Val Glu Met
            35                  40

<210> SEQ ID NO 192
<211> LENGTH: 43
<212> TYPE: PRT
```

<213> ORGANISM: Homo sapiens

<400> SEQUENCE: 192

Phe Leu Ser Met Thr Asp Val Gly Thr Glu Gly Lys Phe Thr Tyr Pro
1               5                   10                  15

Thr Gly Glu Ala Leu Val Tyr Ser Asn Trp Ala Pro Gly Gln Pro Asp
            20                  25                  30

Asn Asn Gly Gly Ala Glu Asn Cys Val Glu Ile
            35                  40

<210> SEQ ID NO 193
<211> LENGTH: 44
<212> TYPE: PRT
<213> ORGANISM: Homo sapiens

<400> SEQUENCE: 193

Trp Ile Gly Ile Arg Lys Val Asn Asn Val Trp Val Trp Val Gly Thr
1               5                   10                  15

Gln Ala Pro Leu Thr Glu Glu Ala Lys Asn Trp Ala Pro Gly Glu Pro
            20                  25                  30

Asn Asn Arg Gln Lys Asp Glu Asp Cys Val Glu Ile
            35                  40

<210> SEQ ID NO 194
<211> LENGTH: 44
<212> TYPE: PRT
<213> ORGANISM: Homo sapiens

<400> SEQUENCE: 194

Trp Ile Gly Ile Arg Lys Val Asn Asn Val Trp Val Trp Val Gly Thr
1               5                   10                  15

Gln Lys Pro Leu Thr Glu Glu Ala Ala Asn Trp Ala Pro Gly Glu Pro
            20                  25                  30

Asn Asn Arg Gln Lys Asp Glu Asp Cys Val Glu Ile
            35                  40

<210> SEQ ID NO 195
<211> LENGTH: 44
<212> TYPE: PRT
<213> ORGANISM: Homo sapiens

<400> SEQUENCE: 195

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Ala Gln Ala Asp Glu Asp Cys Val Glu Ile
            35                  40

<210> SEQ ID NO 196
<211> LENGTH: 44
<212> TYPE: PRT
<213> ORGANISM: Homo sapiens

<400> SEQUENCE: 196

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Ala Gln Lys Asp Glu Asp Cys Val Glu Ile
            35                  40

<210> SEQ ID NO 197
<211> LENGTH: 44
<212> TYPE: PRT
<213> ORGANISM: Homo sapiens

<400> SEQUENCE: 197

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Lys Gln Lys Asp Glu Asp Cys Val Glu Ile
            35                  40

<210> SEQ ID NO 198
<211> LENGTH: 44
<212> TYPE: PRT
<213> ORGANISM: Homo sapiens

<400> SEQUENCE: 198

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Lys Gln Lys Asp Glu Gly Cys Val Glu Ile
            35                  40

<210> SEQ ID NO 199
<211> LENGTH: 44
<212> TYPE: PRT
<213> ORGANISM: Homo sapiens

<400> SEQUENCE: 199

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Lys Pro Gly Glu Pro
            20                  25                  30

Asn Asn Arg Gln Lys Asp Glu Asp Cys Val Glu Ile
            35                  40

<210> SEQ ID NO 200
<211> LENGTH: 44
<212> TYPE: PRT
<213> ORGANISM: Homo sapiens

<400> SEQUENCE: 200

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Lys Lys Gly Glu Pro
            20                  25                  30

Asn Asn Arg Gln Lys Asp Glu Asp Cys Val Glu Ile
            35                  40

<210> SEQ ID NO 201
<211> LENGTH: 44
<212> TYPE: PRT
<213> ORGANISM: Homo sapiens

<400> SEQUENCE: 201

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Lys Gly Pro
            20                  25                  30

Asn Asn Ala Gln Lys Asp Glu Asp Cys Val Glu Ile
            35                  40

<210> SEQ ID NO 202
<211> LENGTH: 44
<212> TYPE: PRT
<213> ORGANISM: Homo sapiens

<400> SEQUENCE: 202

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Arg Gln Lys Glu Glu Asp Cys Val Glu Ile
            35                  40

<210> SEQ ID NO 203
<211> LENGTH: 44
<212> TYPE: PRT
<213> ORGANISM: Homo sapiens

<400> SEQUENCE: 203

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Arg Gln Lys Asn Glu Asp Cys Val Glu Ile
            35                  40

<210> SEQ ID NO 204
<211> LENGTH: 44
<212> TYPE: PRT
<213> ORGANISM: Homo sapiens

<400> SEQUENCE: 204

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Arg Gln Lys Asp Glu Asn Cys Val Glu Ile
            35                  40

<210> SEQ ID NO 205
<211> LENGTH: 44
<212> TYPE: PRT
<213> ORGANISM: Homo sapiens

<400> SEQUENCE: 205

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Ala Pro Gly Glu Pro
            20                  25                  30

Asn Asn Arg Gln Lys Asp Glu Glu Cys Val Glu Ile
            35                  40

<210> SEQ ID NO 206
<211> LENGTH: 44
<212> TYPE: PRT
<213> ORGANISM: Homo sapiens -continued

<400> SEQUENCE: 206

Trp Ile Gly Ile Arg Lys Val Asn Asn Val Trp Val Trp Val Gly Thr
1               5                   10                  15

Gln Lys Pro Leu Thr Glu Glu Ala Lys Asn Trp Lys Pro Gly Gln Pro
            20                  25                  30

Asp Asn Arg Gln Lys Asp Glu Asp Cys Val Glu Ile
        35                  40

<210> SEQ ID NO 207
<211> LENGTH: 44
<212> TYPE: PRT
<213> ORGANISM: Homo sapiens

<400> SEQUENCE: 207

Trp Ile Gly Ile Arg Lys Asn Asn Lys Thr Trp Thr Trp Val Gly Thr
1               5                   10                  15

Lys Lys Ala Leu Thr Asn Glu Ala Glu Asn Trp Lys Asp Asn Glu Pro
            20                  25                  30

Asn Asn Lys Arg Asn Asn Glu Asp Cys Val Glu Ile
        35                  40

<210> SEQ ID NO 208
<211> LENGTH: 44
<212> TYPE: PRT
<213> ORGANISM: Homo sapiens

<400> SEQUENCE: 208

Trp Ile Gly Ile Arg Lys Asn Asn Lys Thr Thr Thr Trp Val Gly Thr
1               5                   10                  15

Lys Lys Ala Leu Thr Asn Glu Ala Glu Asn Trp Lys Asp Asn Gln Pro
            20                  25                  30

Asp Asn Lys Arg Asn Asn Glu Asp Cys Val Glu Ile
        35                  40

<210> SEQ ID NO 209
<211> LENGTH: 48
<212> TYPE: PRT
<213> ORGANISM: Homo sapiens

<400> SEQUENCE: 209

Trp Ile Gly Leu Thr Asp Gln Asn Gly Pro Trp Arg Trp Val Asp Gly
1               5                   10                  15

Thr Asp Tyr Glu Lys Gly Phe Thr His Trp Arg Pro Lys Gln Pro Asp
            20                  25                  30

Asn Trp Tyr Gly His Gly Leu Gly Gly Gly Glu Asp Cys Ala His Phe
        35                  40                  45

<210> SEQ ID NO 210
<211> LENGTH: 48
<212> TYPE: PRT
<213> ORGANISM: Homo sapiens

<400> SEQUENCE: 210

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Gly Gln Pro Asp
            20                  25                  30

Asn Trp Tyr Gly His Gly Leu Gly Gly Gly Glu Asp Cys Ala His Phe
        35                  40                  45

-continued

<210> SEQ ID NO 211
<211> LENGTH: 48
<212> TYPE: PRT
<213> ORGANISM: Homo sapiens

<400> SEQUENCE: 211

Trp Ile Gly Leu Thr Asp Gln Asn Gly Pro Trp Arg Trp Val Asp Gly
1               5                   10                  15

Thr Asp Tyr Glu Lys Gly Phe Thr His Trp Arg Pro Gly Gln Pro Asp
            20                  25                  30

Asn Trp Tyr Gly His Gly Leu Gly Gly Gly Glu Asp Cys Ala His Phe
        35                  40                  45

<210> SEQ ID NO 212
<211> LENGTH: 48
<212> TYPE: PRT
<213> ORGANISM: Homo sapiens

<400> SEQUENCE: 212

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Gly Glu Asp Cys Ala His Ile
        35                  40                  45

<210> SEQ ID NO 213
<211> LENGTH: 48
<212> TYPE: PRT
<213> ORGANISM: Homo sapiens

<400> SEQUENCE: 213

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Gly Glu Asp Cys Ala Ala Phe
        35                  40                  45

<210> SEQ ID NO 214
<211> LENGTH: 48
<212> TYPE: PRT
<213> ORGANISM: Homo sapiens

<400> SEQUENCE: 214

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Gly Glu Asp Cys Ala Glu Phe
        35                  40                  45

<210> SEQ ID NO 215
<211> LENGTH: 48
<212> TYPE: PRT
<213> ORGANISM: Homo sapiens

<400> SEQUENCE: 215

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Glu Asp Cys Ala Gln Phe
        35                  40                  45

<210> SEQ ID NO 216
<211> LENGTH: 48
<212> TYPE: PRT
<213> ORGANISM: Homo sapiens

<400> SEQUENCE: 216

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Glu Asp Cys Ala Asn Phe
        35                  40                  45

<210> SEQ ID NO 217
<211> LENGTH: 48
<212> TYPE: PRT
<213> ORGANISM: Homo sapiens

<400> SEQUENCE: 217

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Glu Asp Cys Ala Tyr Phe
        35                  40                  45

<210> SEQ ID NO 218
<211> LENGTH: 48
<212> TYPE: PRT
<213> ORGANISM: Homo sapiens

<400> SEQUENCE: 218

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Glu Asp Cys Ala Asp Phe
        35                  40                  45

<210> SEQ ID NO 219
<211> LENGTH: 48
<212> TYPE: PRT
<213> ORGANISM: Homo sapiens

<400> SEQUENCE: 219

Trp Ile Gly Leu Thr Asp Gln Asn Gly Pro Trp Arg Trp Val Asp Gly
1               5                   10                  15

Thr Asp Tyr Glu Lys Gly Phe Thr His Trp Ala Pro Lys Gln Pro Asp
            20                  25                  30

Asn Trp Tyr Gly His Gly Leu Gly Gly Glu Asp Cys Ala Lys Phe
        35                  40                  45

<210> SEQ ID NO 220
<211> LENGTH: 48
<212> TYPE: PRT
<213> ORGANISM: PRT

<400> SEQUENCE: 220

Trp Ile Gly Leu Thr Asp Gln Asn Gly Pro Trp Arg Trp Val Asp Gly
1               5                   10                  15

Thr Asp Tyr Glu Lys Gly Phe Thr His Trp Arg Pro Gly Gln Pro Asp
                20                  25                  30

Asn Trp Tyr Gly His Gly Leu Gly Gly Glu Asp Cys Ala Ala Phe
            35                  40                  45

<210> SEQ ID NO 221
<211> LENGTH: 48
<212> TYPE: PRT
<213> ORGANISM: Rattus sp.

<400> SEQUENCE: 221

Trp Ile Gly Leu Thr Asp Gln Asn Gly Pro Trp Lys Trp Val Asp Gly
1               5                   10                  15

Thr Asp Tyr Glu Thr Gly Phe Lys Asn Trp Arg Pro Gly Gln Pro Asp
                20                  25                  30

Asp Trp Tyr Gly His Gly Leu Gly Gly Glu Asp Cys Ala Ala Phe
            35                  40                  45

<210> SEQ ID NO 222
<211> LENGTH: 45
<212> TYPE: PRT
<213> ORGANISM: Gallus sp.

<400> SEQUENCE: 222

Trp Ile Gly Leu Thr Asp Glu Asn Gln Glu Gly Glu Trp Gln Trp Val
1               5                   10                  15

Asp Gly Thr Asp Thr Arg Ser Ser Phe Thr Phe Trp Lys Glu Gly Glu
                20                  25                  30

Pro Asn Asn Ala Gly Phe Asn Glu Asp Cys Ala His Val
            35                  40                  45

<210> SEQ ID NO 223
<211> LENGTH: 45
<212> TYPE: PRT
<213> ORGANISM: Gallus sp.

<400> SEQUENCE: 223

Trp Ile Gly Leu Thr Asp Glu Asn Gln Glu Gly Glu Trp Gln Trp Val
1               5                   10                  15

Asp Gly Thr Asp Thr Arg Ser Ser Phe Thr Phe Trp Lys Glu Gly Glu
                20                  25                  30

Pro Asn Asn Arg Ala Phe Asn Glu Asp Cys Ala His Val
            35                  40                  45

<210> SEQ ID NO 224
<211> LENGTH: 45
<212> TYPE: PRT
<213> ORGANISM: Gallus sp.

<400> SEQUENCE: 224

Trp Ile Gly Leu Thr Asp Glu Asn Gln Glu Gly Glu Trp Gln Trp Val
1               5                   10                  15

Asp Gly Thr Asp Thr Arg Ser Ser Phe Thr Phe Trp Lys Glu Gly Glu
                20                  25                  30

Pro Asn Asn Arg Gly Ala Asn Glu Asp Cys Ala His Val
            35                  40                  45

<210> SEQ ID NO 225
<211> LENGTH: 45

```
<212> TYPE: PRT
<213> ORGANISM: Gallus sp.

<400> SEQUENCE: 225

Trp Ile Gly Leu Thr Asp Glu Asn Gln Glu Gly Glu Trp Gln Trp Val
1               5                   10                  15

Asp Gly Thr Asp Thr Arg Ser Ser Phe Thr Phe Trp Lys Glu Gly Glu
                20                  25                  30

Pro Asn Asn Arg Gly Phe Ala Glu Asp Cys Ala His Val
            35                  40                  45

<210> SEQ ID NO 226
<211> LENGTH: 17
<212> TYPE: PRT
<213> ORGANISM: Homo sapiens

<400> SEQUENCE: 226

Cys Ala Val Leu Ser Gly Ala Ala Asn Gly Ala Trp Phe Asp Lys Arg
1               5                   10                  15

Cys

<210> SEQ ID NO 227
<211> LENGTH: 17
<212> TYPE: PRT
<213> ORGANISM: Homo sapiens

<400> SEQUENCE: 227

Cys Ala Val Leu Ser Gly Ala Ala Asn Gly Lys Trp Phe Asp Ala Arg
1               5                   10                  15

Cys

<210> SEQ ID NO 228
<211> LENGTH: 17
<212> TYPE: PRT
<213> ORGANISM: Homo sapiens

<400> SEQUENCE: 228

Cys Ala Val Leu Ser Gly Ala Ala Asn Gly Lys Trp Phe Asp Lys Ala
1               5                   10                  15

Cys

<210> SEQ ID NO 229
<211> LENGTH: 17
<212> TYPE: PRT
<213> ORGANISM: Homo sapiens

<400> SEQUENCE: 229

Cys Ala Val Leu Ser Gly Ala Ala Asn Gly Lys Trp Leu Asp Lys Arg
1               5                   10                  15

Cys

<210> SEQ ID NO 230
<211> LENGTH: 17
<212> TYPE: PRT
<213> ORGANISM: Homo sapiens

<400> SEQUENCE: 230

Cys Ala Val Leu Ser Gly Ala Ala Asn Gly Lys Trp Phe Ala Lys Arg
1               5                   10                  15

Cys
```

```
<210> SEQ ID NO 231
<211> LENGTH: 17
<212> TYPE: PRT
<213> ORGANISM: Homo sapiens

<400> SEQUENCE: 231

Cys Ala Val Leu Ser Gly Ala Ala Asn Gly Lys Trp Phe Glu Lys Arg
1               5                   10                  15

Cys

<210> SEQ ID NO 232
<211> LENGTH: 17
<212> TYPE: PRT
<213> ORGANISM: Homo sapiens

<400> SEQUENCE: 232

Cys Ala Val Leu Ser Gly Ala Ala Asn Gly Lys Trp Phe Asn Lys Arg
1               5                   10                  15

Cys

<210> SEQ ID NO 233
<211> LENGTH: 15
<212> TYPE: PRT
<213> ORGANISM: Rattus sp.

<400> SEQUENCE: 233

Cys Val Thr Ile Val Asp Asn Gly Leu Trp Asn Asp Val Ser Cys
1               5                   10                  15

<210> SEQ ID NO 234
<211> LENGTH: 15
<212> TYPE: PRT
<213> ORGANISM: Rattus sp.

<400> SEQUENCE: 234

Cys Val Thr Ile Val Asp Asn Gly Leu Trp Asn Asp Leu Ser Cys
1               5                   10                  15

<210> SEQ ID NO 235
<211> LENGTH: 15
<212> TYPE: PRT
<213> ORGANISM: Rattus sp.

<400> SEQUENCE: 235

Cys Val Thr Ile Val Asp Asn Gly Leu Trp Asn Asp Ala Ser Cys
1               5                   10                  15

<210> SEQ ID NO 236
<211> LENGTH: 15
<212> TYPE: PRT
<213> ORGANISM: Rattus sp.

<400> SEQUENCE: 236

Cys Val Thr Ile Val Asp Asn Gly Leu Trp Asn Asp Glu Ser Cys
1               5                   10                  15

<210> SEQ ID NO 237
<211> LENGTH: 21
<212> TYPE: PRT
<213> ORGANISM: Rattus sp.

<400> SEQUENCE: 237

Cys Val Thr Ile Val Tyr Ile Lys Arg Glu Lys Asp Asn Gly Leu Trp
1               5                   10                  15
```

```
Asn Asp Ile Ser Cys
            20

<210> SEQ ID NO 238
<211> LENGTH: 21
<212> TYPE: PRT
<213> ORGANISM: Rattus sp.

<400> SEQUENCE: 238

Cys Val Thr Ile Val Tyr Ile Lys Ser Pro Ser Asp Asn Gly Leu Trp
1               5                   10                  15

Asn Asp Ile Ser Cys
            20

<210> SEQ ID NO 239
<211> LENGTH: 15
<212> TYPE: PRT
<213> ORGANISM: Rattus sp.

<400> SEQUENCE: 239

Cys Val Thr Ile Val Asp Asn Gly Leu Trp Asn Asp Val Tyr Cys
1               5                   10                  15

<210> SEQ ID NO 240
<211> LENGTH: 15
<212> TYPE: PRT
<213> ORGANISM: Rattus sp.

<400> SEQUENCE: 240

Cys Ala His Val Trp Thr Ser Gly Gln Trp Asn Asp Val Tyr Cys
1               5                   10                  15

<210> SEQ ID NO 241
<211> LENGTH: 20
<212> TYPE: PRT
<213> ORGANISM: Homo sapiens

<400> SEQUENCE: 241

Cys Val Glu Ile Phe Ile Lys Arg Glu Lys Asp Val Gly Met Trp Asn
1               5                   10                  15

Asp Glu Arg Cys
            20

<210> SEQ ID NO 242
<211> LENGTH: 20
<212> TYPE: PRT
<213> ORGANISM: Homo sapiens

<400> SEQUENCE: 242

Cys Val Glu Ile Arg Ile Lys Arg Glu Lys Asp Val Gly Met Trp Asn
1               5                   10                  15

Asp Glu Arg Cys
            20

<210> SEQ ID NO 243
<211> LENGTH: 20
<212> TYPE: PRT
<213> ORGANISM: Homo sapiens

<400> SEQUENCE: 243

Cys Val Glu Ile Asp Ile Lys Arg Glu Lys Asp Val Gly Met Trp Asn
1               5                   10                  15

Asp Glu Arg Cys
            20
```

<210> SEQ ID NO 244
<211> LENGTH: 20
<212> TYPE: PRT
<213> ORGANISM: Homo sapiens

<400> SEQUENCE: 244

Cys Val Glu Ile Ala Ile Lys Arg Glu Lys Asp Val Gly Met Trp Asn
1               5                   10                  15

Asp Glu Arg Cys
            20

<210> SEQ ID NO 245
<211> LENGTH: 20
<212> TYPE: PRT
<213> ORGANISM: Homo sapiens

<400> SEQUENCE: 245

Cys Val Glu Ile Ser Ile Lys Arg Glu Lys Asp Val Gly Met Trp Asn
1               5                   10                  15

Asp Glu Arg Cys
            20

<210> SEQ ID NO 246
<211> LENGTH: 20
<212> TYPE: PRT
<213> ORGANISM: Homo sapiens

<400> SEQUENCE: 246

Cys Val Glu Ile Tyr Ile Lys Arg Glu Lys Asp Val Gly Met Trp Asn
1               5                   10                  15

Asp Asp Arg Cys
            20

<210> SEQ ID NO 247
<211> LENGTH: 20
<212> TYPE: PRT
<213> ORGANISM: Homo sapiens

<400> SEQUENCE: 247

Cys Val Glu Ile Tyr Ile Lys Arg Glu Lys Asp Val Gly Met Trp Asn
1               5                   10                  15

Asp Ala Arg Cys
            20

<210> SEQ ID NO 248
<211> LENGTH: 20
<212> TYPE: PRT
<213> ORGANISM: Homo sapiens

<400> SEQUENCE: 248

Cys Val Glu Ile Tyr Ile Lys Arg Glu Lys Asp Val Gly Met Trp Asn
1               5                   10                  15

Asp Asn Arg Cys
            20

<210> SEQ ID NO 249
<211> LENGTH: 20
<212> TYPE: PRT
<213> ORGANISM: Homo sapiens

<400> SEQUENCE: 249

Cys Val Glu Ile Tyr Ile Lys Arg Glu Lys Asp Val Gly Met Trp Asn

```
1               5                   10                  15

Asp Lys Arg Cys
            20

<210> SEQ ID NO 250
<211> LENGTH: 20
<212> TYPE: PRT
<213> ORGANISM: Homo sapiens

<400> SEQUENCE: 250

Cys Val Glu Ile Tyr Ile Lys Arg Glu Lys Asp Val Gly Met Trp Asn
1               5                   10                  15

Asp Gln Arg Cys
            20

<210> SEQ ID NO 251
<211> LENGTH: 20
<212> TYPE: PRT
<213> ORGANISM: Homo sapiens

<400> SEQUENCE: 251

Cys Val Glu Ile Tyr Ile Lys Asp Glu Lys Asp Val Gly Met Trp Asn
1               5                   10                  15

Asp Glu Arg Cys
            20

<210> SEQ ID NO 252
<211> LENGTH: 20
<212> TYPE: PRT
<213> ORGANISM: Homo sapiens

<400> SEQUENCE: 252

Cys Val Glu Ile Tyr Ile Lys Ser Glu Lys Asp Val Gly Met Trp Asn
1               5                   10                  15

Asp Glu Arg Cys
            20

<210> SEQ ID NO 253
<211> LENGTH: 20
<212> TYPE: PRT
<213> ORGANISM: Homo sapiens

<400> SEQUENCE: 253

Cys Val Glu Ile Tyr Ile Lys Glu Glu Lys Asp Val Gly Met Trp Asn
1               5                   10                  15

Asp Glu Arg Cys
            20

<210> SEQ ID NO 254
<211> LENGTH: 20
<212> TYPE: PRT
<213> ORGANISM: Homo sapiens

<400> SEQUENCE: 254

Cys Val Glu Ile Tyr Ile Gln Ser Pro Ser Ala Pro Gly Met Trp Asn
1               5                   10                  15

Asp Glu His Cys
            20

<210> SEQ ID NO 255
<211> LENGTH: 20
<212> TYPE: PRT
```

<400> SEQUENCE: 255

Cys Val Glu Ile Tyr Ile Arg Ser Pro Ser Ala Pro Gly Met Trp Asn
1               5                   10                  15

Asp Glu His Cys
            20

<210> SEQ ID NO 256
<211> LENGTH: 20
<212> TYPE: PRT
<213> ORGANISM: Homo sapiens

<400> SEQUENCE: 256

Cys Val Glu Ile Tyr Ile Glu Ser Pro Ser Ala Pro Gly Met Trp Asn
1               5                   10                  15

Asp Glu His Cys
            20

<210> SEQ ID NO 257
<211> LENGTH: 20
<212> TYPE: PRT
<213> ORGANISM: Homo sapiens

<400> SEQUENCE: 257

Cys Val Glu Ile Tyr Ile Lys Ala Pro Ser Ala Pro Gly Met Trp Asn
1               5                   10                  15

Asp Glu His Cys
            20

<210> SEQ ID NO 258
<211> LENGTH: 20
<212> TYPE: PRT
<213> ORGANISM: Homo sapiens

<400> SEQUENCE: 258

Cys Val Glu Ile Tyr Ile Lys Asp Pro Ser Ala Pro Gly Met Trp Asn
1               5                   10                  15

Asp Glu His Cys
            20

<210> SEQ ID NO 259
<211> LENGTH: 20
<212> TYPE: PRT
<213> ORGANISM: Homo sapiens

<400> SEQUENCE: 259

Cys Val Glu Ile Tyr Ile Lys Arg Pro Ser Ala Pro Gly Met Trp Asn
1               5                   10                  15

Asp Glu His Cys
            20

<210> SEQ ID NO 260
<211> LENGTH: 20
<212> TYPE: PRT
<213> ORGANISM: Homo sapiens

<400> SEQUENCE: 260

Cys Val Glu Ile Tyr Ile Lys Arg Glu Lys Ala Pro Gly Met Trp Asn
1               5                   10                  15

Asp Glu His Cys
            20

<210> SEQ ID NO 261
<211> LENGTH: 20
<212> TYPE: PRT
<213> ORGANISM: Homo sapiens

<400> SEQUENCE: 261

Cys Val Glu Ile Tyr Ile Lys Ser Pro Asp Ala Pro Gly Met Trp Asn
1               5                   10                  15

Asp Glu His Cys
            20

<210> SEQ ID NO 262
<211> LENGTH: 15
<212> TYPE: PRT
<213> ORGANISM: Gallus sp.

<400> SEQUENCE: 262

Cys Ala His Val Trp Thr Ser Gly Gln Trp Asn Asp Ala Tyr Cys
1               5                   10                  15

<210> SEQ ID NO 263
<211> LENGTH: 15
<212> TYPE: PRT
<213> ORGANISM: Gallus sp.

<400> SEQUENCE: 263

Cys Ala His Val Trp Thr Ser Gly Gln Trp Asn Asp Val Ala Cys
1               5                   10                  15

<210> SEQ ID NO 264
<211> LENGTH: 16
<212> TYPE: PRT
<213> ORGANISM: Homo sapiens

<400> SEQUENCE: 264

Ser Gly Ala Ala Asn Gly Lys Trp Phe Asp Lys Arg Cys Ala Asp Gln
1               5                   10                  15

<210> SEQ ID NO 265
<211> LENGTH: 13
<212> TYPE: PRT
<213> ORGANISM: Homo sapiens

<400> SEQUENCE: 265

Cys Ile Ser Arg Gly Gly Thr Leu Gly Thr Pro Gln Thr
1               5                   10

<210> SEQ ID NO 266
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 266

Asn Asp Met Ala Ala Glu Gly Thr Trp Val Asp Met Thr Gly Thr Arg
1               5                   10                  15

Ile Ala Tyr Lys Asn Trp Glu Thr Glu Ile Thr Ala Gln Pro Asp Gly
            20                  25                  30

Gly Lys Thr Glu Asn Xaa Xaa Xaa Xaa Xaa Ser Gly Ala Ala Asn Gly
        35                  40                  45

Lys Trp Phe Asp
    50

<210> SEQ ID NO 267
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 267

Asn Asp Met Ala Ala Glu Gly Thr Trp Val Asp Met Thr Gly Thr Arg
1               5                   10                  15

Ile Ala Tyr Lys Asn Trp His Gly Trp Arg Thr Arg Gln Pro Asp Ala
            20                  25                  30

Asn Glu Gln Glu Asn Xaa Xaa Xaa Xaa Ser Gly Ala Ala Asn Gly
        35                  40                  45

Lys Trp Val Asp
    50

<210> SEQ ID NO 268
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 268

Asn Asp Met Ala Ala Glu Gly Thr Trp Val Asp Met Thr Gly Thr Arg
1               5                   10                  15

Ile Ala Tyr Lys Asn Trp Ile Gln Ser Glu Val Glu Gln Pro Asp Asp
            20                  25                  30

Trp Gln Thr Glu Asn Xaa Xaa Xaa Xaa Xaa Ser Gly Ala Ala Asn Gly
        35                  40                  45

Lys Trp Gly Asp
    50

<210> SEQ ID NO 269
<211> LENGTH: 51
<212> TYPE: PRT
<213> ORGANISM: Homo sapiens
<220> FEATURE:
<221> NAME/KEY: DOMAIN
<222> LOCATION: (37)..(41)
<223> OTHER INFORMATION: Beta3 sheet
<220> FEATURE:
<221> NAME/KEY: DOMAIN
<222> LOCATION: (38)..(42)
<223> OTHER INFORMATION: Beta3 sheet

<400> SEQUENCE: 269

Asn Asp Met Ala Ala Glu Gly Thr Trp Val Asp Met Thr Gly Thr Arg
1               5                   10                  15

Ile Ala Tyr Lys Asn Trp Ala Gly Gly Lys Trp Arg Pro Asp Gly Gly
            20                  25                  30

Leu Gly Glu Asn Xaa Xaa Xaa Xaa Xaa Ser Gly Ala Ala Asn Gly Lys
        35                  40                  45

Trp Lys Asp
    50

<210> SEQ ID NO 270
<211> LENGTH: 52

```
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 270

Asn Asp Met Ala Ala Glu Gly Thr Trp Val Asp Met Thr Gly Thr Arg
1               5                   10                  15

Ile Ala Tyr Lys Asn Trp Gln Arg Val Glu Cys Gly Gln Pro Asp Glu
            20                  25                  30

Ala Val Cys Glu Asn Xaa Xaa Xaa Xaa Ser Gly Ala Ala Asn Gly
        35                  40                  45

Lys Trp Asn Asp
    50

<210> SEQ ID NO 271
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 271

Asn Asp Ala Met Ser Glu Gly Arg Trp Val Asp Met Thr Gly Thr Arg
1               5                   10                  15

Ile Ala Tyr Lys Asn Trp Glu Thr Glu Ile Thr Ala Gln Pro Asp Pro
            20                  25                  30

Ile Cys Arg Glu Asn Xaa Xaa Xaa Xaa Xaa Ser Gly Ala Ala Asn Gly
        35                  40                  45

Lys Trp Phe Asp
    50

<210> SEQ ID NO 272
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 272

Asn Asp Glu Ala Trp Glu Thr Glu Trp Val Asp Met Thr Gly Thr Arg
1               5                   10                  15

Ile Ala Tyr Lys Asn Trp Glu Thr Glu Ile Thr Ala Gln Pro Asp Gln
            20                  25                  30

His Cys Ser Glu Asn Xaa Xaa Xaa Xaa Xaa Ser Gly Ala Ala Asn Gly
        35                  40                  45

Lys Trp Phe Asp
    50

<210> SEQ ID NO 273
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 273
```

```
Asn Asp Ala Gln Asp Glu Pro Arg Trp Val Asp Met Thr Gly Thr Arg
1               5                   10                  15

Ile Ala Tyr Lys Asn Trp Glu Thr Glu Ile Thr Ala Gln Pro Asp Ser
            20                  25                  30

Leu Leu Thr Glu Asn Xaa Xaa Xaa Xaa Ser Gly Ala Ala Asn Gly
                35                  40                  45

Lys Trp Phe Asp
    50

<210> SEQ ID NO 274
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 274

Asn Asp Lys Ala Arg Glu Lys Arg Trp Val Asp Met Thr Gly Thr Arg
1               5                   10                  15

Ile Ala Tyr Lys Asn Trp Glu Thr Glu Ile Thr Ala Gln Pro Asp Asp
            20                  25                  30

Pro Pro Pro Glu Asn Xaa Xaa Xaa Xaa Xaa Ser Gly Ala Ala Asn Gly
                35                  40                  45

Lys Trp Phe Asp
    50

<210> SEQ ID NO 275
<211> LENGTH: 52
<212> TYPE: PRT
<213> ORGANISM: Homo sapiens
<220> FEATURE:
<221> NAME/KEY: DOMAIN
<222> LOCATION: (38)..(42)
<223> OTHER INFORMATION: Beta3 sheet

<400> SEQUENCE: 275

Asn Asp Met Ala Ala Glu Arg Pro Trp Val Asp Met Thr Gly Thr Arg
1               5                   10                  15

Ile Ala Tyr Lys Asn Trp Glu Thr Glu Ile Thr Ala Gln Pro Asp Ile
            20                  25                  30

Ala Arg Gln Glu Asn Xaa Xaa Xaa Xaa Xaa Ser Gly Ala Ala Asn Gly
                35                  40                  45

Lys Trp Phe Asp
    50

<210> SEQ ID NO 276
<211> LENGTH: 137
<212> TYPE: PRT
<213> ORGANISM: Homo sapiens

<400> SEQUENCE: 276

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
                35                  40                  45

Asn Asp Ala Leu Tyr Glu Tyr Leu Arg Gln Ser Val Gly Asn Glu Ala
    50                  55                  60
```

Glu Ile Trp Leu Gly Leu Asn Asp Met Ala Ala Glu Gly Thr Trp Val
65                  70                  75                  80

Asp Met Thr Gly Ala Arg Ile Ala Tyr Lys Asn Trp Glu Thr Glu Ile
                85                  90                  95

Thr Ala Gln Pro Asp Gly Gly Lys Thr Glu Asn Cys Ala Val Leu Ser
            100                 105                 110

Gly Ala Ala Asn Gly Lys Trp Phe Asp Lys Arg Cys Arg Asp Gln Leu
        115                 120                 125

Pro Tyr Ile Cys Gln Phe Gly Ile Val
    130                 135

<210> SEQ ID NO 277
<211> LENGTH: 126
<212> TYPE: PRT
<213> ORGANISM: Homo sapiens

<400> SEQUENCE: 277

Asn Lys Leu His Ala Phe Ser Met Gly Lys Lys Ser Gly Lys Lys Phe
1               5                   10                  15

Phe Val Thr Asn His Glu Arg Met Pro Phe Ser Lys Val Lys Ala Leu
                20                  25                  30

Cys Ser Glu Leu Arg Gly Thr Val Ala Ile Pro Arg Asn Ala Glu Glu
            35                  40                  45

Asn Lys Ala Ile Gln Glu Val Ala Lys Thr Ser Ala Phe Leu Gly Ile
        50                  55                  60

Thr Asp Glu Val Thr Glu Gly Gln Phe Met Tyr Val Thr Gly Gly Arg
65                  70                  75                  80

Leu Thr Tyr Ser Asn Trp Lys Lys Asp Glu Pro Asn Asp His Gly Ser
                85                  90                  95

Gly Glu Asp Cys Val Thr Ile Val Asp Asn Gly Leu Trp Asn Asp Ile
            100                 105                 110

Ser Cys Gln Ala Ser His Thr Ala Val Cys Glu Phe Pro Ala
        115                 120                 125

<210> SEQ ID NO 278
<211> LENGTH: 127
<212> TYPE: PRT
<213> ORGANISM: Homo sapiens

<400> SEQUENCE: 278

Lys Lys Val Glu Leu Phe Pro Asn Gly Gln Ser Val Gly Glu Lys Ile
1               5                   10                  15

Phe Lys Thr Ala Gly Phe Val Lys Pro Phe Thr Glu Ala Gln Leu Leu
                20                  25                  30

Cys Thr Gln Ala Gly Gly Gln Leu Ala Ser Pro Arg Ser Ala Ala Glu
            35                  40                  45

Asn Ala Ala Leu Gln Gln Leu Val Val Ala Lys Asn Gly Ala Ala Phe
        50                  55                  60

Leu Ser Met Thr Asp Ser Lys Thr Glu Gly Lys Phe Thr Tyr Pro Thr
65                  70                  75                  80

Gly Glu Ser Leu Val Tyr Ser Asn Trp Ala Pro Gly Glu Pro Asn Asp
                85                  90                  95

Asp Gly Gly Ser Glu Asp Cys Val Glu Ile Phe Thr Asn Gly Lys Trp
            100                 105                 110

Asn Asp Arg Ala Cys Gly Glu Lys Arg Leu Val Val Cys Glu Phe
        115                 120                 125

<210> SEQ ID NO 279
<211> LENGTH: 124
<212> TYPE: PRT
<213> ORGANISM: Homo sapiens

<400> SEQUENCE: 279

Lys Val Tyr Trp Phe Cys Tyr Gly Met Lys Cys Tyr Tyr Phe Val Met
1               5                   10                  15

Asp Arg Lys Thr Trp Ser Gly Cys Lys Gln Thr Cys Gln Ser Ser Ser
            20                  25                  30

Leu Ser Leu Leu Lys Ile Asp Asp Glu Asp Glu Leu Lys Phe Leu Gln
        35                  40                  45

Leu Leu Val Val Lys Val Tyr Trp Phe Cys Tyr Gly Met Lys Cys Tyr
    50                  55                  60

Tyr Phe Val Met Asp Arg Lys Thr Trp Ser Gly Cys Lys Gln Thr Cys
65                  70                  75                  80

Gln Ser Ser Ser Leu Ser Leu Leu Lys Ile Asp Asp Glu Asp Glu Leu
                85                  90                  95

Lys Phe Leu Gln Leu Leu Val Val Asn Gly Asn Cys Asp Gln Val Phe
            100                 105                 110

Ile Cys Ile Cys Gly Lys Arg Leu Asp Lys Phe Pro
        115                 120

<210> SEQ ID NO 280
<211> LENGTH: 128
<212> TYPE: PRT
<213> ORGANISM: Homo sapiens

<400> SEQUENCE: 280

Cys Pro Val Asn Trp Val Glu His Glu Arg Ser Cys Tyr Trp Phe Ser
1               5                   10                  15

Arg Ser Gly Lys Ala Trp Ala Asp Ala Asp Asn Tyr Cys Arg Leu Glu
            20                  25                  30

Asp Ala His Leu Val Val Val Thr Ser Trp Glu Glu Gln Leu Phe Val
        35                  40                  45

Gln His His Ile Gly Pro Val Asn Thr Trp Met Gly Leu His Asp Gln
    50                  55                  60

Asn Gly Pro Trp Lys Trp Val Asp Gly Thr Asp Tyr Glu Thr Gly Phe
65                  70                  75                  80

Lys Asn Trp Arg Pro Glu Gln Pro Asp Trp Tyr Gly His Gly Leu
                85                  90                  95

Gly Gly Gly Glu Asp Cys Ala His Phe Thr Asp Asp Gly Arg Trp Asn
            100                 105                 110

Asp Asp Val Cys Gln Arg Pro Tyr Arg Trp Val Cys Glu Thr Glu Leu
        115                 120                 125

<210> SEQ ID NO 281
<211> LENGTH: 147
<212> TYPE: PRT
<213> ORGANISM: Homo sapiens

<400> SEQUENCE: 281

Gly Ile Pro Lys Cys Pro Glu Asp Trp Gly Ala Ser Ser Arg Thr Ser
1               5                   10                  15

Leu Cys Phe Lys Leu Tyr Ala Lys Gly Lys His Glu Lys Lys Thr Trp
            20                  25                  30

Phe Glu Ser Arg Asp Phe Cys Arg Ala Leu Gly Gly Asp Leu Ala Ser
        35                  40                  45

```
Ile Asn Asn Lys Glu Glu Gln Gln Thr Ile Trp Arg Leu Ile Thr Ala
     50                  55                  60

Ser Gly Ser Tyr His Lys Leu Phe Trp Leu Gly Leu Thr Tyr Gly Ser
 65                  70                  75                  80

Pro Ser Glu Gly Phe Thr Trp Ser Asp Gly Ser Pro Val Ser Tyr Glu
                 85                  90                  95

Asn Trp Ala Tyr Gly Glu Pro Asn Asn Tyr Gln Asn Val Glu Tyr Cys
                100                 105                 110

Gly Glu Leu Lys Gly Asp Pro Thr Met Ser Trp Asn Asp Ile Asn Cys
            115                 120                 125

Glu His Leu Asn Asn Trp Ile Cys Gln Ile Gln Lys Gly Gln Thr Pro
130                 135                 140

Lys Pro Asp
145

<210> SEQ ID NO 282
<211> LENGTH: 129
<212> TYPE: PRT
<213> ORGANISM: Homo sapiens

<400> SEQUENCE: 282

Asp Cys Leu Ser Gly Trp Ser Ser Tyr Glu Gly His Cys Tyr Lys Ala
 1               5                  10                  15

Phe Glu Lys Tyr Lys Thr Trp Glu Asp Ala Glu Arg Val Cys Thr Glu
                20                  25                  30

Gln Ala Lys Gly Ala His Leu Val Ser Ile Glu Ser Ser Gly Glu Ala
            35                  40                  45

Asp Phe Val Ala Gln Leu Val Thr Gln Asn Met Lys Arg Leu Asp Phe
 50                  55                  60

Tyr Ile Trp Ile Gly Leu Arg Val Gln Gly Lys Val Lys Gln Cys Asn
 65                  70                  75                  80

Ser Glu Trp Ser Asp Gly Ser Ser Val Ser Tyr Glu Asn Trp Ile Glu
                 85                  90                  95

Ala Glu Ser Lys Thr Cys Leu Gly Leu Glu Lys Glu Thr Asp Phe Arg
                100                 105                 110

Lys Trp Val Asn Ile Tyr Cys Gly Gln Gln Asn Pro Phe Val Cys Glu
            115                 120                 125

Ala

<210> SEQ ID NO 283
<211> LENGTH: 122
<212> TYPE: PRT
<213> ORGANISM: Homo sapiens

<400> SEQUENCE: 283

Asp Cys Pro Ser Asp Trp Ser Ser Tyr Glu Gly His Cys Tyr Lys Pro
 1               5                  10                  15

Phe Ser Glu Pro Lys Asn Trp Ala Asp Ala Glu Asn Phe Cys Thr Gln
                20                  25                  30

Gln His Ala Gly Gly His Leu Val Ser Phe Gln Ser Ser Glu Glu Ala
            35                  40                  45

Asp Phe Val Val Lys Leu Ala Phe Gln Thr Phe His Ser Ile Phe Trp
 50                  55                  60

Met Gly Leu Ser Asn Val Trp Asn Gln Cys Asn Trp Gln Trp Ser Asn
 65                  70                  75                  80

Ala Ala Met Leu Arg Tyr Lys Ala Trp Ala Glu Glu Ser Tyr Cys Val
```

-continued

```
              85                  90                  95
Tyr Phe Lys Ser Thr Asn Asn Lys Trp Arg Ser Arg Ala Cys Arg Met
            100                 105                 110

Met Ala Gln Phe Val Cys Glu Phe Gln Ala
            115                 120

<210> SEQ ID NO 284
<211> LENGTH: 135
<212> TYPE: PRT
<213> ORGANISM: Homo sapiens

<400> SEQUENCE: 284

Ala Arg Ile Ser Cys Pro Glu Gly Thr Asn Ala Tyr Arg Ser Tyr Cys
1               5                  10                  15

Tyr Tyr Phe Asn Glu Asp Arg Glu Thr Trp Val Asp Ala Asp Leu Tyr
            20                  25                  30

Cys Gln Asn Met Asn Ser Gly Asn Leu Val Ser Val Leu Thr Gln Ala
            35                  40                  45

Glu Gly Ala Phe Val Ala Ser Leu Ile Lys Glu Ser Gly Thr Asp Asp
    50                  55                  60

Phe Asn Val Trp Ile Gly Leu His Asp Pro Lys Asn Arg Arg Trp
65                  70                  75                  80

His Trp Ser Ser Gly Ser Leu Val Ser Tyr Lys Ser Trp Gly Ile Gly
                85                  90                  95

Ala Pro Ser Ser Val Asn Pro Gly Tyr Cys Val Ser Leu Thr Ser Ser
            100                 105                 110

Thr Gly Phe Gln Lys Trp Lys Asp Val Pro Cys Glu Asp Lys Phe Ser
            115                 120                 125

Phe Val Cys Lys Phe Lys Asn
            130                 135

<210> SEQ ID NO 285
<211> LENGTH: 123
<212> TYPE: PRT
<213> ORGANISM: Homo sapiens

<400> SEQUENCE: 285

Asp Tyr Glu Ile Leu Phe Ser Asp Glu Thr Met Asn Tyr Ala Asp Ala
1               5                  10                  15

Gly Thr Tyr Cys Gln Ser Arg Gly Met Ala Leu Val Ser Ser Ala Met
            20                  25                  30

Arg Asp Ser Thr Met Val Lys Ala Ile Leu Ala Phe Thr Glu Val Lys
            35                  40                  45

Gly His Asp Tyr Trp Val Gly Ala Asp Asn Leu Gln Asp Gly Ala Tyr
    50                  55                  60

Asn Phe Asn Trp Asn Asp Gly Val Ser Leu Pro Thr Asp Ser Asp Leu
65                  70                  75                  80

Trp Ser Pro Asn Glu Pro Ser Asn Pro Gln Ser Trp Gln Leu Cys Val
                85                  90                  95

Gln Ile Trp Ser Lys Tyr Asn Leu Leu Asp Asp Val Gly Cys Gly Gly
            100                 105                 110

Ala Arg Arg Val Ile Cys Glu Lys Glu Leu Asp
            115                 120

<210> SEQ ID NO 286
<211> LENGTH: 546
<212> TYPE: DNA
<213> ORGANISM: Homo sapiens
```

```
<220> FEATURE:
<221> NAME/KEY: CDS
<222> LOCATION: (1)..(546)

<400> SEQUENCE: 286 gag cca cca acc cag aag ccc aag aag att gta aat gcc aag aaa gat      48
Glu Pro Pro Thr Gln Lys Pro Lys Lys Ile Val Asn Ala Lys Lys Asp
1               5                   10                  15 gtt gtg aac aca aag atg ttt gag gag ctc aag agc cgt ctg gac acc      96
Val Val Asn Thr Lys Met Phe Glu Glu Leu Lys Ser Arg Leu Asp Thr
            20                  25                  30 ctg gcc cag gag gtg gcc ctg ctg aag gag cag cag gcc ctg cag acg     144
Leu Ala Gln Glu Val Ala Leu Leu Lys Glu Gln Gln Ala Leu Gln Thr
        35                  40                  45 gtc tgc ctg aag ggg acc aag gtg cac atg aaa tgc ttt ctg gcc ttc     192
Val Cys Leu Lys Gly Thr Lys Val His Met Lys Cys Phe Leu Ala Phe
    50                  55                  60 acc cag acg aag acc ttc cac gag gcc agc gag gac tgc atc tcg cgc     240
Thr Gln Thr Lys Thr Phe His Glu Ala Ser Glu Asp Cys Ile Ser Arg
65                  70                  75                  80 ggg ggc acc ctg agc acc cct cag act ggc tcg gag aac gac gcc ctg     288
Gly Gly Thr Leu Ser Thr Pro Gln Thr Gly Ser Glu Asn Asp Ala Leu
                85                  90                  95 tat gag tac ctg cgc cag agc gtg ggc aac gag gcc gag atc tgg ctg     336
Tyr Glu Tyr Leu Arg Gln Ser Val Gly Asn Glu Ala Glu Ile Trp Leu
            100                 105                 110 ggc ctc aac gac atg gcg gcc gag ggc acc tgg gtg gac atg acc ggc     384
Gly Leu Asn Asp Met Ala Ala Glu Gly Thr Trp Val Asp Met Thr Gly
        115                 120                 125 gcc cgc atc gcc tac aag aac tgg gag act gag atc acc gcg caa ccc     432
Ala Arg Ile Ala Tyr Lys Asn Trp Glu Thr Glu Ile Thr Ala Gln Pro
    130                 135                 140 gat ggc ggc aag acc gag aac tgc gcg gtc ctg tca ggc gcg gcc aac     480
Asp Gly Gly Lys Thr Glu Asn Cys Ala Val Leu Ser Gly Ala Ala Asn
145                 150                 155                 160 ggc aag tgg ttc gac aag cgc tgc cgc gat cag ctg ccc tac atc tgc     528
Gly Lys Trp Phe Asp Lys Arg Cys Arg Asp Gln Leu Pro Tyr Ile Cys
                165                 170                 175 cag ttc ggg atc gtg taa                                             546
Gln Phe Gly Ile Val
            180

<210> SEQ ID NO 287
<211> LENGTH: 181
<212> TYPE: PRT
<213> ORGANISM: Homo sapiens

<400> SEQUENCE: 287

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95
```

```
Tyr Glu Tyr Leu Arg Gln Ser Val Gly Asn Glu Ala Glu Ile Trp Leu
            100                 105                 110

Gly Leu Asn Asp Met Ala Ala Glu Gly Thr Trp Val Asp Met Thr Gly
            115                 120                 125

Ala Arg Ile Ala Tyr Lys Asn Trp Glu Thr Glu Ile Thr Ala Gln Pro
130                 135                 140

Asp Gly Gly Lys Thr Glu Asn Cys Ala Val Leu Ser Gly Ala Ala Asn
145                 150                 155                 160

Gly Lys Trp Phe Asp Lys Arg Cys Arg Asp Gln Leu Pro Tyr Ile Cys
                165                 170                 175

Gln Phe Gly Ile Val
            180

<210> SEQ ID NO 288
<211> LENGTH: 546
<212> TYPE: DNA
<213> ORGANISM: Murinae gen. sp.
<220> FEATURE:
<221> NAME/KEY: CDS
<222> LOCATION: (1)..(546)

<400> SEQUENCE: 288 gag tca ccc act ccc aag gcc aag aag gct gca aat gcc aag aaa gat      48
Glu Ser Pro Thr Pro Lys Ala Lys Lys Ala Ala Asn Ala Lys Lys Asp
1               5                   10                  15 ttg gtg agc tca aag atg ttc gag gag ctc aag aac agg atg gat gtc      96
Leu Val Ser Ser Lys Met Phe Glu Glu Leu Lys Asn Arg Met Asp Val
            20                  25                  30 ctg gcc cag gag gtg gcc ctg ctg aag gag aag cag gcc tta cag act     144
Leu Ala Gln Glu Val Ala Leu Leu Lys Glu Lys Gln Ala Leu Gln Thr
        35                  40                  45 gtg tgc ctg aag ggc acc aag gtg aac ttg aag tgc ctc ctg gcc ttc     192
Val Cys Leu Lys Gly Thr Lys Val Asn Leu Lys Cys Leu Leu Ala Phe
    50                  55                  60 acc caa ccg aag acc ttc cat gag gcg agc gag gac tgc atc tcg caa     240
Thr Gln Pro Lys Thr Phe His Glu Ala Ser Glu Asp Cys Ile Ser Gln
65                  70                  75                  80 ggg ggc acg ctg ggc acc ccg cag tca gag cta gag aac gag gcg ctg     288
Gly Gly Thr Leu Gly Thr Pro Gln Ser Glu Leu Glu Asn Glu Ala Leu
                85                  90                  95 ttc gag tac gcg cgc cac agc gtg ggc aac gat gcg aac atc tgg ctg     336
Phe Glu Tyr Ala Arg His Ser Val Gly Asn Asp Ala Asn Ile Trp Leu
            100                 105                 110 ggc ctc aac gac atg gcc gcg gaa ggc gcc tgg gtg gac atg acc ggc     384
Gly Leu Asn Asp Met Ala Ala Glu Gly Ala Trp Val Asp Met Thr Gly
        115                 120                 125 ggc ctc ctg gcc tac aag aac tgg gag acg gag atc acg acg caa ccc     432
Gly Leu Leu Ala Tyr Lys Asn Trp Glu Thr Glu Ile Thr Thr Gln Pro
130                 135                 140 gac ggc ggc aaa gcc gag aac tgc gcc gcc ctg tct ggc gca gcc aac     480
Asp Gly Gly Lys Ala Glu Asn Cys Ala Ala Leu Ser Gly Ala Ala Asn
145                 150                 155                 160 ggc aag tgg ttc gac aag cga tgc cgc gat cag ttg ccc tac atc tgc     528
Gly Lys Trp Phe Asp Lys Arg Cys Arg Asp Gln Leu Pro Tyr Ile Cys
                165                 170                 175 cag ttt gcc att gtg tag                                              546
Gln Phe Ala Ile Val
            180

<210> SEQ ID NO 289
<211> LENGTH: 181
```

<212> TYPE: PRT
<213> ORGANISM: Murinae gen. sp.

<400> SEQUENCE: 289

```
Glu Ser Pro Thr Pro Lys Ala Lys Lys Ala Asn Ala Lys Lys Asp
1               5                   10                  15

Leu Val Ser Ser Lys Met Phe Glu Glu Leu Lys Asn Arg Met Asp Val
            20                  25                  30

Leu Ala Gln Glu Val Ala Leu Leu Lys Glu Lys Gln Ala Leu Gln Thr
        35                  40                  45

Val Cys Leu Lys Gly Thr Lys Val Asn Leu Lys Cys Leu Leu Ala Phe
    50                  55                  60

Thr Gln Pro Lys Thr Phe His Glu Ala Ser Glu Asp Cys Ile Ser Gln
65                  70                  75                  80

Gly Gly Thr Leu Gly Thr Pro Gln Ser Glu Leu Glu Asn Glu Ala Leu
                85                  90                  95

Phe Glu Tyr Ala Arg His Ser Val Gly Asn Asp Ala Asn Ile Trp Leu
            100                 105                 110

Gly Leu Asn Asp Met Ala Ala Glu Gly Ala Trp Val Asp Met Thr Gly
        115                 120                 125

Gly Leu Leu Ala Tyr Lys Asn Trp Glu Thr Glu Ile Thr Thr Gln Pro
    130                 135                 140

Asp Gly Gly Lys Ala Glu Asn Cys Ala Ala Leu Ser Gly Ala Ala Asn
145                 150                 155                 160

Gly Lys Trp Phe Asp Lys Arg Cys Arg Asp Gln Leu Pro Tyr Ile Cys
                165                 170                 175

Gln Phe Ala Ile Val
            180
```

<210> SEQ ID NO 290
<211> LENGTH: 546
<212> TYPE: DNA
<213> ORGANISM: Homo sapiens
<220> FEATURE:
<221> NAME/KEY: CDS
<222> LOCATION: (1)..(546)

<400> SEQUENCE: 290

```
gag cca cca acc cag aag ccc aag aag att gta aat gcc aag aaa gat      48
Glu Pro Pro Thr Gln Lys Pro Lys Lys Ile Val Asn Ala Lys Lys Asp
1               5                   10                  15 gtt gtg aac aca aag atg ttt gag gag ctc aag agc cgt ctg gac acc      96
Val Val Asn Thr Lys Met Phe Glu Glu Leu Lys Ser Arg Leu Asp Thr
            20                  25                  30 ctg gcc cag gag gtg gcc ctg ctg aag gag cag cag gcc ctg cag acg     144
Leu Ala Gln Glu Val Ala Leu Leu Lys Glu Gln Gln Ala Leu Gln Thr
        35                  40                  45 gtc gtc ctg aag ggg acc aag gtg cac atg aaa gtc ttt ctg gcc ttc     192
Val Val Leu Lys Gly Thr Lys Val His Met Lys Val Phe Leu Ala Phe
    50                  55                  60 acc cag acg aag acc ttc cac gag gcc agc gag gac tgc atc tcg cgc     240
Thr Gln Thr Lys Thr Phe His Glu Ala Ser Glu Asp Cys Ile Ser Arg
65                  70                  75                  80 ggg ggc acc ctg agc acc cct cag act ggc tcg gag aac gac gcc ctg     288
Gly Gly Thr Leu Ser Thr Pro Gln Thr Gly Ser Glu Asn Asp Ala Leu
                85                  90                  95 tat gag tac ctg cgc cag agc gtg ggc aac gag gcc gag atc tgg ctg     336
Tyr Glu Tyr Leu Arg Gln Ser Val Gly Asn Glu Ala Glu Ile Trp Leu
            100                 105                 110
```

```
ggc ctc aac gac atg gcg gcc gag ggc acc tgg gtg gac atg acc ggt      384
Gly Leu Asn Asp Met Ala Ala Glu Gly Thr Trp Val Asp Met Thr Gly
        115                 120                 125 acc cgc atc gcc tac aag aac tgg gag act gag atc acc gcg caa ccc      432
Thr Arg Ile Ala Tyr Lys Asn Trp Glu Thr Glu Ile Thr Ala Gln Pro
    130                 135                 140 gat ggc ggc aag acc gag aac tgc gcg gtc ctg tca ggc gcg gcc aac      480
Asp Gly Gly Lys Thr Glu Asn Cys Ala Val Leu Ser Gly Ala Ala Asn
145                 150                 155                 160 ggc aag tgg ttc gac aag cgc tgc cgc gat caa ttg ccc tac atc tgc      528
Gly Lys Trp Phe Asp Lys Arg Cys Arg Asp Gln Leu Pro Tyr Ile Cys
                165                 170                 175 cag ttc ggg atc gtg tag                                              546
Gln Phe Gly Ile Val
            180

<210> SEQ ID NO 291
<211> LENGTH: 181
<212> TYPE: PRT
<213> ORGANISM: Homo sapiens

<400> SEQUENCE: 291

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Val Leu Lys Gly Thr Lys Val His Met Lys Val Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Asp Met Ala Ala Glu Gly Thr Trp Val Asp Met Thr Gly
        115                 120                 125

Thr Arg Ile Ala Tyr Lys Asn Trp Glu Thr Glu Ile Thr Ala Gln Pro
    130                 135                 140

Asp Gly Gly Lys Thr Glu Asn Cys Ala Val Leu Ser Gly Ala Ala Asn
145                 150                 155                 160

Gly Lys Trp Phe Asp Lys Arg Cys Arg Asp Gln Leu Pro Tyr Ile Cys
                165                 170                 175

Gln Phe Gly Ile Val
            180

<210> SEQ ID NO 292
<211> LENGTH: 546
<212> TYPE: DNA
<213> ORGANISM: Murinae gen. sp.
<220> FEATURE:
<221> NAME/KEY: CDS
<222> LOCATION: (1)..(546)

<400> SEQUENCE: 292 gag tca ccc act ccc aag gcc aag aag gct gca aat gcc aag aaa gat       48
Glu Ser Pro Thr Pro Lys Ala Lys Lys Ala Ala Asn Ala Lys Lys Asp
1               5                   10                  15 ttg gtg agc tca aag atg ttc gag gag ctc aag aac agg atg gat gtc       96
Leu Val Ser Ser Lys Met Phe Glu Glu Leu Lys Asn Arg Met Asp Val
```

```
Leu Val Ser Ser Lys Met Phe Glu Glu Leu Lys Asn Arg Met Asp Val
            20                  25                  30 ctg gcc cag gag gtg gcc ctg ctg aag gag aag cag gcc tta cag act    144
Leu Ala Gln Glu Val Ala Leu Leu Lys Glu Lys Gln Ala Leu Gln Thr
        35                  40                  45 gtg gtc ctg aag ggc acc aag gtg aac ttg aag gtc ctc ctg gcc ttc    192
Val Val Leu Lys Gly Thr Lys Val Asn Leu Lys Val Leu Leu Ala Phe
    50                  55                  60 acc caa ccg aag acc ttc cat gag gcg agc gag gac tgc atc tcg caa    240
Thr Gln Pro Lys Thr Phe His Glu Ala Ser Glu Asp Cys Ile Ser Gln
65                  70                  75                  80 ggg ggc acg ctg ggc acc ccg cag tca gag cta gag aac gag gcg ctg    288
Gly Gly Thr Leu Gly Thr Pro Gln Ser Glu Leu Glu Asn Glu Ala Leu
                85                  90                  95 ttc gag tac gcg cgc cac agc gtg ggc aac gat gcg gag atc tgg ctg    336
Phe Glu Tyr Ala Arg His Ser Val Gly Asn Asp Ala Glu Ile Trp Leu
            100                 105                 110 ggc ctc aac gac atg gcc gcg gaa ggc gcc tgg gtg gac atg acc ggt    384
Gly Leu Asn Asp Met Ala Ala Glu Gly Ala Trp Val Asp Met Thr Gly
        115                 120                 125 acc ctc ctg gcc tac aag aac tgg gag acg gag atc acg acg caa ccc    432
Thr Leu Leu Ala Tyr Lys Asn Trp Glu Thr Glu Ile Thr Thr Gln Pro
130                 135                 140 gac ggc ggc aaa gcc gag aac tgc gcc gcc ctg tct ggc gca gcc aac    480
Asp Gly Gly Lys Ala Glu Asn Cys Ala Ala Leu Ser Gly Ala Ala Asn
145                 150                 155                 160 ggc aag tgg ttc gac aag cga tgc cgc gat caa ttg ccc tac atc tgc    528
Gly Lys Trp Phe Asp Lys Arg Cys Arg Asp Gln Leu Pro Tyr Ile Cys
                165                 170                 175 cag ttt gcc att gtg tag                                             546
Gln Phe Ala Ile Val
            180

<210> SEQ ID NO 293
<211> LENGTH: 181
<212> TYPE: PRT
<213> ORGANISM: Murinae gen. sp.

<400> SEQUENCE: 293

Glu Ser Pro Thr Pro Lys Ala Lys Lys Ala Asn Ala Lys Lys Asp
1               5                   10                  15

Leu Val Ser Ser Lys Met Phe Glu Glu Leu Lys Asn Arg Met Asp Val
            20                  25                  30

Leu Ala Gln Glu Val Ala Leu Leu Lys Glu Lys Gln Ala Leu Gln Thr
        35                  40                  45

Val Val Leu Lys Gly Thr Lys Val Asn Leu Lys Val Leu Leu Ala Phe
    50                  55                  60

Thr Gln Pro Lys Thr Phe His Glu Ala Ser Glu Asp Cys Ile Ser Gln
65                  70                  75                  80

Gly Gly Thr Leu Gly Thr Pro Gln Ser Glu Leu Glu Asn Glu Ala Leu
                85                  90                  95

Phe Glu Tyr Ala Arg His Ser Val Gly Asn Asp Ala Glu Ile Trp Leu
            100                 105                 110

Gly Leu Asn Asp Met Ala Ala Glu Gly Ala Trp Val Asp Met Thr Gly
        115                 120                 125

Thr Leu Leu Ala Tyr Lys Asn Trp Glu Thr Glu Ile Thr Thr Gln Pro
130                 135                 140

Asp Gly Gly Lys Ala Glu Asn Cys Ala Ala Leu Ser Gly Ala Ala Asn
145                 150                 155                 160
```

```
Gly Lys Trp Phe Asp Lys Arg Cys Arg Asp Gln Leu Pro Tyr Ile Cys
            165                 170                 175
Gln Phe Ala Ile Val
            180

<210> SEQ ID NO 294
<211> LENGTH: 414
<212> TYPE: DNA
<213> ORGANISM: Homo sapiens
<220> FEATURE:
<221> NAME/KEY: CDS
<222> LOCATION: (1)..(414)

<400> SEQUENCE: 294 gcc ctg cag acg gtc gtc ctg aag ggg acc aag gtg cac atg aaa gtc       48
Ala Leu Gln Thr Val Val Leu Lys Gly Thr Lys Val His Met Lys Val
1               5                   10                  15 ttt ctg gcc ttc acc cag acg aag acc ttc cac gag gcc agc gag gac       96
Phe Leu Ala Phe Thr Gln Thr Lys Thr Phe His Glu Ala Ser Glu Asp
            20                  25                  30 tgc atc tcg cgc ggg ggc acc ctg agc acc cct cag act ggc tcg gag      144
Cys Ile Ser Arg Gly Gly Thr Leu Ser Thr Pro Gln Thr Gly Ser Glu
        35                  40                  45 aac gac gcc ctg tat gag tac ctg cgc cag agc gtg ggc aac gag gcc      192
Asn Asp Ala Leu Tyr Glu Tyr Leu Arg Gln Ser Val Gly Asn Glu Ala
    50                  55                  60 gag atc tgg ctg ggc ctc aac gac atg gcg gcc gag ggc acc tgg gtg      240
Glu Ile Trp Leu Gly Leu Asn Asp Met Ala Ala Glu Gly Thr Trp Val
65                  70                  75                  80 gac atg acc ggt acc cgc atc gcc tac aag aac tgg gag act gag atc      288
Asp Met Thr Gly Thr Arg Ile Ala Tyr Lys Asn Trp Glu Thr Glu Ile
                85                  90                  95 acc gcg caa ccc gat ggc ggc aag acc gag aac tgc gcg gtc ctg tca      336
Thr Ala Gln Pro Asp Gly Gly Lys Thr Glu Asn Cys Ala Val Leu Ser
            100                 105                 110 ggc gcg gcc aac ggc aag tgg ttc gac aag cgc tgc cgc gat caa ttg      384
Gly Ala Ala Asn Gly Lys Trp Phe Asp Lys Arg Cys Arg Asp Gln Leu
        115                 120                 125 ccc tac atc tgc cag ttc ggg atc gtg tag                              414
Pro Tyr Ile Cys Gln Phe Gly Ile Val
    130                 135

<210> SEQ ID NO 295
<211> LENGTH: 137
<212> TYPE: PRT
<213> ORGANISM: Homo sapiens

<400> SEQUENCE: 295

Ala Leu Gln Thr Val Val Leu Lys Gly Thr Lys Val His Met Lys Val
1               5                   10                  15

Phe Leu Ala Phe Thr Gln Thr Lys Thr Phe His Glu Ala Ser Glu Asp
            20                  25                  30

Cys Ile Ser Arg Gly Gly Thr Leu Ser Thr Pro Gln Thr Gly Ser Glu
        35                  40                  45

Asn Asp Ala Leu Tyr Glu Tyr Leu Arg Gln Ser Val Gly Asn Glu Ala
    50                  55                  60

Glu Ile Trp Leu Gly Leu Asn Asp Met Ala Ala Glu Gly Thr Trp Val
65                  70                  75                  80

Asp Met Thr Gly Thr Arg Ile Ala Tyr Lys Asn Trp Glu Thr Glu Ile
                85                  90                  95
```

```
Thr Ala Gln Pro Asp Gly Gly Lys Thr Glu Asn Cys Ala Val Leu Ser
        100                 105                 110

Gly Ala Ala Asn Gly Lys Trp Phe Asp Lys Arg Cys Arg Asp Gln Leu
        115                 120                 125

Pro Tyr Ile Cys Gln Phe Gly Ile Val
        130                 135

<210> SEQ ID NO 296
<211> LENGTH: 414
<212> TYPE: DNA
<213> ORGANISM: Murinae gen. sp.
<220> FEATURE:
<221> NAME/KEY: CDS
<222> LOCATION: (1)..(414)

<400> SEQUENCE: 296 gcc tta cag act gtg gtc ctg aag ggc acc aag gtg aac ttg aag gtc      48
Ala Leu Gln Thr Val Val Leu Lys Gly Thr Lys Val Asn Leu Lys Val
1               5                   10                  15 ctc ctg gcc ttc acc caa ccg aag acc ttc cat gag gcg agc gag gac      96
Leu Leu Ala Phe Thr Gln Pro Lys Thr Phe His Glu Ala Ser Glu Asp
            20                  25                  30 tgc atc tcg caa ggg ggc acg ctg ggc acc ccg cag tca gag cta gag     144
Cys Ile Ser Gln Gly Gly Thr Leu Gly Thr Pro Gln Ser Glu Leu Glu
        35                  40                  45 aac gag gcg ctg ttc gag tac gcg cgc cac agc gtg ggc aac gat gcg     192
Asn Glu Ala Leu Phe Glu Tyr Ala Arg His Ser Val Gly Asn Asp Ala
    50                  55                  60 gag atc tgg ctg ggc ctc aac gac atg gcc gcg gaa ggc gcc tgg gtg     240
Glu Ile Trp Leu Gly Leu Asn Asp Met Ala Ala Glu Gly Ala Trp Val
65                  70                  75                  80 gac atg acc ggt acc ctc ctg gcc tac aag aac tgg gag acg gag atc     288
Asp Met Thr Gly Thr Leu Leu Ala Tyr Lys Asn Trp Glu Thr Glu Ile
                85                  90                  95 acg acg caa ccc gac ggc ggc aaa gcc gag aac tgc gcc gcc ctg tct     336
Thr Thr Gln Pro Asp Gly Gly Lys Ala Glu Asn Cys Ala Ala Leu Ser
            100                 105                 110 ggc gca gcc aac ggc aag tgg ttc gac aag cga tgc cgc gat caa ttg     384
Gly Ala Ala Asn Gly Lys Trp Phe Asp Lys Arg Cys Arg Asp Gln Leu
        115                 120                 125 ccc tac atc tgc cag ttt gcc att gtg tag                             414
Pro Tyr Ile Cys Gln Phe Ala Ile Val
    130                 135

<210> SEQ ID NO 297
<211> LENGTH: 137
<212> TYPE: PRT
<213> ORGANISM: Murinae gen. sp.

<400> SEQUENCE: 297

Ala Leu Gln Thr Val Val Leu Lys Gly Thr Lys Val Asn Leu Lys Val
1               5                   10                  15

Leu Leu Ala Phe Thr Gln Pro Lys Thr Phe His Glu Ala Ser Glu Asp
            20                  25                  30

Cys Ile Ser Gln Gly Gly Thr Leu Gly Thr Pro Gln Ser Glu Leu Glu
        35                  40                  45

Asn Glu Ala Leu Phe Glu Tyr Ala Arg His Ser Val Gly Asn Asp Ala
    50                  55                  60

Glu Ile Trp Leu Gly Leu Asn Asp Met Ala Ala Glu Gly Ala Trp Val
65                  70                  75                  80

Asp Met Thr Gly Thr Leu Leu Ala Tyr Lys Asn Trp Glu Thr Glu Ile
```

-continued

```
                         85                  90                  95
Thr Thr Gln Pro Asp Gly Gly Lys Ala Glu Asn Cys Ala Ala Leu Ser
            100                 105                 110

Gly Ala Ala Asn Gly Lys Trp Phe Asp Lys Arg Cys Arg Asp Gln Leu
        115                 120                 125

Pro Tyr Ile Cys Gln Phe Ala Ile Val
    130                 135

<210> SEQ ID NO 298
<211> LENGTH: 31
<212> TYPE: DNA
<213> ORGANISM: Artificial
<220> FEATURE:
<223> OTHER INFORMATION: artificial
<220> FEATURE:
<221> NAME/KEY: CDS
<222> LOCATION: (4)..(30)

<400> SEQUENCE: 298 cat atg gga tcg cat cac cat cac cat cac g                       31
    Met Gly Ser His His His His His His
    1               5

<210> SEQ ID NO 299
<211> LENGTH: 9
<212> TYPE: PRT
<213> ORGANISM: Artificial
<220> FEATURE:
<223> OTHER INFORMATION: Synthetic Construct

<400> SEQUENCE: 299

Met Gly Ser His His His His His His
1               5

<210> SEQ ID NO 300
<211> LENGTH: 11
<212> TYPE: DNA
<213> ORGANISM: Artificial
<220> FEATURE:
<223> OTHER INFORMATION: artificial

<400> SEQUENCE: 300
agcttgaatt c                                                    11

<210> SEQ ID NO 301
<211> LENGTH: 13
<212> TYPE: DNA
<213> ORGANISM: Artificial
<220> FEATURE:
<223> OTHER INFORMATION: artificial
<220> FEATURE:
<221> NAME/KEY: CDS
<222> LOCATION: (1)..(12)

<400> SEQUENCE: 301 tat gcg gcc cag c                                               13
Tyr Ala Ala Gln
1

<210> SEQ ID NO 302
<211> LENGTH: 4
<212> TYPE: PRT
<213> ORGANISM: Artificial
<220> FEATURE:
<223> OTHER INFORMATION: Synthetic Construct

<400> SEQUENCE: 302
```

Tyr Ala Ala Gln
1

<210> SEQ ID NO 303
<211> LENGTH: 13
<212> TYPE: DNA
<213> ORGANISM: Artificial
<220> FEATURE:
<223> OTHER INFORMATION: artificial
<220> FEATURE:
<221> NAME/KEY: CDS
<222> LOCATION: (2)..(13)

<400> SEQUENCE: 303 g gcc gca ggt gcg                                                        13
  Ala Ala Gly Ala
   1

<210> SEQ ID NO 304
<211> LENGTH: 4
<212> TYPE: PRT
<213> ORGANISM: Artificial
<220> FEATURE:
<223> OTHER INFORMATION: Synthetic Construct

<400> SEQUENCE: 304

Ala Ala Gly Ala
1

<210> SEQ ID NO 305
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X can be any amino acid

<400> SEQUENCE: 305

Trp Ile Gly Xaa
1

<210> SEQ ID NO 306
<211> LENGTH: 4
<212> TYPE: PRT
<213> ORGANISM: Artificial
<220> FEATURE:
<223> OTHER INFORMATION: Synthetic

<400> SEQUENCE: 306

Trp Ile Gly Leu
1

<210> SEQ ID NO 307
<211> LENGTH: 4
<212> TYPE: PRT
<213> ORGANISM: Artificial
<220> FEATURE:
<223> OTHER INFORMATION: Synthetic

<400> SEQUENCE: 307

Trp Ile Gly Ile
1

<210> SEQ ID NO 308
<211> LENGTH: 4
<212> TYPE: PRT

```
<213> ORGANISM: Artificial
<220> FEATURE:
<223> OTHER INFORMATION: Synthetic

<400> SEQUENCE: 308

Trp Ile Gly Val
 1

<210> SEQ ID NO 309
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X can be any amino acid

<400> SEQUENCE: 309

Trp Leu Gly Xaa
 1

<210> SEQ ID NO 310
<211> LENGTH: 4
<212> TYPE: PRT
<213> ORGANISM: Artificial
<220> FEATURE:
<223> OTHER INFORMATION: Synthetic

<400> SEQUENCE: 310

Trp Leu Gly Leu
 1

<210> SEQ ID NO 311
<211> LENGTH: 4
<212> TYPE: PRT
<213> ORGANISM: Artificial
<220> FEATURE:
<223> OTHER INFORMATION: Synthetic

<400> SEQUENCE: 311

Trp Leu Gly Val
 1

<210> SEQ ID NO 312
<211> LENGTH: 4
<212> TYPE: PRT
<213> ORGANISM: Artificial
<220> FEATURE:
<223> OTHER INFORMATION: Synthetic

<400> SEQUENCE: 312

Trp Leu Gly Ala
 1

<210> SEQ ID NO 313
<211> LENGTH: 4
<212> TYPE: PRT
<213> ORGANISM: Artificial
<220> FEATURE:
<223> OTHER INFORMATION: Synthetic

<400> SEQUENCE: 313

Trp Met Gly Leu
 1

<210> SEQ ID NO 314
```

```
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X can be any amino acid

<400> SEQUENCE: 314

Tyr Leu Xaa Met
1

<210> SEQ ID NO 315
<211> LENGTH: 4
<212> TYPE: PRT
<213> ORGANISM: Artificial
<220> FEATURE:
<223> OTHER INFORMATION: Synthetic

<400> SEQUENCE: 315

Tyr Leu Ser Met
1

<210> SEQ ID NO 316
<211> LENGTH: 4
<212> TYPE: PRT
<213> ORGANISM: Artificial
<220> FEATURE:
<223> OTHER INFORMATION: Synthetic

<400> SEQUENCE: 316

Tyr Leu Gly Met
1

<210> SEQ ID NO 317
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X can be any amino acid

<400> SEQUENCE: 317

Trp Val Gly Xaa
1

<210> SEQ ID NO 318
<211> LENGTH: 4
<212> TYPE: PRT
<213> ORGANISM: Artificial
<220> FEATURE:
<223> OTHER INFORMATION: Synthetic

<400> SEQUENCE: 318

Trp Val Gly Leu
1

<210> SEQ ID NO 319
<211> LENGTH: 4
<212> TYPE: PRT
<213> ORGANISM: Artificial
<220> FEATURE:
<223> OTHER INFORMATION: Synthetic

<400> SEQUENCE: 319
```

Trp Val Gly Ala
1

<210> SEQ ID NO 320
<211> LENGTH: 5
<212> TYPE: PRT
<213> ORGANISM: Artificial
<220> FEATURE:
<223> OTHER INFORMATION: Synthetic

<400> SEQUENCE: 320

Phe Phe Leu Gly Ile
1               5

<210> SEQ ID NO 321
<211> LENGTH: 4
<212> TYPE: PRT
<213> ORGANISM: Artificial
<220> FEATURE:
<223> OTHER INFORMATION: Synthetic

<400> SEQUENCE: 321

Phe Val Gly Leu
1

<210> SEQ ID NO 322
<211> LENGTH: 4
<212> TYPE: PRT
<213> ORGANISM: Artificial
<220> FEATURE:
<223> OTHER INFORMATION: Synthetic

<400> SEQUENCE: 322

Phe Ile Gly Val
1

<210> SEQ ID NO 323
<211> LENGTH: 4
<212> TYPE: PRT
<213> ORGANISM: Artificial
<220> FEATURE:
<223> OTHER INFORMATION: Synthetic

<400> SEQUENCE: 323

Phe Leu Ser Met
1

<210> SEQ ID NO 324
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X can be any amino acid

<400> SEQUENCE: 324

Cys Val Xaa Ile
1

<210> SEQ ID NO 325
<211> LENGTH: 4
<212> TYPE: PRT
<213> ORGANISM: Artificial
<220> FEATURE:
<223> OTHER INFORMATION: Synthetic

```
<400> SEQUENCE: 325

Cys Val Glu Ile
1

<210> SEQ ID NO 326
<211> LENGTH: 4
<212> TYPE: PRT
<213> ORGANISM: Artificial
<220> FEATURE:
<223> OTHER INFORMATION: Synthetic

<400> SEQUENCE: 326

Cys Val Thr Ile
1

<210> SEQ ID NO 327
<211> LENGTH: 4
<212> TYPE: PRT
<213> ORGANISM: Artificial
<220> FEATURE:
<223> OTHER INFORMATION: Synthetic

<400> SEQUENCE: 327

Cys Val Gln Ile
1

<210> SEQ ID NO 328
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X can be any amino acid

<400> SEQUENCE: 328

Cys Val Xaa Met
1

<210> SEQ ID NO 329
<211> LENGTH: 4
<212> TYPE: PRT
<213> ORGANISM: Artificial
<220> FEATURE:
<223> OTHER INFORMATION: Synthetic

<400> SEQUENCE: 329

Cys Val Glu Met
1

<210> SEQ ID NO 330
<211> LENGTH: 4
<212> TYPE: PRT
<213> ORGANISM: Artificial
<220> FEATURE:
<223> OTHER INFORMATION: Synthetic

<400> SEQUENCE: 330

Cys Val Val Met
1

<210> SEQ ID NO 331
<211> LENGTH: 4
<212> TYPE: PRT
<213> ORGANISM: Artificial
```

```
<220> FEATURE:
<223> OTHER INFORMATION: Synthetic

<400> SEQUENCE: 331

Cys Val Met Met
1

<210> SEQ ID NO 332
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X can be any amino acid

<400> SEQUENCE: 332

Cys Val Xaa Leu
1

<210> SEQ ID NO 333
<211> LENGTH: 4
<212> TYPE: PRT
<213> ORGANISM: Artificial
<220> FEATURE:
<223> OTHER INFORMATION: Synthetic

<400> SEQUENCE: 333

Cys Val Val Leu
1

<210> SEQ ID NO 334
<211> LENGTH: 4
<212> TYPE: PRT
<213> ORGANISM: Artificial
<220> FEATURE:
<223> OTHER INFORMATION: Synthetic

<400> SEQUENCE: 334

Cys Val Ser Leu
1

<210> SEQ ID NO 335
<211> LENGTH: 4
<212> TYPE: PRT
<213> ORGANISM: Artificial
<220> FEATURE:
<223> OTHER INFORMATION: Synthetic

<400> SEQUENCE: 335

Cys Val His Leu
1

<210> SEQ ID NO 336
<211> LENGTH: 4
<212> TYPE: PRT
<213> ORGANISM: Artificial
<220> FEATURE:
<223> OTHER INFORMATION: Synthetic

<400> SEQUENCE: 336

Cys Val Ala Leu
1

<210> SEQ ID NO 337
<211> LENGTH: 4
```

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X can be any amino acid

<400> SEQUENCE: 337

Cys Ala Xaa Leu
1

<210> SEQ ID NO 338
<211> LENGTH: 4
<212> TYPE: PRT
<213> ORGANISM: Artificial
<220> FEATURE:
<223> OTHER INFORMATION: Synthetic

<400> SEQUENCE: 338

Cys Ala Val Leu
1

<210> SEQ ID NO 339
<211> LENGTH: 4
<212> TYPE: PRT
<213> ORGANISM: Artificial
<220> FEATURE:
<223> OTHER INFORMATION: Synthetic

<400> SEQUENCE: 339

Cys Ala Ser Leu
1

<210> SEQ ID NO 340
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X can be any amino acid

<400> SEQUENCE: 340

Cys Ala Xaa Phe
1

<210> SEQ ID NO 341
<211> LENGTH: 4
<212> TYPE: PRT
<213> ORGANISM: Artificial
<220> FEATURE:
<223> OTHER INFORMATION: Synthetic

<400> SEQUENCE: 341

Cys Ala His Phe
1

<210> SEQ ID NO 342
<211> LENGTH: 4
<212> TYPE: PRT
<213> ORGANISM: Artificial
<220> FEATURE:
<223> OTHER INFORMATION: Synthetic

<400> SEQUENCE: 342
```

Cys Ala Glu Phe
1

<210> SEQ ID NO 343
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X can be any amino acid

<400> SEQUENCE: 343

Cys Leu Xaa Leu
1

<210> SEQ ID NO 344
<211> LENGTH: 4
<212> TYPE: PRT
<213> ORGANISM: Artificial
<220> FEATURE:
<223> OTHER INFORMATION: Synthetic

<400> SEQUENCE: 344

Cys Leu Glu Leu
1

<210> SEQ ID NO 345
<211> LENGTH: 4
<212> TYPE: PRT
<213> ORGANISM: Artificial
<220> FEATURE:
<223> OTHER INFORMATION: Synthetic

<400> SEQUENCE: 345

Cys Leu Gly Leu
1

<210> SEQ ID NO 346
<211> LENGTH: 4
<212> TYPE: PRT
<213> ORGANISM: Artificial
<220> FEATURE:
<223> OTHER INFORMATION: Synthetic

<400> SEQUENCE: 346

Cys Val Tyr Phe
1

<210> SEQ ID NO 347
<211> LENGTH: 4
<212> TYPE: PRT
<213> ORGANISM: Artificial
<220> FEATURE:
<223> OTHER INFORMATION: Synthetic

<400> SEQUENCE: 347

Cys Val Ala Gln
1

<210> SEQ ID NO 348
<211> LENGTH: 4
<212> TYPE: PRT
<213> ORGANISM: Artificial
<220> FEATURE:
<223> OTHER INFORMATION: Synthetic

```
<400> SEQUENCE: 348

Cys Ala His Val
1

<210> SEQ ID NO 349
<211> LENGTH: 4
<212> TYPE: PRT
<213> ORGANISM: Artificial
<220> FEATURE:
<223> OTHER INFORMATION: Synthetic

<400> SEQUENCE: 349

Cys Ala His Ile
1

<210> SEQ ID NO 350
<211> LENGTH: 4
<212> TYPE: PRT
<213> ORGANISM: Artificial
<220> FEATURE:
<223> OTHER INFORMATION: Synthetic

<400> SEQUENCE: 350

Cys Leu Glu Ile
1

<210> SEQ ID NO 351
<211> LENGTH: 4
<212> TYPE: PRT
<213> ORGANISM: Artificial
<220> FEATURE:
<223> OTHER INFORMATION: Synthetic

<400> SEQUENCE: 351

Cys Ile Ala Tyr
1

<210> SEQ ID NO 352
<211> LENGTH: 4
<212> TYPE: PRT
<213> ORGANISM: Artificial
<220> FEATURE:
<223> OTHER INFORMATION: Synthetic

<400> SEQUENCE: 352

Cys Met Leu Leu
1
```

COMBINATORIAL LIBRARIES OF PROTEINS HAVING THE SCAFFOLD STRUCTURE OF C-TYPE LECTIN-LIKE DOMAINS

CROSS-REFERENCE TO RELATED APPLICATION

This application is a divisional of U.S. patent application Ser. No. 10/450,472, filed Jun. 13, 2003, now abandoned which was a national phase of International Application PCT/DK01/00825, filed Dec. 13, 2001. The entire contents of U.S. patent application Ser. No. 10/450,472 and the International Application, including new claims 1-29, attached to the International Preliminary Examination Report, are incorporated herein by reference. The International Application and this application claim priority from Denmark application PA 2000 01872, filed Dec. 13, 2000 and U.S. Application No. 60/272,098, filed Feb. 28, 2001.

FIELD OF THE INVENTION

This invention describes a system which relates to the generation of randomised libraries of ligand-binding protein units derived from proteins containing the so-called C-type lectin like domain (CTLD) of which the carbohydrate recognition domain (CRD) of C-type lectins represents one example of a family of this protein domain.

BACKGROUND OF THE INVENTION

The C-type lectin-like domain (CTLD) is a protein domain family which has been identified in a number of proteins isolated from many animal species (reviewed in Drickamer and Taylor (1993) and Drickamer (1999)). Initially, the CTLD domain was identified as a domain common to the so-called C-type lectins (calcium-dependent carbohydrate binding proteins) and named "Carbohydrate Recognition Domain" ("CRD"). More recently, it has become evident that this domain is shared among many eukaryotic proteins, of which several do not bind sugar moieties, and hence, the canonical domain has been named as CTLD.

CTLDs have been reported to bind a wide diversity of compounds, including carbohydrates, lipids, proteins, and even ice [Aspberg et al. (1997), Bettler et al. (1992), Ewart et al. (1998), Graversen et al. (1998), Mizumo et al. (1997), Sano et al. (1998), and Tormo et al. (1999)]. Only one copy of the CTLD is present in some proteins, whereas other proteins contain from two to multiple copies of the domain. In the physiologically functional unit multiplicity in the number of CTLDs is often achieved by assembling single copy protein protomers into larger structures.

The CTLD consists of approximately 120 amino acid residues and, characteristically, contains two or three intra-chain disulfide bridges. Although the similarity at the amino acid sequence level between CTLDs from different proteins is relatively low, the 3D-structures of a number of CTLDs have been found to be highly conserved, with the structural variability essentially confined to a so-called loop-region, often defined by up to five loops. Several CTLDs contain either one or two binding sites for calcium and most of the side chains which interact with calcium are located in the loop-region.

On the basis of CTLDs for which 3D structural information is available, it has been inferred that the canonical CTLD is structurally characterised by seven main secondary-structure elements (i.e. five β-strands and two α-helices) sequentially appearing in the order β1; α1; α2; β2; β3; β4; and β5 (FIG. 1, and references given therein). In all CTLDs, for which 3D structures have been determined, the β-strands are arranged in two anti-parallel β-sheets, one composed of β1 and β5, the other composed of β2, β3 and β4. An additional β-strand, β0, often precedes β1 in the sequence and, where present, forms an additional strand integrating with the β1, β5-sheet. Further, two disulfide bridges, one connecting α1 and β5 ($C_I$-$C_{IV}$, FIG. 1) and one connecting β3 and the polypeptide segment connecting β4 and β5 ($C_{II}$-$C_{III}$, FIG. 1) are invariantly found in all CTLDs characterised so far. In the CTLD 3D-structure, these conserved secondary structure elements form a compact scaffold for a number of loops, which in the present context collectively are referred to as the "loop-region", protruding out from the core. These loops are in the primary structure of the CTLDs organised in two segments, loop segment A, LSA, and loop segment B, LSB. LSA represents the long polypeptide segment connecting β2 and β3 which often lacks regular secondary structure and contains up to four loops. LSB represents the polypeptide segment connecting the β-strands β3 and β4. Residues in LSA, together with single residues in β4, have been shown to specify the $Ca^{2+}$- and ligand-binding sites of several CTLDs, including that of tetranectin. E.g. mutagenesis studies, involving substitution of single or a few residues, have shown, that changes in binding specificity, $Ca^{2+}$-sensitivity and/or affinity can be accommodated by CTLD domains [Weis and Drickamer (1996), Chiba et al. (1999), Graversen et al. (2000)].

As noted above, overall sequence similarities between CTLDs are often limited, as assessed e.g. by aligning a prospective CTLD sequence with the group of structure-characterized CTLDs presented in FIG. 1, using sequence alignment procedures and analysis tools in common use in the field of protein science. In such an alignment, typically 22-30% of the residues of the prospective CTLD will be identical with the corresponding residue in at least one of the structure-characterized CTLDs. The sequence alignment shown in FIG. 1 was strictly elucidated from actual 3D structure data, so the fact that the polypeptide segments of corresponding structural elements of the framework also exhibit strong sequence similarities provide a set of direct sequence-structure signatures, which can readily be inferred from the sequence alignment.

The implication is that also CTLDs, for which precise 3D structural information is not yet available, can nonetheless be used as frameworks in the construction of new classes of CTLD libraries. The specific additional steps involved in preparing starting materials for the construction of such a new class of CTLD library on the basis of a CTLD, for which no precise 3D structure is available, would be the following: (1) Alignment of the sequence of the new CTLD with the sequence shown in FIG. 1; and (2) Assignment of approximate locations of framework structural elements as guided by the sequence alignment, observing any requirement for minor adjustment of the alignment to ensure precise alignment of the four canonical cysteine residues involved in the formation of the two conserved disulfide bridges ($C_I$-$C_{IV}$ and $C_{II}$-$C_{III}$, in FIG. 1). The main objective of these steps would be to identify the sequence location of the loop-region of the new CTLD, as flanked in the sequence by segments corresponding to the β2-, β3-, and β4-strands. To provide further guidance in this the results of an analysis of the sequences of 29 bona fide CTLDs are given in Table 1 below in the form of typical tetrapeptide sequences, and their consensus sequences, found as parts of CTLD β2- and β3-strands, and the precise location of the β4-strand by position and sequence characteristics as elucidated.

TABLE I

β2 and β3 consensus elements analysis

| CTLD | β2 | --- | LSA | --- | β3 | LSB | β4 | SEQ ID NO |
|---|---|---|---|---|---|---|---|---|
| IX-A | WIGLRW | ---QGKVKQCNSEWSDGSSVS | --YENWIE | --------AESKT | ---------- | CLGLEKETDFR | KWVNIYC | 92 |
| MGL | WIGLTDQ | --NGP--WRWVDGTDFEKGFKNWAP | -------- | LQPDNWFGHGLGGGED | CAHITTG | --G | FWNDDVC | 93 |
| LIT | WIGLHDPKKNRR | --WHWSSGSLVS | --YKSWGI | --------GAPSSVNP | -----GY- | CVSLTSSTGF | QKWKDVPC | 94 |
| CHL | WIGLTDENQEGE | --WQWVDGTDTRSSFTFWKE | -------- | GEPNNRGF | -----NED | CAHVWTS | --G | QWNDVYC | 95 |
| IGE-FCR | WIGLRNLDLKGEFIWV | --DGSHVD | --YSNWAP | --------GEPTSRSQ | -----GED | CVMMRGS | --G | RWNDAFC | 96 |
| TCL-1 | WIGLTDKDSEGT | --WKWVDGTPLT | --TAFWST | --------DEPNDGAVN | ----GED | CVSLYYHTQPEF | KNWNDLAC | 97 |
| KUCR | WIGLTDQGTEGN | --WRWVDGTPFDYVQSRRFWRK | -------- | GQPDWRHGNGE | --RED | CVHLQ | ----R | MWNDMAC | 98 |
| CD94 | WIGLSYSEEHTA | --WLWENGSALSQ | -YLSFET | -----------FNTKN | ------- | CIAYNPN | --G | NALDESC | 99 |
| CPCP | WIGLNDRTIEGDFRWS | --DGHPMQ | --FENWRP | --------NQPDNFFAA | ----GED | CVVMIWHEKG | EWNDVPC | 100 |
| PAP | WIGLHDPTQGTEPNGEG | -WEWSSSDVMN | --YFAWER | --------N-PSTISSPGH | ----- | CASLSRSTAFL | RWKDYNC | 101 |
| NEU | WIGLNDRIVEQD | --FQWTDNTGLQ | --YENWRE | --------NQPDNFFAG | ----GED | CVVLVSHEIG | KWNDVPC | 102 |
| ESL | WIGIRKVNNV | ----WVV-VGTQKPLTEEAKNWAP | -------- | GEPNNRQK | -----DED | CVEIYIKREKDVG | MWNDERC | 103 |
| NKg2A | WIGVFRNSSHHP | --WVTMNGLAFKHEIKDSDNA | ------------------- | ELN | CAVLQV | ---N | RLKSAQC | 104 |
| GP120 | WMGLSDLNQEGT | --WQWVDGSPLLPS | -FKQYWNR | --------GEPNNVG | ------EED | CAEFSGN | --G-WNDDKC | 105 |
| MMR | WIGLFRNV | -EGT--WLWINNSPVS | --FVNWNT | --------GDPSGE | -------RND | CVALHASS | -G | FWSNIHC | 106 |
| TN | WLGLNDMAAEGT | ----WVDMTGARIAYKNWETEIT | -----AQPDGGK | ------TEN | CAVLSGAANG | KWFDKRC | 107 |
| SCGF | WLGVHDRRAEGL | --YLFENGQRVS | --FFAWHRSPRPELGAQPSASPHPLSPDQPNGGT | ------LEN | CVAQASDD | -G | SWWDHDC | 108 |
| PLC | WLGASDLNIEGR | --WLW-EGQRRMN | -YTNWSP | --------GQPDNAGG | -----IEH | CLELRRDLGNYL | WNDYQC | 109 |
| H1-ASR | WMGLHD | --QNGP--WKWVDGTDYETGFKNWRP | -------- | EQPDDWYGHGLGGGED | CAHFTDD | --G | RWNDDVC | 110 |
| IX-B | WMGLSNVWNQCN | --WQWSNAAMLR | --YKAWAE | --------ESY | ------------- | CVYFKSTN | -N | KWRSRAC | 111 |
| LY49A | WVGLSYDNKKKD | --WAWIDNRPSKLALNTRKY | -------- | NIRDGG | ---------- | CMLLSKT | ----R | LDNGNC | 112 |
| TU14 | WVGADN | -LQDGAYNFNWNDGVSLPTDSDLWSP | --------NEPSNPQSWQL | ----- | CVQIWSKY | -N | LLDDVGC | 113 |
| rSP-A | YLGMIEDQTPGD | --FHYLDGASVN | --YTNWYP | --------GEPRGQG | ------KEK | CVEMYTD | -G | TWNDRGC | 114 |
| BCON | YLSMNDISTEGR | --FTYPTGEILV | --YSNWAD | --------GEPNNSDEGQ | ---PEN | CVEIFPD | --G | KWNDVPC | 115 |
| BCL43 | YLSMNDISKEGK | --FTYPTGGSLD | --YSNWAP | --------GEPNNRAKDEG | --PEN | CLEIYSD | --G | NWNDIEC | 116 |
| MBP-A | FLGITDEVTEGQ | --FMYVTGGRLT | --YSNWKK | --------DEPNDHGS | -----GED | CVTIVDN | --G | LWNDISC | 117 |
| SP-D | FLSMTDSKTEGK | --FTYPTGESLV | --YSNWAP | --------GEPNDDGG | -----SED | CVEIFTN | --G | KWNDRAC | 118 |
| CL-L1 | FIGVNDLEREGQ | --YMFTDNTPLQN | -YSNWNE | --------GEPSDPYG | -----HED | CVEMLSS | --G | RWNDTEC | 119 |
| DCIR | FVGLSDP | --EGQRHWQWVDQTP | ----YNESSTFWHP | --------REPSDPN | -------ER | CVVLNFRKSPKRWG | -WNDVNC | 120 |

Notes:
LSA, Loop Segment A; LSB, Loop Segment B. Sequences taken from: Berglund and Petersen (1992) [TN, tetranectin]; Bartrand et al. (1996) [LIT, lithostatin]; Mann et al. (2000) [MGL, mouse macrophage galactose lectin, KUCR, Kupffer cell receptor, NEU, chicken neurocan, PLC, perlucin, H1-ASR, asialoglycoprotein receptor]; Mio et al. (1998) [CPCP, cartilage proteoglycan core protein, IGE-FCR, IgE Fc receptor, PAP, pancreatitis-associated protein, MMR, mouse macrophage receptor, NKG2, Natural Killer group, SCGF, stem cell growth factor]; Mizuno et al. (1997) [IX-A and B, factor IX/X binding protein, MBP, mannose binding protein]; Obtani et al. (1999) [BCON, bovine conglutinin, BCL43, bovine CL43, CL-L1, collectin liver 1, SP-A, surfactant protein A, SP-D, surfactant protein D]; Poget et al. (1999) [ESL, e-selectin, TU14, tunicate c-type lectin]; Tormo et al. (1999) [CD94, CD94 NK receptor domain, LY49A, LY49A NK receptor domain]; Zhang et al. (2000) [CHL, chicken hepatic lectin, TCL-1, trout c-type lectin, GP120, HIV gp 120-binding c-type lectin, DCIR, dendritic cell immuno receptor]

Of the 29 β2-strands,
14 were found to conform to the consensus sequence WIGX [SEQ ID NO: 305] (of which 12 were WIGL [SEQ ID NO: 306] sequences, 1 was a WIGI [SEQ ID NO: 307] sequence and 1 was a WIGV [SEQ ID NO: 308] sequence);
3 were found to conform to the consensus sequence WLGX [SEQ ID NO: 309] (of which 1 was a WLGL [SEQ ID NO: 310] sequence, 1 was a WLGV [SEQ ID NO: 311] sequence and 1 was a WLGA [SEQ ID NO: 312] sequence);
3 were found to be WMGL [SEQ ID NO: 313] sequences;
3 were found to conform to the consensus sequence YLXM [SEQ ID NO: 314] (of which 2 were YLSM [SEQ ID NO: 315] sequences and 1 was an YLGM [SEQ ID NO: 316] sequence);
2 were found to conform to the consensus sequence WVGX [SEQ ID NO: 317] (of which 1 was a WVGL [SEQ ID NO: 318] sequence and 1 was a WVGA [SEQ ID NO: 319] sequence); and
the sequences of the remaining 4 β2-strands in the collection were FLGI [SEQ ID NO:320], FVGL [SEQ ID NO:321], FIGV [SEQ ID NO: 322] and FLSM [SEQ ID NO: 323] sequences, respectively.

Therefore, it is concluded that the four-residue β2 consensus sequence ("β2cseq") may be specified as follows:
Residue 1: An aromatic residue, most preferably Trp, less preferably Phe and least preferably Tyr.
Residue 2: An aliphatic or non-polar residue, most preferably Ile, less preferably Leu or Met and least preferably Val.
Residue 3: An aliphatic or hydrophilic residue, most preferably Gly and least preferably Ser.
Residue 4: An aliphatic or non-polar residue, most preferably Leu and less preferably Met, Val or Ile.

Accordingly the β2 consensus sequence may be summarized as follows:

β2cseq:
($\underline{W}$, Y, F)-($\underline{I}$, L, V, M)-($\underline{G}$, S)-($\underline{L}$, M, V, I), where the underlined residue denotes the most commonly found residue at that sequence position.

All 29 β3-strands analysed are initiated with the $CYS_{II}$ residue canonical for all known CTLD sequences, and of the 29 β3-strands,
5 were found to conform to the consensus sequence CVXI [SEQ ID NO: 324] (of which 3 were CVEI [SEQ ID NO: 325] sequences, 1 was a CVTI [SEQ ID NO: 326] sequence and 1 was a CVQI [SEQ ID NO: 327] sequence);
4 were found to conform to the consensus sequence CVXM [SEQ ID NO: 328] (of which 2 were CVEM [SEQ ID NO: 329] sequences, 1 was a CVVM [SEQ ID NO: 330] sequence and 1 was a CVMM [SEQ ID NO: 331] sequence);
6 were found to conform to the consensus sequence CVXL [SEQ ID NO: 332] (of which 2 were CVVL [SEQ ID NO: 333] sequences, 2 were a CVSL [SEQ ID NO: 334] sequence, 1 was a CVHL [SEQ ID NO: 335] sequence and 1 was CVAL[SEQ ID NO: 336] sequence);
3 were found to conform to the consensus sequence CAXL [SEQ ID NO: 337] (of which 2 were CAVL [SEQ ID NO: 338] and 1 was a CASL [SEQ ID NO: 339] sequence);
2 were found to conform to the consensus sequence CAXF [SEQ ID NO: 340] (of which 1 was 1 CAHF [SEQ ID NO: 341] sequence and 1 was a CAEF [SEQ ID NO: 342] sequence);
2 were found to conform to the consensus sequence CLXL [SEQ ID NO: 343] (of which 1 was a CLEL [SEQ ID NO: 344] sequence and 1 was a CLGL [SEQ ID NO: 345] sequence); and
the sequences of the remaining 7 β3-strands in the collection were CVYF [SEQ ID NO: 346], CVAQ [SEQ ID NO: 347], CAHV [SEQ ID NO: 348], CAHI [SEQ ID NO: 349], CLEI [SEQ ID NO: 350], CIAY [SEQ ID NO: 351], and CMLL [SEQ ID NO: 352] sequences, respectively.

Therefore, it is concluded that the four-residue β3 consensus sequence ("β3cseq") may be specified as follows:
Residue 1: Cys, being the canonical $Cys_{II}$ residue of CTLDs
Residue 2: An aliphatic or non-polar residue, most preferably Val, less preferably Ala or Leu and least preferably Ile or Met
Residue 3: Most commonly an aliphatic or charged residue, which most preferably is Glu
Residue 4: Most commonly an aliphatic, non-polar, or aromatic residue, most preferably Leu or Ile, less preferably Met or Phe and least preferably Tyr or Val.

Accordingly the β3 consensus sequence may be summarized as follows:

β3cseq:
($\underline{C}$)-($\underline{V}$, A, L, I, M)-($\underline{E}$, X)-($\underline{L}$, I, M, F, Y, V), where the underlined residue denotes the most commonly found residue at that sequence position.

It is observed from the known 3D-structures of CTLDs (FIG. 1), that the β4-strands most often are comprised by five residues located in the primary structure at positions −6 to −2 relative to the canonical $Cys_{III}$ residue of all known CTLDs, and less often are comprised by four residues located at positions −5 to −2 relative to the canonical $Cys_{III}$ residue of all known CTLDs. The residue located at position −3, relative to $Cys_{III}$, is involved in co-ordination of the site 2 calcium ion in CTLDs housing this site, and this notion is reflected in the observation, that of the 29 CTLD sequences analysed in Table 1, 27 have an Asp-residue or an Asn-residue at this position, whereas 2 CTLDs have a Ser at this position. From the known CTLD 3D-structures it is also noted, that the residue located at position −5, relative to the $Cys_{III}$ residue, is involved in the formation of the hydrophobic core of the CTLD scaffold. This notion is reflected in the observation, that of the 29 CTLD sequences analysed 25 have a Trp-residue, 3 have a Leu-residue, and 1 an Ala-residue at this position. 18 of the 29 CTLD sequences analysed have an Asn-residue at position −4. Further, 19 of the 29 β4-strand segments are preceded by a Gly residue.

Of the 29 central three residue motifs located at positions −5, −4 and −3 relative to the canonical $Cys_{III}$ residue in the β4-strand:
22 were of the sequence WXD (18 were WND, 2 were WKD, 1 was WFD and 1 was WWD),
2 were of the sequence WXN (1 was WVN and 1 was WSN), and the remaining 5 motifs (WRS, LDD, LDN, LKS and ALD) were each represented once in the analysis.

It has now been found that each member of the family of CTLD domains represents an attractive opportunity for the construction of new protein libraries from which members with affinity for new ligand targets can be identified and isolated using screening or selection methods. Such libraries may be constructed by combining a CTLD framework structure in which the CTLD's loop-region is partially or completely replaced with one or more randomised polypeptide segments.

One such system, where the protein used as scaffold is tetranectin or the CTLD domain of tetranectin, is envisaged as a system of particular interest, not least because the stability of the trimeric complex of tetranectin protomers is very high (International Patent Application Publication No. WO 98/56906 A2).

Tetranectin is a trimeric glycoprotein [Holtet et al. (1997), Nielsen et al. (1997)], which has been isolated from human plasma and found to be present in the extracellular matrix in certain tissues. Tetranectin is known to bind calcium, complex polysaccharides, plasminogen, fibrinogen/fibrin, and apolipoprotein (a). The interaction with plasminogen and apolipoprotein (a) is mediated by the so-called kringle 4-protein domain therein. This interaction is known to be sensitive to calcium and to derivatives of the amino acid lysine [Graversen et al. (1998)].

A human tetranectin gene has been characterised, and both human and murine tetranectin cDNA clones have been isolated. Both the human and the murine mature protein comprise 181 amino acid residues (FIG. 2). The 3D-structures of full length recombinant human tetranectin and of the isolated tetranectin CTLD have been determined independently in two separate studies [Nielsen et al. (1997) and Kastrup et al. (1998)]. Tetranectin is a two- or possibly three-domain protein, i.e. the main part of the polypeptide chain comprises the CTLD (amino acid residues Qly53 to Val181), whereas the region Leu26 to Lys52 encodes an alpha-helix governing trimerisation of the protein via the formation of a homotrimeric parallel coiled coil. The polypeptide segment Glu1 to Glu25 contains the binding site for complex polysaccharides (Lys6 to Lys15) [Lorentsen et al. (2000)] and appears to contribute to stabilisation of the trimeric structure [Holtet et al. (1997)]. The two amino acid residues Lys148 and Glu150, localised in loop 4, and Asp165 (localised in β4) have been shown to be of critical importance for plasminogen kringle 4 binding, whereas the residues Ile140 (in loop 3) and Lys166 and Arg167 (in β4) have been shown to be of some importance [Graversen et al. (1998)]. Substitution of Thr149 (in loop 4) with an aromatic residue has been shown to significantly increase affinity of tetranectin to kringle 4 and to increase affinity for plasminogen kringle 2 to a level comparable to the affinity of wild type tetranectin for kringle 4 [Graversen et al. (2000)].

OBJECT OF THE INVENTION

The object of the invention is to provide a new practicable method for the generation of useful protein products endowed with binding sites able to bind substance of interest with high affinity and specificity.

The invention describes one way in which such new and useful protein products may advantageously be obtained by applying standard combinatorial protein chemistry methods, commonly used in the recombinant antibody field, to generate randomised combinatorial libraries of protein modules, in which each member contains an essentially common core structure similar to that of a CTLD.

The variation of binding site configuration among naturally occurring CTLDs shows that their common core structure can accommodate many essentially different configurations of the ligand binding site. CTLDs are therefore particularly well suited to serve as a basis for constructing such new and useful protein products with desired binding properties.

In terms of practical application, the new artificial CTLD protein products can be employed in applications in which antibody products are presently used as key reagents in technical biochemical assay systems or medical in vitro or in vivo diagnostic assay systems or as active components in therapeutic compositions.

In terms of use as components of in vitro assay systems, the artificial CTLD protein products are preferable to antibody derivatives as each binding site in the new protein product is harboured in a single structurally autonomous protein domain. CTLD domains are resistant to proteolysis, and neither stability nor access to the ligand-binding site is compromised by the attachment of other protein domains to the N- or C-terminus of the CTLD. Accordingly, the CTLD binding module may readily be utilized as a building block for the construction of modular molecular assemblies, e.g. harbouring multiple CLTDs of identical or nonidentical specificity in addition to appropriate reporter modules like peroxidases, phosphatases or any other signal-mediating moiety.

In terms of in vivo use as essential component of compositions to be used for in vivo diagnostic or therapeutic purposes, artificial CTLD protein products constructed on the basis of human CTLDs are virtually identical to the corresponding natural CTLD protein already present in the body, and are therefore expected to elicit minimal immunological response in the patient. Single CTLDs are about half the mass of the smallest functional antibody derivative, the single-chain Fv derivative, and this small size may in some applications be advantageous as it may provide better tissue penetration and distribution, as well as a shorter half-life in circulation. Multivalent formats of CTLD proteins, e.g. corresponding to the complete tetranectin trimer or the further multimerized collecting, like e.g. mannose binding protein, provide increased binding capacity and avidity and longer circulation half-life.

One particular advantage of the preferred embodiment of the invention, arises from the fact that mammalian tetranectins, as exemplified by murine and human tetranectin, are of essentially identical structure. This conservation among species is of great practical importance as it allows straightforward swapping of polypeptide segments defining ligand-binding specificity between e.g. murine and human tetranectin derivatives. The option of facile swapping of species genetic background between tetranectin derivatives is in marked contrast to the well-known complications of effecting the "humanisation" of murine antibody derivatives.

Further advantages of the invention are:

The availability of a general and simple procedure for reliable conversion of an initially selected protein derivative into a final protein product, which without further reformatting may be produced in bacteria (e.g. *Escherichia coli*) both in small and in large scale (International Patent Application Publication No. WO 94/18227 A2).

The option of including several identical or non-identical binding sites in the same functional protein unit by simple and general means, thereby enabling the exploitation even of weak affinities by means of avidity in the interaction, or the construction of bi- or heterofunctional molecular assemblies (International Patent Application Publication No. WO 98/56906 A2).

The possibility of modulating binding by addition or removal of divalent metal ions (e.g. calcium ions) in combinational libraries with one or more preserved metal binding site(s) in the CTLDs.

SUMMARY OF THE INVENTION

The present invention provides a great number of novel and useful proteins each being a protein having the scaffold structure of C-type lectin-like domains (CTLD), said protein comprising a variant of a model CTLD wherein the α-helices and β-strands and connecting segments are conserved to such a degree that the scaffold structure of the CTLD is substantially maintained, while the loop region is altered by amino acid substitution, deletion, insertion or any combination thereof, with the proviso that said protein is not any of the known CTLD loop derivatives of C-type lectin-like proteins or C-type lectins listed in the following Table 2.

TABLE 2

Known β2, β3, β4, LSA and LSB CTLD derivatives

Table 2A: LSA derivatives (β2 and β3 consensus elements are underlined)

| CTLD | Mut. | LSA sequence (one letter code) | Reference | SEQ ID NO |
|---|---|---|---|---|
| hTN | TND116A | WLGLNAMAAEGTWVDMTGARIAYKNWETEITAQPDGGKTENCAVL | Graversen et al. (1998) | 121 |
| | TNE120A | WLGLNDMAAAGTWVDMTGARIAYKNWETEITAQPDGGKTENCAVL | Graversen et al. (1998) | 122 |
| | TNK134A | WLGLNDMAAEGTWVDMTGARIAYANWETEITAQPDGGKTENCAVL | Graversen et al. (1998) | 123 |
| | TNK140A | WLGLNDMAAEGTWVDMTGARIAYKNWETEATAQPDGGKTENCAVL | Graversen et al. (1998) | 124 |
| | TNQ143A | WLGLNDMAAEGTWVDMTGARIAYKNWETEITAAPDGGKTENCAVL | Graversen et al. (1998) | 125 |
| | TND145A | WLGLNDMAAEGTWVDMTGARIAYKNWETEITAQPAGGKTENCAVL | Graversen et al. (1998) | 126 |
| | TNK148A | WLGLNDMAAEGTWVDMTGARIAYKNWETEITAQPDGGATENCAVL | Graversen et al. (1998) | 127 |
| | TNK148M | WLGLNDMAAEGTWVDMTGARIAYKNWETEITAQPDGGMTENCAVL | Graversen et al. (2000) | 128 |
| | TNK148R | WLGLNDMAAEGTWVDMTGARIAYKNWETEITAQPDGGRTENCAVL | Graversen et al. (2000) | 129 |
| | TNT149F | WLGLNDMAAEGTWVDMTGARIAYKNWETEITAQPDGGKFENCAVL | Graversen et al. (2000) | 130 |
| | TNT149M | WLGLNDMAAEGTWVDMTGARIAYKNWETEITAQPDGGKMENCAVL | Graversen et al. (2000) | 131 |
| | TNT149R | WLGLNDMAAEGTWVDMTGARIAYKNWETEITAQPDGGKRENCAVL | Graversen et al. (2000) | 132 |
| | TN149Y | WLGLNDMAAEGTWVDMTGARIAYKNWETEITAQPDGGKYENCAVL | Graversen et al. (2000) | 133 |
| | TNE150A | WLGLNDMAAEGTWVDMTGARIAYKNWETEITAQPDGGKTANCAVL | Graversen et al. (1998) | 134 |
| | TNE150D | WLGLNDMAAEGTWVDMTGARIAYKNWETEITAQPDGGKTDNCAVL | Graversen et al. (2000) | 135 |
| | TNE150Q | WLGLNDMAAEGTWVDMTGARIAYKNWETEITAQPDGGKTQNCAVL | Graversen et al. (2000) | 136 |
| | TNN151A | WLGLNDMAAEGTWVDMTGARIAYKNWETEITAQPDGGKTEACAVL | Graversen et al. (1998) | 137 |
| | TNK148R, T149Y | WLGLNDMAAEGTWVDMTGARIAYKNWETEITAQPDGGRYENCAVL | Graversen et al. (2000) | 138 |
| | TNT149Y, E150Q | WLGLNDMAAEGTWVDMTGARIAYKNWETEITAQPDGGKYQNCAVL | Graversen et al. (2000) | 139 |
| | TNT149Y, D165N | WLGLNDMAAEGTWVDMTGARIAYKNWETEITAQPDGGKYENCAVL | Graversen et al. (2000) | 140 |

TABLE 2-continued

Known β2, β3, β4, LSA and LSB CTLD derivatives

| rMBP | QPD | FLGITDEVTEGQFMYVTGGRLTYSNWKKDQPDDHGSGEDCVTI | Drickamer (1992) | 141 |
|---|---|---|---|---|
| | N187D | FLGITDEVTEGQFMYVTGGRLTYSNWKKDEPDDHGSGEDCVTI | Iobst et al. (1994) | 142 |
| | H189A | FLGITDEVTEGQFMYVTGGRLTYSNWKKDEPNDAGSGEDCVTI | Iobst et al. (1994) | 143 |
| | H189G | FLGITDEVTEGQFMYVTGGRLTYSNWKKDEPNDGGSGEDCVTI | Iobst et al. (1994) | 144 |
| | QPDW | FLGITDEVTEGQFMYVTGGRLTYSNWKKDQPDDWGSGEDCVTI | Iobst & Drickamer (1994) | 145 |
| | QPDWG | FLGITDEVTEGQFMYVTGGRLTYSNWKKDQPDDWYGHGLGGGEDCVTI | Iobst & Drickamer (1994) | 146 |
| | QPDWG/Y/A | FLGITDEVTEGQFMYVTGGRLTYSNWKKDQPDDWAGHGLGGGEDCVTI | Iobst & Drickamer (1994) | 147 |
| | QPDWG/Y/Q | FLGITDEVTEGQFMYVTGGRLTYSNWKKDQPDDWQGHGLGGGEDCVTI | Iobst & Drickamer (1994) | 148 |
| | QPDWG/G/A | FLGITDEVTEGQFMYVTGGRLTYSNWKKDQPDDWYAHGLGGGEDCVTI | Iobst & Drickamer (1994) | 149 |
| | QPDWG/H/A | FLGITDEVTEGQFMYVTGGRLTYSNWKKDQPDDWYGAGLGGGEDCVTI | Iobst & Drickamer (1994) | 150 |
| | QPDWG/H/Q | FLGITDEVTEGQFMYVTGGRLTYSNWKKDQPDDWYGQGLGGGEDCVTI | Iobst & Drickamer (1994) | 151 |
| | QPDWG/H/E | FLGITDEVTEGQFMYVTGGRLTYSNWKKDQPDDWYGEGLGGGEDCVTI | Iobst & Drickamer (1994) | 152 |
| | QPDWG/H/Y | FLGITDEVTEGQFMYVTGGRLTYSNWKKDQPDDWYGYGLGGGEDCVTI | Iobst & Drickamer (1994) | 153 |
| | QPDWG/-/G | FLGITDEVTEGQFMYVTGGRLTYSNWKKDQPDDWYGHGLGGEDCVTI | Iobst & Drickamer (1994) | 154 |
| | QPDF | FLGITDEVTEGQFMYVTGGRLTYSNWKKDQPDDFGSGEDCVTI | Iobst & Drickamer (1994) | 155 |
| | QPDFG | FLGITDEVTEGQFMYVTGGRLTYSNWKKDQPDDFYGHGLGGGEDCVTI | Iobst & Drickamer (1994) | 156 |
| | REGION 1 | FLGIRKVNNVFMYVTGGRLTYSNWKKDEPNDHGSGEDCVTI | Blanck et al. (1996) | 157 |
| | REGION 2 | FLGITDEVTEGQFMYVTGGRLTYSNWKKDEPNNRQKDEDCVTI | Blanck et al. (1996) | 158 |
| | RES. 189 | FLGITDEVTEGQFMYVTGGRLTYSNWKKDEPNDGGSGEDCVTI | Torgersen et al. (1998) | 159 |
| | RES. 197 | FLGITDEVTEGQFMYVTGGRLTYSNWKKDEPNDHGSGEDCVEI | Torgersen et al. (1998) | 160 |
| | LOOP 3E | FLGITDEVTEGQFMYVTGGRLTYSNWAPGEPNDHGSGEDCVTI | Torgersen et al. (1998) | 161 |
| | LOOP 3P | FLGITDEVTEGQFMYVTGGRLTYSNWADNEPNDHGSGEDCVTI | Torgersen et al. (1998) | 162 |

TABLE 2-continued

Known β2, β3, β4, LSA and LSB CTLD derivatives

| | | | | |
|---|---|---|---|---|
| | REGION 4 | <u>FLGI</u>TDEVTEGQFMYVTGGRLTYSNWKKDQPDDWYGHGLGGGED<u>CVHI</u> | Kolatkar et al. (1998) | 163 |
| | REGION 4' | <u>FLGI</u>TDEVTEGQFMYVTGGRLTYSNWRPGQPDDWYGHGLGGGED<u>CVHI</u> | Kolatkar et al. (1998) | 164 |
| | QPDWG/QNG | <u>FLGI</u>TDQNGQFMYVTGGRLTYSNWKKDQPDDWYGHGLGGGED<u>CVTI</u> | Wragg & Drickamer (1999) | 165 |
| | QPDWG/QNGP | <u>FLGI</u>TDQNGPFMYVTGGRLTYSNWKKDQPDDWYGHGLGGGED<u>CVTI</u> | Wragg & Drickamer (1999) | 166 |
| | MBP/CHL189 | <u>FLGI</u>TDEVTEGQFMYVTGGRLTYSNWKEGEPNNRGSGED<u>CVTI</u> | Burrows et al. (1997) | 167 |
| | MBP/CHL192 | <u>FLGI</u>TDEVTEGQFMYVTGGRLTYSNWKEGEPNNRGFNED<u>CVTI</u> | Burrows et al. (1997) | 168 |
| | MBP/CHL208 | <u>FLGI</u>TDEVTEGQFMYVTGGRLTYSNWKEGEPNNRGFNED<u>CAHV</u> | Burrows et al. (1997) | 169 |
| rSP-A | E195Q, R197D | <u>YLGMI</u>EDQTPGDFHYLDGASVNYTNWYPGQPDGQGKEK<u>CVEM</u> | McCormack et al. (1994) | 170 |
| | AM2 | <u>YLGMI</u>EDQTPGDFHYLDGASVNYTNWYPGEPRGQGKEK<u>CVTI</u> | Honma et al. (1997) | 171 |
| | AM3 | <u>YLGMI</u>EDQTPGDFHYLDGASVNYTNWYPGEPNDHGSGED<u>CVTI</u> | Honma et al. (1997) | 172 |
| | E195A | <u>YLGMI</u>EDQTPGDFHYLDGASVNYTNWYPGAPRGQGKEK<u>CVEM</u> | Mccormack et al. (1997) | 173 |
| | R197G | <u>YLGMI</u>EDQTPGDFHYLDGASVNYTNWYPGEPGGQGKEK<u>CVEM</u> | McCormack et al. (1997) | 174 |
| | E202A | <u>YLGMI</u>EDQTPGDFHYLDGASVNYTNWYPGEPRGQGKAK<u>CVEM</u> | McCormack et al. (1997) | 175 |
| | N187S | <u>YLGMI</u>EDQTPGDFHYLDGASVSYTNWYPGEPRGQGKEK<u>CVEM</u> | McCormack et al. (1997) | 176 |
| | R197A | <u>YLGMI</u>EDQTPGDFHYLDGASVNYTNWYPGEPAGQGKEK<u>CVEM</u> | Pattanajitvilai et al. (1998) | 177 |
| | P197K | <u>YLGMI</u>EDQTPGDFHYLDGASVNYTNWYPGEPKGQGKEK<u>CVEM</u> | Pattanajitvilai et al. (1998) | 178 |
| | R197H | <u>YLGMI</u>EDQTPGDFHYLDGASVNYTNWYPGEPHGQGKEK<u>CVEM</u> | Pattanajitvilai et al. (1998) | 179 |
| | R197D | <u>YLGMI</u>EDQTPGDFHYLDGASVNYTNWYPGEPDGQGKEK<u>CVEM</u> | Pattanajitvilai et al. (1998) | 180 |
| | R197N | <u>YLGMI</u>EDQTPGDFHYLDGASVNYTNWYPGEPNGQGKEK<u>CVEM</u> | Pattanajitvilai et al. (1998) | 181 |
| | E195Q | <u>YLGMI</u>EDQTPGDFHYLDGASVNYTNWYPGQPRGQGKEK<u>CVEM</u> | Tsunezawa et al. (1998) | 182 |
| | K201A | <u>YLGMI</u>EDQTPGDFHYLDGASVNYTNWYPGEPRGQGAEK<u>CVEM</u> | Tsunezawa et al. (1998) | 183 |
| | K203A | <u>YLGMI</u>EDQTPGDFHYLDGASVNYTNWYPGEPRGQGKEA<u>CVEM</u> | Tsunezawa et al. (1998) | 184 |
| | E197A, K201A, K203A | <u>YLGMI</u>EDQTPGDFHYLDGASVNYTNWYPGAPRGQGAEA<u>CVEM</u> | Tsunezawa et al. (1998) | 185 |
| | ad3 | <u>YLGMI</u>EDQTPGDFHYLDGASVNYTNWYPGEPNNNGGAEN<u>CVEI</u> | Sano et al. (1998) | 186 |
| | ad4 | <u>YLGMI</u>EDQTEGKFTYPTGEALVYSNWAPGEPNNNGGAEN<u>CVEI</u> | Sano et al. (1998) | 187 |

TABLE 2-continued

Known β2, β3, β4, LSA and LSB CTLD derivatives

| | | | | |
|---|---|---|---|---|
| | rat ama4 | YLGMIEDQTEGQFMYVTGGRLTYSNWKKDEPRGQGKEKCVEM | Chiba et al (1999) | 188 |
| hSP-A | R199A | YVGLTEGPSPGDFRYSDGTPVNYTNWYRGEPAGAGKEQCVEM | Tsunezawa et al. (1998) | 189 |
| | K201A | YVGLTEGPSPGDFRYSDGTPVNYTNWYRGEPAGRGAEQCVEM | Tsunezawa et al. (1998) | 190 |
| | hum ama4 | YVGLTEGPTEGQFMYVTGGRLTYSNWKKDEPRGRGKEQCVEM | Chiba et al (1999) | 191 |
| rSP-D | E321Q, N323D | FLSMTDVGTEGKFTYPTGEALVYSNWAPGQPDNNGGAENCVEI | Ogasawara & Voelker (1995) | 192 |
| h-esl | K67A | WIGIRKVNNVWVWVGTQAPLTEEAKNWAPGEPNNRQKDEDCVEI | Erbe et al. | 193 |
| | K74A | WIGIRKVNNVWVWVGTQKPLTEEAANWAPGEPNNRQKDEDCVEI | Erbe et al. | 194 |
| | R84A, K86A | WIGIRKVNNVWVWVGTQKPLTEEAKNWAPGEPNNAQADEDCVEI | Erbe et al. | 195 |
| | R84A | WIGIRKVNNVWVWVGTQKPLTEEAKNWAPGEPNNAQKDEDCVEI | Kogan et al. (1995) | 196 |
| | R84K | WIGIRKVNNVWVWVGTQKPLTEEAKNWAPGEPNNKQKDEDCVEI | Kogan et al. (1995) | 197 |
| | R84K, D89G | WIGIRKVNNVWVWVGTQKPLTEEAKNWAPGEPNNKQKDEGCVEI | Kogan et al. (1995) | 198 |
| | A77K | WIGIRKVNNVWVWVGTQKPLTEEAKNWKPGEPNNRQKDHDCVEI | Kogan et al. (1995) | 199 |
| | A77K, P78K | WIGIRKVNNVWVWVGTQKPLTEEAKNWKKGEPNNRQKDEDCVEI | Kogan et al. (1995) | 200 |
| | A77K, P78K, R84A | WIGIRKVNNVWVWVGTQKPLTEEAKNWKKGEPNNAQKDEDCVEI | Kogan et al. (1995) | 201 |
| | D87E | WIGIRKVNNVWVWVGTQKPLTEEAKNWAPGEPNNRQKEEDCVEI | Kogan et al. (1995) | 202 |
| | D87N | WIGIRKVNNVWVWVGTQKPLTEEAKNWAPGEPNNRQKNEDCVEI | Kogan et al. (1995) | 203 |
| | D89N | WIGIRKVNNVWVWVGTQKPLTEEAKNWAPGEPNNRQKDENCVEI | Kogan et al. (1995) | 204 |
| | D89E | WIGIRKVNNVWVWVGTQKPLTEEAKNWAPGEPNNRQKDEECVEI | Kogan et al. (1995) | 205 |
| | A77K, E80Q, N82D | WIGIRKVNNVWVWVGTQKPLTEEAKNWKPGQPDNRQKDEDCVEI | Kogan et al. (1995) | 206 |
| h-psl | A77K | WIGIRKNNKTWTWVGTKKALTNEAENWKDNEPNNKRNNEDCVEI | Revelle et al. (1996) | 207 |
| | A77K, E80D, N82D | WIGIRKNNKTWTWVGTKKALTNEAENWKDNQPDNKRNNEDCVEI | Revelle et al. (1996) | 208 |
| MGR | 2A/R | WIGLTDQNGPWRWVDGTDYEKGFTHWRPKQPDNWYGHGLGGGEDCAHF | Iobst & Drickamer (1996) | 209 |
| | 2K/G | WIGLTDQNGPWRWVDGTDYEKGFTHWAPGQPDNWYGHGLGGGEDCAHF | Iobst & Drickamer (1996) | 210 |
| | 2A/R, 2K/G | WIGLTDQNGPWRWVDGTDYEKGFTHWRPGQPDNWYGHGLGGGEDCAHF | Iobst & Drickamer (1996) | 211 |

TABLE 2-continued

Known β2, β3, β4, LSA and LSB CTLD derivatives

|   |   |   |   |   |
|---|---|---|---|---|
|   | 4F/I | WIGLTDQNGPWRWVDGTDYEKGFTHWAPKQPDNWYGHGLGGGED<u>CAHI</u> | Iobst & Drickamer (1996) | 212 |
|   | 4H/A | WIGLTDQNGPWRWVDGTDYEKGFTHWAPKQPDNWYGHGLGGGED<u>CAAF</u> | Iobst & Drickamer (1996) | 213 |
|   | 4H/E | WIGLTDQNGPWRWVDGTDYEKGFTHWAPKQPDNWYGHGLGGGED<u>CAEF</u> | Iobst & Drickamer (1996) | 214 |
|   | 4H/Q | WIGLTDQNGPWRWVDGTDYEKGFTHWAPKQPDNWYGHGLGGGED<u>CAQF</u> | Iobst & Drickamer (1996) | 215 |
|   | 4H/N | WIGLTDQNGPWRWVDGTDYEKGFTHWAPKQPDNWYGHGLGGGED<u>CANF</u> | Iobst & Drickamer (1996) | 216 |
|   | 4H/Y | WIGLTDQNGPWRWVDGTDYEKGFTHWAPKQPDNWYGHGLGGGED<u>CAYF</u> | Iobst & Drickamer (1996) | 217 |
|   | 4H/D | WIGLTDQNGPWRWVDGTDYEKGFTHWAPKQPDNWYGHGLGGGED<u>CADF</u> | Iobst & Drickamer (1996) | 218 |
|   | 4H/K | WIGLTDQNGPWRWVDGTDYEKGFTHWAPKQPDNWYGHGLGGGED<u>CAKF</u> | Iobst & Drickamer (1996) | 219 |
|   | 2A/R, 2K/G, 4H/A | WIGLTDQNGPWRWVDGTDYEKGFTHWRPGQPDNWYGHGLGGGED<u>CAAF</u> | Iobst & Drickamer (1996) | 220 |
| RHL | 4H/A | WIGLTDQNGPWKWVDGTDYETGFKNWRPGQPDDWYGHGLGGGED<u>CAAF</u> | Iobst & Drickamer (1996) | 221 |
| CHL | R173A | WIGLTDENQEGEWQWVDGTDTRSSFTFWKEGEPNNAGFNED<u>CAHV</u> | Burrows et al. (1997) | 222 |
|   | G174A | WIGLTDENQEGEWQWVDGTDTRSSFTFWKEGEPNNRAFNED<u>CAHV</u> | Burrows et al. (1997) | 223 |
|   | F175A | WIGLTDENQEGEWQWVDGTDTRSSFTFWKEGEPNNRGANED<u>CAHV</u> | Burrows et al. (1997) | 224 |
|   | N176A | WIGLTDENQEGEWQWVDGTDTRSSFTFWKEGEPNNRGFAED<u>CAHV</u> | Burrows et al. (1997) | 225 |

Table 2B: LSB derivatives (β3 and β4 consensus elements are underlined)

| CTLD | Mut. | LSB sequence (one letter code) | Reference | SEQ ID NO |
|---|---|---|---|---|
| hTN | TNK163A | <u>CAVL</u>SGAANGA<u>WFD</u>KRC | Graversen et al. (1998) | 226 |
|   | TNK166A | <u>CAVL</u>SGAANGK<u>WFD</u>ARC | Graversen et al. (1998) | 227 |
|   | TNR167A | <u>CAVL</u>SGAANGK<u>WFD</u>KAC | Graversen et al. (1998) | 228 |
|   | TNF164L | <u>CAVL</u>SGAANGK<u>WLD</u>KRC | Graversen et al. (1998) | 229 |
|   | TND165A | <u>CAVL</u>SGAANGK<u>WFA</u>KRC | Graversen et al. (1998) | 230 |
|   | TND165E | <u>CAVL</u>SGAANGK<u>WFE</u>KRC | Graversen et al. (2000) | 231 |

TABLE 2-continued

Known β2, β3, β4, LSA and LSB CTLD derivatives

| | | | | |
|---|---|---|---|---|
| | TND165N | CAVLSGAANGKWFNKRC | Graversen et al. (2000) | 232 |
| rMBP | I207V | CVTIVDNGLWNDVSC | Iobst et al. (1994) | 233 |
| | I207L | CVTIVDNGLWNDLSC | Iobst et al. (1994) | 234 |
| | I207A | CVTIVDNGLWNDASC | Iobst et al. (1994) | 235 |
| | I207E | CVTIVDNGLWNDESC | Torgensen et al. (1996) | 236 |
| | Region 4E | CVTIVYIKREKDNGLWNDISC | Torgensen et al. (1996) | 237 |
| | Region4P | CVTIVYIKSPSDNGLWNDISC | Torgensen et al. (1996) | 238 |
| | 207VY | CVTIVDNGLWNDVYC | Burrows et al. (1997) | 239 |
| | β34 | CAHVWTSGQWNDVYC | Burrows et al. (1997) | 240 |
| h-esl | Y94F | CVEIFIKREKDVGMWNDERC | Kogan et al. (1995) | 241 |
| | Y94R | CVEIRIKREKDVGMWNDERC | Kogan et al. (1995) | 242 |
| | Y94D | CVEIDIKREKDVGMWNDERC | Kogan et al. (1995) | 243 |
| | Y94A | CVEIAIKREKDVGMWNDERC | Kogan et al. (1995) | 244 |
| | Y94S | CVEISIKREKDVGMWNDERC | Kogan et al. (1995) | 245 |
| | E107D | CVEIYIKREKDVGMWNDDRC | Kogan et al. (1995) | 246 |
| | E107A | CVEIYIKREKDVGMWNDARC | Kogan et al. (1995) | 247 |
| | E107N | CVEIYIKREKDVGMWNDNRC | Kogan et al. (1995) | 248 |
| | E107K | CVEIYIKREKDVGMWNDKRC | Kogan et al. (1995) | 249 |
| | E107Q | CVEIYIKREKDVGMWNDQRC | Kogan et al. (1995) | 250 |
| | R97D | CVEIYIKDEKDVGMWNDERC | Revelle et al. (1996) | 251 |
| | R97S | CVEIYIKSEKDVGMWNDERC | Revelle et al. (1996) | 252 |
| | R97E | CVEIYIKEEKDVGMWNDERC | Revelle et al. (1996) | 253 |
| h-psl | K96Q | CVEIYIQSPSAPGMWNDEHC | Revelle et al. (1996) | 254 |
| | K96R | CVEIYIRSPSAPGMWNDEHC | Revelle et al. (1996) | 255 |
| | K96E | CVEIYIESPSAPGMWNDEHC | Revelle et al. (1996) | 256 |
| | S97A | CVEIYIKAPSAPGMWHDEHC | Revelle et al. (1996) | 257 |

TABLE 2-continued

Known β2, β3, β4, LSA and LSB CTLD derivatives

|  |  |  |  | SEQ ID NO |
|---|---|---|---|---|
|  | S97D | <u>CVEIYI</u>KDPSAPG<u>MWNDE</u>HC | Revelle et al. (1996) | 258 |
|  | S97R | <u>CVEIYI</u>KRPSAPG<u>MWNDE</u>HC | Revelle et al. (1996) | 259 |
|  | REK | <u>CVEIYI</u>KREKAPG<u>MWNDE</u>HC | Revelle et al. (1996) | 260 |
|  | S99D | <u>CVEIYI</u>KSPDAPG<u>MWNDE</u>HC | Revelle et al. (1996) | 261 |
| CHL | V191A | <u>CAHVW</u>TSG<u>QWNDA</u>YC | Burrows et al. (1997) | 262 |
|  | Y192A | <u>CAHVW</u>TSG<u>QWNDV</u>AC | Burrows et al. (1997) | 263 |

2C: Other TN CTLD derivatives

| CTLD | Mut. | TN sequence (one letter-code) | Reference | SEQ ID NO |
|---|---|---|---|---|
| hTN | TNR169A | SGAANGKWFDKRCADQ | Graversen et al. (1998) | 264 |
|  | TNS85G | CISRGGTLGTPQT | Jaquinod et al. (1999) | 265 |

Notes:
hTN: human tetranectin;
rMBP: rat mannose binding protein,
rSP-A: rat surfactant protein-A,
hSP-A: human surfactant protein-A,
rSP-D: rat surfactant protein-D;
h-esl: human e-selectin;
h-psl: human p-selectin;
MGR: macrophage galactose receptor;
RHL: rat hepatic lectin,
CHL: chicken hepatic lectin?

Normally the model CTLD is defined by having a 3D structure that conforms to the secondary-structure arrangement illustrated in FIG. 1 characterized by the following main secondary structure elements:

five β-strands and two a-helices sequentially appearing in the order β1, α1, α2, β2, β3, β4, and β5, the β-strands being arranged in two anti-parallel β-sheets, one composed of β1 and β5, the other composed of β2, β3 and β4, at least two disulfide bridges, one connecting α1 and β5 and one connecting β3 and the polypeptide segment connecting β4 and β5, a loop region consisting of two polypeptide segments, loop segment A (LSA) connecting β2 and β3 and comprising typically 15-70 or, less typically, 5-14 amino acid residues, and loop segment B (LSB) connecting β3 and β4 and comprising typically 5-12 or less typically, 2-4 amino acid residues.

However, also a CTLD, for which no precise 3D structure is available, can be used as a model CTLD, such CTLD being defined by showing sequence similarity to a previously recognised member of the CTLD family as expressed by an amino acid sequence identity of at least 22%, preferably at least 25% and more preferably at least 30%, and by containing the cysteine residues necessary for establishing the conserved two-disulfide bridge topology (i.e. $Cys_I$, $Cys_{II}$, $Cys_{III}$ and $Cys_{IV}$). The loop region, consisting of the loop segments LSA and LSB, and its flanking N-strand structural elements can then be identified by inspection of the sequence alignment with the collection of CTLDs shown in FIG. 1, which provides identification of the sequence locations of the β2- and β3-strands with the further corroboration provided by comparison of these sequences with the four-residue consensus sequences, β2cseq and β3cseq, and the β4 strand segment located typically at positions −6 to −2 and less typically at positions −5 to −2 relative to the conserved $Cys_{III}$ residue and with the characteristic residues at positions −5 and −3 as elucidated from Table 1 and deducted above under BACKGROUND OF THE INVENTION.

The same considerations apply for determining whether in a model CTLD the α-helices and β-strands and connecting segments are conserved to such a degree that the scaffold structure of the CTLD is substantially maintained.

It may be desirable that up to 10, preferably up to 4, and more preferably 1 or 2, amino acid residues are substituted, deleted or inserted in the α-helices and/or β-strands and/or connecting segments of the model CTLD. In particular, changes of up to 4 residues may be made in the β-strands of the model CTLD as a consequence of the introduction of recognition sites for one or more restriction endonucleases in the nucleotide sequence encoding the CTLD to facilitate the excision of part or all of the loop region and the insertion of an altered amino acid sequence instead while the scaffold structure of the CTLD is substantially maintained.

Of particular interest are proteins wherein the model CTLD is that of a tetranectin. Well known tetranectins the CTLDs of which can be used as model CTLDs are human tetranectin and murine tetranectin. The proteins according to the invention thus comprise variants of such model CTLDs.

The proteins according to the invention may comprise N-terminal and/or C-terminal extensions of the CTLD variant, and such extensions may for example contain effector, enzyme, further binding and/or multimerising functions. In particular, said extension may be the non-CTLD-portions of a native C-type lectin-like protein or C-type lectin or a "soluble" variant thereof lacking a functional transmembrane domain.

The proteins according to the invention may also be multimers of a moiety comprising the CTLD variant, e.g. derivatives of the native tetranectin trimer.

In a preferred aspect the present invention provides a combinatorial library of proteins having the scaffold structure of C-type lectin-like domains (CTLD), said proteins comprising variants of a model CTLD wherein the α-helices and β-strands are conserved to such a degree that the scaffold structure of the CTLD is substantially maintained, while the loop region or parts of the loop region of the CTLD is randomised with respect to amino acid sequence and/or number of amino acid residues.

The proteins making up such a library comprise variants of model CTLDs defined as for the above proteins according to the invention, and the variants may include the changes stated for those proteins.

In particular, the combinatorial library according to the invention may consist of proteins wherein the model CTLD is that of a tetranectin, e.g. that of human tetranectin or that of murine tetranectin.

The combinatorial library according to the invention may consist of proteins comprising N-terminal and/or C-terminal extensions of the CTLD variant, and such extensions may for example contain effector, enzyme, further binding and/or multimerising functions. In particular, said extensions may be the non-CTLD-portions of a native C-type lectin-like protein or C-type lectin or a "soluble" variant thereof lacking a functional transmembrane domain.

The combinatorial library according to the invention may also consist of proteins that are multimers of a moiety comprising the CTLD variant, e.g. derivatives of the native tetranectin trimer.

The present invention also provides derivatives of a native tetranectin wherein up to 10, preferably up to 4, and more preferably 1 or 2, amino acid residues are substituted, deleted or inserted in the x-helices and/or β-strands and/or connecting segments of its CTLD as well as nucleic acids encoding such derivatives. Specific derivatives appear from SEQ ID Nos: 02, 04, 09, 11, 13, 15, 29, 31, 36, and 38; and nucleic acids comprising nucleotide inserts encoding specific tetranectin derivatives appear from SEQ ID Nos: 12, 14, 35, and 37.

The invention comprises a method of constructing a tetranectin derivative adapted for the preparation of a combinatorial library according to the invention, wherein the nucleic acid encoding the tetranectin derivative has been modified to generate endonuclease restriction sites within nucleic acid segments encoding β2, β3 or β4, or up to 30 nucleotides upstream or downstream in the sequence from any nucleotide which belongs to a nucleic acid segment encoding β2, β3 or β4.

The invention also comprises the use of a nucleotide sequence encoding a tetranectin, or a derivative thereof wherein the scaffold structure of its CTLD is substantially maintained, for preparing a library of nucleotide sequences encoding related proteins by randomising part or all of the nucleic acid sequence encoding the loop region of its CTLD.

Further, the present invention provides nucleic acid comprising any nucleotide sequence encoding a protein according to the invention.

In particular, the invention provides a library of nucleic acids encoding proteins of a combinatorial library according to the invention, in which the members of the ensemble of nucleic acids, that collectively constitute said library of nucleic acids, are able to be expressed in a display system, which provides for a logical, physical or chemical link between entities displaying phenotypes representing properties of the displayed expression products and their corresponding genotypes.

In such a library the display system may be selected from
(I) a phage display system such as
  (1) a filamentous phage fd in which the library of nucleic acids is inserted into
    (a) a phagemid vector,
    (b) the viral genome of a phage
    (c) purified viral nucleic acid in purified single- or double-stranded form, or
  (2) a phage lambda in which the library is inserted into
    (a) purified phage lambda DNA, or
    (b) the nucleic acid in lambda phage particles; or
(II) a viral display system in which the library of nucleic acids is inserted into the viral nucleic acid of a eukaryotic virus such as baculovirus; or
(III) a cell-based display system in which the library of nucleic acids is inserted into, or adjoined to, a nucleic acid carrier able to integrate either into the host genome or into an extrachromosomal element able to maintain and express itself within the cell and suitable for cell-surface display on the surface of
  (a) bacterial cells,
  (b) yeast cells, or
  (c) mammalian cells; or
(IV) a nucleic acid entity suitable for ribosome linked display into which the library of nucleic acid is inserted; or
(V) a plasmid suitable for plasmid linked display into which the library of nucleic acid is inserted.

A well-known and useful display system is the "Recombinant Phage Antibody System" with the phagemid vector "pCANTAB 5E" supplied by Amersham Pharmacia Biotech (code no. 27-9401-01).

Further, the present invention provides a method of preparing a protein according to the invention, wherein the protein comprises at least one or more, identical or not identical, CTLD domains with novel loop-region sequences which has (have) been isolated from one or more CTLD libraries by screening or selection. At least one such CTLD domain may have been further modified by mutagenesis; and the protein containing at least one CTLD domain may have been assembled from two or more components by chemical or enzymatic coupling or crosslinking.

Also, the present invention provides a method of preparing a combinatorial library according to the invention comprising the following steps:
1) inserting nucleic acid encoding a protein comprising a model CTLD into a suitable vector,
2) if necessary, introducing restriction endonuclease recognition sites by site directed mutagenesis, said recognition sites being properly located in the sequence at or close to the ends of the sequence encoding the loop region of the CTLD or part thereof, 3) excising the DNA fragment encoding the loop region or part thereof by use of the proper restriction endonucleases,
4) ligating mixtures of DNA fragments into the restricted vector, and
5) inducing the vector to express randomised proteins having the scaffold structure of CTLDs in a suitable medium.

In a further aspect, the present invention provides a method of screening a combinatorial library according to the invention for binding to a specific target which comprises the following steps:
1) expressing a nucleic acids library to display the library of proteins in the display system;
2) contacting the collection of entities displayed with a suitably tagged target substance for which isolation of a CTLD-derived exhibiting affinity for said target substance is desired;
3) harvesting subpopulations of the entities displayed that exhibit affinity for said target substance by means of affinity-based selective extractions, utilizing the tag to which said target substance is conjugated or physically attached or adhering to as a vehicle or means of affinity purification, a procedure commonly referred to in the field as "affinity panning", followed by re-amplification of the sub-library;
4) isolating progressively better binders by repeated rounds of panning and re-amplification until a suitably small number of good candidate binders is obtained; and,
5) if desired, isolating each of the good candidates as an individual clone and subjecting it to ordinary functional and structural characterisation in preparation for final selection of one or more preferred product clones.

In a still further aspect, the present invention provides a method of reformatting a protein according to the invention or selected from a combinatorial library according to the invention and containing a CTLD variant exhibiting desired binding properties, in a desired alternative species-compatible framework by excising the nucleic acid fragment encoding the loop region-substituting polypeptide and any required single framework mutations from the nucleic acid encoding said protein using PCR technology, site directed mutagenesis or restriction enzyme digestion and inserting said nucleic acid fragment into the appropriate location(s) in a display- or protein expression vector that harbours a nucleic acid sequence encoding the desired alternative CTLD framework.

BRIEF DESCRIPTION OF THE DRAWINGS

FIG. 1 shows an alignment of the amino acid sequences of ten CTLDs of known 3D-structure. The sequence locations of main secondary structure elements are indicated above each sequence, labelled in sequential numerical order as "αN", denoting a α-helix number N, and "βM", denoting β-strand number M.

The four cysteine residues involved in the formation of the two conserved disulfide bridges of CTLDs are indicated and enumerated in the Figure as "$C_I$", "$C_{II}$", "$C_{III}$" and "$C_{IV}$" respectively. The two conserved disulfide bridges are $C_I$-$C_{IV}$ and $C_{II}$-$C_{III}$, respectively.

The ten C-type lectins are
hTN: human tetranectin [Nielsen et al. (1997)];
MBP: mannose binding protein [Weis et al. (1991); Sheriff et al. (1994)];
SP-D: surfactant protein D [Hakansson et al. (1999)];
LY49A: NK receptor LY49A [Tormo et al. (1999)];
H1-ASR: H1 subunit of the asialoglycoprotein receptor [Meier et al. (2000)];
MMR-4: macrophage mannose receptor domain 4 [Feinberg et al. (2000)];
IX-A and IX-B: coagulation factors IX/X-binding protein domain A and B. respectively [Mizuno et al. (1997)];
Lit: lithostatine [Bertrand et al. (1996)];
TU14: tunicate C-type lectin [Poget et al. (1999)].

Figure 2:
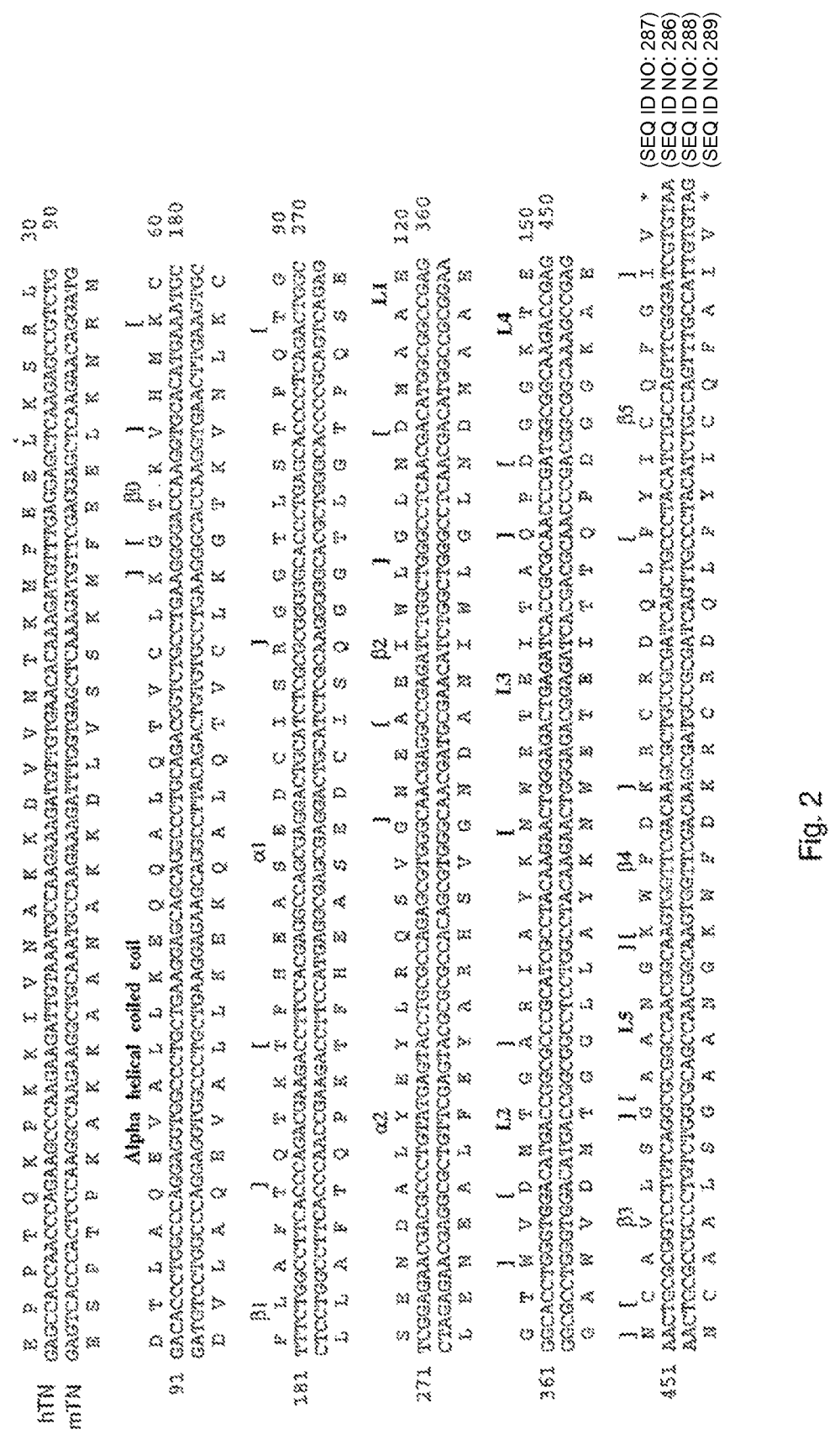

FIG. 2 shows an alignment of the nucleotide and amino acid sequences of the coding regions of the mature forms of human and murine tetranectin with an indication of known secondary structural elements.
hTN: human tetranectin; nucleotide sequence from Berglund and Petersen (1992).
mTN: murine tetranectin; nucleotide sequence from Sørensen et al. (1995).
Secondary structure elements from Nielsen et al. (1997). "α" denotes an α-helix; "β" denotes a β-strand; and "L" denotes a loop.

Figure 3:
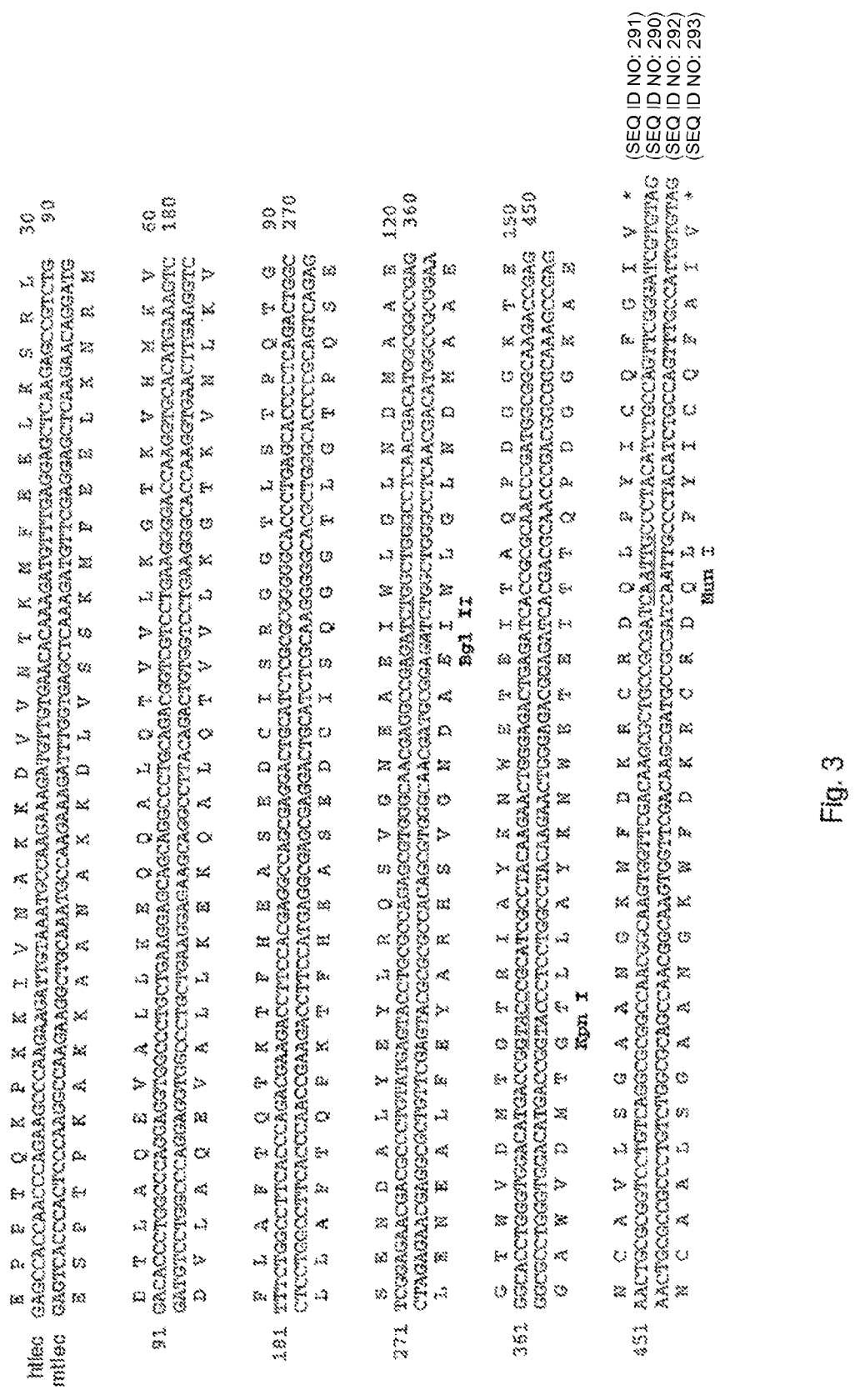

FIG. 3 shows an alignment of the nucleotide and amino acid sequences of human and murine tlec coding regions. htlec: the sequence derived from hTN; mtlec: the sequence derived from mTN. The position of the restriction endonuclease sites for Bgl II, Kpn I, and Mun I are indicated.

FIG. 4 shows an alignment of the nucleotide and amino acid sequences of human and murine tCTLD coding regions. htCTLD: the sequence derived from hTN; mtCTLD: the sequence derived from mTN. The position of the restriction endonuclease sites for Bgl II, Kpn I, and Mun I are indicated.

FIG. 5 shows an outline of the pT7H6FX-htlec expression plasmid. The FX-htlec fragment was inserted into pT7H6 [Christensen et al. (1991)] between the Bam HI and Hind III cloning sites.

FIG. 6 shows the amino acid sequence (one letter code) of the FX-htlec part of the H6FX-htlec fusion protein produced by pT7H6FX-htlec.

Figure 7:
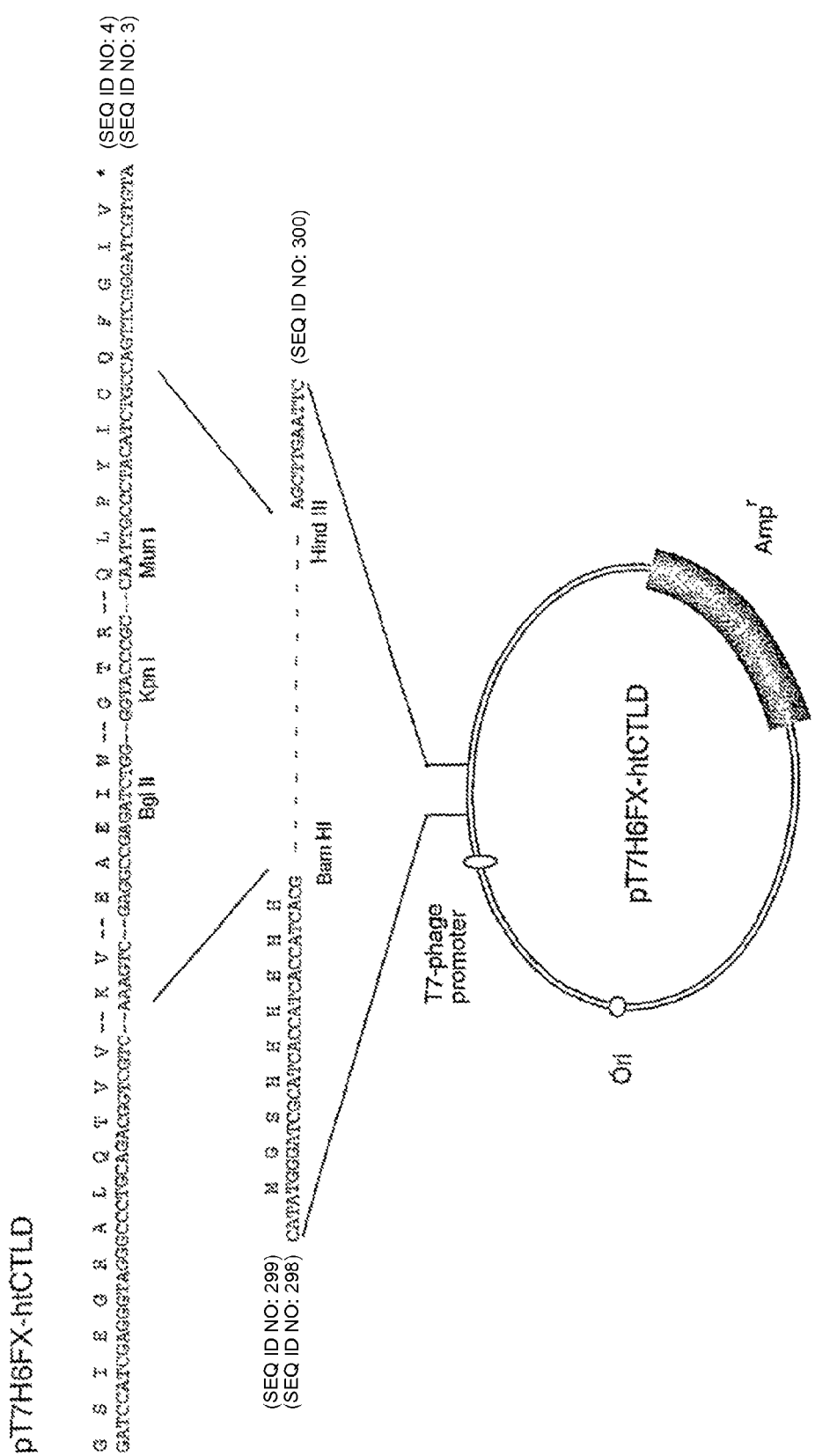

FIG. 7 shows an outline of the pT7H6FX-htCTLD expression plasmid. The FX-htCTLD fragment was inserted into pT7H6 [Christensen et al. (1991)] between the Bam HI and Hind III cloning sites.

FIG. 8 shows the amino acid sequence (one letter code) of the FX-htCTLD part of the H6FX-htCTLD fusion protein produced by pT7H6FX-htCTLD.

Figure 9:
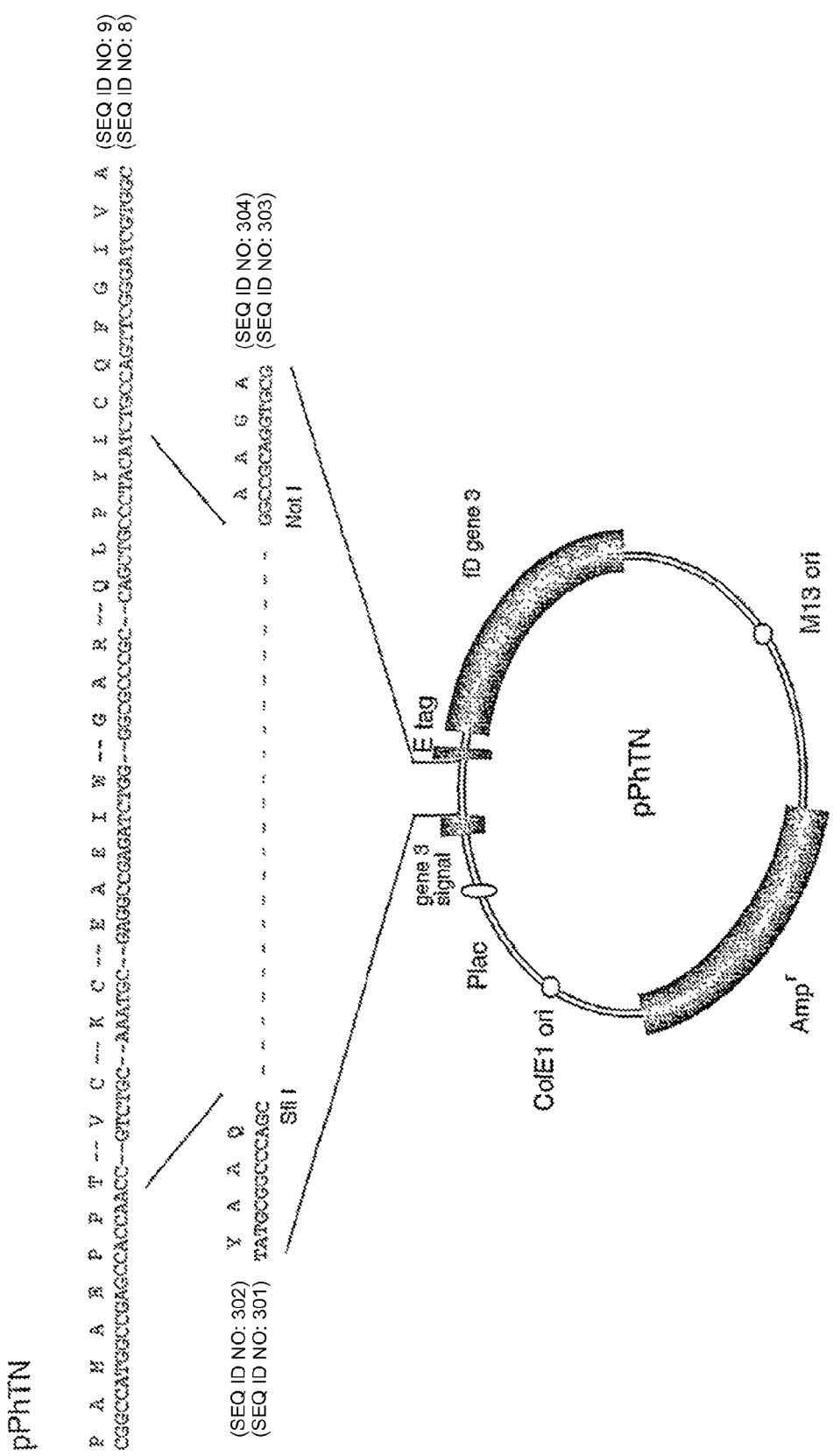

FIG. 9 shows an outline of the pPhTN phagemid. The PhTN fragment was inserted into the phagemid pCANTAB 5E (Amersham Pharmacia Biotech, code no. 27-9401-01) between the Sfi I and Not I restriction sites.

FIG. 10 shows the amino acid sequence (one letter code) of the PhTN part of the PhTN-gene III fusion protein produced by pPhTN.

Figure 11:
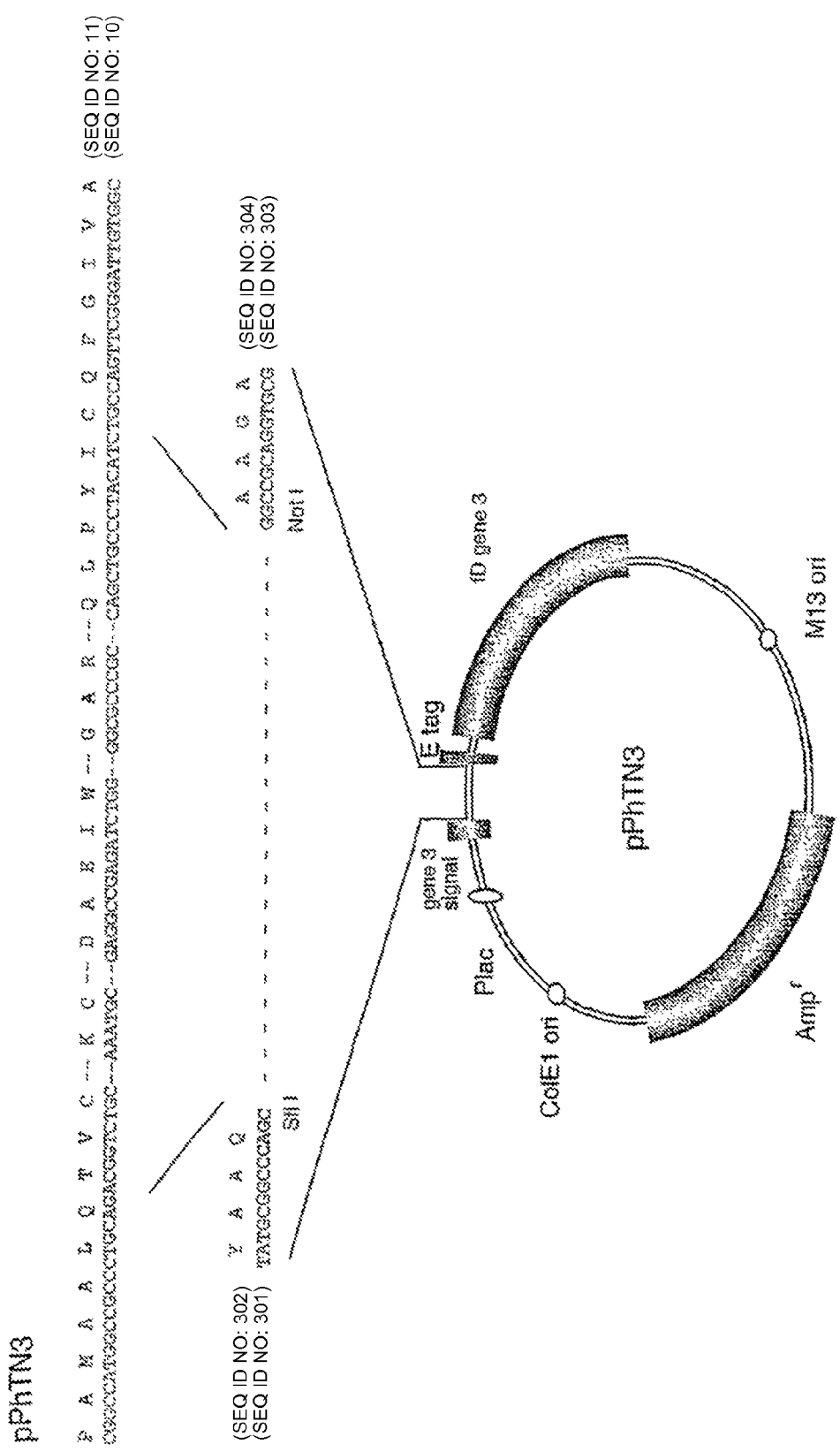

FIG. 11 shows an outline of the pPhTN3 phagemid. The PhTN3 fragment was inserted into the phagemid pCANTAB 5E (Amersham Pharmacia Biotech, code no. 27-9401-01) between the Sfi I and Not I restriction sites.

FIG. 12 shows the amino acid sequence (one letter code) of the PhTN3 part of the PhTN3-gene III fusion protein produced by pPhTN3.

Figure 13:
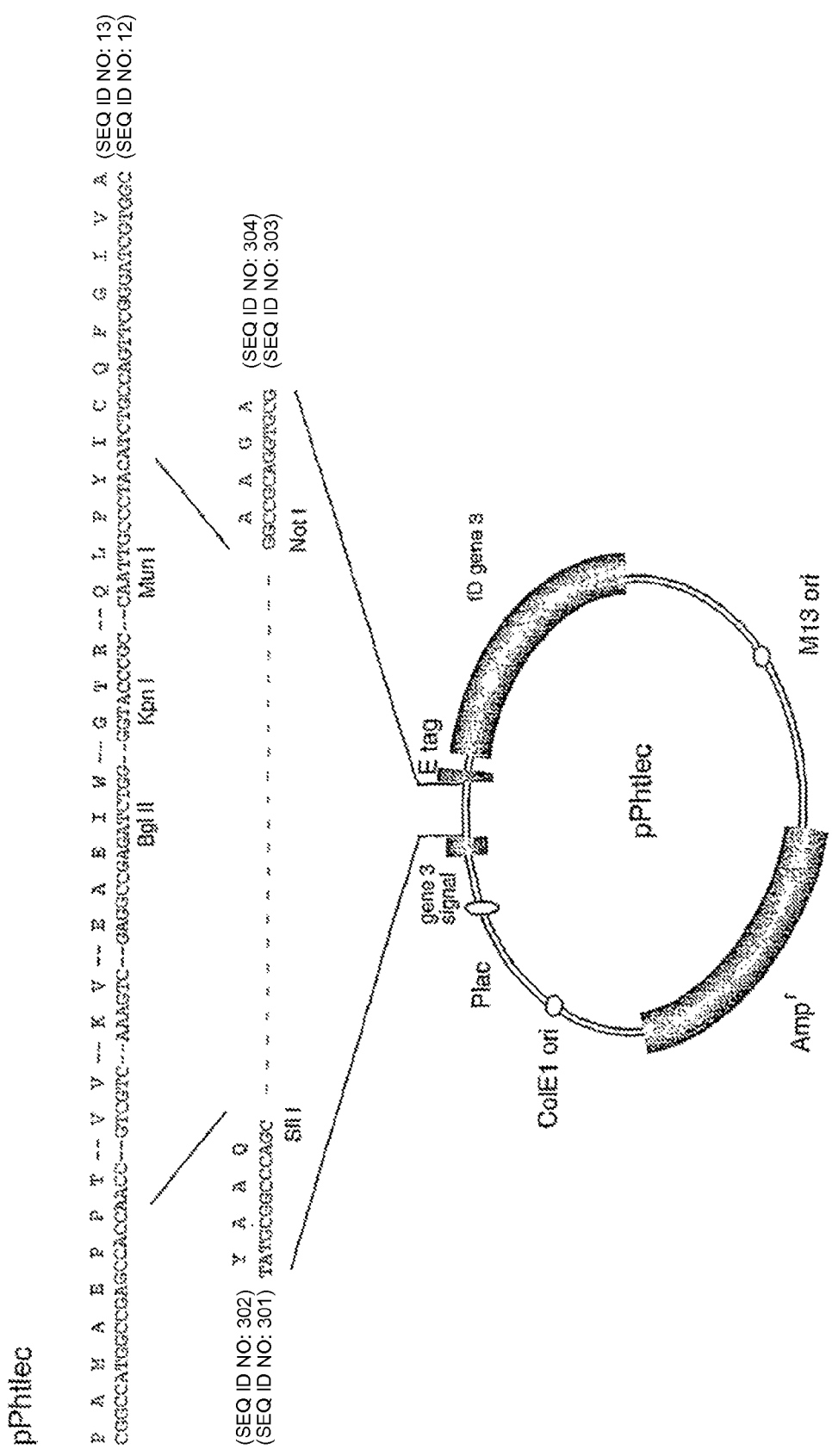

FIG. 13 shows an outline of the pPhtlec phagemid. The Phtlec fragment was inserted into the phagemid pCANTAB 5E (Amersham Pharmacia Biotech, code no. 27-9401-01) between the Sfi I and Not I restriction sites.

FIG. 14 shows the amino acid sequence (one letter code) of the Phtlec part of the Phtlec-gene III fusion protein produced by pPhtlec.

Figure 15:
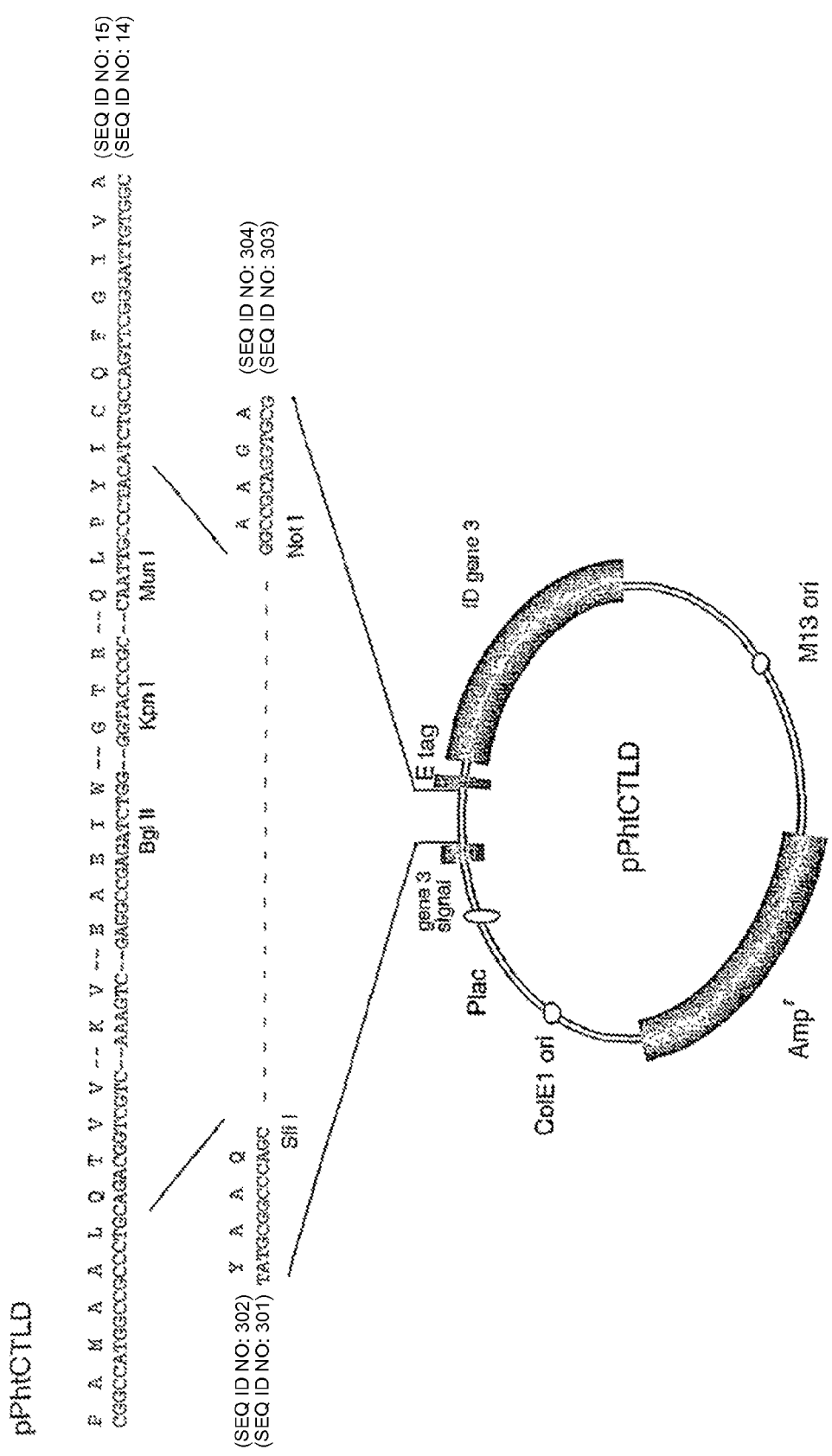

FIG. 15 shows an outline of the pPhtCTLD phagemid. The PhtCTLD fragment was inserted into the phagemid PCANTAB 5E (Amersham Pharmacia Biotech, code no. 27-9401-01) between the Sfi I and Not I restriction sites.

FIG. 16 shows the amino acid sequence (one letter code) of the PhtCTLD part of the PhtCTLD-gene III fusion protein produced by pPhtCTLD.

Figure 17:
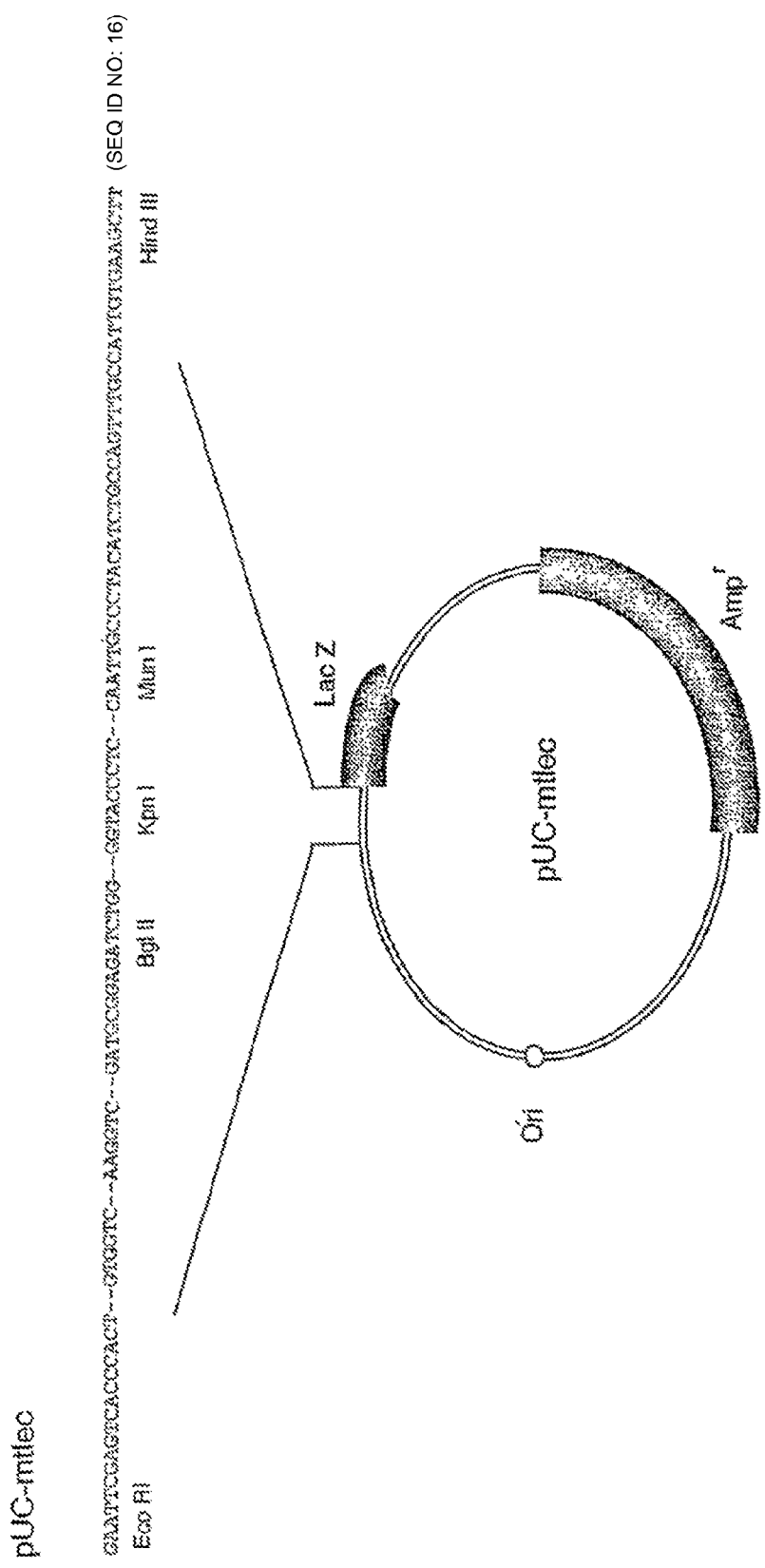

FIG. 17 shows an outline of the pUC-mtlec.

Figure 18:
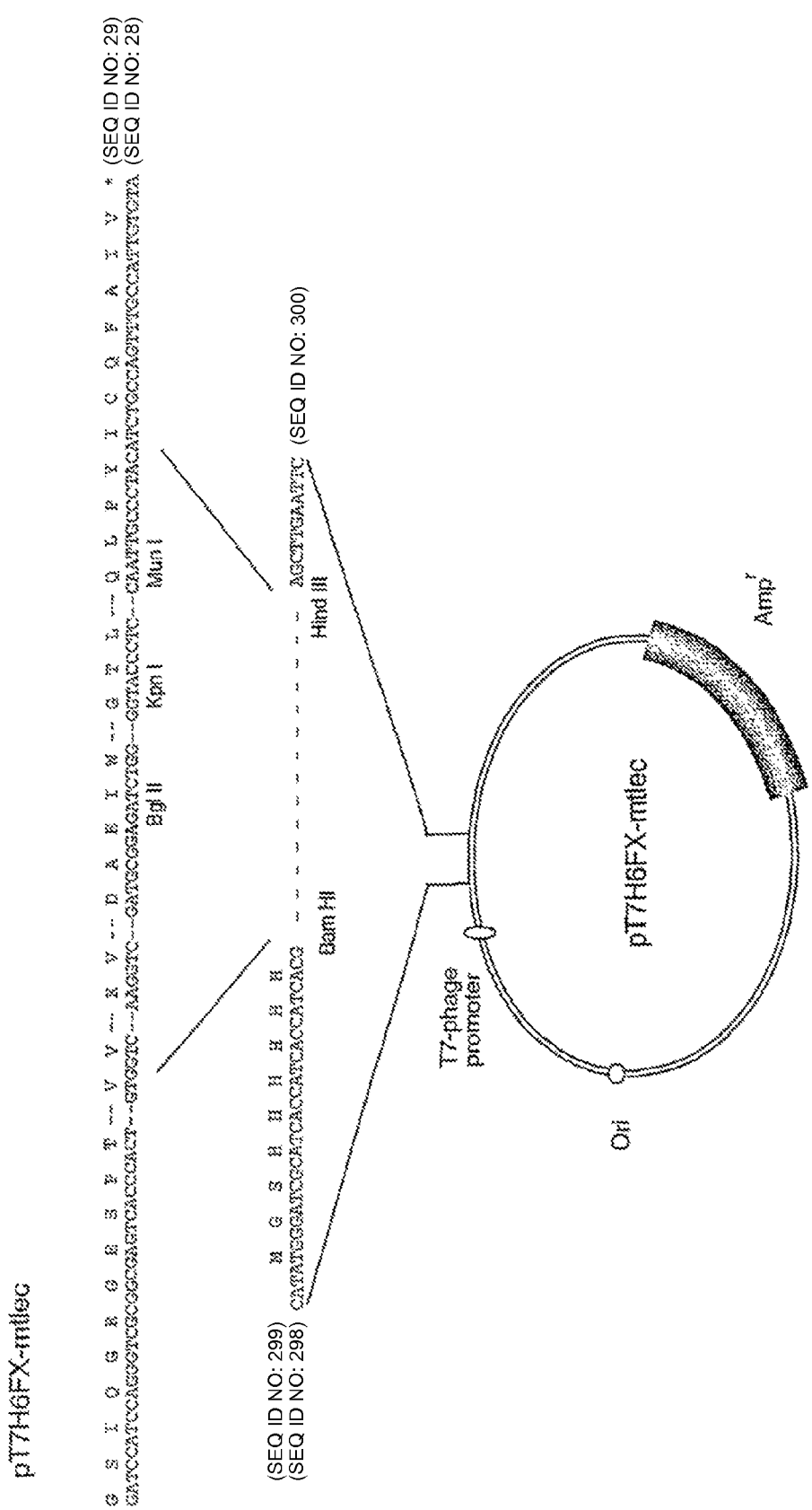

FIG. 18 shows an outline of the pT7H6FX-mtlec expression plasmid. The FX-mtlec fragment was inserted into pT7H6 [Christensen et al. (1991)] between the Bam HI and Hind III cloning sites.

FIG. 19 shows the amino acid sequence (one letter code) of the FX-mtlec part of the H6FX-mtlec fusion protein produced by pT7H6FX-mtlec.

Figure 20:
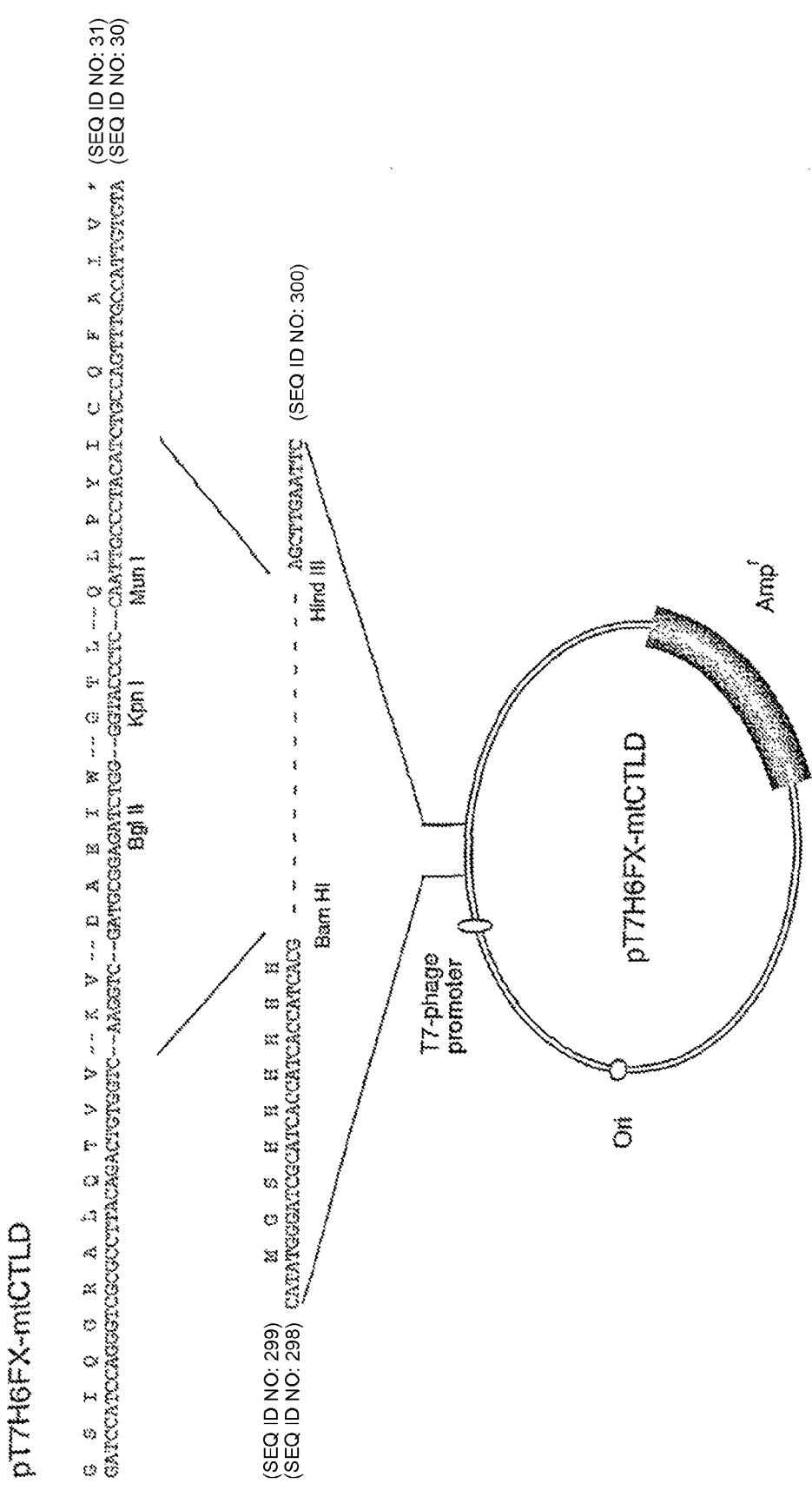

FIG. 20 shows an outline of the pT7H6FX-mtCTLD expression plasmid. The FX-mtCTLD fragment was inserted into pT7H6 [Christensen et al. (1991)] between the Bam HI and Hind III cloning sites.

FIG. 21 shows the amino acid sequence (one letter code) of the FX-mtCTLD part of the H6FX-mtCTLD fusion protein produced by pT7H6FX-mtCTLD.

Figure 22:
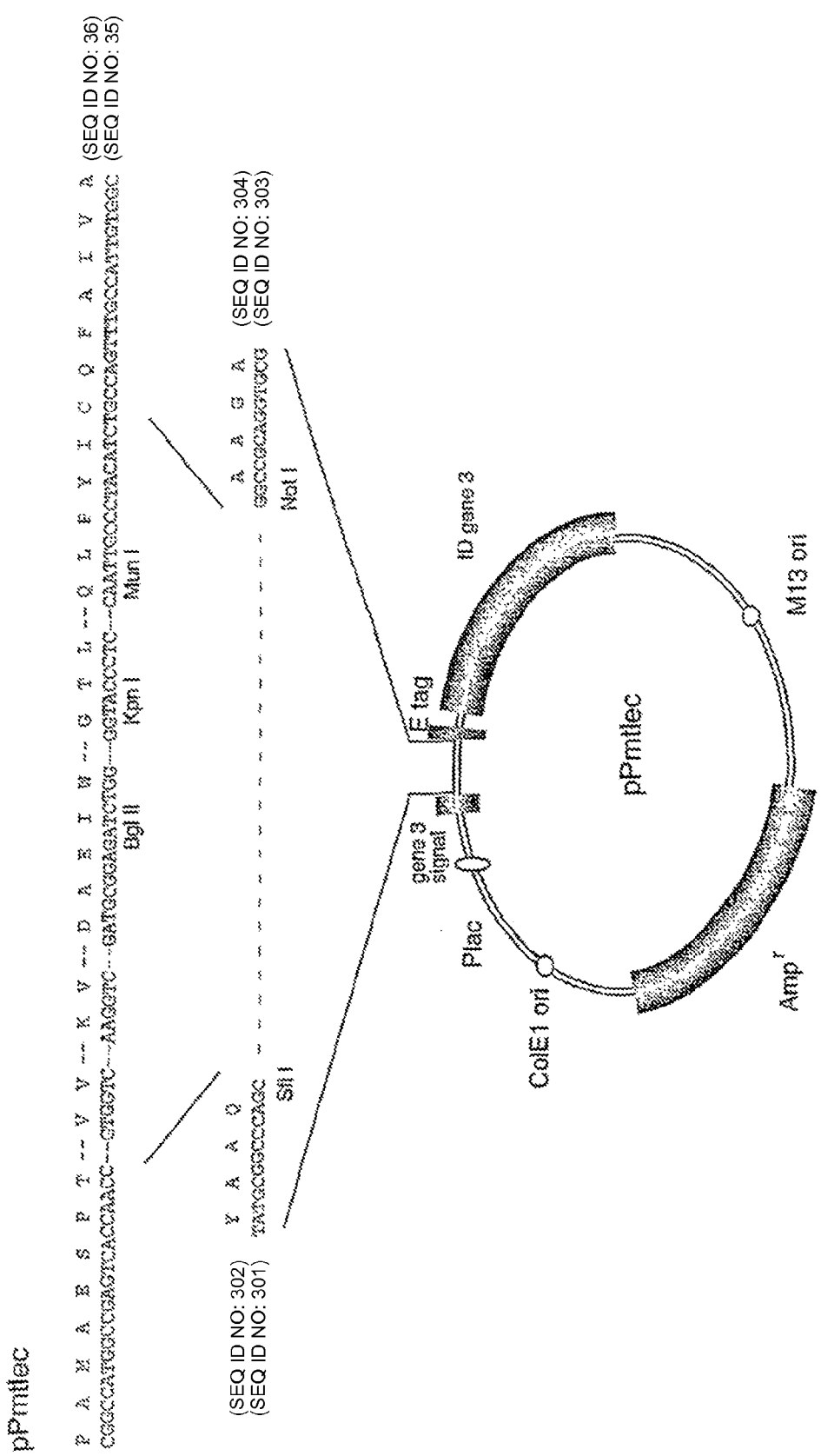

FIG. 22 shows an outline of the pPmtlec phagemid. The Pmtlec fragment was inserted into the phagemid pCANTAB 5E (Amersham Pharmacia Biotech, code no. 27-9401-01) between the Sfi I and Not I restriction sites.

FIG. 23 shows the amino acid sequence (one letter code) of the Pmtlec part of the Pmtlec-gene III fusion protein produced by pPmtlec.

Figure 24:
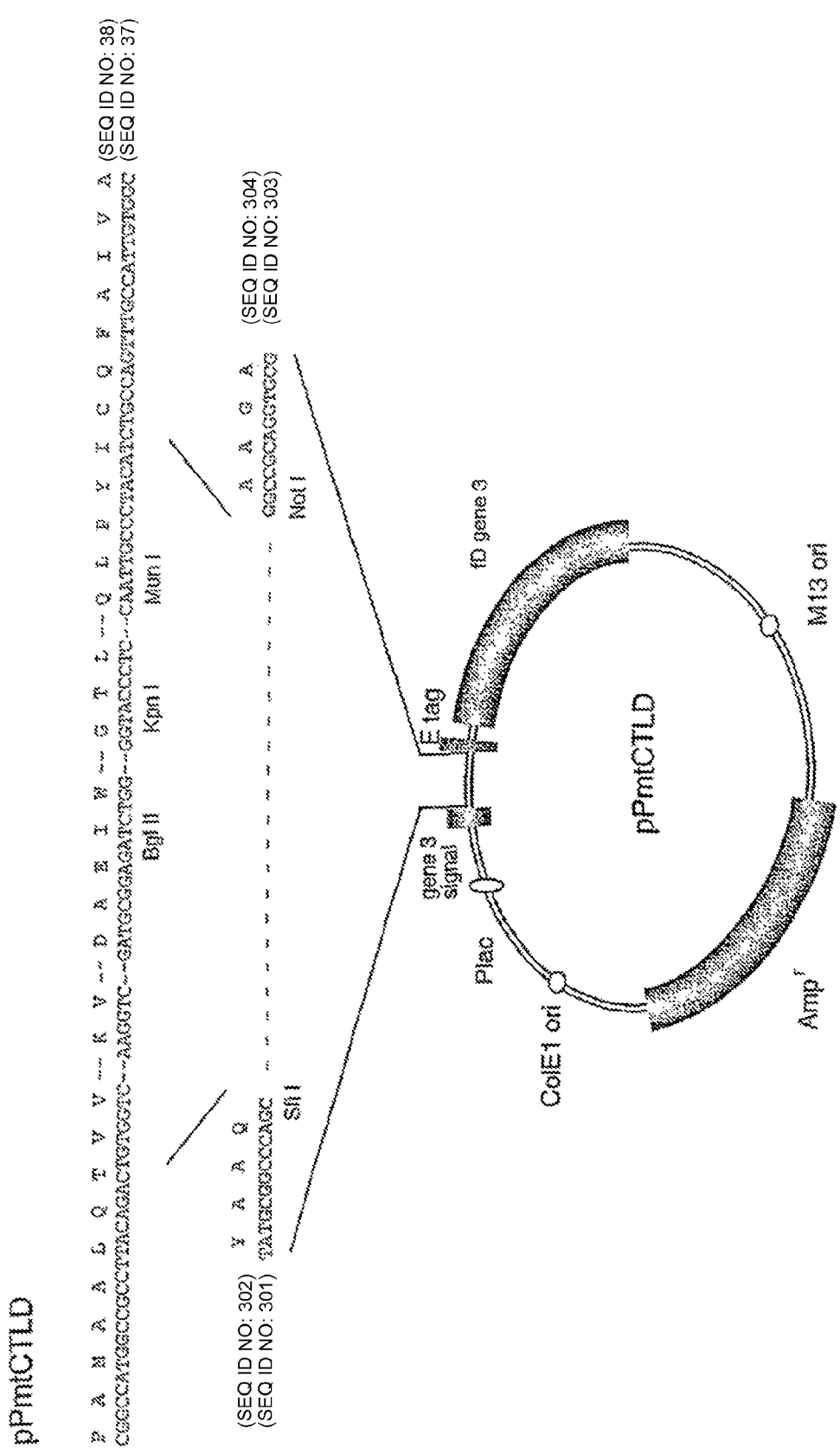

FIG. 24 shows an outline of the pPmtCTLD phagemid. The PmtCTLD fragment was inserted into the phagemid pCANTAB 5E (Amersham Pharmacia Biotech, code no. 27-9401-01) between the Sfi I and Not I restriction sites.

FIG. 25 shows the amino acid sequence (one letter code) of the PmtCTLD part of the PmtCTLD-gene III fusion protein produced by pPmtCTLD.

Figure 26:
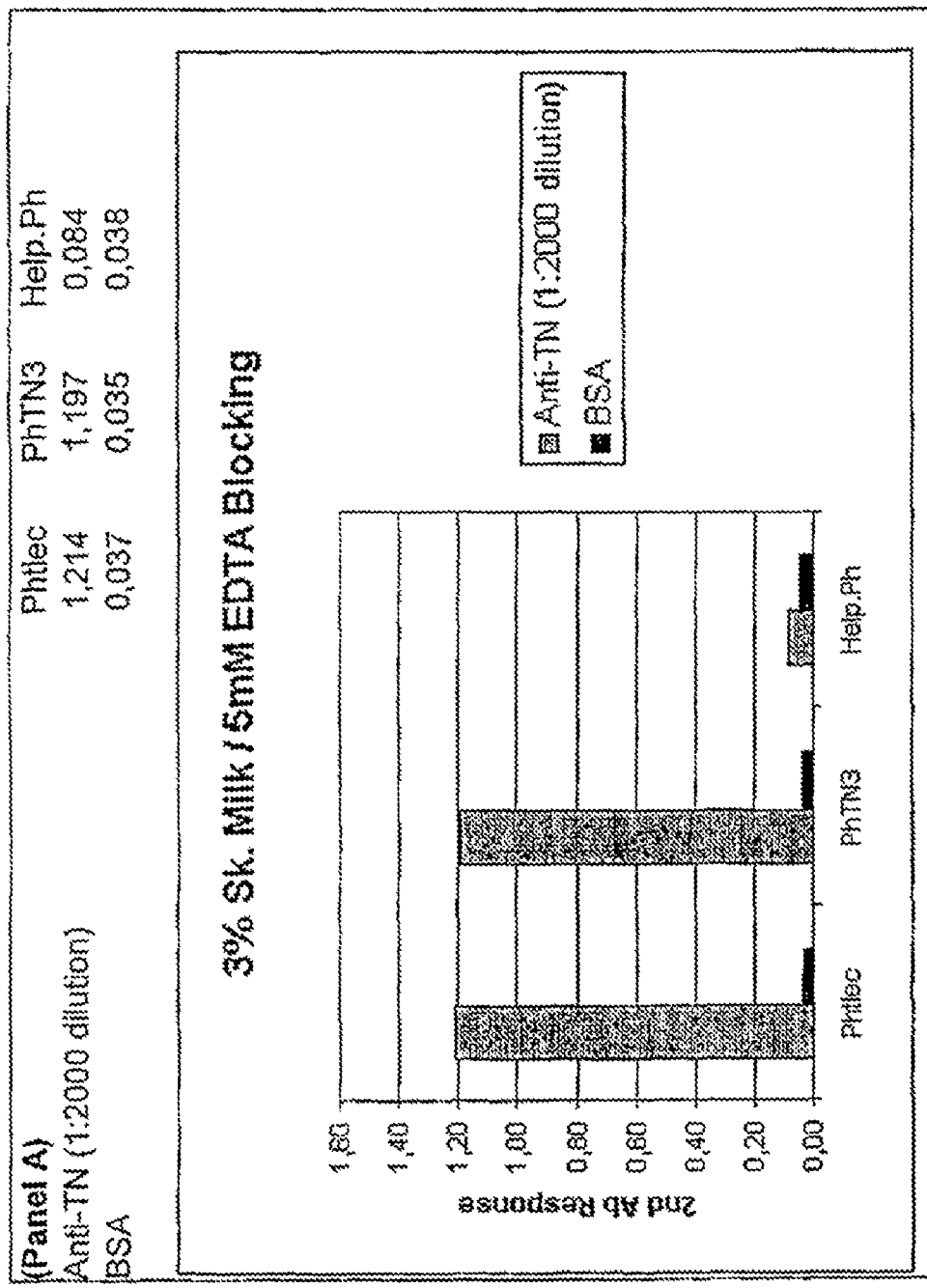
Figure 26:
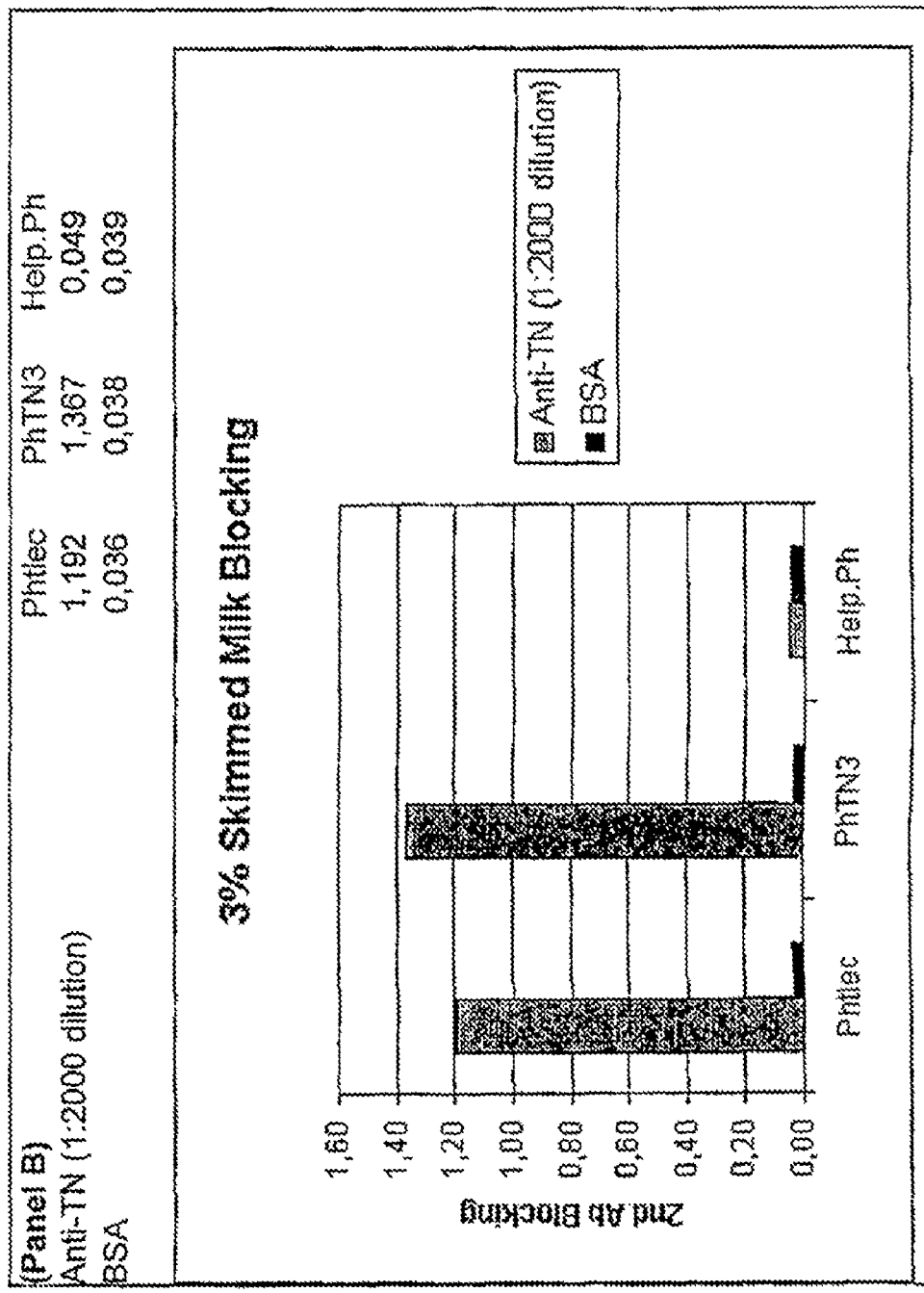

FIG. 26 shows an ELISA-type analysis of Phtlec-, PhTN3-, and M13KO7 helper phage binding to anti-tetranectin or BSA. Panel A: Analysis with 3% skimmed milk/5 mM EDTA as blocking reagent. Panel B: Analysis with 3% skimmed milk as blocking reagent.

Figure 27:
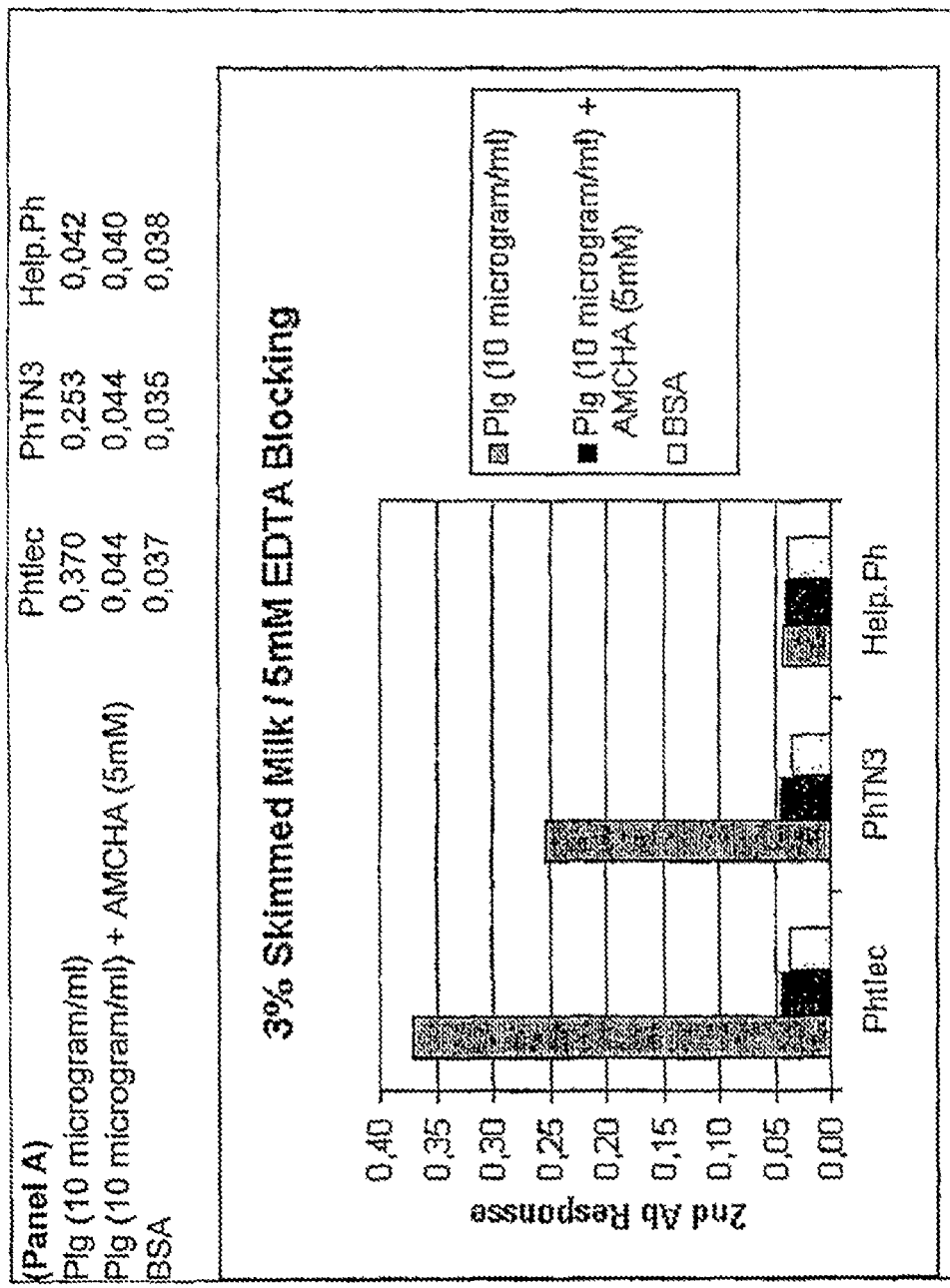
Figure 27:
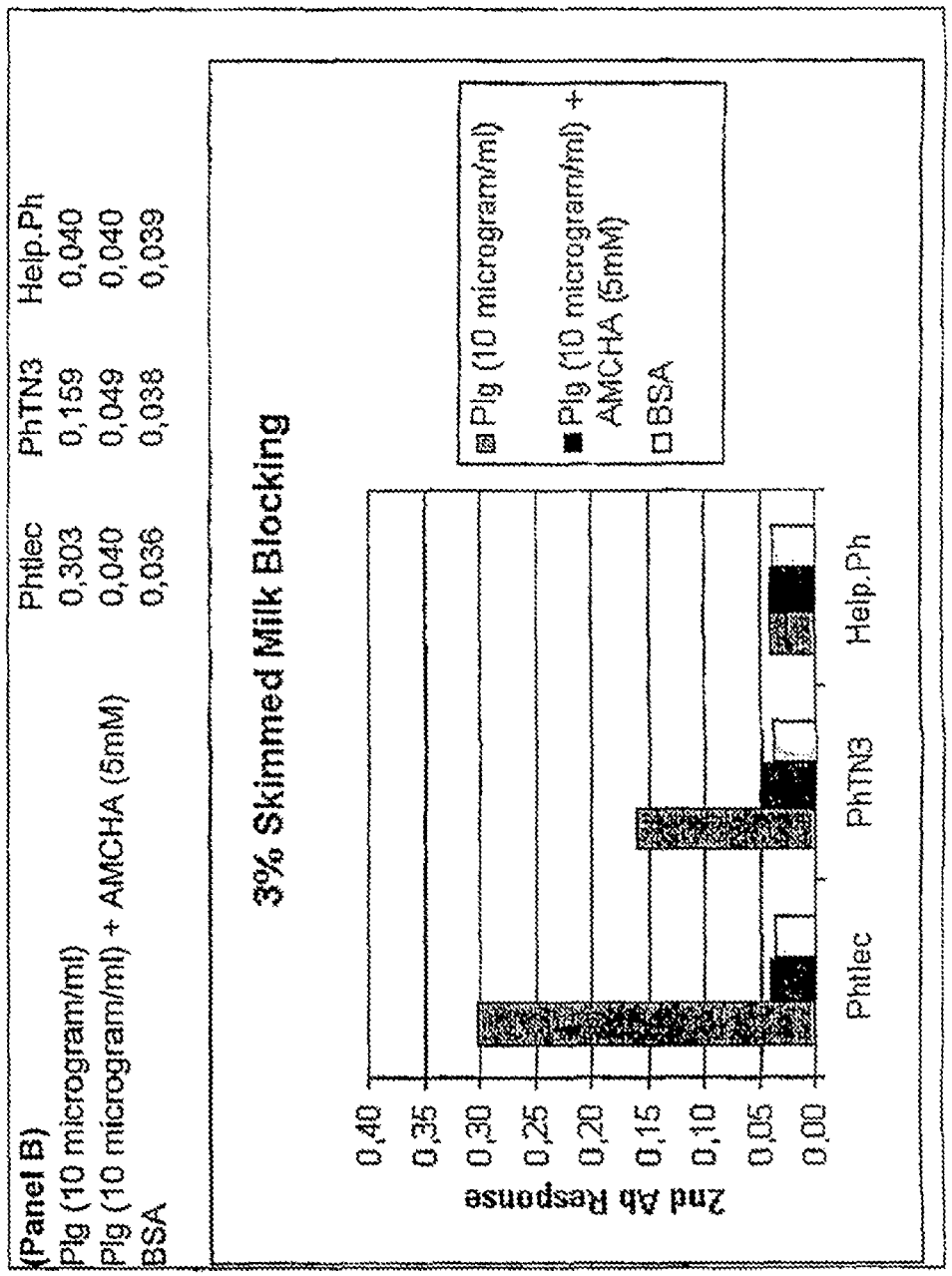

FIG. 27 shows an ELISA-type analysis of Phtlec-, PhTN3-, and M13KO7 helper phage binding to plasminogen (Plg) and BSA. Panel A: Analysis with 3% skimmed milk/5 mM EDTA as blocking reagent. Panel B: Analysis with 3% skimmed milk as blocking reagent.

Figure 28:
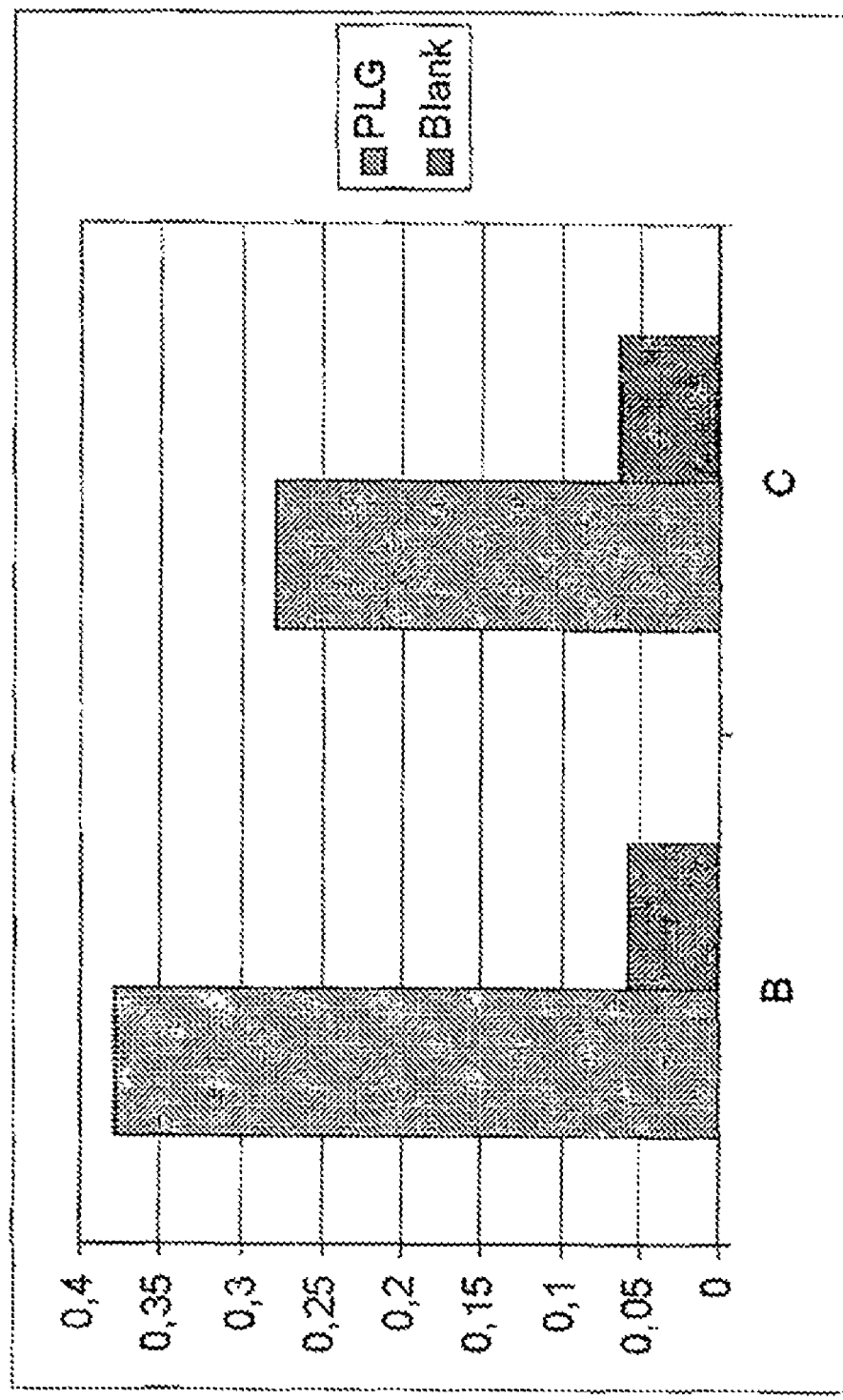

FIG. 28 shows an ELISA-type analysis of the B series and C series polyclonal populations, from selection round 2, binding to plasminogen (Plg) compared to background.

Figure 29:
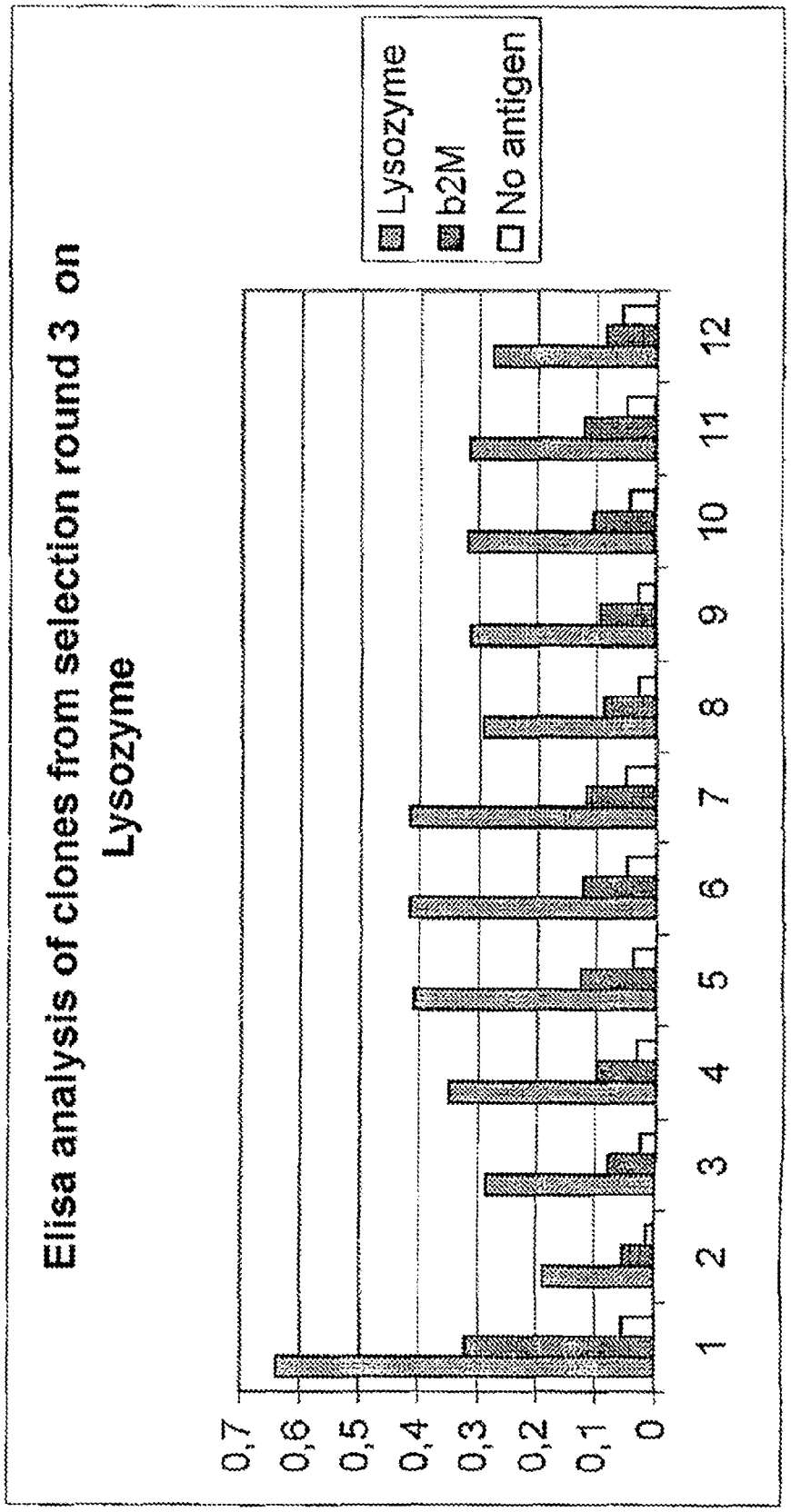

FIG. 29 Phages from twelve clones isolated from the third round of selection analysed for binding to hen egg white lysozyme, human $\beta_2$-microglobulin and background in an ELISA-type assay.

FIG. 30 shows the amino acid sequence (one letter code) of the PrMBP part of the PrMBP-gene III fusion protein produced by pPrMBP.

Figure 31:
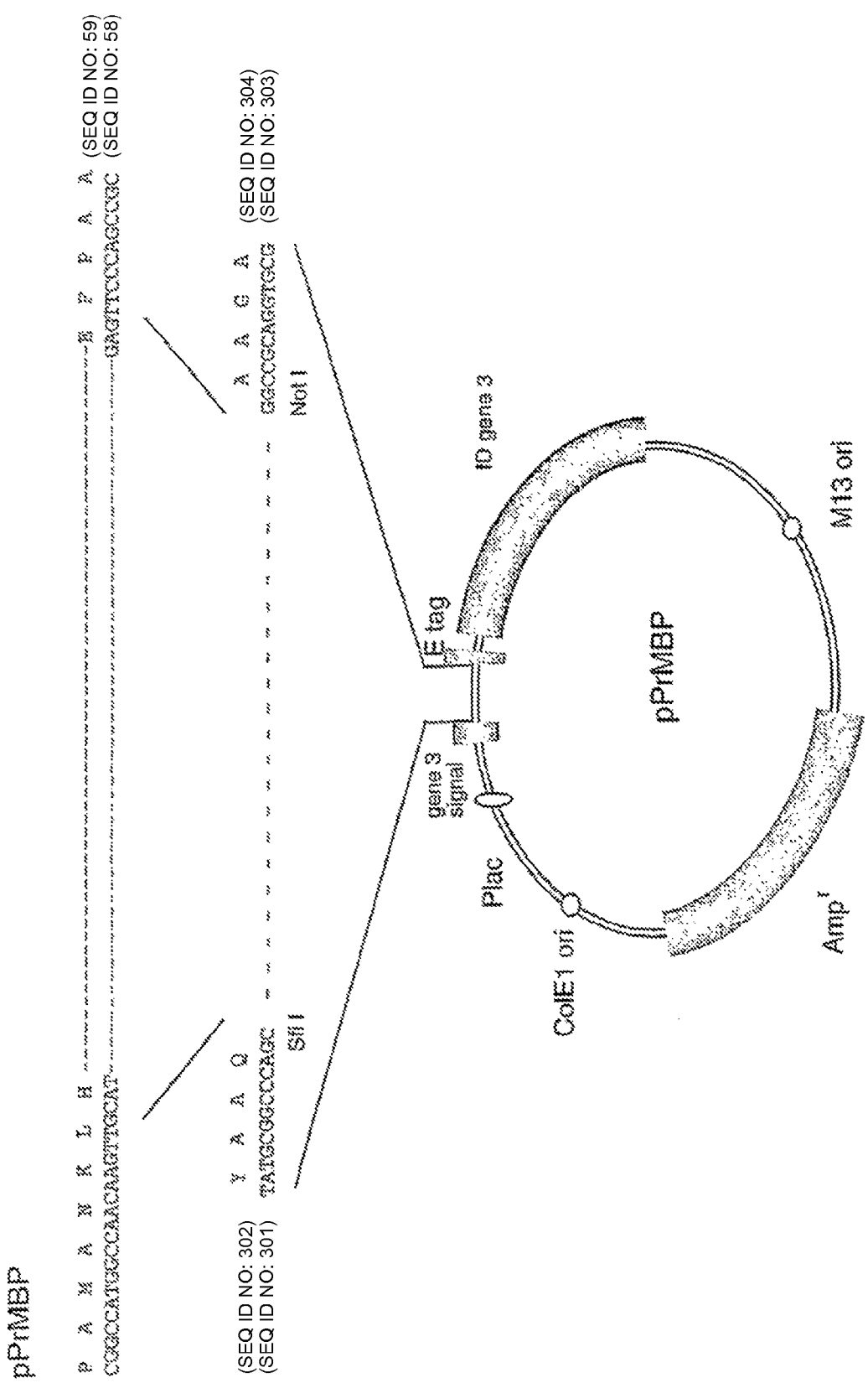

FIG. 31 shows an outline of the pPrMBP phagemid. The PrMBP fragment was inserted into the phagemid pCANTAB 5E (Amersham Pharmacia Biotech, code no. 27-9401-01) between the Sfi I and Not I restriction sites.

FIG. 32 shows the amino acid sequence (one letter code) of the PhSP-D part of the PhSP-D-gene III fusion protein produced by pPhSP-D.

Figure 33:
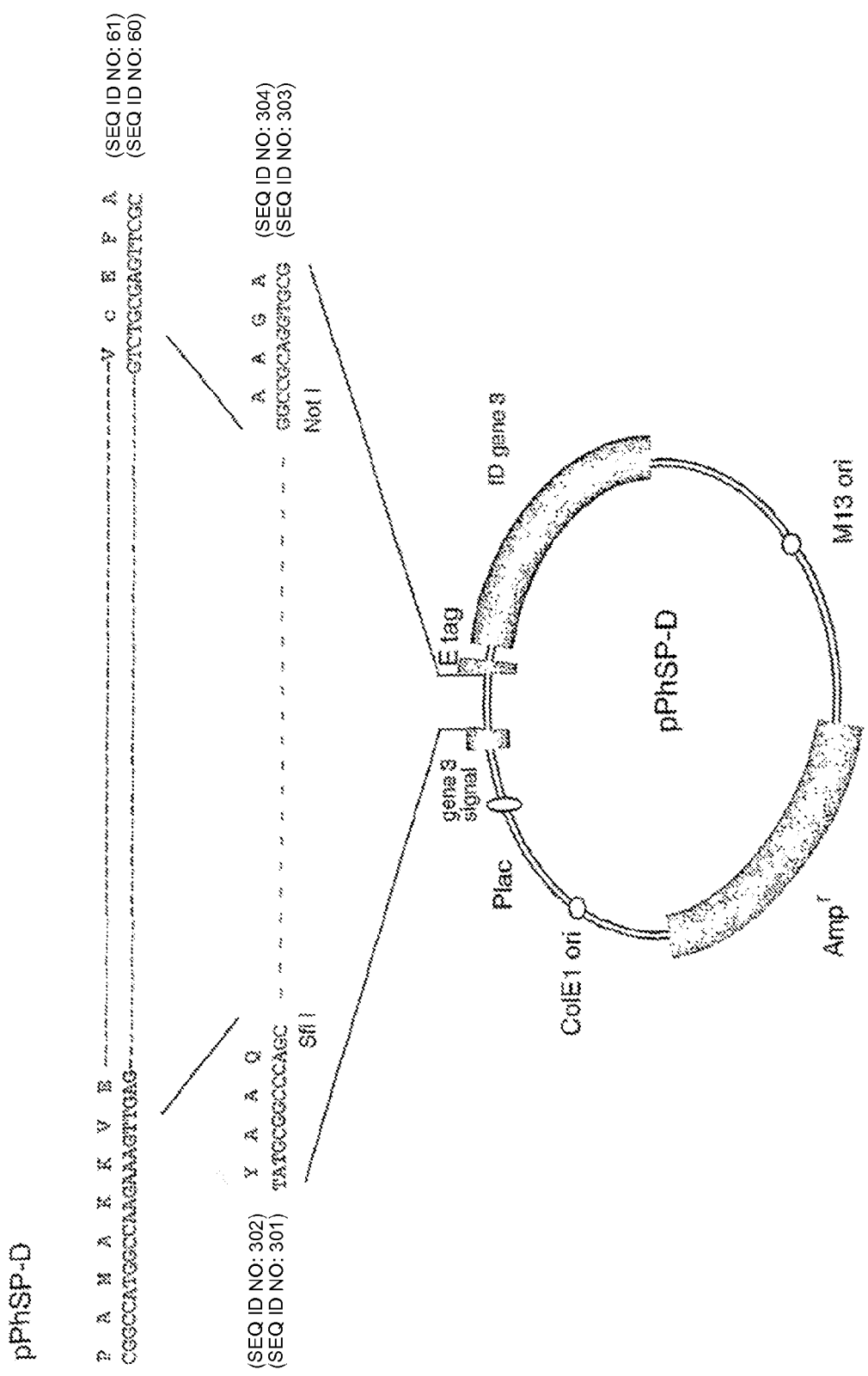

FIG. 33 shows an outline of the pPhSP-D phagemid. The PhSP-D fragment was inserted into the phagemid pCANTAB 5E (Amersham Pharmacia Biotech, code no. 27-9401-01) between the Sfi I and Not I restriction sites.

Figure 34:
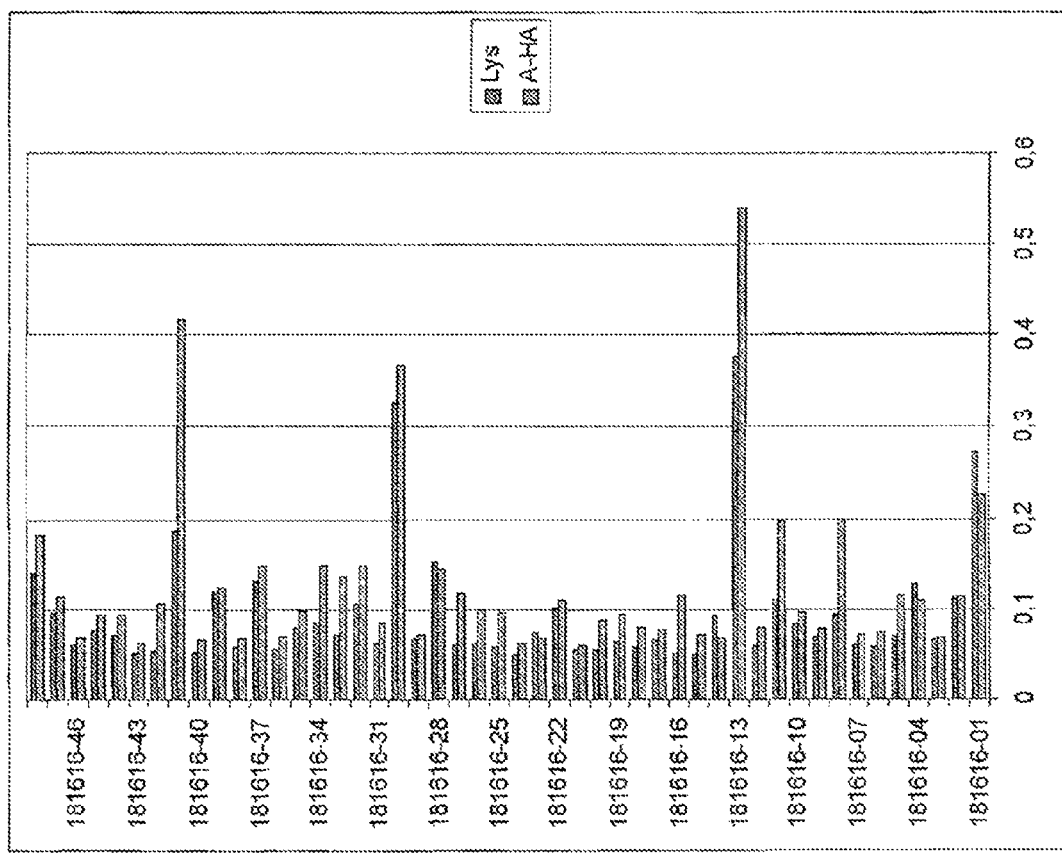

FIG. 34. Phages from 48 clones isolated from the third round of selection in the #1 series analysed for binding to hen egg white lysozyme and to A-HA in an ELISA-type assay.

Figure 35:
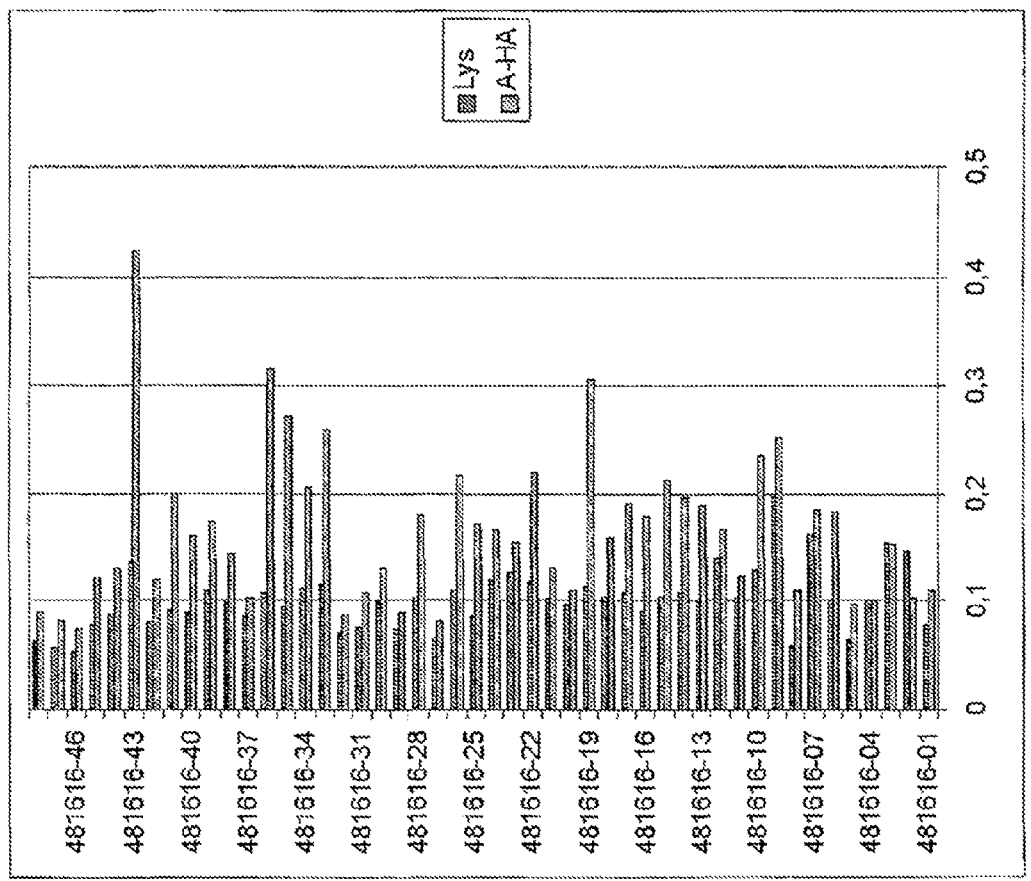

FIG. 35. Phages from 48 clones isolated from the third round of selection in the #4 series analysed for binding to hen egg white lysozyme and to A-HA in an ELISA-type assay.

DETAILED DESCRIPTION OF THE INVENTION

I. Definitions

The terms "C-type lectin-like protein" and "C-type lectin" are used to refer to any protein present in, or encoded in the genomes of, any eukaryotic species, which protein contains one or more CTLDs or one or more domains belonging to a subgroup of CTLDs, the CRDs, which bind carbohydrate ligands. The definition specifically includes membrane attached C-type lectin-like proteins and C-type lectins, "soluble" C-type lectin-like proteins and C-type lectins lacking a functional transmembrane domain and variant C-type lectin-like proteins and C-type lectins in which one or more amino acid residues have been altered in vivo by glycosylation or any other post-synthetic modification, as well as any product that is obtained by chemical modification of C-type lectin-like proteins and C-type lectins.

In the claims and throughout the specification certain alterations may be defined with reference to amino acid residue numbers of a CTLD domain or a CTLD-containing protein. The amino acid numbering starts at the first N-terminal amino acid of the CTLD or the native or artificial CTLD-containing protein product, as the case may be, which shall in each case be indicated by unambiguous external literature reference or internal reference to a figure contained herein within the textual context.

The terms "amino acid", "amino acids" and "amino acid residues" refer to all naturally occurring L-α-amino acids. This definition is meant to include norleucine, ornithine, and homocysteine. The amino acids are identified by either the single-letter or three-letter designations:

| Asp | D | aspartic acid |
|-----|---|---------------|
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Nle | J | norleucine |
| Hcy | U | homocysteine |
| Ile | I | isoleucine |
| Leu | L | leucine |
| Tyr | Y | tyrosine |
| Phe | F | phenylalanine |
| His | H | histidine |
| Lys | K | lysine |
| Arg | R | arginine |
| Trp | W | tryptophan |
| Gln | Q | glutamine |
| Asn | N | asparagine |
| Orn | O | ornithine |
| Xxx | X | any L-α-amino acid. |

The naturally occurring L-α-amino acids may be classified according to the chemical composition and properties of their side chains. They are broadly classified into two groups, charged and uncharged. Each of these groups is divided into subgroups to classify the amino acids more accurately:

A. Charged Amino Acids

| Acidic Residues: | Asp, Glu |
| Basic Residues: | Lys, Arg, His, Orn |

B. Uncharged Amino Acids

| Hydrophilic Residues: | Ser, Thr, Asn, Gln |
| Aliphatic Residues: | Gly, Ala, Val, Leu, Ile, Nle |
| Non-polar Residues: | Cys, Met, Pro, Hcy |
| Aromatic Residues: | Phe, Tyr, Trp |

The terms "amino acid alteration" and "alteration" refer to amino acid substitutions, deletions or insertions or any combinations thereof in a CTLD amino acid sequence. In the CTLD variants of the present invention such alteration is at a site or sites of a CTLD amino acid sequence. Substitutional variants herein are those that have at least one amino acid residue in a native CTLD sequence removed and a different amino acid inserted in its place at the same position. The substitutions may be single, where only one amino acid in the molecule has been substituted, or they may be multiple, where two or more amino acids have been substituted in the same molecule.

The designation of the substitution variants herein consists of a letter followed by a number followed by a letter. The first (leftmost) letter designates the amino acid in the native (unaltered) CTLD or CTLD-containing protein. The number refers to the amino acid position where the amino acid substitution is being made, and the second (righthand) letter designates the amino acid that is used to replace the native amino acid. As mentioned above, the numbering starts with "1" designating the N-terminal amino acid sequence of the CTLD or the CTLD-containing protein, as the case may be. Multiple alterations are separated by a comma (,) in the notation for ease of reading them.

The terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide chain. The DNA sequence thus encodes the amino acid sequence.

The terms "mutationally randomised sequence", "randomised polypeptide segment", "randomised amino acid sequence", "randomised oligonucleotide" and "mutationally randomised sequence", as well as any similar terms used in any context to refer to randomised sequences, polypeptides or nucleic acids, refer to ensembles of polypeptide or nucleic acid sequences or segments, in which the amino acid residue or nucleotide at one or more sequence positions may differ between different members of the ensemble of polypeptides or nucleic acids, such that the amino acid residue or nucleotide occurring at each such sequence position may belong to a set of amino acid residues or nucleotides that may include all possible amino acid residues or nucleotides or any restricted subset thereof. Said terms are often used to refer to ensembles in which the number of amino acid residues or nucleotides is the same for each member of the ensemble, but may also be used to refer to such ensembles in which the number of amino acid residues or nucleotides in each member of the ensemble may be any integer number within an appropriate range of integer numbers.

II. Construction and Utility of Combinatorial CTLD Libraries

Several systems displaying phenotype, in terms of putative ligand binding modules or modules with putative enzymatic activity, have been described. These include: phage display (e.g. the filamentous phage fd [Dunn (1996), Griffiths and Duncan (1998), Marks et al. (1992)], phage lambda [Mikawa et al. (1996)]), display on eukarotic virus (e.g. baculovirus [Ernst et al. (2000)]), cell display (e.g. display on bacterial cells [Benhar et al. (2000)], yeast cells [Boder and Wittrup (1997)], and mammalian cells [Whitehorn et al. (1995)], ribosome linked display [Schaffitzel et al. (1999)], and plasmid linked display [Gates et al. (1996)].

The most commonly used method for phenotype display and linking this to genotype is by phage display. This is accomplished by insertion of the reading frame encoding the scaffold protein or protein of interest into an intradomain segment of a surface exposed phage protein. The filamentous phage fd (e.g. M13) has proven most useful for this purpose. Polypeptides, protein domains, or proteins are the most frequently inserted either between the "export" signal and domain 1 of the fd gene III protein or into a so-called hinge region between domain 2 and domain 3 of the fd-phage gene III protein. Human antibodies are the most frequently used proteins for the isolation of new binding units, but other proteins and domains have also been used (e.g. human growth hormone [Bass et al. (1990)], alkaline phosphatase [McCafferty et al. (1991)], β-lactamase inhibitory protein [Huang et al. (2000)], and cytotoxic T lymphocyte-associated antigen 4 [Hufton et al. (2000)]. The antibodies are often expressed and presented as scFv or Fab fusion proteins. Three strategies have been employed. Either a specific antibody is used as a scaffold for generating a library of mutationally randomised sequences within the antigen binding clefts [e.g. Fuji et al. (1998)] or libraries representing large ensembles of human antibody encoding genes from non-immunised hosts [e.g. Nissim et al. (1994)] or from immunised hosts [e.g. Cyr and Hudspeth (2000)] are cloned into the fd phage vector.

Figure 1:
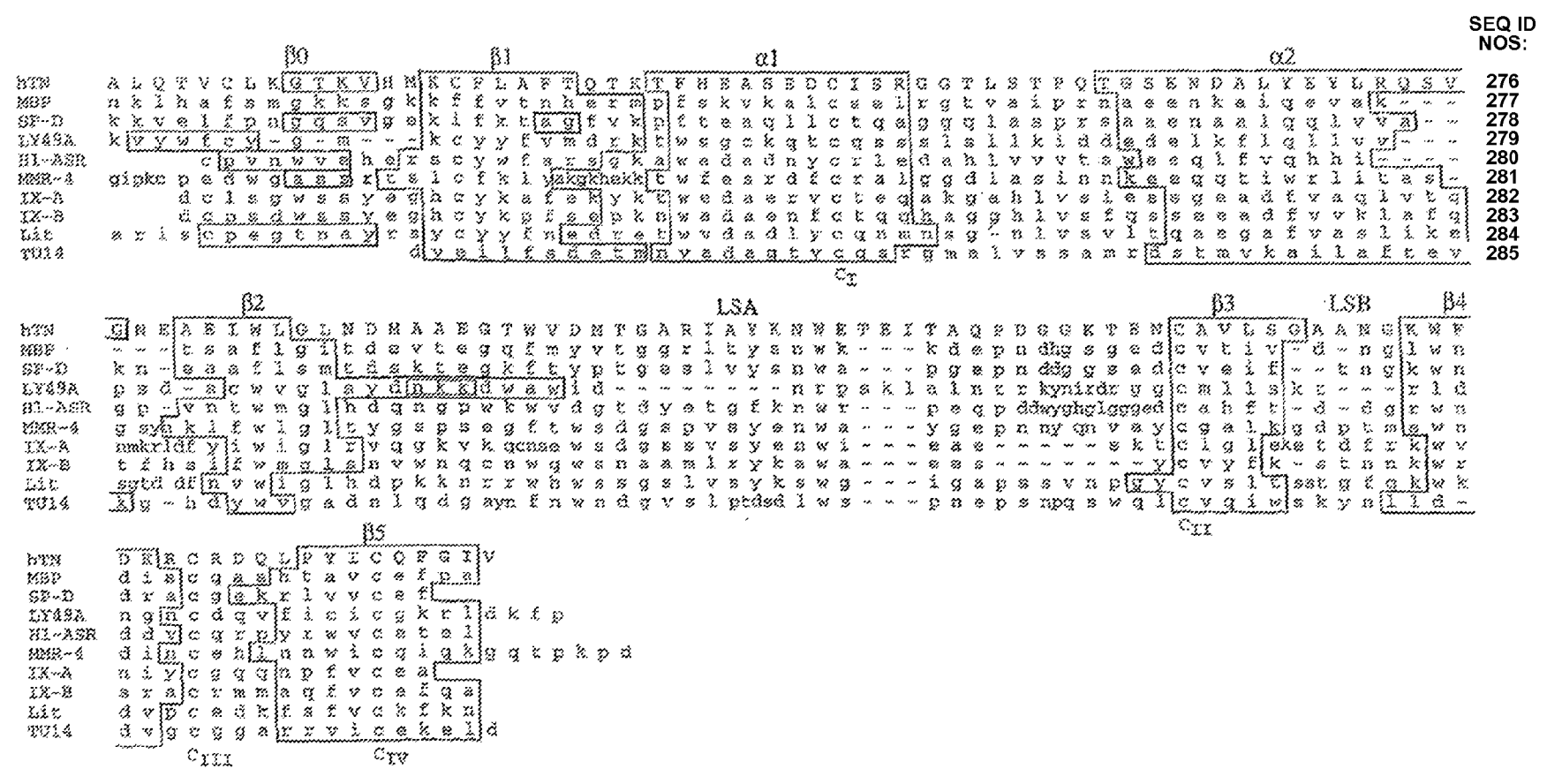

The general procedure for accomplishing the generation of a display system for the generation of CTLD libraries comprise essentially (1) identification of the location of the loop-region, by referring to the 3D structure of the CTLD of choice, if such information is available, or, if not, identification of the sequence locations of the β2-, β3- and β4 strands by sequence alignment with the sequences shown in FIG. 1, as aided by the further corroboration by identification of sequence elements corresponding to the β2 and β3 consensus sequence elements and β4-strand characteristics, also disclosed above;

(2) subcloning of a nucleic acid fragment encoding the CTLD of choice in a protein display vector system with or without prior insertion of endonuclease restriction sites close to the sequences encoding β2, β3 and β4; and (3) substituting the nucleic acid fragment encoding some or all of the loop-region of the CTLD of choice with randomly selected members of an ensemble consisting of a multitude of nucleic acid fragments which after insertion into the nucleic acid context encoding the receiving framework will substitute the nucleic acid fragment encoding the original loop-region polypeptide fragments with randomly selected nucleic acid fragments. Each of the cloned nucleic acid fragments, encoding a new polypeptide replacing an original loop-segment or the entire loop-region, will be decoded in the reading frame determined within its new sequence context.

Nucleic acid fragments may be inserted in specific locations into receiving nucleic acids by any common method of molecular cloning of nucleic acids, such as by appropriately designed PCR manipulations in which chemically synthesized nucleic acids are copy-edited into the receiving nucleic acid, in which case no endonuclease restriction sites are required for insertion. Alternatively, the insertion/excision of nucleic acid fragments may be facilitated by engineering appropriate combinations of endonuclease restriction sites into the target nucleic acid into which suitably designed oligonucleotide fragments may be inserted using standard methods of molecular cloning of nucleic acids.

It will be apparent that interesting CTLD variants isolated from CTLD libraries in which restriction endonuclease sites have been inserted for convenience may contain mutated or additional amino acid residues that neither correspond to residues present in the original CTLD nor are important for maintaining the interesting new affinity of the CTLD variant. If desirable, e.g. in case the product needs to be rendered as non-immunogenic as possible, such residues may be altered or removed by back-mutation or deletion in the specific clone, as appropriate.

The ensemble consisting of a multitude of nucleic acid fragments may be obtained by ordinary methods for chemical synthesis of nucleic acids by directing the step-wise synthesis to add pre-defined combinations of pure nucleotide monomers or a mixture of any combination of nucleotide monomers at each step in the chemical synthesis of the nucleic acid fragment. In this way it is possible to generate any level of sequence degeneracy, from one unique nucleic acid sequence to the most complex mixture, which will represent a complete or incomplete representation of maximum number unique sequences of $4^N$, where N is the number of nucleotides in the sequence.

Complex ensembles consisting of multitudes of nucleic acid fragments may, alternatively, be prepared by generating mixtures of nucleic acid fragments by chemical, physical or enzymatic fragmentation of high-molecular mass nucleic acid compositions like, e.g., genomic nucleic acids extracted from any organism. To render such mixtures of nucleic acid fragments useful in the generation of molecular ensembles, as described here, the crude mixtures of fragments, obtained in the initial cleavage step, would typically be size-fractionated to obtain fragments of an approximate molecular mass range which would then typically be adjoined to a suitable pair of linker nucleic acids, designed to facilitate insertion of the linker-embedded mixtures of size-restricted oligonucleotide fragments into the receiving nucleic acid vector.

To facilitate the construction of combinatorial CTLD libraries in tetranectin, the model CTLD of the preferred embodiment of the invention, suitable restriction sites located in the vicinity of the nucleic acid sequences encoding β2, β3 and β4 in both human and murine tetranectin were designed with minimal perturbation of the polypeptide sequence encoded by the altered sequences. It was found possible to establish a design strategy, as detailed below, by which identical endonuclease restriction sites could be introduced at corresponding locations in the two sequences, allowing interesting loop-region variants to be readily excised from a recombinant murine CTLD and inserted correctly into the CTLD framework of human tetranectin or vice versa.

Analysis of the nucleotide sequence encoding the mature form of human tetranectin reveals (FIG. 2) that a recognition site for the restriction endonuclease Bgl II is found at position 326 to 331 (AGATCT), involving the encoded residues Glu109, Ile110, and Trp111 of β2, and that a recognition site for the restriction endonuclease Kas I is found at position 382 to 387 (GGCGCC), involving the encoded amino acid residues Gly128 and Ala129 (located C-terminally in loop 2).

Mutation, by site directed mutagenesis, of G513 to A and of C514 to T in the nucleotide sequence encoding human tetranectin would introduce a Mun I restriction endonuclease recognition site therein, located at position 511 to 516, and mutation of G513 to A in the nucleotide sequence encoding murine tetranectin would introduce a Mun I restriction endonuclease site therein at a position corresponding to the Mun I site in human tetranectin, without affecting the amino acid sequence of either of the encoded protomers. Mutation, by site directed mutagenesis, of C327 to G and of G386 to C in the nucleotide sequence encoding murine tetranectin would introduce a Bgl II and a Kas I restriction endonuclease recognition site, respectively, therein. Additionally, A325 in the nucleotide sequence encoding murine tetranectin is mutagenized to a G. These three mutations would affect the encoded amino acid sequence by substitution of Asn109 to Glu and Gly129 to Ala, respectively. Now, the restriction endonuclease Kas I is known to exhibit marked site preference and cleaves only slowly the tetranectin coding region. Therefore, a recognition site for another restriction endonuclease substituting the Kas I site is preferred (e.g. the recognition site for the restriction endonuclease Kpn I, recognition sequence GGTACC). The nucleotide and amino acid sequences of the resulting tetranectin derivatives, human tetranectin lectin (htlec) and murine tetranectin lectin (mtlec) are shown in FIG. 3. The nucleotide sequences encoding the htlec and mtlec protomers may readily be subcloned into devices enabling protein display of the linked nucleotide sequence (e.g. phagemid vectors) and into plasmids designed for heterologous expression of protein [e.g. pT7H6, Christensen et al. (1991)]. Other derivatives encoding only the mutated CTLDs of either htlec or mtlec (htCTLD and mtCTLD, respectively) have also been constructed and subcloned into phagemid vectors and expression plasmids, and the nucleotide and amino acid sequences of these CTLD derivatives are shown in FIG. 4.

The presence of a common set of recognition sites for the restriction endonucleases Bgl II, Kas I or Kpn I, and Mun I in the ensemble of tetranectin and CTLD derivatives allows for the generation of protein libraries with randomised amino acid sequence in one or more of the loops and at single residue positions in β4 comprising the lectin ligand binding region by ligation of randomised oligonucleotides into properly restricted phagemid vectors encoding htlec, mtlec, htCTLD, or mtCTLD derivatives.

After rounds of selection on specific targets (e.g. eukaryotic cells, virus, bacteria, specific proteins, polysaccharides, other polymers, organic compounds etc.) DNA may be isolated from the specific phages, and the nucleotide sequence of the segments encoding the ligand-binding region determined, excised from the phagemid DNA and transferred to the appropriate derivative expression vector for heterologous production of the desired product. Heterologous production in a prokaryote may be preferred because an efficient protocol for the isolation and refolding of tetranectin and derivatives has been reported (International Patent Application Publication WO 94/18227 A2).

A particular advantage gained by implementing the technology of the invention, using tetranectin as the scaffold structure, is that the structures of the murine and human tetranectin scaffolds are almost identical, allowing loop regions to be swapped freely between murine and human tetranectin derivatives with retention of functionality. Swapping of loop regions between the murine and the human framework is readily accomplished within the described system of tetranectin derivative vectors, and it is anticipated, that the system can be extended to include other species (e.g. rat, old and new world monkeys, dog, cattle, sheep, goat etc.) of relevance in medicine or veterinary medicine in view of the high level of homology between man and mouse sequences, even at the genetic level. Extension of this strategy to include more species may be rendered possible as and when tetranectin is eventually cloned and/or sequenced from such species.

Because the C-type lectin ligand-binding region represents a different topological unit compared to the antigen binding clefts of the antibodies, we envisage that the selected binding specificities will be of a different nature compared to the antibodies. Further, we envisage that the tetranectin derivatives may have advantages compared to antibodies with respect to specificity in binding sugar moieties or polysaccharides. The tetranectin derivatives may also be advantageous in selecting binding specificities against certain natural or synthetic organic compounds.

Several CTLDs are known to bind calcium ions, and binding of other ligands is often either dependent on calcium (e.g. the collectin family of C-type lectins, where the calcium ion bound in site 2 is directly involved in binding the sugar ligand [Weis and Drickamer (1996)]) or sensitive to calcium (e.g. tetranectin, where binding of calcium involves more of the side chains known otherwise to be involved in plasminogen kringle 4 binding [Graversen et al. (1998)]). The calcium binding sites characteristic of the C-type lectin-like protein family are comprised by residues located in loop 1, loop 4 and β-strand 4 and are dependent on the presence of a proline residue (often interspacing loop 3 and loop 4 in the structure), which upon binding is found invariantly in the cis conformation. Moreover, binding of calcium is known to enforce structural changes in the CTLD loop-region [Ng et al. (1998a,b)]. We therefore envisage, that binding to a specific target ligand by members of combinational libraries with preserved CTLD metal binding sites may be modulated by addition or removal of divalent metal ions (e.g. calcium ions) either because the metal ion may be directly involved in binding, because it is a competitive ligand, or because binding of the metal ion enforces structural rearrangements within the putative binding site.

The trimeric nature of several members of the C-type lectin and C-type lectin-like protein family, including tetranectin, and the accompanying avidity in binding may also be exploited in the creation of binding units with very high binding affinity.

As can be appreciated from the disclosure above, the present invention has a broad general scope and a wide area of application. Accordingly, the following examples, describing various embodiments thereof, are offered by way of illustration only, not by way of limitation.

EXAMPLE 1

Construction of Tetranectin Derived *E. coli* Expression Plasmids and Phagemids

The expression plasmid pT7H6FX-htlec, encoding the FX-htlec (SEQ ID NO:01) part of full length H6FX-htlec fusion protein, was constructed by a series of four consecutive site-directed mutagenesis experiments starting from the expression plasmid pT7H6-rTN 123 [Holtet et al. (1997)] using the QuickChange™ Site-Directed Mutagenesis Kit (Stratagene, La Jolla, Calif.) and performed as described by the manufacturer. Mismatching primer pairs introducing the desired mutations were supplied by DNA Technology (Aarhus, Denmark). An outline of the resulting pT7H6FX-htlec expression plasmid is shown in FIG. 5, and the nucleotide sequence of the FX-htlec encoding insert is given as SEQ ID NO:01. The amino acid sequence of the FX-htlec part of the H6FX-htlec fusion protein is shown in FIG. 6 and given as SEQ ID NO:02.

The expression plasmid pT7H6FX-htCTLD, encoding the FX-htCTLD (SEQ ID NO: 03) part of the H6FX-htCTLD fusion protein, was constructed by amplification and subcloning into the plasmid pT7H6 (i.e. amplification in a polymerase chain reaction using the expression plasmid pT7H6-htlec as template, and otherwise the primers, conditions, and subcloning procedure described for the construction of the expression plasmid pT7H6TN3 [Holtet et al. (1997)]. An outline of the resulting pT7H6FX-htCTLD expression plasmid is shown in FIG. 7, and the nucleotide sequence of the FX-htCTLD encoding insert is given as SEQ ID NO:03. The amino acid sequence of the FX-htCTLD part of the H6FX-htCTLD fusion protein is shown in FIG. 8 and given as SEQ ID NO:04.

The phagemids, pPhTN and pPhTN3, were constructed by ligation of the Sfi I and Not I restricted DNA fragments amplified from the expression plasmids pT7H6-rTN 123 (with the oligonucleotide primers 5-CGGCTGAGCGGC-CCAGCCGGCCATGGCCGAGCCACCAAC-CCAGAAGC-3' [SEQ ID NO:05] and 5'-CCTGCGGCCGC-CACGATCCCGAACTGG-3' [SEQ ID NO:06]) and pT7H6FX-htCTLD (with the oligonucleotide primers 5'-CG-GCTGAGCGGCCCAGCCGGCCATGGCCGC-CCTGCAGACGGTC-3' [SEQ ID NO:07] and 5'-CCTGCG-GCCGCCACGATCCCGAACTGG-3' [SEQ ID NO:06]), respectively, into a Sfi I and Not I precut vector, pCANTAB 5E supplied by Amersham Pharmacia Biotech (code no. 27-9401-01) using standard procedures. Outlines of the resulting pPhTN and pPhTN3 phagemids are shown in FIG. 9 and FIG. 11, respectively, and the nucleotide sequences of the PhTN and PhTN3 inserts are given as SEQ ID NO:08 and SEQ ID NO:10, respectively. The amino acid sequences encoded by the PhTN and PhTN3 inserts are shown in FIG. 10 (SEQ ID NO:09) and FIG. 12 (SEQ ID NO:11), respectively.

The phagemids, pPhtlec and pPhtCTLD, were constructed by ligation of the Sfi I and Not I restricted DNA fragments amplified from the expression plasmids pT7H6FX-htlec (with the oligonucleotide primers 5-CGGCTGAGCGGC-CCAGCCGGCCATGGCCGAGCCACCAAC-CCAGAAGC-3' [SEQ ID NO:05] and 5'-CCTGCGGCCGC-CACGATCCCGAACTGG-3' [SEQ ID NO:06]) and pT7H6FX-htCTLD (with the oligonucleotide primers 5'-CG-GCTGAGCGGCCCAGCCGGCCATGGCCGC-CCTGCAGACGGTC-3' [SEQ ID NO:07] and 5'-CCTGCG-GCCGCCACGATCCCGAACTGG-3' [SEQ ID NO:06]), respectively, into a Sfi I and Not I precut vector, pCANTAB 5E supplied by Amersham Pharmacia Biotech (code no. 27-9401-01) using standard procedures. Outlines of the resulting pPhtlec and pPhtCTLD phagemids are shown in FIG. 13 and FIG. 15, respectively, and the nucleotide sequences of the Phtlec and PhtCTLD inserts are given as SEQ ID NO:12 and SEQ ID NO:14, respectively. The amino acid sequences encoded by the Phtlec and PhtCTLD inserts are shown in FIG. 14 (SEQ ID NO:13) and FIG. 16 (SEQ ID NO:15), respectively.

A plasmid clone, pUC-mtlec, containing the nucleotide sequence corresponding to the murine tetranectin derivative mtlec (FIG. 3 and SEQ ID NO:16) was constructed by four succesive subclonings of DNA subfragments in the following way: First, two oligonucleotides 5'-CGGAATTCGAGT-CACCCACTCCCAAGGCCAAGAAGGCTG-CAAATGCCAAGAAAGATTTGGTGAGCT-CAAAGATGTTC-3' (SEQ ID NO:17) and 5'-GCGGATCCAGGCCTGCTTCTCCTTCAG-CAGGGCCACCTCCTGGGCCAGGACATC-CATCCTGTTCTTGAGCTCCTCGAA-CATCTTTGAGCTCACC-3' (SEQ ID NO: 18) were annealed and after a filling in reaction cut with the restriction endonucleases Eco RI (GAATTC) and Bam HI (GGATCC) and ligated into Eco RI and Bam HI precut pUC18 plasmid DNA. Second, a pair of oligonucleotides 5'-GCAGGCCTTA-CAGACTGTGTGCCTGAAGGGCACCAAG-GTGAACTTGAAGTGCCTCCTGGCCT-TCACCCAACCGAAGACCTTCCATGAGGCGAGCGAG-3' (SEQ ID NO:19) and 5'-CCGCATGCTTCGAACAGCGC-CTCGTTCTCTAGCTCTGACTGCGGGGT-GCCCAGCGTGCCCCCTTGCGAGATG-CAGTCCTCGCTCGCCTCATGG-3 , (SEQ ID NO:20) was annealed and after a filling in reaction cut with the restriction endonucleases Stu I (AGGCCT) and Sph I (GCATGC) and ligated into the Stu I and Sph I precut plasmid resulting from the first ligation. Third, an oligonucleotide pair 5'-GGTTC-GAATACGCGCGCCACAGCGTGGGCAAC-GATGCGGAGATCTAAATGCTCCCAATTGC-3' (SEQ ID NO:21) and 5'-CCAAGCTTCACAATGGCAAACTGGCA-GATGTAGGGCAATTGGGAGCATTTAGATC-3' (SEQ ID NO: 22) was annealed and after a filling in reaction cut with the restriction endonucleases BstB I (TTCGAA) and Hind III (AAGCTT) and ligated into the BstB I and Hind III precut plasmid resulting from the second ligation. Fourth, an oligonucleotide pair 5'-CGGAGATCTGGCTGGGCCTCAAC-GACATGGCCGCGGAAGGCGCCTGGGTG-GACATGACCGGTACCCTCCTGGCCTACAAGAACTGG-3' (SEQ ID NO:23) and 5'-GGGCAATTGATCGCG-GCATCGCTTGTCGAACCTCTTGCCGTTG-GCTGCGCCAGACAGGGCGGCGCAGT-TCTCGGCTTTGCCGCCGTCGGGTTGCGTCGTGATCT CCGTCTCCCAGTTCTTGTAGGCCAGG-3' (SEQ ID NO:24) was annealed and after a filling in reaction cut with the restriction endonucleases Bgl II (AGATCT) and Mun I (CAATTG) and ligated into the Bgl II and Mun I precut plasmid resulting from the third ligation. An outline of the pUC-mtlec plasmid is shown in FIG. 17, and the resulting nucleotide sequence of the Eco RI to Hind III insert is given as SEQ ID NO:16.

The expression plasmids pT7H6FX-mtlec and pT7H6FX-mtCTLD may be constructed by ligation of the Bam HI and Hind III restricted DNA fragments, amplified from the pUC-mtlec plasmid with the oligonucleotide primer pair 5-CTGG-GATCCATCCAGGGTCGCGAGTCAC-CCACTCCCAAGG-3' (SEQ ID NO:25) and 5'-CCGAAGCTTACACAATGGCAAACTGGC-3' (SEQ ID NO:26), and with the oligonucleotide primer pair 5'-CTGG-GATCCATCCAGGGTCGCGCCTTACAGACTGTGGTC-3' (SEQ ID NO:27), and 5'-CCGAAGCTTACACAATG-GCAAACTGGC-3' (SEQ ID NO:26), respectively, into Bam HI and Hind III precut pT7H6 vector using standard procedures. An outline of the expression plasmids pT7H6FX-mtlec and pT7H6FX-mtCTLD is shown in FIG. 18 and FIG. 20, respectively, and the nucleotide sequences of the FX-mtlec and FX-mtCTLD inserts are given as SEQ ID NO:28 and SEQ ID NO:30, respectively. The amino acid sequences of the FX-mtlec and FX-mtCTLD parts of the fusion proteins H6FX-mtlec and H6FX-mtCTLD fusion proteins are shown in FIG. 19 (SEQ ID NO:29) and FIG. 21 (SEQ ID NO:31), respectively.

The phagemids pPmtlec and pPmtCTLD may be constructed by ligation of the Sfi I and Not I restricted DNA fragments (amplified from the pUC-mtlec plasmid with the oligonucleotide primer pair 5-CGGCTGAGCGGCCCAGC-CGGCCATGGCCGAGTCACCCACTCCCAAGG-3' [SEQ ID NO:32], and 5'-CCTGCGGCCGCCACGATC-CCGAACTGG-3' [SEQ ID NO:33] and with the oligonucleotide primers 5'-CGGCTGAGCGGCCCAGCCGGCCATG-GCCGCCTTACAGACTGTGGTC-3' [SEQ ID NO:34] and 5'-CCTGCGGCCGCCACGATCCCGAACTGG-3' [SEQ ID NO:33], respectively) into a Sfi I and Not I precut vector pCANTAB 5E supplied by Amersham Pharmacia Biotech (code no. 27-9401-01) using standard procedures. Outlines of the pPmtlec and pPmtCTLD plasmids are shown in FIG. 22 and FIG. 24, respectively, and the resulting nucleotide sequences of the Pmtlec and PmtCTLD inserts are given as SEQ ID NO:35 and SEQ ID NO:37, respectively. The amino acid sequences encoded by the Pmtlec and PmtCTLD inserts are shown in FIG. 23 (SEQ ID NO: 36) and FIG. 25 (SEQ ID NO: 38), respectively.

EXAMPLE 2

Demonstration of Successful Display of Phtlec and PhTN3 on Phages

In order to verify that the Phtlec and PhTN3 Gene III fusion proteins can indeed be displayed by the recombinant phage particles, the phagemids pPhtlec and pPhTN3 (described in Example 1) were transformed into *E. coli* TG1 cells and recombinant phages produced upon infection with the helper phage M13KO7. Recombinant phages were isolated by precipitation with poly(ethylene glycol) (PEG 8000) and samples of Phtlec and PhTN3 phage preparations as well as a sample of helper phage were subjected to an ELISA-type sandwich assay, in which wells of a Maxisorb (Nunc) multi-well plate were first incubated with antihuman tetranectin or bovine serum albumin (BSA) and blocked in skimmed milk or skimmed milk/EDTA. Briefly, cultures of pPhtlec and pPhTN3 phagemid transformed TG1 cells were grown at 37° C. in 2×TY-medium supplemented with 2% glucose and 100 mg/L ampicillin until $A_{600}$ reached 0.5. By then the helper phage, M13KO7, was added to a concentration of $5 \times 10^9$ pfu/mL. The cultures were incubated at 37° C. for another 30 min before cells were harvested by centrifugation and resuspended in the same culture volume of 2×TY medium supplemented with 50 mg/L kanamycin and 100 mg/L ampicillin and transferred to a fresh set of flasks and grown for 16 hours at 25° C. Cells were removed by centrifugation and the phages precipitated from 20 mL culture supernatant by the addition of 6 mL of ice cold 20% PEG 8000, 2.5 M NaCl. After mixing the solution was left on ice for one hour and centrifuged at 4° C. to isolate the precipitated phages. Each phage pellet was resuspended in 1 mL of 10 mM tris-HCl pH 8, 1 mM EDTA (TE) and incubated for 30 min before centrifugation. The phage containing supernatant was transferred to a fresh tube. Along with the preparation of phage samples, the wells of a Maxisorb plate was coated overnight with (70 μL) rabbit anti-human tetranectin (a polyclonal antibody from DAKO A/S, code no. A0371) in a 1:2000 dilution or with (70 μL) BSA (10 mg/mL). Upon coating, the wells were washed three times with PBS (2.68 mM KCl, 1.47 mM $KH_2PO_4$, 137 mM NaCl, 8.10 mM $Na_2HPO_4$, pH 7.4) and blocked for one hour at 37° C. with 280 μL of either 3% skimmed milk in PBS, or 3% skimmed milk, 5mM EDTA in PBS. Anti-tetranectin coated and BSA coated wells were then incubated with human Phtlec-, PhTN3-, or helper phage samples for 1 hour and then washed 3 times in PBS buffer supplemented with the appropriate blocking agent. Phages in the wells were detected after incubation with HRP-conjugated anti-phage conjugate (Amersham Pharmacia, code no. 27-9421-01) followed by further washing. HRP activities were then measured in a 96-well ELISA reader using a standard HRP chromogenic substrate assay.

Phtlec and PhTN3 phages produced strong responses (14 times background) in the assay, irrespective of the presence or absence of EDTA in the blocking agent, whereas helper phage produced no response above background readings in either blocking agent. Only low binding to BSA was observed (FIG. 26).

It can therefore be concluded that the human Phtlec and PhTN3 phages both display epitopes that are specifically recognized by the anti-human tetranectin antibody.

EXAMPLE 3

Demonstration of Authentic Ligand Binding Properties of Phtlec and PhTN3 Displayed on Phage The apo-form of the CTLD domain of human tetranectin binds in a lysine-sensitive manner specifically to the kringle 4 domain of human plasminogen [Graversen et al. (1998)]. Binding of tetranectin to plasminogen can be inhibited by calcium which binds to two sites in the ligand-binding site in the CTLD domain (Kd approx. 0.2 millimolar) or by lysine-analogues like AMCHA (6-aminocyclohexanoic acid), which bind specifically in the two stronger lysine-binding sites in plasminogen of which one is located in kringle 1 and one is located in kringle 4 (Kd approx. 15 micromolar).

To demonstrate specific AMCHA-sensitive binding of human Phtlec and PhTN3 phages to human plasminogen, an ELISA assay, in outline similar to that employed to demonstrate the presence of displayed Phlec and PhCTLD GIII fusion proteins on the phage particles (cf. Example 2), was devised.

Wells were coated with solutions of human plasminogen (10 μg/mL), with or without addition of 5 mM AMCHA. Control wells were coated with BSA. Two identical arrays were established, one was subjected to blocking of excess binding capacity with 3% skimmed milk, and one was blocked using 3% skimmed milk supplemented with 5 mM EDTA. Where appropriate, blocking, washing and phage stock solutions were supplemented by 5 mM AMCHA. The two arrays of wells were incubated with either Phtlec-, or PhTN3-, or helper phage samples, and after washing the amount of phage bound in each well was measured using the HRP-conjugated antiphage antibody as above. The results are shown in FIG. 27, panels A and B, and can be summarized as follows (a) In the absence of AMCHA, binding of human Phtlec phages to plasminogen-coated wells generated responses at 8-10 times background levels using either formulation of blocking agent, whereas human PhTN3 phages generated responses at 4 (absence of EDTA) or 7 (presence of EDTA) times background response levels.

(b) In the presence of 5 mM AMCHA, binding of human Phtlec- and PhTN3 phages to plasminogen was found to be completely abolished.

(c) Phtlec and PhTN3 phages showed no binding to BSA, and control helper phages showed no binding to any of the immobilized substances.

(d) Specific binding of human Phtlec and PhTN3 phages to a specific ligand at moderate binding strength (about 20 micromolar level) can be detected with high efficiency at virtually no background using a skimmed-milk blocking agent, well-known in the art of combinatorial phage technology as a preferred agent effecting the reduction of non-specific binding.

In conclusion, the results show that the Phtlec and PhTN3 Gene III fusion proteins displayed on the phage particles exhibit plasminogen-binding properties corresponding to those of authentic tetranectin, and that the physical and biochemical properties of Phtlec and PhTN3 phages are compatible with their proposed use as vehicles for the generation of combinatorial libraries from which CTLD derived units with new binding properties can be selected.

EXAMPLE 4

Construction of the Phage Libraries Phtlec-lb001 and Phtlec-lb002

All oligonucleotides used in this example were supplied by DNA Technology (Aarhus, Denmark).

The phage library Phtlec-lb001, containing random amino acid residues corresponding to Phtlec (SEQ ID NO: 12) positions 141-146 (loop 3), 150-153 (part of loop 4), and residue 168 (Phe in β4), was constructed by ligation of 20 μg KpnI and MunI restricted pPhtlec phagemid DNA (cf, Example 1) with 10 μg of KpnI and MunI restricted DNA fragment amplified from the oligonucleotide htlec-lib1-tp (SEQ ID NO: 39), where N denotes a mixture of 25% of each of the nucleotides T, C, G, and A, respectively and S denotes a mixture of 50% of C and G, encoding the appropriately randomized nucleotide sequence and the oligonucleotides htlec-lib1-rev (SEQ ID NO: 40) and htlec-lib1/2-fo (SEQ ID NO: 41) as primers using standard conditions. The ligation mixture was used to transform so-called electrocompetent E. coli TG-1 cells by electroporation using standard procedures. After transformation the E. coli TG-1 cells were plated on 2×TY-agar plates containing 0.2 mg ampicillin/mL and 2% glucose and incubated over night at 30° C.

The phage library Phtlec-lb002, containing random amino acid residues corresponding to Phtlec (SEQ ID NO: 12) positions 121-123, 125 and 126 (most of loop 1), and residues 150-153 (part of loop 4) was constructed by ligation of 20 μg BglII and MunI restricted pPhtlec phagemid DNA (cf, EXAMPLE 1) with 15 μg of BglII and MunI restricted DNA fragment amplified from the pair of oligonucleotides htlec-lib2-tprev (SEQ ID NO: 42) and htlec-lib2-tpfo (SEQ ID NO: 43), where N denotes a mixture of 25% of each of the nucleotides T, C, G, and A, respectively and S denotes a mixture of 50% of C and G, encoding the appropriately randomized nucleotide sequence and the oligonucleotides htlec-lib2-rev (SEQ ID NO: 44) and htlec-lib1/2-fo (SEQ ID NO: 41) as primers using standard conditions. The ligation mixture was used to transform so-called electrocompetent E. coli TG-1 cells by electroporation using standard procedures. After transformation the E. coli TG-1 cells were plated on 2×TY-agar plates containing 0.2 mg ampicillin/mL and 2% glucose and incubated overnight at 30° C.

The titer of the libraries Phtlec-lb001 and -lb002 was determined to $1.4*10^9$ and $3.2*10^9$ clones, respectively. Six clones from each library were grown and phagemid DNA isolated using a standard miniprep procedure, and the nucleotide sequence of the loop-region determined (DNA Technology, Aarhus, Denmark). One clone from each library failed, for technical reasons, to give reliable nucleotide sequence, and one clone from Phtlec-lib001 apparently contained a major deletion. The variation of nucleotide sequences, compared to Phtlec (SEQ ID NO: 12), of the loop-regions of the other nine clones (lb001-1, lb001-2, lb001-3, lb001-4, lb002-1, lb002-2, lb002-3, lb002-4, and lb002-5) is shown in Table 3.

TABLE 3

Variation of Phtlec loop derivatives isolated from the libraries Phtlec-lb001 and -lb002. (β2 and β3 consensus elements are indicated)

| Clone | Loop-region sequence |
|---|---|
| Phtlec | 120                                130                                140<br>β2-N D M A A E G T W V D M T G T R I A Y K N W E T E I T A Q P D<br>- AACGACATGGCGGCCGAGGGCACCTGGGTGGACATGACCGGTACCCGCATCGCCTACAAGAACTGGGAGACTGAGATCACCGCGCAACCCGAT |
| lb001-1 |                                                                                               H G W R T R<br>CACGGCTGGCGGACCCGG |
| lb001-2 |                                                                                               I*/Q S E V E<br>ATCTAGACGGAGGTCGAG |
| lb001-3 |                                                                                               A G G K W R<br>GCGGGCGGGAAGTGGCGG |
| lb001-4 |                                                                                               Q R V E C G<br>CAGAGGGTGGAGTCGGGG |
| lb002-1 |     A M S      G R<br>    GGCATGAGC   GGGCGG |
| lb002-2 |     E A W      T E<br>    GAGGCCTGG   ACGGAG |
| lb002-3 |     A Q D      P R<br>    GCGCAGGAC   CCGCGG |
| lb002-4 |     K A R      K R<br>    AAGGCGCGG   AAGAGG |
| lb002-5 |     - - - -     R P<br>    ------------CGCCCG |

| Clone | Loop-region sequence | SEQ ID NO |
|---|---|---|
| Phtlec | 150                        160<br>G G K T E N -β3- S G A A N G K W F D<br>GGCGGCAAGACCGAGAAC -- TCAGGCGCGGCCAACGGCAAGTGGTTCGAC | 266 |
| lb001-1 | A N E */Q                                       V<br>GCCAACGAGTAG                                   GTC | 267 |
| lb001-2 | D W */Q T                                       G<br>GACTGGTAGACC                                   GGG | 268 |
| lb001-3 | G G L G                                          K<br>GCCGGCCTGGGC                                   AAG | 269 |
| lb001-4 | E A V C                                          N<br>GAGGCGGTCTGC                                   AAC | 270 |
| lb002-1 | P I C R<br>CCCATCTGCCGG | 271 |
| lb002-2 | Q H C S<br>CAGCACTGCTCC | 272 |
| lb002-3 | S L L T<br>TCGCTCCTGACC | 273 |
| lb002-4 | D P P P<br>GACCCCCCCCCC | 274 |
| lb002-5 | I A R */Q<br>ATCGCGAGGTAG | 275 |

EXAMPLE 5

Construction of the Phage Library PhtCTLD-lb003

All oligonucleotides used in this example were supplied by DNA Technology (Aarhus, Denmark).

The phage library PhtCTLD-lb003, containing random amino acid residues corresponding to PhtCTLD (SEQ ID NO: 15) positions 77 to 79 and 81 to 82 (loop 1) and 108 to 109 (loop 4) was constructed by ligation of 20 μg BglII and MunI restricted pPhtCTLD phagemid DNA (cf. Example 1) with 10 □g of a BglII and MunI restricted DNA fragment population encoding the appropriately randomised loop 1 and 4 regions with or without two and three random residue insertions in loop 1 and with three and four random residue insertions in loop 4. The DNA fragment population was amplified, from six so-called assembly reactions combining each of the three loop 1 DNA fragments with each of the two loop 4 DNA fragments as templates and the oligonucleotides TN-lib3-rev (SEQ ID NO: 45) and loop 3-4-5 tagfo (SEQ ID NO: 46) as primers using standard procedures. Each of the three loop 1 fragments was amplified in a reaction with either the oligonucleotides loop1b (SEQ ID NO: 47), loop1c (SEQ ID NO: 48), or loop 1d (SEQ ID NO: 49) as template and the oligonucleotides TN-lib3-rev (SEQ ID NO: 45) and TN-KpnI-fo (SEQ ID NO: 50) as primers, and each of the two DNA loop 4 fragments was amplified in a reaction with either the oligonucleotide loop4b (SEQ ID NO: 51) or loop4c (SEQ ID NO: 52) as template and the oligonucleotides loop3-4rev (SEQ ID NO: 53) and loop3-4fo (SEQ ID NO: 54) as primers using standard procedures. In the oligonucleotide sequences N denotes a mixture of 25% of each of the nucleotides T, C, G, and A, respectively and S denotes a mixture of 50% of C and G, encoding the appropriately randomized nucleotide sequence. The ligation mixture was used to transform so-called electrocompetent *E. coli* TG-1 cells by electroporation using standard procedures. After transformation the *E. coli* TG-1 cells were plated on 2×TY-agar plates containing 0.2 mg ampicillin/mL and 2% glucose and incubated over night at 30° C.

The size of the resulting library, PhtCTLD-lb003, was determined to $1.4*10^{10}$ clones. Twenty four clones from the library were grown and phages and phagemid DNA isolated. The nucleotide sequences of the loop-regions were determined (DNA Technology, Aarhus, Denmark) and binding to a polyclonal antibody against tetranectin, anti-TN (DAKO A/S, Denmark), analysed in an ELISA-type assay using HRP conjugated anti-gene VIII (Amersham Pharmacia Biotech) as secondary antibody using standard procedures. Eighteen clones were found to contain correct loop inserts, one clone contained the wild type loop region sequence, one a major deletion, two contained two or more sequences, and two clones contained a frameshift mutation in the region. Thirteen of the 18 clones with correct loop inserts, the wild type clone, and one of the mixed isolates reacted strongly with the polyclonal anti-TN antibody. Three of the 18 correct clones reacted weakly with the antibody, whereas, two of the correct clones, the deletion mutant, one of the mixed, and the two frameshift mutants did not show a signal above background.

EXAMPLE 6

Phage Selection by Biopanning on Anti-TN Antibody.

Approximately $10^{11}$ phages from the PhtCTLD-lb003 library was used for selection in two rounds on the polyclonal anti-TN antibody by panning in Maxisorb immunotubes (NUNC, Denmark) using standard procedures. Fifteen clones out of $7*10^7$ from the plating after the second selection round were grown and phagemid DNA isolated and the nucleotide sequence determined. All 15 clones were found to encode correct and different loop sequences.

EXAMPLE 7

Model Selection of CTLD-phages on Plasminogen

I: Elution by Trypsin Digestion after Panning

In order to demonstrate that tetranectin derived CTLD bearing phages can be selected from a population of phages, mixtures of PhtCTLD phages isolated from a *E. coli* TG1 culture transformed with the phagemid pPhtCTLD (cf. EXAMPLE 1) after infection with M13K07 helper phage and phages isolated from a culture transformed with the phagemid pPhtCPB after infection with M13K07 helper phage at ratios of 1:10 and $1:10^5$, respectively were used in a selection experiment using panning in 96-well Maxisorb micro-titerplates (NUNC, Denmark) and with hu ran plasminogen as antigen. The pPhtCPB phagemid was constructed by ligation of the double stranded oligonucleotide (SEQ ID NO: 55) with the appropriate restriction enzyme overhang sequences into KpnI and MunI restricted pPhtCTLD phagemid DNA. The pPhtCBP phages derived upon infection with the helper phages displays only the wild type M13 gene III protein because of the translation termination codons introduced into the CTLD coding region of the resulting pPhtCPB phagemid (SEQ ID NO: 56).

The selection experiments were performed in 96 well micro titer plates using standard procedures. Briefly, in each well 3 μg of human plasminogen in 100 AL PBS (PBS, 0.2 g KCl, 0.2 g $KH_2PO_4$, 8 g NaCl, 1.44 g $Na_2HPO_4$, $2H_2O$, water to 1 L, and adjusted to pH 7.4 with NaOH) or 100 μL PBS (for analysis of non specific binding) was used for over night coating at 4° C. and at 37° C. for one hour. After washing once with PBS, wells were blocked with 400 μL PBS and 3% non fat dried milk for one hour at 37° C. After blocking wells were washed once in PBS and 0.1% Tween 20 and three times with PBS before the addition of phages suspended in 100 μL PBS, 3% non fat dried milk. The phages were allowed to bind at 37° C. for one hour before washing three times with PBS, Tween 20 and three times with PBS. Bound phages were eluted from each well by trypsin digestion in 100 μL (1 mg/mL trypsin in PBS) for 30 min. at room temperature, and used for infection of exponentially growing *E. coli* TG1 cells before plating and titration on 2×TY agar plates containing 2% glucose and 0.1 mg/mL ampicillin.

Initially (round 1), $10^{12}$ PhtCTLD phages (A series), a mixture of $10^{10}$ PhtCTLD phages and $10^{11}$ PhtCPB phages (B series), or a mixture of $10^6$ PhtCTLD and $10^{11}$ PhtCPB phages (C series) were used. In the following round (round 2) $10^{11}$ phages of the output from each series were used. Results from the two rounds of selection are summarised in Table 4.

TABLE 4

Selection of mixtures of PhtCTLD and PhtCPB by panning and elution with trypsin.

|  |  | Plasminogen ($*10^5$ colonies) | Blank ($*10^5$ colonies) |
| --- | --- | --- | --- |
| Round 1 | A | 113.0 | 19.50 |
|  | B | 1.8 | 1.10 |
|  | C | 0.1 | 0.30 |
| Round 2 | A | 49 | 0.10 |
|  | B | 5.2 | 0.20 |
|  | C | 0.3 | 0.04 |

Phagemid DNA from 12 colonies from the second round of plating together with 5 colonies from a plating of the initial phage mixtures was isolated and the nucleotide sequence of the CTLD region determined. From the initial 1/10 mixture (B series) of PhtCTLD/PhtCPB one out of five were identified as the CTLD sequence. From the initial $1/10^5$ mixture (C series) all five sequences were derived from the pPhtCPB phagemid. After round 2 nine of the twelve sequences analysed from the B series and all twelve sequences from the C series were derived from the pPhtCTLD phagemid.

EXAMPLE 8

Model Selection of CTLD-phages on Plasminogen.
II: Elution by 0.1 M Triethylamine after Panning.

In order to demonstrate that tetranectin derived CTLD-bearing phages can be selected from a population of phages, mixtures of PhtCTLD phages isolated from a *E. coli* TG1 culture transformed with the phagemid pPhtCTLD (cf, EXAMPLE 1) after infection with M13K07 helper phage and phages isolated from a culture transformed with the phagemid pPhtCPB (cf, EXAMPLE 6) after infection with M13K07 helper phage at ratios of $1:10^2$ and $1:10^6$, respectively were used in a selection experiment using panning in 96-well Maxisorb microtiterplates (NUNC, Denmark) and with human plasminogen as antigen using standard procedures.

Briefly, in each well 3 µg of human plasminogen in 100 µL PBS (PBS, 0.2 g KCl, 0.2 g $KH_2PO_4$, 8 g NaCl, 1.44 g $Na_2HPO_4$, $2H_2O$, water to 1 L, and adjusted to pH 7.4 with NaOH) or 100 µL PBS (for analysis of non specific binding) was used for over night coating at 4° C. and at 37° C. for one hour. After washing once with PBS, wells were blocked with 400 □L PBS and 3% non fat dried milk for one hour at 37° C. After blocking wells were washed once in PBS and 0.1% Tween 20 and three times with PBS before the addition of phages suspended in 100 µL PBS, 3% non fat dried milk. The phages were allowed to bind at 37° C. for one hour before washing 15 times with PBS, Tween 20, and 15 times with PBS. Bound phages were eluted from each well by 100 µL 0.1 M triethylamine for 10 min at room temperature, and upon neutralisation with 0.5 vol. 1 M Tris-HCl pH 7.4, used for infection of exponentially growing *E. coli* TG1 cells before plating and titration on 2×TY agar plates containing 2% glucose and 0.1 mg/mL ampicillin.

Initially (round 1) $10^{12}$ PhtCTLD phages (A series), a mixture of $10^9$ PhtCTLD phages and $10^{11}$ PhtCPB phages (B series), or a mixture of $10^5$ PhtCTLD and $10^{11}$ PhtCPB phages (C series) were used. In the following round (round 2) $10^{11}$ phages of the output from each series were used. Results from the two rounds of selection are summarised in Table 5.

TABLE 5

Selection of mixtures of PhtCTLD and PhtCPB by panning elution with triethylamine.

|  |  | Plasminogen ($*10^4$ colonies) | Blank ($*10^4$ colonies) |
| --- | --- | --- | --- |
| Round 1 | A | 18 | 0.02 |
|  | B | 0.5 | 0.00 |
|  | C | 0.25 | 0.02 |
| Round 2 | A | n.d. | n.d. |
|  | B | 5.0 | 0.00 |
|  | C | 1.8 | 0.02 |
| Round 3 | A | n.d. | n.d. |
|  | B | 11 | 0.00 |
|  | C | 6.5 | 0.02 | n.d. = not determined

Phage mixtures from the A and the B series from the second round of selection were grown using a standard procedure, and analysed for binding to plasminogen in an ELISA-type assay. Briefly, in each well 3 µg of plasminogen in 100 µL PBS (PBS, 0.2 g KCl, 0.2 g KH2PO4, 8 g NaCl, 1.44 g $Na_2HPO_4$, $2H_2O$, water to 1 L, and adjusted to pH 7.4 with NaOH) or 100 µL PBS (for analysis of non specific binding) was used for over night coating at 4° C. and at 37° C. for one hour. After washing once with PBS, wells were blocked with 400 µL PBS and 3% non fat dried milk for one hour at 37° C. After blocking wells were washed once in PBS and 0.1% Tween 20 and three times with PBS before the addition of phages suspended in 100 µL PBS, 3% non fat dried milk. The phage mixtures were allowed to bind at 37° C. for one hour before washing three times with PBS, Tween 20, and three times with PBS. After washing, 50 µL of a 1:5000 dilution of a HRP-conjugated anti-gene VIII antibody (Amersham Pharmacia Biotech) in PBS, 3% non fat dried milk was added to each well and incubated at 37° C. for one hour. After binding of the "secondary" antibody wells were washed three times with PBS, Tween 20, and three times with PBS before the addition of 50 µL of TMB substrate (DAKO-TMB One-Step Substrate System, code: S1600, DAKO, Denmark). Reaction was allowed to proceed for 20 min. before quenching with 0.5 vol. 0.5 M $H_2SO_4$, and analysis. The result of the ELISA analysis confirmed specific binding to plasminogen of phages in both series (FIG. 28).

EXAMPLE 9

Selection of Phages from the Library Phtlec-lb002 Binding to Hen Egg White Lysozyme $1.2*10^{12}$ phages, approximately 250 times the size of the original library, derived from the Phtlec-lb002 library (cf, EXAMPLE 4) were used in an experimental procedure for the selection of phages binding to hen egg white lysozyme involving sequential rounds of panning using standard procedures.

Briefly, 30 µg of hen egg white lysozyme in 1 mL PBS (PBS, 0.2 g KCl, 0.2 g $KH_2PO_4$, 8 g NaCl, 1.44 g $Na_2HPO_4$, $2H_2O$, water to 1 L, and adjusted to pH 7.4 with NaOH) or 1 mL PBS (for analysis of non specific binding) was used for over night coating of Maxisorb immunotubes (NUNC, Denmark) at 4° C. and at 37° C. for one hour. After washing once with PBS, tubes were filled and blocked with PBS and 3% non fat dried milk for one hour at 37° C. After blocking tubes were washed once in PBS, 0.1% Tween 20 and three times with PBS before the addition of phages suspended in 1 mL PBS, 3% non fat dried milk. The phages were allowed to bind at 37° C. for one hour before washing six times with PBS, Tween 20 and six times with PBS. Bound phages were eluted from each well by 1 mL 0.1 M triethylamine for 10 min at room temperature, and upon neutralisation with 1 M Tris-HCl pH 7.4, used for infection of exponentially growing *E. coli* TG1 cells before plating and titration on 2×TY agar plates containing 2% glucose and 0.1 mg/mL ampicillin. In the subsequent rounds of selection approximately $10^{12}$ phages derived from a culture grown from the colonies plated after infection with the phages eluted from the lysozyme coated tube were used in the panning procedure. However, the stringency in binding was increased by increasing the number of washing step after phage panning from six to ten.

The results from the selection procedure is shown in Table 7.

TABLE 7

Selection by panning of lysozyme binding phages from Phtlec-lb002 library.

| | Lysozyme | Blank | Ratio |
|---|---|---|---|
| Round 1 | $2.4*10^4$ | n.a. | n.a. |
| Round 2 | $3.5*10^3$ | $4.0*10^2$ | 9 |
| Round 3 | $3.2*10^5$ | $2.5*10^2$ | $1.3*10^3$ | n.a. = not applicable

Phages were grown from twelve clones isolated from the third round of selection in order to analyse the specificity of binding using a standard procedure, and analysed for binding to hen egg white lysozyme and human $\beta_2$-microglobulin in an ELISA-type assay. Briefly, in each well 3 μg of hen egg white lysozyme in 100 μL PBS (PBS, 0.2 g KCl, 0.2 g $KH_2PO_4$, 8 g NaCl, 1.44 g $Na_2HPO_4$, $2H_2O$, water to 1 L, and adjusted to, pH 7.4 with NaOH), or 3 μg of human $\beta_2$-microglobulin, or 100 μL PBS (for analysis of non specific binding) was used for over night coating at 4° C. and at 37° C. for one hour. After washing once with PBS, wells were blocked with 400 μL PBS and 3% non fat dried milk for one hour at 37° C. After blocking wells were washed once in PBS and 0.1% Tween 20 and three times with PBS before the addition of phages suspended in 100 μL PBS, 3% non fat dried milk. The phages were allowed to bind at 37° C. for one hour before washing three times with PBS, Tween 20 and three times with PBS. After washing, 50 μL of a 1 to 5000 dilution of a HRP-conjugated anti-gene VIII antibody (Amersham Pharmacia Biotech) in PBS, 3% non fat dried milk was added to each well and incubated at 37° C. for one hour. After binding of the "secondary" antibody wells were washed three times with PBS, Tween 20 and three times with PBS before the addition of 50 μL of TMB substrate (DAKO-TMB One-Step Substrate System, code: S1600, DAKO, Denmark). Reaction was allowed to proceed for 20 min before quenching with 0.5 M $H_2SO_4$.

Results showing relatively weak but specific binding to lysozyme are summarised in FIG. 29.

EXAMPLE 10

Construction of the Rat Mannose-Binding Protein CTLD (r-MBP) Derived Phagemid (pPrMBP) and Human Lung Surfactant Protein D CTLD (h-SP-D) Derived Phagemid (pPhSP-D)

The phagemid, pPrMBP, is constructed by ligation of the Sfi I and Not I restricted DNA fragment amplified from cDNA, isolated from rat liver (Drickamer, K., et al., *J. Biol. Chem.* 1987, 262(6):2582-2589) (with the oligonucleotide primers SfiMBP 5'-CGGCTGAGCGGCCCAGCCGGC-CATGGCCGAGCCAAACAAGTTGCATGCCTTCTCC-3' [SEQ ID NO:62] and NotMBP 5'-GCACTCCTGCGGC-CGCGGCTGGGAACTCGCAGAC-3' [SEQ ID NO:63]) into a Sfi I and Not I precut vector, PCANTAB 5E supplied by Amersham Pharmacia Biotech (code no. 27-9401-01) using standard procedures. Outlines of the resulting pPrMBP is shown in FIG. 31 and the nucleotide sequence of PrMBP is given as (SEQ ID NO:58). The amino acid sequence encoded by the PrMBP insert is shown in FIG. 30 (SEQ ID NO:59).

The phagemid, pPhSP-D, is constructed by ligation of the Sfi I and Not I restricted DNA fragment amplified from cDNA, isolated from human lung (Lu, J., et al., *Biochem J.* 1992 jun 15; 284:795-802) (with the oligonucleotide primers SfiSP-D 5'-CGGCTGAGCGGCCCAGCCGGCCATGGC-CGAGCCAAAGAAAGTTGAGCTCTTCCC-3' [SEQ ID NO:64] and NotSP-D 5'-GCACTCCTGCGGCCGC-GAACTCGCAGACCACAAGAC-3' [SEQ ID NO:65]) into a Sfi I and Not I precut vector, pCANTAB 5E supplied by Amersham Pharmacia Biotech (code no. 27-9401-01) using standard procedures. Outlines of the resulting pPhSP-D is shown in FIG. 33 and the nucleotide sequence of PhSP-D, is given as (SEQ ID NO:60). The amino acid sequences encoded by the PhSP-D insert is shown in FIG. 32 (SEQ ID NO:61).

EXAMPLE 11

Construction of the Phage Library PrMBP-lb001

The phage library PrMBP-lb001, containing random amino acid residues corresponding to PrMBP CTLD (SEQ ID NO:59) positions 71 to 73 or 70 to 76 (loop 1) and 97 to 101 or 100 to 101 (loop 4) is constructed by ligation of 20 μg SfiI and NotI restricted pPrMBP phagemid DNA (cf. Example 10) with 10 μg of a SfiI and NotI restricted DNA fragment population encoding the appropriately randomised loop 1 and 4 regions. The DNA fragment population is amplified, from nine assembly reactions combining each of the three loop 1 DNA fragments with each of the three loop 4 DNA fragments as templates and the oligonucleotides Sfi-tag 5'-CGGCTGAGCGGCCCAGC-3' (SEQ ID NO:74) and Not-tag 5'-GCACTCCTGCGGCCGCG3' (SEQ ID NO:75) as primers using standard procedures. Each of the three loop 1 fragments is amplified in a primary PCR reaction with pPrMBP phagmid DNA (cf. Example 10) as template and the oligonucleotides MBPloop1a fo (SEQ ID NO:66), MBPloop1b fo (SEQ ID NO:67)or MBPloop1c fo (SEQ ID NO:68) and SfiMBP (SEQ ID NO:62) as primers, and further amplified in a secondary PCR reaction using Sfi-tag (SEQ ID NO:74) and MBPloop1-tag fo (SEQ ID NO:69). Each of the three DNA loop 4 fragments is amplified in a primary PCR reaction with pPrMBP phagemid DNA (cf. Example 10) as template and the oligonucleotides MBPloop4a rev (SEQ ID NO:71), MBPloop4b rev (SEQ ID NO:72) or MBPloop4c rev (SEQ ID NO:73) and NotMBP (SEQ ID NO:63) as primers using standard procedures and further amplified in a secondary PCR reaction using MBPloop4-tag rev (SEQ ID NO:70) and Not-tag (SEQ ID NO:63). In the oligonucleotide sequences N denotes a mixture of 25% of each of the nucleotides T, C, G, and A, respectively, and S denotes a mixture of 50% of C and G, encoding the appropriately randomized nucleotide sequence. The ligation mixture is used to transform so-called electrocompetent *E. coli* TG-1 cells by electroporation using standard procedures. After transformation the *E. coli* TG-1 cells are plated on 2×TY-agar plates containing 0.2 mg ampicillin/mL and 2% glucose and incubated over night at 30° C.

EXAMPLE 12

Construction of the Phage Library PhSP-D-lb001

The phage library PhSP-D-lb001, containing random amino acid residues corresponding to PhSP-D CTLD insert (SEQ ID NO:61) positions 74 to 76 or 73 to 79 (loop 1) and 100 to 104 or 103 to 104 (loop 4) is constructed by ligation of 20 μg SfiI and NotI restricted pPhSP-D phagemid DNA (cf. Example 10) with 10 μg of a SfiI and NotI restricted DNA fragment population encoding the appropriately randomised loop 1 and 4 regions. The DNA fragment population is amplified, from nine assembly reactions combining each of the three loop 1 DNA fragments with each of the three loop 4 DNA fragments as templates and the oligonucleotides Sfi-tag 5'-CGGCTGAGCGGCCCAGC-3' (SEQ ID NO:74 ) and Not-tag 5'-GCACTCCTGCGGCCGCG-3' (SEQ ID NO:75) as primers using standard procedures. Each of the three loop 1 fragments is amplified in a primary PCR reaction with pPhSP-D phagemid DNA (cf. Example 10) as template and the oligonucleotides Sp-dloop1a fo (SEQ ID NO:76), Sp-dloop1b fo (SEQ ID NO:77)or Sp-dloop1c fo (SEQ ID NO:78) and SfiSP-D (SEQ ID NO:64) as primers, and further amplified in a PCR reaction using Sfi-tag (SEQ ID NO:74) and Sp-dloop1-tag fo (SEQ ID NO:79) as primers. Each of the three DNA loop 4 fragments is amplified in a primary PCR reaction with pPhSP-D phagemid DNA (cf. Example 10) as template and the oligonucleotides Sp-dloop4a rev (SEQ ID NO:81), Sp-dloop4b rev (SEQ ID ,NO:82) or Sp-dloop4c rev (SEQ ID NO:83) and NotSP-D (SEQ ID NO:65) as primers using standard procedures and further amplified in a PCR reaction using Sp-dloop4-tag rev (SEQ ID NO:80) and Not-tag (SEQ ID NO:75) as primers. In the oligonucleotide sequences N denotes a mixture of 25% of each of the nucleotides T, C, G, and A, respectively, and S denotes a mixture of 50% of C and G, encoding the appropriately randomized 3 nucleotide sequence. The ligation mixture is used to transform so-called electrocompetent $E.$ $coli$ TG-1 cells by electroporation using standard procedures. After transformation the $E.$ $coli$ TG-1 cells are plated on 2×TY-agar plates containing 0.2 mg ampicillin/mL and 2% glucose and incubated over night at 30° C.

EXAMPLE 13

Construction of the Phage Library PhtCTLD-lb004

All oligonucleotides used in this example were supplied by DNA Technology (Aarhus, Denmark).

The phage library PhtCTLD-lb004, containing random amino acid residues corresponding to PhtCTLD (SEQ ID NO:15) positions 97 to 102 or 98 to 101 (loop 3) and positions 116 to 122 or 118 to 120 (loop 5) was constructed by ligation of 20 μg KpnI and MunI restricted pPhtCTLD phagemid DNA (cf. Example 1) with 10 μg of a KpnI and MunI restricted DNA fragment population encoding the randomised loop 3 and 5 regions. The DNA fragment population was amplified from nine primary PCR reactions combining each of the three loop 3 DNA fragments with each of the three loop 5 DNA fragments. The fragments was amplified with either of the oligonucleotides loop3a (SEQ ID NO:84), loop3b (SEQ ID NO: 85), or loop3c (SEQ ID NO:86) as template and loop5a(SEQ ID NO:87), loop5b(SEQ ID NO:88)or loop5c(SEQ ID NO:89) and loop3-4rev(SEQ ID NO:91) as primers. The DNA fragments were further amplified in PCR reactions, using the primary PCR product as template and the oligonucleotide loop3-4rev (SEQ ID NO:91) and loop3-4-5tag fo (SEQ ID NO:90) as primers. All PCR reactions were performed using standard procedures.

In the oligonucleotide sequences N denotes a mixture of 25% of each of the nucleotides T, C, G, and A, respectively and S denotes a mixture of 50% of C and G, encoding the appropriately randomised nucleotide sequence. The ligation mixture was used to transform so-called electrocompetent $E.$ $coli$ TG-1 cells by electroporation using standard procedures. After transformation the $E.$ $coli$ TG-1 cells were plated on 2×TY-agar plates containing 0.2 mg ampicillin/mL and 2% glucose and incubated over night at 30° C.

The size of the resulting library, PhtCTLD-1b004, was determined to $7*10^9$ clones. Sixteen clones from the library were picked and phagemid DNA isolated. The nucleotide sequence of the loop-regions were determined (DNA Technology, Aarhus, Denmark). Thirteen clones were found to contain correct loop inserts and three clones contained a frameshift mutation in the region.

EXAMPLE 14

Selection of Phtlec-Phages and PhtCTLD-Phages Binding to the Blood Group A Sugar Moiety Immobilised on Human Serum Albumin Phages grown from glycerol stocks of the libraries Phtlec-1b001 and Phtlec-1b002 (cf. Example 4) and phages grown from a glycerol stock of the library PhtCTLD-1b003 (cf. Example 5), using a standard procedure, were used in an experiment designed for the selection of Phtlec- and PhtCTLD derived phages with specific affinity to the blood group A sugar moiety immobilized on human serum albumin, A-HA, by panning in 96-well Maxisorb micro-titerplates (NUNC, Denmark) using standard procedures.

Initially, the phage supernatants were precipitated with 0.3 volume of a solution of 20% polyethylene glycol 6000 (PEG) and 2.5 M NaCl, and the pellets re-suspended in TE-buffer (10 mM Tris-HC1 pH 8, 1 mM EDTA). After titration on $E.$ $coli$ TG-1 cells, phages derived from Phtlec-1b001 and -1b002 were mixed (#1) in a 1:1 ratio and adjusted to $5*10^{12}$ pfu/mL in 2*TY medium, and phages grown from the PhtCTLD-1b003 library (#4) were adjusted to $2.5*10^{12}$ pfu/mL in 2*TY medium.

One microgram of the "antigen", human blood group A trisaccharide immobilised on human serum albumin, A-HA, (Glycorex AB, Lund, Sweden) in 100 μL PBS (PBS, 0.2 g KCl, 0.2 g $KH_2PO_4$, 8 g NaCl, 1.44 g $Na_2HPO_4$, $2H_2O$, water to 1 L, and adjusted to pH 7.4 with NaOH), in each of three wells, was coated over night at 4° C. and at room temperature for one hour, before the first round of panning. After washing once with PBS, wells were blocked with 300 μL PBS and 3% non fat dried milk for one hour at room temperature. After blocking wells were washed once in PBS and 0.1% Tween 20 and three times with PBS before the addition of a mixture of 50 μL of the phage suspension and 50 μL PBS, 6% non fat dried milk. The phages were allowed to bind at room temperature for two hours before washing eight times with PBS, Tween 20, and eight times with PBS. Bound phages were eluted from each well by trypsin digestion in 100 μL (1 mg/mL trypsin in PBS) for 30 min. at room temperature, and used for infection of exponentially growing $E.$ $coli$ TG1 cells before plating and titration on 2×TY agar plates containing 2% glucose and 0.1 mg/mL ampicillin.

In the second round of selection, 150 μL of crude phage supernatant, grown from the first round output colonies, was mixed with 150 μL PBS, 6% non fat dried milk, and used for panning distributing 100 μL of the mixture in each of three A-HA coated wells, as previously described. Stringency in binding was increased by increasing the number of washing steps from 16 to 32. 300 μL of phage mixture was also used for panning in three wells, which had received no antigen as control.

In the third round of selection, 150 μL of crude phage supernatant, grown from the second round output colonies, was mixed with 150 μL PBS, 6% non fat dried milk, and used for panning distributing 100 μL of the mixture in each of three A-HA coated wells, as previously described. The number of washing steps was again 32. 300 μL of phage mixture was also used for panning in three wells, which had received no antigen as control.

The results from the selection procedure are summarised in Table 8

TABLE 8

Selection of Phtlec phages (#1) and PhtCTLD phages (#4) binding to A-HA by panning and elution with trypsin digestion.

|  |  | A-HA | Blank | Ratio |
|---|---|---|---|---|
| Round 1 | #1 | $0.8*10^3$ | n.a. | n.a. |
|  | #4 | $1.1*10^3$ | n.a. | n.a. |
| Round 2 | #1 | $1.0*10^3$ | $0.5*10^2$ | 20 |
|  | #4 | $1.3*10^3$ | $0.5*10^2$ | 26 |
| Round 3 | #1 | $8.0*10^4$ | $0.5*10^2$ | 1600 |
|  | #4 | $9.0*10^5$ | $0.5*10^2$ | 18000 | n.a. not applicable.

48 clones from each of the #1 and #4 series were picked and grown in a 96 well microtiter tray and phages produced by infection with M13K07 helper phage using a standard procedure. Phages from the 96 phage supernatants were analysed for binding to the A-HA antigen and for non-specific binding to hen egg white lysozyme using an ELISA-type assay. Briefly, in each well 1 μg of A-HA in 100 μL PBS (PBS, 0.2 g KCl, 0.2 g $KH_2PO_4$, 8 g NaCl, 1.44 g $Na_2HPO_4$, $2H_2O$, water to 1 L, and adjusted to pH 7.4 with NaOH) or 1 μg of hen egg white lysozyme in 100 μL PBS (for analysis of non specific binding) was used for over night coating at 4° C. and at room temperature for one hour. After washing once with PBS, wells were blocked with 300 μL PBS and 3% non fat dried milk for one hour at room temperature. After blocking wells were washed once in PBS and 0.1% Tween 20 and three times with PBS before the addition of 50 μL phage supernatant in 50 μL PBS, 6% non fat dried milk. The phage mixtures were allowed to bind at room temperature for two hours before washing three times with PBS, Tween 20, and three times with PBS. After washing, 50 μL of a 1:5000 dilution of a HRP-conjugated anti-gene VIII antibody (Amersham Pharmacia Biotech) in PBS, 3% non fat dried milk, was added to each well and incubated at room temperature for one hour. After binding of the "secondary" antibody wells were washed three times with PBS, Tween 20, and three times with PBS before the addition of 50 μL of TMB substrate (DAKO-TMB One-Step Substrate System, DAKO, Denmark). Reaction was allowed to proceed for 20 min. before quenching with 0.5 M $H_2SO_4$, and analysis. The result of the ELISA analysis showed "hits" in terms of specific binding to A-HA of phages in both series (FIGS. 34 and 35), as judged by a signal ratio between signal on A-HA to signal on lysozyme at or above 1.5, and with a signal above background. From the #1 series 13 hits were identified and 28 hits were identified from the #4 series.

REFERENCES

Aspberg, A., Miura, R., Bourdoulous, S., Shimonaka, M., Heinegård, D., Schachner, M., Ruoslahti, E., and Yamaguchi, Y. (1997). "The C-type lectin domains of lecticans, a family of aggregating chondroitin sulfate proteoglycans, bind tenascin-R by protein-protein interactions independent of carbohydrate moiety". *Proc. Natl. Acad. Sci. (USA)* 94: 10116-10121

Bass, S., Greene, R., and Wells, J. A. (1990). "Hormone phage: an enrichment method for variant proteins with altered binding properties". *Proteins* 8: 309-314

Benhar, I., Azriel, R., Nahary, L., Shaky, S., Berdichevsky, Y., Tamarkin, A., and Wels, W. (2000). "Highly efficient selection of phage antibodies mediated by display of antigen as Lpp-OmpA' fusions on live bacteria". *J. Mol. Biol.* 301: 893-904

Berglund, L. and Petersen, T. E. (1992). "The gene structure of tetranectin, a plasminogen binding protein". *FEBS Letters* 309: 15-19

Bertrand, J. A., Pignol, D., Bernard, J-P., Verdier, J-M., Dagorn, J-C., and Fontecilla-Camps, J. C. (1996). "Crystal structure of human lithostathine, the pancreatic inhibitor of stone formation". *EMBO J.* 15: 2678-2684

Bettler, B., Texido, G., Raggini, S., Ruegg, D., and Hofstetter, H. (1992). "Immunoglobulin E-binding site in Fc epsilon receptor (Fc epsilon RII/CD23) identified by homolog-scanning mutagenesis". *J. Biol. Chem.* 267: 185-191

Blanck, O., Iobst, S. T., Gabel, C., and Drickamer, K. (1996). "Introduction of selectin-like binding specificity into a homologous mannose-binding protein". *J. Biol. Chem.* 271: 7289-7292

Boder, E. T. and Wittrup, K. D. (1997). "Yeast surface display for screening combinatorial polypeptide libraries". *Nature Biotech.* 15: 553-557

Burrows L, Iobst S T, Drickamer K. (1997) "Selective binding of N-acetylglucosamine to the chicken hepatic lectin". *Biochem J.* 324:673-680

Chiba, H., Sano, H., Saitoh, M., Sohma, H., Voelker, D. R., Akino, T., and Kuroki, Y. (1999). "Introduction of mannose binding protein-type phosphatidylinositol recognition into pulmonary surfactant protein A". *Biochemistry* 38: 7321-7331

Christensen, J. H., Hansen, P. K., Lillelund, O., and Thøgersen, H. C. (1991). "Sequence-specific binding of the N-terminal three-finger fragment of *Xenopus* transcription factor IIIA to the internal control region of a 5S RNA gene". *FEBS Letters* 281: 181-184

Cyr, J. L. and Hudspeth, A. J. (2000). "A library of bacteriophage-displayed antibody fragments directed against proteins of the inner ear". *Proc. Natl. Acad. Sci (USA)* 97: 2276-2281

Drickamer, K. (1992). "Engineering galactose-binding activity into a C-type mannose-binding protein". *Nature* 360: 183-186

Drickamer, K. and Taylor, M. E. (1993). "Biology of animal lectins". *Annu. Rev. Cell Biol.* 9: 237-264

Drickamer, K. (1999). "C-type lectin-like domains". *Curr. Opinion Struc. Biol.* 9: 585-590

Dunn, I. S. (1996). "Phage display of proteins". *Curr. Opinion Biotech.* 7: 547-553

Erbe, D. V., Lasky, L. A., and Presta, L. G. "Selectin variants". U.S. Pat. No. 5,593,882

Ernst, W. J., Spenger, A., Toellner, L., Katinger, H., Grabherr, R. M. (2000). "Expanding baculovirus surface display. Modification of the native coat protein gp64 of *Autographa californica* NPV". *Eur. J. Biochem.* 267: 4033-4039

Ewart, K. V., Li, Z., Yang, D. S. C., Fletcher, G. L., and Hew, C. L. (1998). "The ice-binding site of Atlantic herring antifreeze protein corresponds to the carbohydrate-binding site of C-type lectins". *Biochemistry* 37: 4080-4085

Feinberg, H., Park-Snyder, S., Kolatkar, A. R., Heise, C. T., Taylor, M. E., and Weis, W. I. (2000). "Structure of a C-type carbohydrate recognition domain from the macrophage mannose receptor". *J. Biol. Chem.* 275: 21539-21548

Fujii, I., Fukuyama, S., Iwabuchi, Y., and Tanimura, R. (1998). "Evolving catalytic antibodies in a phage-displayed combinatorial library". *Nature Biotech.* 16: 463-467

Gates, C. M., Stemmer, W. P. C., Kaptein, R., and Schatz, P. J. (1996). "Affinity selective isolation of ligands from peptide libraries through display on a lac repressor "headpiece dimer"". *J. Mol. Biol.* 255: 373-386

Graversen, J. H., Lorentsen, R. H., Jacobsen, C., Moestrup, S. K., Sigurskjold, B. W., Thøgersen, H. C., and Etzerodt, M. (1998). "The plasminogen binding site of the C-type lectin tetranectin is located in the carbohydrate recognition domain, and binding is sensitive to both calcium and lysine". *J. Biol. Chem.* 273:29241-29246

Graversen, J. H., Jacobsen, C., Sigurskjold, B. W., Lorentsen, R. H., Moestrup, S. K., Thøgersen, H. C., and Etzerodt, M. (2000). "Mutational Analysis of Affinity and Selectivity of Kringle-Tetranectin Interaction. Grafting novel kringle affinity onto the tetranectin lectin scaffold". *J. Biol. Chem.* 275: 37390-37396

Griffiths, A. D. and Duncan, A. R. (1998). "Strategies for selection of antibodies by phage display". *Curr. Opinion Biotech.* 9: 102-108

Holtet, T. L., Graversen, J. H., Clemmensen, I., Thøgersen, H. C., and Etzerodt, M. (1997). "Tetranectin, a trimeric plasminogen-binding C-type lectin". *Prot. Sci.* 6: 1511-1515

Honma, T., Kuroki, Y., Tzunezawa, W., Ogasawara, Y., Sohma, H., Voelker, D. R., and Akino, T. (1997). "The mannose-binding protein A region of glutamic acid185-alanine221 can functionally replace the surfactant protein A region of glutamic acid195-phenylalanine228 without loss of interaction with lipids and alveolar type II cells". *Biochemistry* 36: 7176-7184

Huang, W., Zhang, Z., and Palzkill, T. (2000). "Design of potent beta-lactamase inhibitors by phage display of beta-lactamase inhibitory protein". *J. Biol. Chem.* 275: 14964-14968

Hufton, S. E., van Neer, N., van den Beuken, T., Desmet, J., Sablon, E., and Hoogenboom, H. R. (2000). "Development and application of cytotoxic T lymphocyte-associated antigen 4 as a protein scaffold for the generation of novel binding ligands". *FEBS Letters* 475: 225-231

Håkansson, K., Lim, N. K., Hoppe, H-J., and Reid, K. B. M. (1999). "Crystal structure of the trimeric alpha-helical coiled-coil and the three lectin domains of human lung surfactant protein D". *Structure Folding and Design* 7: 255-264

Iobst, S. T., Wormald, M. R., Weis, W. I., Dwek, R. A., and Drickamer, K. (1994). "Binding of sugar ligands to Ca(2+)-dependent animal lectins. I. Analysis of mannose binding by site-directed mutagenesis and NMR". *J. Biol. Chem.* 269: 15505-15511

Iobst, S. T. and Drickamer, K. (1994). "Binding of sugar ligands to Ca(2+)-dependent animal lectins. II. Generation of high-affinity galactose binding by site-directed mutagenesis". *J. Biol. Chem.* 269: 15512-15519

Iobst, S. T. and Drickamer, K. (1996). "Selective sugar binding to the carbohydrate recognition domains of the rat hepatic and macrophage asialoglycoprotein receptors". *J. Biol. Chem.* 271: 6686-6693

Jaquinod, M., Holtet, T. L., Etzerodt, M., Clemmensen, I., Thøgersen, H. C., and Roepstorff, P. (1999). "Mass Spectrometric Characterisation of Post-Translational Modification and Genetic Variation in Human Tetranectin". *Biol. Chem.* 380: 1307-1314

Kastrup, J. S., Nielsen, B. B., Rasmussen, H., Holtet, T. L., Graversen, J. H., Etzerodt, M., Thøgersen, H. C., and Larsen, I. K. (1998). "Structure of the C-type lectin carbohydrate recognition domain of human tetranectin". *Acta. Cryst. D* 54: 757-766

Kogan, T. P., Revelle, B. M., Tapp, S., Scott, D., and Beck, P. J. (1995). "A single amino acid residue can determine the ligand specificity of E-selectin". *J. Biol. Chem.* 270: 14047-14055

Kolatkar, A. R., Leung, A. K., Isecke, R., Brossmer, R., Drickamer, K., and Weis, W. I. (1998). "Mechanism of N-acetylgalactosamine binding to a C-type animal lectin carbohydrate-recognition domain". *J. Biol. Chem.* 273: 19502-19508

Lorentsen, R. H., Graversen, J. H., Caterer, N. R., Thøgersen, H. C., and Etzerodt, M. (2000). "The heparin-binding site in tetranectin is located in the N-terminal region and binding does not involve the carbohydrate recognition domain". *Biochem. J.* 347: 83-87

Marks, J. D., Hoogenboom, H. R., Griffiths, A. D., and Winter, G. (1992). "Molecular evolution of proteins on filamentous phage. Mimicking the strategy of the immune system". *J. Biol. Chem.* 267: 16007-16010

Mann K, Weiss I M, Andre S, Gabius H J, Fritz M. (2000). "The amino-acid sequence of the abalone (Haliotis laevigata) nacre protein perlucin. Detection of a functional C-type lectin domain with galactose/mannose specificity". *Eur. J. Biochem.* 267: 5257-5264

McCafferty, J., Jackson, R. H., and Chiswell, D. J. (1991). "Phage-enzymes: expression and affinity chromatography of functional alkaline phosphatase on the surface of bacterio-phage". *Prot. Eng.* 4: 955-961

McCormack, F. X., Kuroki, Y., Stewart, J. J., Mason, R. J., and Voelker, D. R. (1994). "Surfactant protein A amino acids Glu195 and Arg197 are essential for receptor binding, phospholipid aggregation, regulation of secretion, and the facilitated uptake of phospholipid by type II cells". *J. Biol. Chem.* 269: 29801-29807

McCormack, F. X., Festa, A. L., Andrews, R. P., Linke, M., and Walzer, P. D. (1997). "The carbohydrate recognition domain of surfactant protein A mediates binding to the major surface glycoprotein of Pneumocystis carinii". *Biochemistry* 36: 8092-8099

Meier, M., Bider, M. D., Malashkevich, V. N., Spiess, M., and Burkhard, P. (2000). "Crystal structure of the carbohydrate recognition domain of the Hi subunit of the asialoglycoprotein receptor". *J. Mol. Biol.* 300: 857-865

Mikawa, Y. G., Maruyama, I. N., and Brenner, S. (1996). "Surface display of proteins on bacteriophage lambda heads". *J. Mol. Biol.* 262: 21-30

Mio H, Kagami N, Yokokawa S, Kawai H, Nakagawa S, Takeuchi K, Sekine S, Hiraoka A. (1998). "Isolation and characterization of a cDNA for human mouse, and rat full-length stem cell growth factor, a new member of C-type lectin superfamily". *Biochem. Biophys. Res. Commun.* 249: 124-130

Mizuno, H., Fujimoto, Z., Koizumi, M., Kano, H., Atoda, H., and Morita, T. (1997). "Structure of coagulation factors IX/X-binding protein, a heterodimer of C-type lectin domains". *Nat. Struc. Biol.* 4: 438-441

Ng, K. K., Park-Snyder, S., and Weis, W. I. (1998a) . "$Ca^{2+}$-dependent structural changes in C-type mannose-binding proteins". *Biochemistry* 37: 17965-17976

Ng, K. K. and Weis, W. I. (1998b). "Coupling of prolyl peptide bond isomerization and Ca2+ binding in a C-type mannose-binding protein". *Biochemistry* 37: 17977-17989

Nielsen, B. B., Kastrup, J. S., Rasmussen, H., Holtet, T. L., Graversen, J. H., Etzerodt, M., Thøgersen, H. C., and Larsen, I. K. (1997). "Crystal structure of tetranectin, a trimeric plasminogen-binding protein with an alpha-helical coiled coil". *FEBS Letters* 412: 388-396

Nissim A., Hoogenboom, H. R., Tomlinson, I. M., Flynn, G., Midgley, C., Lane, D., and Winter, G. (1994). "Antibody fragments from a 'single pot' phage display library as immunochemical reagents". *EMBO J.* 13: 692-698

Ogasawara, Y. and Voelker, D. R. (1995). "Altered carbohydrate recognition specificity engineered into surfactant protein D reveals different binding mechanisms for phosphatidylinositol and glucosylceramide". *J. Biol. Chem.* 270: 14725-14732

Ohtani, K., Suzuki, Y., Eda, S., Takao, K., Kase, T., Yamazaki, H., Shimada, T., Keshi, H., Sakai, Y., Fukuoh, A., Sakamoto, T., and Wakamiya, N. (1999). "Molecular cloning of a novel human collectin from liver (CL-L1)". *J. Biol. Chem.* 274: 13681-13689

Pattanajitvilai, S., Kuroki, Y., Tsunezawa, W., McCormack, F. X., and Voelker, D. R. (1998). "Mutational analysis of Arg197 of rat surfactant protein A. His197 creates specific lipid uptake defects". *J. Biol. Chem.* 273: 5702-5707

Poget, S. F., Legge, G. B., Proctor, M. R., Butler, P. J., Bycroft, M., and Williams, R. L. (1999). "The structure of a tunicate C-type lectin from Polyandrocarpa misakiensis complexed with D-galactose". *J. Mol. Biol.* 290: 867-879

Revelle, B. M., Scott, D., Kogan, T. P., Zheng, J., and Beck, P. J. (1996). "Structure-function analysis of P-selectinsialyl LewisX binding interactions. Mutagenic alteration of ligand binding specificity". *J. Biol. Chem.* 271: 4289-4297

Sano, H., Kuroki, Y., Honma, T., Ogasawara, Y., Sohma, H., Voelker, D. R., and Akino, T. (1998). "Analysis of chimeric proteins identifies the regions in the carbohydrate recognition domains of rat lung collections that are essential for interactions with phospholipids, glycolipids, and alveolar type II cells". *J. Biol. Chem.* 273: 4783-4789

Schaffitzel, C., Hanes, J., Jermutus, L., and Plucktun, A. (1999). "Ribosome display: an in vitro method for selection and evolution of antibodies from libraries". *J. Immunol. Methods* 231: 119-135

Sheriff, S., Chang, C. Y., and Ezekowitz, R. A. (1994). "Human mannose-binding protein carbohydrate recognition domain trimerizes through a triple alpha-helical coiled-coil". *Nat. Struc. Biol.* 1: 789-794

Sørensen, C. B., Berglund, L., and Petersen, T. E. (1995). "Cloning of a cDNA encoding murine tetranectin". *Gene* 152: 243-245

Torgersen, D., Mullin, N. P., and Drickamer, K. (1998). "Mechanism of ligand binding to E- and P-selectin analyzed using selectin/mannose-binding protein chimeras". *J. Biol. Chem.* 273: 6254-6261

Tormo, J., Natarajan, K., Margulies, D. H., and Mariuzza, R. A. (1999). "Crystal structure of a lectin-like natural killer cell receptor bound to its MHC class I ligand". *Nature* 402: 623-631

Tsunezawa, W., Sano, H., Sohma, H., McCormack, F. X., Voelker, D. R., and Kuroki, Y. (1998). "Site-directed mutagenesis of surfactant protein A reveals dissociation of lipid aggregation and lipid uptake by alveolar type II cells". *Biochim. Biophys. Acta* 1387: 433-446

Weis, W. I., Kahn, R., Fourme, R., Drickamer, K., and Hendrickson, W. A. (1991). "Structure of the calcium-dependent lectin domain from a rat mannose-binding protein determined by MAD phasing". *Science* 254: 1608-1615

Weis, W. I., and Drickamer, K. (1996). "Structural basis of lectin-carbohydrate recognition". *Annu. Rev. Biochem.* 65: 441-473

Whitehorn, E. A., Tate, E., Yanofsky, S. D., Kochersperger, L., Davis A., Mortensen, R. B., Yonkovic, S., Bell, K., Dower, W. J., and Barrett, R. W. (1995). "A generic method for expression and use of "tagged" soluble versions of cell surface receptors". *Bio/Technology* 13: 1215-1219

Wragg, S. and Drickamer, K. (1999). "Identification of amino acid residues that determine pH dependence of ligand binding to the asialoglycoprotein receptor during endocytosis". *J. Biol. Chem.* 274: 35400-35406

Zhang, H., Robison, B., Thorgaard, G. H., and Ristow, S. S. (2000). "Cloning, mapping and genomic organization of a fish C-type lectin gene from homozygous clones of rainbow trout (Oncorhynchos Mykiss)". *Biochim. et Biophys. Acta* 1494: 14-22

The invention claimed is:

1. A method for the identification and isolation of a polypeptide capable of specifically binding to a target, said method comprising the steps of:
   (1) providing a nucleic acid library, wherein said library comprises a collection of nucleic acid molecules encoding an ensemble of polypeptides having the scaffold structure of a C-type lectin-like domain (CTLD) and a randomized CTLD loop region, said CTLD scaffold comprising the following structural elements:
      a) five β-strands and two α-helices sequentially appearing in the order β1, α1, α2, β2, β3, β4, and β5, the β-strands being arranged in two anti-parallel β-sheet composed of β1 and β5, the other β-sheet composed of β2, β3 and β4, and
      b) at least two disulfide bridges, one connecting α1 and β5 and one connecting β3 and a polypeptide segment connecting β4 and β5, and said randomized CTLD loop region consisting of two loop polypeptide segments, loop segment A (LSA) containing loops 1-4 and connecting β2 and β3, and loop segment B (LSB) containing loop 5 and connecting β3 and β4, wherein said CTLD loop region is randomized by substituting the portion of the nucleic acid molecules encoding some or all of the loop region with a nucleic acid fragment randomly selected from a multitude of nucleic acid fragments;
   (2) expressing the nucleic acid library in a display system to obtain an ensemble of polypeptides, in which the amino acid residues at least at one sequence position in the loop region differ between different members of said ensemble of polypeptides, wherein the amino acid residues differ at least at one sequence position in the loop region of amino acid residues 72-79 (loop 1), 81-85 (loop 2), 91-99 (loop 3), 101-107 (loop 4), and 114-117 (loop 5) of tetranectin SEQ ID NO: 276;

(3) contacting the ensemble of polypeptides in step (2) with said target; and
(4) isolating a polypeptide that is capable of specifically binding to said target from the ensemble of polypeptides in step (3).

2. The method according to claim 1, wherein the amino acid residues differ between different members of said ensemble of polypeptides at least at two amino acid sequence positions in the loop region.

3. The method according to claim 1, wherein the display system is selected from the group consisting of:
(I) a phage display system selected from
  (1) a filamentous phage fd in which the library of nucleic acids is inserted into (a) a phagemid vector, (b) the viral genome of a phage, (c) purified viral nucleic acid in purified single- or double-stranded form, or
  (2) a phage lambda in which the library of nucleic acids is inserted into (a) purified phage lambda DNA, or (b) the nucleic acid in lambda phage particles;
(II) a viral display system in which the library of nucleic acids is inserted into the viral nucleic acid of a eukaryotic virus such as baculovirus;
(III) a cell-based display system in which the library of nucleic acids is inserted into, or adjoined to, a nucleic acid carrier able to integrate either into the host genome or into an extrachromosomal element able to maintain and express itself within the cell and suitable for cell-surface display on the surface of (a) bacterial cells, (b) yeast cells, or (c) mammalian cells;
(IV) a nucleic acid entity suitable for ribosome linked display into which the library of nucleic acid is inserted; and
(V) a plasmid suitable for plasmid linked display into which the library of nucleic acid is inserted.

4. The method according to claim 1, wherein the target is selected from the group consisting of eukaryotic cells, viruses, bacteria, proteins, polysaccharides, lipids, lipoproteins, polymers and organic compounds.

5. The method of claim 1, wherein the amino acid residues differ at any of the sequence positions of 73-78 in loop 1, 93-98 in loop 3, 102-105 in loop 4, and 114-117 (loop 5) of tetranectin SEQ ID NO: 276.

6. The method of claim 5, wherein the amino acid residues differ at any of the sequence positions of 73-75 in loop 1, 77-78 in loop 1, and 102-105 in loop 4 of tetranectin SEQ ID NO: 276.

7. The method of claim 5, wherein the amino acid residues differ at any of the sequence positions of 93-98 in loop 3 and 102-105 in loop 4 of tetranectin SEQ ID NO: 276.

8. The method of claim 7, wherein the amino acid residues further differ at the sequence position of 120 of tetranectin SEQ ID NO: 276.

9. The method of claim 5, wherein the amino acid residues differ at any of the sequence positions of 93-98 in loop 3 and 114-117 (loop 5) of tetranectin SEQ ID NO: 276.

10. The method of claim 9, wherein the amino acid residues further differ at any of the sequence positions of 112, 113, and 118 of tetranectin SEQ ID NO: 276.

11. The method of claim 9, wherein the amino acid residues differ at any of the sequence positions of 94-97 in loop 3 and 114-116 in loop 5 of tetranectin SEQ ID NO: 276.

12. The method of claim 5, wherein the amino acid residues differ at any of the sequence positions of 73-75 in loop 1, 77-78 in loop 1, and 104-105 in loop 4 of tetranectin SEQ ID NO: 276.

13. A method for the identification and isolation of a polypeptide capable of specifically binding to a target, said method comprising the steps of:
(1) providing a nucleic acid library, wherein said library comprises a collection of nucleic acid molecules encoding an ensemble of polypeptides having the scaffold structure of a C-type lectin-like domain (CTLD) and a randomized CTLD loop region, said CTLD scaffold comprising the following structural elements:
  a) five β-strands and two α-helices sequentially appearing in the order β1, α1, α2, β2, β3, β4, and β5, the β-strands being arranged in two anti-parallel β-sheet composed of β1 and β5, the other β-sheet composed of β2, β3 and β4, and
  b) at least two disulfide bridges, one connecting α1 and β5 and one connecting β3 and a polypeptide segment connecting β4 and β5, and
said randomized CTLD loop region consisting of two loop polypeptide segments, loop segment A (LSA) containing loops 1-4 and connecting β2 and β3, and loop segment B (LSB) containing loop 5 and connecting β3 and β4, wherein said CTLD loop region is randomized by substituting the portion of the nucleic acid molecules encoding some or all of the loop region with a nucleic acid fragment randomly selected from a multitude of nucleic acid fragments;
(2) expressing the nucleic acid library in a display system to obtain an ensemble of polypeptides, in which the amino acid residues at least at one sequence position in the loop region differ between different members of said ensemble of polypeptides, wherein the amino acid residues differ at least at one sequence position in the loop region corresponding to amino acid residues 66-73 (loop 1), 75-79 (loop 2), 85-90 (loop 3), 92-99 (loop 4), and 105-107 (loop 5) of mannose binding protein (MBP) SEQ ID NO: 277;
(3) contacting the ensemble of polypeptides in step (2) with said target; and
(4) isolating a polypeptide that is capable of specifically binding to said target from the ensemble of polypeptides in step (3).

14. The method of claim 13, wherein the amino acid residues differ at any of the sequence positions of 66-72 in loop 1 and 93-97 in loop 4 of MBP SEQ ID NO: 277.

15. The method of claim 14, wherein the amino acid residues differ at any of the sequence positions of 67-69 in loop 1 and 96-97 in loop 4 of MBP SEQ ID NO: 277.

16. The method according to claim 13, wherein the target is selected from the group consisting of eukaryotic cells, viruses, bacteria, proteins, polysaccharides, lipids, lipoproteins, polymers and organic compounds.

17. The method according to claim 13, wherein the display system is selected from the group consisting of:
(I) a phage display system selected from
  (3) a filamentous phage fd in which the library of nucleic acids is inserted into (a) a phagemid vector, (b) the viral genome of a phage, (c) purified viral nucleic acid in purified single- or double-stranded form, or
  (4) a phage lambda in which the library of nucleic acids is inserted into (a) purified phage lambda DNA, or (b) the nucleic acid in lambda phage particles;
(II) a viral display system in which the library of nucleic acids is inserted into the viral nucleic acid of a eukaryotic virus such as baculovirus;
(III) a cell-based display system in which the library of nucleic acids is inserted into, or adjoined to, a nucleic acid carrier able to integrate either into the host genome or into an extrachromosomal element able to maintain and express itself within the cell and suitable for cell-surface display on the surface of (a) bacterial cells, (b) yeast cells, or (c) mammalian cells;

(IV) a nucleic acid entity suitable for ribosome linked display into which the library of nucleic acid is inserted; and (V) a plasmid suitable for plasmid linked display into which the library of nucleic acid is inserted.

18. A method for the identification and isolation of a polypeptide capable of specifically binding to a target, said method comprising the steps of:

(1) providing a nucleic acid library, wherein said library comprises a collection of nucleic acid molecules encoding an ensemble of polypeptides having the scaffold structure of a C-type lectin-like domain (CTLD) and a randomized CTLD loop region, said CTLD scaffold comprising the following structural elements:

a) five β-strands and two α-helices sequentially appearing in the order β1, α1, α2, β2, β3, β4, and β5, the β-strands being arranged in two anti-parallel β-sheet composed of β1 and β5, the other β-sheet composed of β2, β3 and β4, and b) at least two disulfide bridges, one connecting α1 and β5 and one connecting β3 and a polypeptide segment connecting β4 and β5, and said randomized CTLD loop region consisting of two loop polypeptide segments, loop segment A (LSA) containing loops 1-4 and connecting β2 and β3, and loop segment B (LSB) containing loop 5 and connecting β3 and β4, wherein said CTLD loop region is randomized by substituting the portion of the nucleic acid molecules encoding some or all of the loop region with a nucleic acid fragment randomly selected from a multitude of nucleic acid fragments;

(2) expressing the nucleic acid library in a display system to obtain an ensemble of polypeptides, in which the amino acid residues at least at one sequence position in the loop region differ between different members of said ensemble of polypeptides, wherein the amino acid residues differ at least at one sequence position in the loop region of amino acid residues 69-76 (loop 1), 78-82 (loop 2), 88-93 (loop 3), 95-102 (loop 4), and 108-110 (loop 5) of surfactant protein D (SP-D) SEQ ID NO: 278;

(3) contacting the ensemble of polypeptides in step (2) with said target; and (4) isolating a polypeptide that is capable of specifically binding to said target from the ensemble of polypeptides in step (3).

19. The method of claim 18, wherein the amino acid residues differ at any of the sequence positions of 69-75 in loop 1 and 96-100 in loop 4 of SP-D SEQ ID NO: 278.

20. The method of claim 18, wherein the amino acid residues differ at any of the sequence positions of 70-72 in loop 1 and 99-100 in loop 4 of SP-D SEQ ID NO: 278.

21. The method according to claim 18, wherein the target is selected from the group consisting of eukaryotic cells, viruses, bacteria, proteins, polysaccharides, lipids, lipoproteins, polymers and organic compounds.

22. The method according to claim 18, wherein the display system is selected from the group consisting of:

(I) a phage display system selected from (5) a filamentous phage fd in which the library of nucleic acids is inserted into (a) a phagemid vector, (b) the viral genome of a phage, (c) purified viral nucleic acid in purified single- or double-stranded form, or (6) a phage lambda in which the library of nucleic acids is inserted into (a) purified phage lambda DNA, or (b) the nucleic acid in lambda phage particles;

(II) a viral display system in which the library of nucleic acids is inserted into the viral nucleic acid of a eukaryotic virus such as baculovirus;

(III) a cell-based display system in which the library of nucleic acids is inserted into, or adjoined to, a nucleic acid carrier able to integrate either into the host genome or into an extrachromosomal element able to maintain and express itself within the cell and suitable for cell-surface display on the surface of (a) bacterial cells, (b) yeast cells, or (c) mammalian cells;

(IV) a nucleic acid entity suitable for ribosome linked display into which the library of nucleic acid is inserted; and (V) a plasmid suitable for plasmid linked display into which the library of nucleic acid is inserted.

* * * * *

UNITED STATES PATENT AND TRADEMARK OFFICE
CERTIFICATE OF CORRECTION

| | | |
|---|---|---|
| PATENT NO. | : 8,017,559 B2 | Page 1 of 1 |
| APPLICATION NO. | : 11/633040 | |
| DATED | : September 13, 2011 | |
| INVENTOR(S) | : Etzerodt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 649 days.

Signed and Sealed this
Thirteenth Day of December, 2011

David J. Kappos
*Director of the United States Patent and Trademark Office*